United States Patent
Shimizu et al.

(10) Patent No.: US 9,854,805 B2
(45) Date of Patent: *Jan. 2, 2018

(54) COMPOSITION AND METHOD FOR CONTROLLING PESTS

(71) Applicant: SUMITOMO CHEMICAL COMPANY, LIMITED, Tokyo (JP)

(72) Inventors: Chie Shimizu, Tokyo (JP); Masashi Kamezaki, Takarazuka (JP); Yoshihiko Nokura, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/764,317

(22) PCT Filed: Jan. 30, 2014

(86) PCT No.: PCT/JP2014/052144
§ 371 (c)(1),
(2) Date: Jul. 29, 2015

(87) PCT Pub. No.: WO2014/119674
PCT Pub. Date: Aug. 7, 2014

(65) Prior Publication Data
US 2015/0366207 A1    Dec. 24, 2015

(30) Foreign Application Priority Data

Jan. 31, 2013 (JP) .................. 2013-016546

(51) Int. Cl.
| C07D 401/00 | (2006.01) |
| C07D 421/00 | (2006.01) |
| C07D 413/00 | (2006.01) |
| A01N 43/90 | (2006.01) |
| A01N 43/56 | (2006.01) |
| A01N 43/52 | (2006.01) |
| A01N 43/76 | (2006.01) |

(52) U.S. Cl.
CPC ............ *A01N 43/90* (2013.01); *A01N 43/52* (2013.01); *A01N 43/56* (2013.01); *A01N 43/76* (2013.01)

(58) Field of Classification Search
None
See application file for complete search history.

(56) References Cited

U.S. PATENT DOCUMENTS

| 9,018,134 | B2 * | 4/2015 | Takahashi | .............. A01N 43/76 504/246 |
| 9,615,580 | B2 * | 4/2017 | Takahashi | .............. A01N 43/90 |
| 2004/0014977 | A1 | 1/2004 | Fukuda et al. | |
| 2005/0233909 | A1 | 10/2005 | Fukuda et al. | |
| 2011/0039843 | A1 | 2/2011 | Iwakoshi et al. | |
| 2013/0045970 | A1 | 2/2013 | Matsuzaki | |
| 2013/0090353 | A1 | 4/2013 | Iwakoshi et al. | |
| 2013/0116294 | A1 | 5/2013 | Matsuzaki | |
| 2014/0018373 | A1 | 1/2014 | Takyo et al. | |
| 2015/0148308 | A1 | 5/2015 | Suzuki et al. | |

FOREIGN PATENT DOCUMENTS

| CN | 102006776 A | 4/2011 |
| CN | 102858162 A | 1/2013 |
| JP | 2002-20384 A | 1/2002 |

(Continued)

OTHER PUBLICATIONS

Carey, FA. Organic Chemistry 6th Ed. McGraw Hill. 2006, chapter 1, p. 9.*
Chinese Office Action and Search Report dated May 24, 2016, for Chinese Application No. 201480006841.1 with the English translation.
European Patent Office Communication including an extended search report issued in the corresponding European Patent Application No. 14745879.8 dated Jun. 27, 2016.
Hisano et al., "Synthesis of Benzoxazoles, Benzothiazoles and Benzimidazoles and Evaluation of Their Antifungal, Insecticidal and Herbicidal Activities," Chemical and Pharmaceutical Bulletin, vol. 30, No. 8, 1982, pp. 2996-3004.

(Continued)

*Primary Examiner* — Andrew D Kosar
*Assistant Examiner* — Ben S Michelson
(74) *Attorney, Agent, or Firm* — Birch, Stewart, Kolasch & Birch, LLP

(57) ABSTRACT

The present invention provides a composition for controlling pests having an excellent control efficacy on pests.
A composition for controlling pests comprising a compound represented by the formula (1):

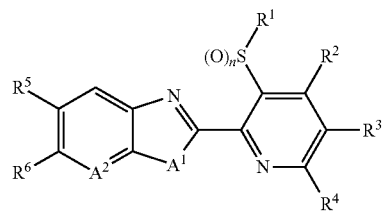

(1)

wherein each of symbols are the same as defined in the Description, or N-oxide thereof; and
a compound represented by the formula (2):

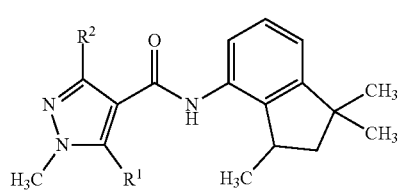

(2)

wherein each of symbols are the same as defined in the Description;
shows an excellent controlling efficacy on pests.

5 Claims, No Drawings

(56) References Cited

FOREIGN PATENT DOCUMENTS

| | | | |
|---|---|---|---|
| JP | 2004-34438 A | | 2/2004 |
| JP | 2011-231038 A | | 11/2011 |
| JP | 2011-231041 A | | 11/2011 |
| JP | 2012-131780 A | | 7/2012 |
| JP | 2014-5263 A | | 1/2014 |
| TW | 201242962 A1 | | 11/2012 |
| WO | WO 2010/125985 A1 | | 11/2010 |
| WO | WO 2011/043404 A1 | | 4/2011 |
| WO | WO 2011/135827 A1 | * | 11/2011 |
| WO | WO 2011/135830 A1 | | 11/2011 |
| WO | WO 2012/074135 A1 | | 6/2012 |
| WO | WO 2012/086848 A1 | | 6/2012 |
| WO | WO 2013/018928 A1 | * | 2/2013 |
| WO | WO 2013/018928 A1 | | 2/2013 |
| WO | WO 2013/187422 A1 | | 12/2013 |
| WO | WO 2013/187424 A1 | | 12/2013 |
| WO | WO 2013/187425 A1 | | 12/2013 |
| WO | WO 2013/187426 A1 | | 12/2013 |
| WO | WO 2014/104407 A1 | * | 7/2014 |

OTHER PUBLICATIONS

International Preliminary Report on Patentability and Written Opinion of the International Searching Authority (Forms PCT/IB/373 and PCT/ISA/237) for International Application No. PCT/JP2014/052144, dated Aug. 4, 2015.

International Search Report (Form PCT/ISA/210) for International Application No. PCT/JP2014/052144, dated Apr. 8, 2014.

European Patent Office Communication pursuant to Article 94(3) EPC issued in the corresponding European Patent Application No. 14745879.8 dated Jun. 26, 2017.

Office Action and Search Report (including an English translation thereof) issued in the corresponding Taiwanese Patent Application No. 103103706 dated May 5, 2017.

Second Office Action (including an English translation thereof) issued in the corresponding Chinese Patent Application No. 201480006841.1 dated Apr. 5, 2017.

* cited by examiner

COMPOSITION AND METHOD FOR CONTROLLING PESTS

TECHNICAL FIELD

This application claims priority to and the benefit of Japanese Patent Application No. 2013-016546, filed Jan. 31, 2013, the entire contents of which is incorporated herein by reference.

The present invention relates to a composition for controlling pests and a method for controlling pests.

BACKGROUND ART

Hitherto, many compounds have been known as active ingredients in a composition for controlling pests (The Pesticide Manual-15th edition, published by British Crop Protection Council (BCPC), ISBN 978-1-901396-18-8).

SUMMARY OF INVENTION

Problems to be Solved by Invention

An object of the present invention is to provide a composition for controlling pests having an excellent control efficacy on pests.

Means to Solve Problems

The present inventors have intensively studied to find out a composition for controlling pests having an excellent control efficacy on pests. As a result, they have found that a composition comprising a compound represented by the following the formula (1) and a compound represented by the following the formula (2) has an excellent controlling effect on pests.

Specifically, the present invention includes:
Item 1.
A composition for controlling pests comprising a compound represented by the formula (1) or N-oxide thereof and a compound represented by the formula (2);
the formula (1):

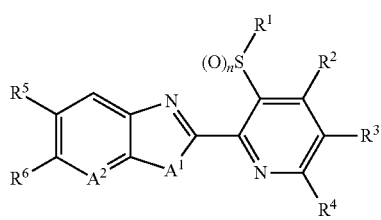

wherein
$A^1$ represents —$NR^7$—, an oxygen atom, or a sulfur atom;
$A^2$ represents a nitrogen atom or =$CR^8$—;
$R^1$ represents a C1-C6 alkyl group which may be substituted with one or more atoms or groups selected from Group X;
$R^2$, $R^3$ and $R^4$ are the same or different to each other and each independently represent a C1-C6 alkyl group which may be substituted with one or more atoms or groups selected from Group X, a —$OR^{10}$ group, a —$C(OR^{10})_3$ group, a —$S(O)_m R^{10}$ group, a —$S(O)_2 NR^{10} R^{11}$ group, a —$NR^{10} R^{11}$ group, a —$NR^{10} CO_2 R^{11}$ group, a —$NR^{10} C(O) R^{10} R^{11}$ group, a —$CO_2 R^{10}$ group, a —$C(O)R^{10}$ group, a —$C(O)NR^{10}R^{11}$ group, a —$SF_5$ group, a cyano group, a nitro group, a halogen atom, or a hydrogen atom;
$R^5$ and $R^6$ are the same or different to each other and each independently represent a C1-C6 alkyl group which may be substituted with one or more atoms or groups selected from Group X, a —$OR^{10}$ group, a —$S(O)_m R^{10}$ group, a —$S(O)_2 NR^{10} R^{11}$ group, a —$NR^{10} R^{11}$ group, a —$NR^{10} CO_2 R^{11}$ group, a —$NR^{10} C(O) R^{11}$ group, a —$CO_2 R^{10}$ group, a —$C(O) R^{10}$ group, a —$C(O)NR^{10}R^{11}$ group, —$OC(O)R^{10}$, a —$SF_5$ group, a —$SH$ group, a cyano group, a nitro group, a halogen atom, or a hydrogen atom, except for a case in which $R^5$ and $R^6$ are both hydrogen atoms;
$R^7$ represents a C1-C6 alkyl group which may be substituted with one or more atoms or groups selected from Group W, a —$CO_2 R^{10}$ group, a —$C(O)R^{10}$ group, a —$CH_2CO_2R^{10}$ group, a C3-C6 cycloalkyl group, or a hydrogen atom;
$R^8$ represents a C1-C6 alkyl group which may be substituted with one or more halogen atoms, a —$OR^{10}$ group, a —$S(O)_m R^{10}$ group, a —$NR^{10} R^{11}$ group, a —$CO_2 R^{10}$ group, a —$C(O)R^{10}$ group, a cyano group, a nitro group, a halogen atom, or a hydrogen atom;
$R^{10}$ and $R^{11}$ are the same or different to each other and each independently represent a C1-C6 alkyl group which may be substituted with one or more atoms or groups selected from Group X or a hydrogen atom, except for a —$S(O)_m R^{10}$ group wherein m is 1 or 2 and $R^{10}$ is a hydrogen atom;
m independently represents 0, 1 or 2; and
n represents 0, 1 or 2;
Group X comprising:
  a C1-C6 alkoxy group which may be substituted with one or more halogen atoms,
  a C3-C6 cycloalkyl group which may be substituted with one or more halogen atoms or one or more C1-C3 alkyl groups,
  a cyano group,
  a hydroxy group, and
  a halogen atom;
Group W comprising:
  a C1-C6 alkoxy group which may be substituted with one or more halogen atoms,
  a C3-C6 cycloalkyl group which may be substituted with one or more halogen atoms,
  a hydroxy group,
  a halogen atom, and
  a cyano group;
the formula (2):

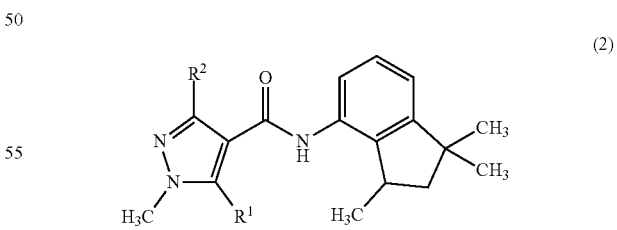

wherein
$R^1$ represents a hydrogen atom or a methyl group; and
$R^2$ represents a methyl group, a difluoromethyl group, or a trifluoromethyl group.
Item 2.
The composition for controlling pests according to Item 1, wherein in the compound represented by the formula (1) or N-oxide thereof, $R^1$ is a C1-C6 alkyl group which may be substituted with one or more atoms or groups selected from Group Y;

$R^2$ and $R^4$ are hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 alkyl group which may be substituted with one or more halogen atoms, a —OR$^{10}$ group, a —S(O)$_m$R$^{10}$ group, a —CO$_2$R$^{10}$ group, a —SF$_5$ group, or a halogen atom;

$R^6$ is a —OR$^{10}$ group, a —NR$^{10}$R$^{11}$ group, a —CO$_2$R$^{10}$ group, a —C(O)NR$^{10}$R$^{11}$ group, —OC(O)R$^{10}$, a cyano group, a halogen atom, or a hydrogen atom;

$R^7$ is a C1-C6 alkyl group which may be substituted with one or more halogen atoms, a —CH$_2$CO$_2$R$^{10}$ group, a C3-C6 cycloalkyl group, or a hydrogen atom, $R^8$ is a C1-C3 alkyl group which may be substituted with one or more halogen atoms, a —OR$^{10}$ group, a —S(O)$_m$R$^{10}$ group, a cyano group, a halogen atom, or a hydrogen atom;

$R^{10}$ and $R^{11}$ are the same or different to each other and each independently represent a C1-C3 alkyl group which may be substituted with one or more halogen atoms or a hydrogen atom, except for a —S(O)$_m$R$^{10}$ group wherein m is 1 or 2 and $R^{10}$ is a hydrogen atom; and Group Y comprising:

a C3-C6 cycloalkyl group which may be substituted with one or more halogen atoms and a halogen atom.

Item 3.

The composition for controlling pests according to Item 1, wherein in the compound represented by the formula (1) or N-oxide thereof, $R^1$ is a C1-C3 alkyl group which may be substituted with one or more halogen atoms;

$R^2$ and $R^4$ are hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 alkyl group which may be substituted with one or more halogen atoms, a —OR$^{10}$ group, a —S(O)$_m$R$^{10}$ group, or a halogen atom;

$R^6$ is a cyano group, a —NR$^{10}$R$^{11}$ group, a halogen atom, or a hydrogen atom;

$R^7$ is a C1-C6 alkyl group which may be substituted with one or more halogen atoms;

$R^8$ is a —S(O)$_m$R$^{10}$ group, a cyano group, a halogen atom, or a hydrogen atom; and $R^{10}$ and $R^{11}$ are the same or different to each other and each independently represent a C1-C3 alkyl group which may be substituted with one or more halogen atoms.

Item 4.

The composition for controlling pests according to Item 1, wherein in the compound represented by the formula (1) or N-oxide thereof:

$R^1$ is an ethyl group;

$R^2$ and $R^4$ are hydrogen atoms;

$R^3$ is a C1-C3 alkyl group which may be substituted with one or more halogen atoms, a —C(OR$^{10}$)$_3$ group, a halogen atom, or a hydrogen atom;

$R^5$ is a C1-C3 haloalkyl group, a —OR$^{20}$ group, a S(O)$_m$R$^{20}$ group, or a halogen atom;

$R^6$ is a cyano group, a —NR$^{10}$R$^{11}$ group, a halogen atom, or a hydrogen atom;

$R^7$ is a C1-C6 alkyl group which may be substituted with one or more halogen atoms;

$R^8$ is a —S(O)$_m$R$^{10}$ group, a cyano group, a halogen atom, or a hydrogen atom;

$R^{10}$ and $R^{11}$ are the same or different to each other and each independently represent a C1-C3 alkyl group which may be substituted with one or more halogen atoms; and $R^{20}$ is a C1-C3 haloalkyl group.

Item 5.

The composition for controlling pests according to any one of Items 1 to 4, wherein in the compound represented by the formula (1) or N-oxide thereof, $A^1$ is —NR$^7$—.

Item 6.

The composition for controlling pests according to any one of Items 1 to 4, wherein in the compound represented by the formula (1) or N-oxide thereof, $A^1$ is an oxygen atom.

Item 7.

The composition for controlling pests according to any one of Items 1 to 4, wherein in the compound represented by the formula (1) or N-oxide thereof, $A^1$ is a sulfur atom.

Item 8.

The composition for controlling pests according to Item 1, wherein the compound represented by the formula (1) or N-oxide thereof is a compound represented by the formula (1-2) or N-oxide thereof;

the formula (1-2):

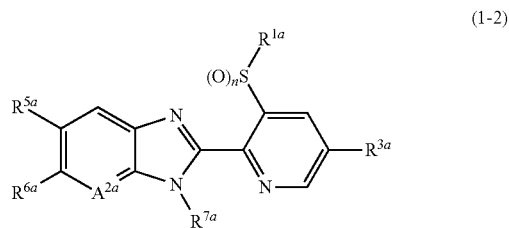

wherein $R^{1a}$ represents a C1-C3 alkyl group;

$A^{2a}$ represents a nitrogen atom or =CR$^{8a}$—;

$R^{3a}$ represents a C1-C3 alkyl group which may be substituted with one or more halogen atoms, a —C(OR$^{10a}$)$_3$ group, a halogen atom, or a hydrogen atom;

$R^{5a}$ represents a C1-C3 haloalkyl group, a —OR$^{20a}$ group, a —S(O)$_m$R$^{20a}$ group, or a halogen atom;

$R^{6a}$ represents a cyano group, a —NR$^{10a}$R$^{11a}$ group, a halogen atom, or a hydrogen atom;

$R^{7a}$ represents a C1-C6 alkyl group which may be substituted with one or more halogen atoms;

$R^{8a}$ represents a —S(O)$_m$R$^{10a}$ group, a cyano group, a halogen atom, or a hydrogen atom;

$R^{10a}$ and $R^{11a}$ are the same or different to each other and each independently represent a C1-C3 alkyl group which may be substituted with one or more halogen atoms;

$R^{20a}$ represents a C1-C3 haloalkyl group;

m independently represents 0, 1 or 2; and n represents 0, 1 or 2.

Item 9.

The composition for controlling pests according to Item 1, wherein the compound represented by the formula (1) or N-oxide thereof is a compound represented by the formula (1-3) or N-oxide thereof;

the formula (1-3):

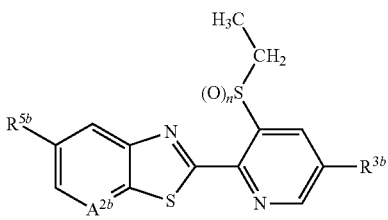

wherein
$A^{2b}$ represents a nitrogen atom or $=CR^{8b}-$;
$R^{3b}$ represents a C1-C3 alkyl group which may be substituted with one or more halogen atoms, a $-C(OR^{10b})_3$ group, a halogen atom, or a hydrogen atom;
$R^{5b}$ represents a C1-C3 haloalkyl group, a $-OR^{20b}$ group, a $-S(O)_m R^{20b}$ group, or a halogen atom;
$R^{8b}$ represents a $-S(O)_m R^{10b}$ group, a cyano group, a halogen atom, or a hydrogen atom;
$R^{10b}$ independently represents a C1-C3 alkyl group which may be substituted with one or more halogen atoms;
$R^{20b}$ represents a C1-C3 haloalkyl group;
m independently represents 0, 1 or 2; and
n represents 0, 1 or 2.

Item 10.

The composition for controlling pests according to Item 9, wherein in the compound represented by the formula (1-3) or N-oxide thereof,
$R^{3b}$ is a halogen atom or a hydrogen atom;
$R^{5b}$ is a C1-C3 perfluoroalkyl group, a $-OR^{30b}$ group, or a $-S(O)_m R^{30b}$ group;
$R^{30b}$ is a C1-C3 perfluoroalkyl group; and
$R^{8b}$ is a halogen atom or a hydrogen atom.

Item 11.

The composition for controlling pests according to Item 1, wherein the compound represented by the formula (1) or N-oxide thereof is a compound represented by the formula (1-4) or N-oxide thereof;
the formula (1-4):

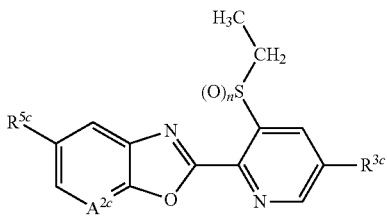

wherein
$A^{2c}$ represents a nitrogen atom or $=CR^{8c}-$;
$R^{3c}$ represents a C1-C3 alkyl group which may be substituted with one or more halogen atoms, a $-C(OR^{10c})_3$ group, a halogen atom, or a hydrogen atom;
$R^{5c}$ represents a C1-C3 haloalkyl group, a $-OR^{20c}$ group, a $-S(O)_m R^{2c}$ group, or a halogen atom;
$R^{8c}$ represents a $-S(O)_m R^{10c}$ group, a cyano group, a halogen atom, or a hydrogen atom;
$R^{10c}$ independently represents a C1-C3 alkyl group which may be substituted with one or more halogen atoms;

$R^{20c}$ represents a C1-C3 haloalkyl group;
m independently represents 0, 1 or 2; and
n represents 0, 1 or 2.

Item 12.

The composition for controlling pests according to Item 11, wherein in the compound represented by the formula (1-4) or N-oxide thereof,
$R^{3c}$ is a halogen atom or a hydrogen atom;
$R^{5c}$ is a C1-C3 perfluoroalkyl group, a $-OR^{30c}$ group, or a $-S(O)_m R^{30c}$ group;
$R^{30c}$ is a C1-C3 perfluoroalkyl group, and
$R^{8c}$ is a halogen atom or a hydrogen atom.

Item 13.

The composition for controlling pests according to any one of Items 1 to 7 wherein a weight ratio of the compound represented by the formula (1) to the compound represented by the formula (2) is in the range of 1,000:1 to 1:1,000.

Item 14.

The composition for controlling pests according to any one of Items 1 to 7 wherein a weight ratio of the compound represented by the formula (1) to the compound represented by the formula (2) is in the range of 500:1 to 1:10.

Item 15.

The composition for controlling pests according to Item 8 wherein a weight ratio of the compound represented by the formula (1-2) to the compound represented by the formula (2) is in the range of 1,000:1 to 1:1,000.

Item 16.

The composition for controlling pests according to Item 8 wherein a weight ratio of the compound represented by the formula (1-2) to the compound represented by the formula (2) is in the range of 500:1 to 1:10.

Item 17.

The composition for controlling pests according to Item 9 or 10 wherein a weight ratio of the compound represented by the formula (1-3) to the compound represented by the formula (2) is in the range of 1,000:1 to 1:1,000.

Item 18.

The composition for controlling pests according to Item 9 or 10 wherein a weight ratio of the compound represented by the formula (1-3) to the compound represented by the formula (2) is in the range of 500:1 to 1:10.

Item 19.

The composition for controlling pests according to Item 11 or 12 wherein a weight ratio of the compound represented by the formula (1-4) to the compound represented by the formula (2) is in the range of 1,000:1 to 1:1,000.

Item 20.

The composition for controlling pests according to Item 11 or 12 wherein a weight ratio of the compound represented by the formula (1-4) to the compound represented by the formula (2) is in the range of 500:1 to 1:10.

Item 21.

A method for controlling pests, which comprises the step of applying an effective amount of the composition for controlling pests according to any one of Items 1 to 20 to plants, plant seeds, bulbs, or a soil where plants grow.

The present invention can control pests.

MODE FOR CARRYING OUT THE INVENTION

A composition for controlling pests of the present invention comprises the compound represented by the formula (1) (hereinafter referred to as "the present fused heterocyclic compound") and the compound represented by the formula (2) (hereinafter referred to as "the present carboxamide compound").

For the present fused heterocyclic compound, "N-oxide" includes a compound wherein one or more ring-constituting nitrogen atoms in one or more the heterocyclic moieties are oxidized. The heterocyclic moieties which may form N-oxide includes, for example, the pyridine ring moiety.

For example, the nitrogen atom of the pyridine ring moiety of the formula (1) may be N-oxide(N→O).

Further, for example, in the formula (1), $A^2$ may be N-oxide(N→O).

The examples of each group as used herein are explained as follows.

In the following "Ca-Cb", "a" means the smallest number of the carbon atoms and "b" means the largest number of carbon atoms.

The term "Ca-Cb alkyl group" as used herein represents a straight- or branched-chain hydrocarbon group having "a" to "b" carbon atoms.

The term "Ca-Cb haloalkyl group represents a straight- or branched-chain hydrocarbon group having "a" to "b" carbon atoms, wherein one or more hydrogen atoms attached to the carbon atoms are replaced with one or more halogen atoms. When two or more halogen atoms are attached to the carbon atoms, the halogen atoms may be the same or different.

The term "Ca-Cb alkoxy group" represents a straight- or branched-chain alkyl-O— group having "a" to "b" carbon atoms.

The term "Ca-Cb cycloalkyl group" represents a saturated cyclic hydrocarbon group having "a" to "b" carbon atoms.

In "which may be substituted with one or more atoms or groups selected from Group X" as used herein, when substituted with two or more atoms or groups selected from Group X, the atoms or groups selected from Group X may be the same or different to each other.

In "which may be substituted with one or more atoms or groups selected from Group Y" as used herein, when substituted with two or more atoms or groups selected from Group Y, the atoms or groups selected from Group Y may be the same or different to each other.

In "which may be substituted with one or more atoms or groups selected from Group W" as used herein, when substituted with two or more atoms or groups selected from Group W, the atoms or groups selected from Group W may be the same or different to each other.

In "which may be substituted with one or more halogen atoms" as used herein, when substituted with two or more halogen atoms, the halogen atoms may be the same or different to each other.

In "which may be substituted with one or more C1-C3 alkyl groups" as used herein, when substituted with two or more C1-C3 alkyl groups, the C1-C3 alkyl groups may be the same or different to each other.

In the present fused heterocyclic compound, the term "halogen atom" includes a fluorine atom, a chlorine atom, a bromine atom, and an iodine atom.

In the present fused heterocyclic compound, "a C1-C6 alkyl group which may be substituted with one or more (for example, 1 to 7, 1 to 5, or 1 to 3) atoms or groups selected from Group X" represents a straight- or branched-chain saturated hydrocarbon group having 1 to 6 carbon atoms, wherein one or more hydrogen atoms attached to the carbon atoms may optionally be replaced with one or more atoms or groups selected from Group X. When substituted with two or more atoms or groups selected from Group X, the atoms or groups selected from Group X may be the same or different to each other.

Examples of "a C1-C6 alkyl group which may be substituted with one or more atoms or groups selected from Group X" include methyl group, ethyl group, propyl group, isopropyl group, butyl group, isobutyl group, sec-butyl group, tert-butyl group, pentyl group, neopentyl group, hexyl group, methoxymethyl group, ethoxymethyl group, propyloxymethyl group, isopropyloxymethyl group, butyloxymethyl group, sec-butyloxymethyl group, tert-butyloxymethyl group, 2-methoxyethyl group, 2-ethoxyethyl group, 2-propyloxyethyl group, 2-isopropyloxyethyl group, 2-butyloxyethyl group, 2-sec-butyloxyethyl group, 2-tert-butyloxyethyl group, trifluoromethyl group, trichloromethyl group, 2-fluoroethyl group, 2,2-difluoroethyl group, 2,2,2-trifluoroethyl group and pentafluoroethyl group, 2-hydroxyethyl group, cyclopropylmethyl group, 1-methylcyclopropylmethyl group, 2,2-difluorocyclopropylmethyl group, trimethoxymethyl group, triethoxymethyl group etc. Examples of subgroups such as "a C1-C3 alkyl group which may be substituted with one or more atoms or groups selected from Group X" may be selected from the above, depending on the indicated number of carbon atom.

In the present fused heterocyclic compound, "a C1-C6 alkyl group which may be substituted with one or more (for example, 1 to 7, 1 to 5, or 1 to 3) halogen atoms" represents a straight- or branched-chain hydrocarbon group having 1 to 6 carbon atoms, wherein one or more hydrogen atoms attached to the carbon atoms may optionally be replaced with one or more halogen atoms. When substituted with two or more halogen atoms, the halogen atoms may be the same or different to each other.

Examples of "a C1-C6 alkyl group which may be substituted with one or more halogen atoms" include methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group, and pentafluoroethyl group, heptafluoroisopropyl group etc. Examples of subgroups such as "a C1-C3 alkyl group which may be substituted with one or more halogen atoms" may be selected from the above, depending on the indicated number of carbon atom.

In the present fused heterocyclic compound, examples of "a C1-C6 alkyl group which may be substituted with one or more (for example, 1 to 7, 1 to 5, or 1 to 3) atoms or groups selected from Group W" include methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group, pentafluoroethyl group, methoxymethyl group, ethoxymethyl group, propyloxymethyl group, isopropyloxymethyl group, butyloxymethyl group, sec-butyloxymethyl group, isobutyloxymethyl group, tert-butyloxymethyl group, methoxyethyl group, ethoxyethyl group, propyloxyethyl group, isopropyloxyethyl group, butyloxyethyl group, sec-butyloxyethyl group, isobutyloxyethyl group, tert-butyloxyethyl group etc. When substituted with two or more atoms or groups selected from Group W, the atoms or groups selected from Group W may be the same or different to each other.

In the present fused heterocyclic compound, examples of "a C1-C6 alkyl group which may be substituted with one or more atoms or groups selected from Group Y" include methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group and pentafluoroethyl group, cyclopropylmethyl group, 1-methylcyclopropylmethyl group, 2,2-difluorocyclopropylmethyl group etc. Examples of subgroups are selected from the above, depending on the indicated number of carbon atom.

In the present fused heterocyclic compound, examples of "a C1-C6 alkoxy group which may be substituted with one or more (for example, 1 to 7, 1 to 5, or 1 to 3) halogen atoms" includes methoxy group, trifluoromethoxy group, ethoxy group, 2,2,2-trifluoroethoxy group, propyloxy group, isopropyloxy group, butyloxy group, isobutyloxy group, sec-butyloxy group, tert-butyloxy group, pentyloxy group, and hexyloxy group.

In the present fused heterocyclic compound, examples of "a C3-C6 cycloalkyl group which may be substituted with one or more (for example, 1 to 7, 1 to 5, or 1 to 3) halogen atoms" include cyclopropyl group, 2,2-difluorocyclopropyl group, 2,2-dichlorocyclopropyl group, 2,2-dibromocyclopropyl group, cyclobutyl group, cyclopentyl group, and cyclohexyl group.

In the present fused heterocyclic compound, examples of "a C3-C6 cycloalkyl group which may be substituted with one or more (for example, 1 to 7, 1 to 5, or 1 to 3) halogen atoms or one or more (for example, 1 to 7, 1 to 5, or 1 to 3) C1-C3 alkyl groups" include cyclopropyl group, 1-methylcyclopropyl group, 2-methylcyclopropyl group, 1-fluorocyclopropyl group, 2,2-difluorocyclopropyl group, 2,2-dichlorocyclopropyl group, 2,2-dibromocyclopropyl group, cyclobutyl group, cyclopentyl group, and cyclohexyl group.

In the present fused heterocyclic compound, the term "a C1-C3 haloalkyl group" represents a straight- or branched-chain hydrocarbon group having 1 to 3 carbon atoms, wherein one or more hydrogen atoms attached to the carbon atoms are replaced with one or more (for example, 1 to 7, 1 to 5, or 1 to 3) halogen atoms. When substituted with two or more halogen atoms, the halogen atoms may be the same or different to each other.

Examples of "a C1-C3 haloalkyl group" include fluoromethyl group, chloromethyl group, bromomethyl group, iodomethyl group, difluoromethyl group, dichloromethyl group, trifluoromethyl group, chlorodifluoromethyl group, bromodifluoromethyl group, trichloromethyl group, 2-fluoroethyl group, 2-chloroethyl group, 2-bromoethyl group, 2,2-difluoroethyl group, 2,2,2-trifluoroethyl group, pentafluoroethyl group, heptafluoropropyl group, heptafluoroisopropyl group etc.

In the present fused heterocyclic compound, examples of "C1-C3 alkyl group" include methyl group, ethyl group, propyl group, and isopropyl group.

In the present fused heterocyclic compound, examples of "C1-C3 perfluoroalkyl group" include trifluoromethyl group, pentafluoroethyl group, heptafluoropropyl group, and heptafluoroisopropyl group.

Examples of the present fused heterocyclic compound include as follows.

The compound represented by the formula (1), wherein
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, a —CO$_2$R$^{10}$ group, a —SF$_5$ group, or a halogen atom;
$R^6$ is a —OR$^{10}$ group, a —NR$^{10}$R$^{11}$ group, a —CO$_2$R$^{10}$ group, a —C(O)NR$^{10}$R$^{11}$ group, —OC(O)R$^{10}$, a cyano group, a halogen atom, or a hydrogen atom;
$R^7$ is a C1-C6 alkyl group which may be substituted with one or more halogen atoms, a —CH$_2$CO$_2$R$^{10}$ group, a C3-C6 cycloalkyl group, or a hydrogen atom;
$R^8$ is a C1-C3 alkyl group which may be substituted with one or more halogen atoms, a —OR$^{10}$ group, a —S(O)$_m$R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —S(O)$_m$R$^{10}$ group wherein m is 1 or 2 and $R^{10}$ is a hydrogen atom; and
Group Y comprising:
a C3-C6 cycloalkyl group which may be substituted with one or more halogen atoms and
a halogen atom; or N-oxide thereof.

The compound represented by the formula (1), wherein
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms; or N-oxide thereof.

The compound represented by the formula (1), wherein
$R^1$ is an ethyl group;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 haloalkyl group, a —OR$^{20}$ group, a —S(O)$_m$ R$^{20}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1), wherein
$A^1$ is —NR$^7$—; or N-oxide thereof.

The compound represented by the formula (1), wherein
$A^1$ is —NR$^7$—;
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, a —CO$_2$R$^{10}$ group, a —SF$_5$ group, or a halogen atom;

$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;

$R^7$ is a C1-C6 alkyl group which may be substituted with one or more halogen atoms, a —$CH_2CO_2R^{10}$ group, a C3-C6 cycloalkyl group, or a hydrogen atom;

$R^8$ is a C1-C3 alkyl group which may be substituted with one or more halogen atoms, a —$OR^{10}$ group, a —$S(O)_mR^{10}$ group, a cyano group, a halogen atom, or a hydrogen atom;

$R^{10}$ and $R^{11}$ are the same or different to each other and each independently represent a C1-C3 alkyl group which may be substituted with one or more halogen atoms or a hydrogen atom, except for a —$S(O)_mR^{10}$ group wherein m is 1 or 2 and $R^{10}$ is a hydrogen atom; and Group Y comprising:
a C3-C6 cycloalkyl group which may be substituted with one or more halogen atoms, and
a halogen atom; or N-oxide thereof.

The compound represented by the formula (1), wherein
$A^1$ is —$NR^7$—;
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms; or N-oxide thereof.

The compound represented by the formula (1), wherein
$A^1$ is —$NR^7$—;
$R^1$ is an ethyl group;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 haloalkyl group, a —$OR^{20}$ group, a —$S(O)_m R^{20}$ group, or a halogen atom;
$R^6$ is a cyano group, a —$NR^{10}R^{11}$ group, a halogen atom, or a hydrogen atom,
$R^7$ is a C1-C6 alkyl group which may be substituted with one or more halogen atoms;
$R^8$ is a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1), wherein $A^1$ is an oxygen atom; or N-oxide thereof.

The compound represented by the formula (1), wherein
$A^1$ is an oxygen atom;
$R^1$ is a C1-C6 alkyl group which may be substituted with one or more atoms or groups selected from Group Y;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom;
$R^6$ is a —$OR^{10}$ group, a —$NR^{10}R^{11}$ group, a —$CO_2R^{10}$ group, a —$C(O)NR^{10}R^{11}$ group, —$OC(O)R^{10}$, a cyano group, a halogen atom, or a hydrogen atom;
$R^7$ is a C1-C6 alkyl group which may be substituted with one or more halogen atoms, a —$CH_2CO_2R^{10}$ group, a C3-C6 cycloalkyl group, or a hydrogen atom;
$R^8$ is a C1-C3 alkyl group which may be substituted with one or more halogen atoms, a —$OR^{10}$ group, a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —$S(O)_mR^{10}$ group wherein m is 1 or 2 and $R^{10}$ is a hydrogen atom; and Group Y comprising:
a C3-C6 cycloalkyl group which may be substituted with one or more halogen atoms, and
a halogen atom; or N-oxide thereof.

The compound represented by the formula (1), wherein
$A^1$ is an oxygen atom;
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 alkyl group which may be substituted with one or more halogen atoms, a —$OR^{10}$ group, a —$S(O)_mR^{10}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms; or N-oxide thereof.

The compound represented by the formula (1), wherein
$A^1$ is a sulfur atom;
$R^1$ is an ethyl group;
$R^2$ and $R^4$ are hydrogen atoms;
$R^3$ is a C1-C3 alkyl group which may be substituted with one or more halogen atoms, a —$C(OR^{10})_3$ group, a halogen atom, or a hydrogen atom;
$R^5$ is a C1-C3 haloalkyl group, a —$OR^{20}$ group, a —$S(O)_mR^{20}$ group, or a halogen atom;
$R^6$ is a cyano group, a —$NR^{10}R^{11}$ group, a halogen atom, or a hydrogen atom;
$R^7$ is a C1-C6 alkyl group which may be substituted with one or more halogen atoms;
$R^8$ is a —$S(O)_mR^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1), wherein $A^1$ is a sulfur atom; or N-oxide thereof.

The compound represented by the formula (1), wherein
$A^1$ is a sulfur atom;
$R^1$ is a C1-C6 alkyl group which may be substituted with one or more atoms or groups selected from Group Y;
$R^2$ and $R^4$ are hydrogen atoms,
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, a —CO$_2$R$^{10}$ group, a —SF$_5$ group, or a halogen atom;
$R^6$ is a —OR$^{10}$ group, a —NR$^{10}$R$^{11}$ group, a —CO$_2$R$^{10}$ group, a —C(O)NR$^{10}$R$^{11}$ group, —OC(O)R$^{10}$, a cyano group, a halogen atom, or a hydrogen atom;
$R^7$ is a C1-C6 alkyl group which may be substituted with one or more halogen atoms, a —CH$_2$CO$_2$R$^{10}$ group, a C3-C6 cycloalkyl group, or a hydrogen atom;
$R^8$ is a C1-C3 alkyl group which may be substituted with one or more halogen atoms, a —OR$^{10}$ group, a —S(O)$_m$R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms or a hydrogen atom, except for a —S(O)$_m$R$^{10}$ group wherein m is 1 or 2 and $R^{10}$ is a hydrogen atom; and
Group Y comprising:
a C3-C6 cycloalkyl group which may be substituted with one or more halogen atoms, and
a halogen atom; or N-oxide thereof.

The compound represented by the formula (1), wherein
$A^1$ is a sulfur atom;
$R^1$ is a C1-C3 alkyl group which may be substituted with one or more halogen atoms;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 alkyl group which may be substituted with one or more halogen atoms, a —OR$^{10}$ group, a —S(O)$_m$R$^{10}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom; and
$R^{10}$ and $R^{11}$ are the same or different to each other and each independently represent a C1-C3 alkyl group which may be substituted with one or more halogen atoms; or N-oxide thereof.

The compound represented by the formula (1), wherein
$A^1$ is a sulfur atom;
$R^1$ is an ethyl group;
$R^2$ and $R^4$ are hydrogen atoms;
$R^3$ is a C1-C3 alkyl group which may be substituted with one or more halogen atoms, a —C(OR$^{10}$)$_3$ group, a halogen atom, or a hydrogen atom;
$R^5$ is a C1-C3 haloalkyl group, a —OR$^{20}$ group, a —S(O)$_m$ R$^{20}$ group, or a halogen atom;
$R^6$ is a cyano group, a —NR$^{10}$R$^{11}$ group, a halogen atom, or a hydrogen atom;
$R^7$ is a C1-C6 alkyl group which may be substituted with one or more halogen atoms;
$R^8$ is a —S(O)$_m$R$^{10}$ group, a cyano group, a halogen atom, or a hydrogen atom;
$R^{10}$ and $R^{11}$ are the same or different to each other and each independently represent a C1-C3 alkyl group which may be substituted with one or more halogen atoms; and
$R^{20}$ is a C1-C3 haloalkyl group; or N-oxide thereof.

The compound represented by the formula (1-2):

(1-2)

wherein
$R^{1a}$ represents a C1-C3 alkyl group;
$A^{2a}$ represents a nitrogen atom or =CR$^{8a}$—;
$R^{3a}$ represents a C1-C3 alkyl group which may be substituted with one or more halogen atoms, a —C(OR$^{10a}$)$_3$ group, a halogen atom, or a hydrogen atom;
$R^{5a}$ represents a C1-C3 haloalkyl group, a —OR$^{20a}$ group, a —S(O)$_m$R$^{20a}$ group, or a halogen atom;
$R^{a6}$ represents a cyano group, a —NR$^{10a}$R$^{11a}$ group, a halogen atom, or a hydrogen atom;
$R^{7a}$ represents a C1-C6 alkyl group which may be substituted with one or more halogen atoms;
$R^{8a}$ represents a —S(O)$_m$R$^{10a}$ group, a cyano group, a halogen atom, or a hydrogen atom;
$R^{10\,a}$ and $R^{11\,a}$ are the same or different to each other and each independently represent a C1-C3 alkyl group which may be substituted with one or more halogen atoms;
$R^{20a}$ represents a C1-C3 haloalkyl group;
m independently represents 0, 1 or 2; and
n represents 0, 1 or 2; or N-oxide thereof.

The compound represented by the formula (1-3):

(1-3)

wherein
$A^{2b}$ represents a nitrogen atom or =CR$^{8b}$—;
$R^{3b}$ represents a C1-C3 alkyl group which may be substituted with one or more halogen atoms, a —C(OR$^{10b}$)$_3$ group, a halogen atom, or a hydrogen atom;
$R^{5b}$ represents a C1-C3 haloalkyl group, a —OR$^{20b}$ group, a —S(O)$_m$R$^{20b}$ group, or a halogen atom;
$R^{8b}$ represents a —S(O)$_m$R$^{10b}$ group, a cyano group, a halogen atom, or a hydrogen atom;
$R^{10b}$ independently represents a C1-C3 alkyl group which may be substituted with one or more halogen atoms;
$R^{20b}$ represents a C1-C3 haloalkyl group;
m independently represents 0, 1 or 2; and
n represents 0, 1 or 2; or N-oxide thereof.

The compound represented by the formula (1-3), wherein
$R^{3b}$ is a halogen atom or a hydrogen atom;
$R^{5b}$ is a C1-C3 perfluoroalkyl group, a —$OR^{30b}$ group, or a —$S(O)_mR^{30b}$ group;
$R^{30b}$ is a C1-C3 perfluoroalkyl group; and
$R^{8b}$ is a halogen atom or a hydrogen atom; or N-oxide thereof.

The compound represented by the formula (1-4):

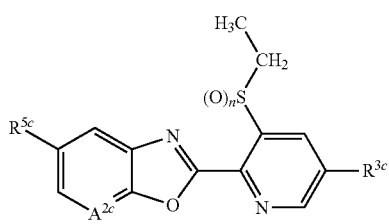

(1-4)

wherein
$A^{2c}$ represents a nitrogen atom or =$CR^{8c}$—;
$R^{3c}$ represents a C1-C3 alkyl group which may be substituted with one or more halogen atoms, a —$C(OR^{10c})_3$ group, a halogen atom, or a hydrogen atom;
$R^{5c}$ represents a C1-C3 haloalkyl group, a —$OR^{20c}$ group, a —$S(O)_mR^{2c}$ group, or a halogen atom;
$R^{8c}$ represents a —$S(O)_mR^{10c}$ group, a cyano group, a halogen atom, or a hydrogen atom;
$R^{10c}$ independently represents a C1-C3 alkyl group which may be substituted with one or more halogen atoms;
$R^{20c}$ represents a C1-C3 haloalkyl group;
m independently represents 0, 1 or 2; and
n represents 0, 1 or 2; or N-oxide thereof.

The compound represented by the formula (1-4), wherein
$R^{3c}$ is a halogen atom or a hydrogen atom;
$R^{5c}$ is a C1-C3 perfluoroalkyl group, a —$OR^{30c}$ group, or a —$S(O)_mR^{30c}$ group;
$R^{30c}$ is a C1-C3 perfluoroalkyl group; and
$R^{8c}$ is a halogen atom or a hydrogen atom; or N-oxide thereof.

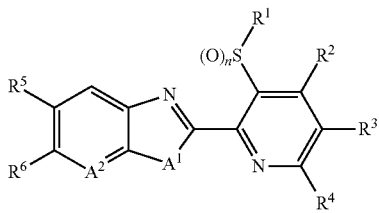

(1)

The compound represented by the formula (1), wherein $A^1$ is —$NR^7$—, and $R^7$ is a C1-C6 alkyl group which may be substituted with one or more halogen atoms, or a hydrogen atom; or N-oxide thereof.

The compound represented by the formula (1), wherein $A^1$ is —$NR^7$—, and $R^7$ is a methyl group, an ethyl group, or a propyl group; or N-oxide thereof.

The compound represented by the formula (1), wherein $A^1$ is —$NR^7$—, and $R^7$ is a methyl group; or N-oxide thereof.

The compound represented by the formula (1), wherein $A^1$ is —$NR^7$—, and $R^7$ is a hydrogen atom; or N-oxide thereof.

The compound represented by the formula (1), wherein $A^2$ is a nitrogen atom; or N-oxide thereof.

The compound represented by the formula (1), wherein $A^2$ is =$N(\rightarrow O)$—: (N-oxide).

The compound represented by the formula (1), wherein $A^2$ is =$CR^8$—; or N-oxide thereof.

The compound represented by the formula (1), wherein $A^2$ is =$CR^8$—, and $R^8$ is a C1-C3 alkoxy group, a C1-C3 alkylsulfonyl group, a halogen atom, or a hydrogen atom; or N-oxide thereof.

The compound represented by the formula (1), wherein $A^2$ is =$CR^8$—, and $R^8$ is a C1-C3 alkoxy group; or N-oxide thereof.

The compound represented by the formula (1), wherein $A^2$ is =$CR^8$—, and $R^8$ is a C1-C3 alkylsulfonyl group; or oxide thereof.

The compound represented by the formula (1), wherein $A^2$ is =$CR^8$—, and $R^8$ is a halogen atom; or N-oxide thereof.

The compound represented by the formula (1), wherein $A^2$ is =CH—; or N-oxide thereof.

The compound represented by the formula (1), wherein $A^1$ is —$NR^7$—, and $A^2$ is a nitrogen atom; or N-oxide thereof.

The compound represented by the formula (1), wherein $A^1$ is —$NR^7$—, and $A^2$ is =$N(\rightarrow O)$—: (N-oxide).

The compound represented by the formula (1), wherein $A^1$ is —$NR^7$—, and $A^2$ is =$CR^8$—; or N-oxide thereof.

The compound represented by the formula (1), wherein $A^1$ is —$NR^7$—, and $A^2$ is =CH—; or N-oxide thereof.

The compound represented by the formula (1), wherein $A^1$ is an oxygen atom, and $A^2$ is a nitrogen atom; or N-oxide thereof.

The compound represented by the formula (1), wherein $A^1$ is an oxygen atom, and $A^2$ is =$N(\rightarrow O)$—: (N-oxide).

The compound represented by the formula (1), wherein $A^1$ is an oxygen atom, and $A^2$ is =$CR^8$—; or N-oxide thereof.

The compound represented by the formula (1), wherein $A^1$ is an oxygen atom, and $A^2$ is =CH—; or N-oxide thereof.

The compound represented by the formula (1), wherein $A^1$ is a sulfur atom, and $A^2$ is a nitrogen atom; or N-oxide thereof.

The compound represented by the formula (1), wherein $A^1$ is a sulfur atom, and $A^2$ is =$N(\rightarrow O)$—: (N-oxide).

The compound represented by the formula (1), wherein $A^1$ is a sulfur atom, and $A^2$ is =$CR^8$—; or N-oxide thereof.

The compound represented by the formula (1), wherein $A^1$ is a sulfur atom, and $A^2$ is =CH—; or N-oxide thereof.

The compound represented by the formula (1), wherein $R^1$ is a C1-C6 alkyl group which may be substituted with one or more halogen atoms or a C3-C6 cycloalkyl group which may be substituted with one or more halogen atoms; or N-oxide thereof.

The compound represented by the formula (1), wherein $R^1$ is a C1-C3 alkyl group which may be substituted with one or more halogen atoms; or N-oxide thereof.

The compound represented by the formula (1), wherein $R^1$ is a methyl group, an ethyl group, or a propyl group, an isopropyl group, a trifluoromethyl group, a 2,2,2-trifluoroethyl group, a cyclopropyl group, or a cyclopropylmethyl group; or N-oxide thereof.

The compound represented by the formula (1), wherein $R^1$ is an ethyl group or a cyclopropylmethyl group; or N-oxide thereof.

The compound represented by the formula (1), wherein $R^1$ is a methyl group; or N-oxide thereof;

The compound represented by the formula (1), wherein $R^1$ is an ethyl group; or N-oxide thereof.

The compound represented by the formula (1), wherein $R^1$ is a propyl group; or N-oxide thereof.

The compound represented by the formula (1), wherein $R^1$ is an isopropyl group; or N-oxide thereof.

The compound represented by the formula (1), wherein $R^3$ is a C1-C6 alkyl group which may be substituted with one or more atoms or groups selected from Group X, a halogen atom, or a hydrogen atom; or N-oxide thereof.

The compound represented by the formula (1), wherein $R^3$ is a C1-C3 alkyl group which may be substituted with one or more halogen atoms, a —$C(OR^{10})_3$ group, a halogen atom, or a hydrogen atom; or N-oxide thereof.

The compound represented by the formula (1), wherein $R^3$ is a C1-C3 alkyl group which may be substituted with one or more halogen atoms or a hydrogen atom; or N-oxide thereof.

The compound represented by the formula (1), wherein $R^3$ is a C1-C3 alkyl group which may be substituted with one or more halogen atoms; or N-oxide thereof.

The compound represented by the formula (1), wherein $R^3$ is a —$C(OR^{10})_3$ group; or N-oxide thereof.

The compound represented by the formula (1), wherein $R^3$ is a halogen atom; or N-oxide thereof.

The compound represented by the formula (1), wherein $R^3$ is a hydrogen atom; or N-oxide thereof.

The compound represented by the formula (1), wherein $R^3$ is a methyl group, a trifluoromethyl group, a pentafluoroethyl group, a hexafluoropropyl group, a hexafluoroisopropyl group, a trimethoxymethyl group, a triethoxymethyl group, a fluorine atom, a chlorine atom, a bromine atom, an iodine atom, or a hydrogen atom; or N-oxide thereof.

The compound represented by the formula (1), wherein $R^3$ is a trifluoromethyl group; or N-oxide thereof.

The compound represented by the formula (1), wherein $R^3$ is a trimethoxymethyl group, or N-oxide thereof;

The compound represented by the formula (1), wherein $R^2$ and $R^4$ are both hydrogen atoms; or N-oxide thereof.

The compound represented by the formula (1), wherein $R^2$ and $R^4$ are both hydrogen atoms, and $R^3$ is a C1-C3 alkyl group which may be substituted with one or more halogen atoms, a —$C(OR^{10})_3$ group, a halogen atom; or N-oxide thereof.

The compound represented by the formula (1), wherein $R^2$ and $R^4$ are both hydrogen atoms, and $R^3$ is a hydrogen atom; or N-oxide thereof.

The compound represented by the formula (1), wherein $R^2$ and $R^4$ are both hydrogen atoms, and $R^3$ is a trifluoromethyl group; or N-oxide thereof.

The compound represented by the formula (1), wherein $R^2$ and $R^4$ are both hydrogen atoms, and $R^3$ is a trimethoxymethyl group; or N-oxide thereof.

The compound represented by the formula (1), wherein $R^5$ is a C1-C3 alkyl group which may be substituted with one or more halogen atoms, a —$OR^{10}$ group, a —$S(O)_mR^{10}$ group, a —$CO_2R^{10}$ group, a —$SF_5$ group, or a halogen atom; or N-oxide thereof.

The compound represented by the formula (1), wherein $R^5$ is a C1-C3 alkyl group which may be substituted with one or more halogen atoms, a —$OR^{10}$ group, a —$S(O)_mR^{10}$ group, or a halogen atom; or N-oxide thereof.

The compound represented by the formula (1), wherein $R^5$ is a C1-C3 haloalkyl group, a C1-C3 haloalkoxy group, a C1-C3 haloalkylsulfanyl group, a C1-C3 haloalkylsulfinyl group, a C1-C3 haloalkylsulfonyl group, or a halogen atom; or N-oxide thereof.

The compound represented by the formula (1), wherein $R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; or N-oxide thereof.

The compound represented by the formula (1), wherein $R^5$ is a C1-C3 perfluoroalkyl group; or N-oxide thereof.

The compound represented by the formula (1), wherein $R^5$ is a C1-C3 perfluoroalkoxy group; or N-oxide thereof.

The compound represented by the formula (1), wherein $R^5$ is a C1-C3 perfluoroalkylsulfanyl group, a C1-C3 perfluoroalkylsulfinyl group, or a C1-C3 perfluoroalkylsulfonyl group; or N-oxide thereof.

The compound represented by the formula (1), wherein $R^5$ is a halogen atom; or N-oxide thereof.

The compound represented by the formula (1), wherein $R^5$ is a trifluoromethyl group, —$CF_2CF_3$, —$CF_2CF_2CF_3$, —$CF(CF_3)_2$, —$OCF_3$, —$OCF_2CF_3$, —$SCF_3$, —$S(O)CF_3$, —$S(O)_2CF_3$, —$SCF_2CF_3$, —$S(O)CF_2CF_3$, —$S(O)_2CF_2CF_3$, —$SF_5$, a fluorine atom, a chlorine atom, a bromine atom, or a iodine atom; or N-oxide thereof.

The compound represented by the formula (1), wherein $R^5$ is a trifluoromethyl group; or N-oxide thereof.

The compound represented by the formula (1), wherein $R^5$ is —$CF_2CF_3$; or N-oxide thereof.

The compound represented by the formula (1), wherein $R^5$ is —$SCF_3$; or N-oxide thereof.

The compound represented by the formula (1), wherein $R^5$ is —$S(O)CF_3$; or N-oxide thereof.

The compound represented by the formula (1), wherein $R^5$ is —$S(O)_2CF_3$; or N-oxide thereof.

The compound represented by the formula (1), wherein $R^6$ is a —$OR^{10}$ group, a —$NR^{10}R^{11}$ group, a —$CO_2R$ group, a —$C(O)NR^{10}R^{11}$ group, a cyano group, a halogen atom, or a hydrogen atom; or N-oxide thereof.

The compound represented by the formula (1), wherein $R^6$ is a cyano group, a —$NR^{10}R^{11}$ group, a halogen atom, or a hydrogen atom; or N-oxide thereof.

The compound represented by the formula (1), wherein $R^6$ is a hydrogen atom; or N-oxide thereof.

The compound represented by the formula (1), wherein $R^5$ is a C1-C3 haloalkyl group, a C1-C3 haloalkoxy group, a C1-C3 haloalkylsulfanyl group, a C1-C3 haloalkylsulfinyl group, a C1-C3 haloalkylsulfonyl group, or a halogen atom, and $R^6$ is a hydrogen atom; or N-oxide thereof.

The compound represented by the formula (1), wherein $R^5$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and $R^6$ is a hydrogen atom; or N-oxide thereof.

The compound represented by the formula (1), wherein $R^5$ is a C1-C3 perfluoroalkyl group, and $R^6$ is a hydrogen atom; or N-oxide thereof.

The compound represented by the formula (1), wherein $R^5$ is a C1-C3 perfluoroalkoxy group, and $R^6$ is a hydrogen atom; or N-oxide thereof.

The compound represented by the formula (1), wherein $R^5$ is a C1-C3 perfluoroalkylsulfanyl group, a C1-C3 perfluoroalkylsulfinyl group, or a C1-C3 perfluoroalkylsulfonyl group, and $R^6$ is a hydrogen atom; or N-oxide thereof.

The compound represented by the formula (1), wherein
$A^1$ is —$NR^7$—;
$R^7$ is a methyl group;

A² is a nitrogen atom;
R¹ is a C1-C3 alkyl group which may be substituted with one or more halogen atoms;
R² and R⁴ are both hydrogen atoms;
R³ is a C1-C3 alkyl group which may be substituted with one or more halogen atoms, a —C(OR¹⁰)₃ group, a halogen atom, or a hydrogen atom;
R⁵ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
R⁶ is a hydrogen atom;
or N-oxide thereof.

The compound represented by the formula (1), wherein
A¹ is —NR⁷—;
R⁷ is a methyl group;
A² is =N(→O)—;
R¹ is a C1-C3 alkyl group which may be substituted with one or more halogen atoms;
R² and R⁴ are both hydrogen atoms;
R³ is a C1-C3 alkyl group which may be substituted with one or more halogen atoms, a —C(OR¹⁰)₃ group, a halogen atom, or a hydrogen atom;
R⁵ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
R⁶ is a hydrogen atom; (N-oxide).

The compound represented by the formula (1), wherein
A¹ is —NR⁷—;
R⁷ is a methyl group;
A² is =CR⁸—;
R⁸ is a C1-C3 alkoxy group, a C1-C3 alkylsulfanyl group, a halogen atom, or a hydrogen atom;
R¹ is a C1-C3 alkyl group which may be substituted with one or more halogen atoms;
R² and R⁴ are both hydrogen atoms;
R³ is a C1-C3 alkyl group which may be substituted with one or more halogen atoms, a —C(OR¹⁰)₃ group, a halogen atom, or a hydrogen atom;
R⁵ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
R⁶ is a hydrogen atom;
or N-oxide thereof.

The compound represented by the formula (1), wherein
A¹ is an oxygen atom;
A² is a nitrogen atom;
R¹ is a C1-C3 alkyl group which may be substituted with one or more halogen atoms;
R² and R⁴ are both hydrogen atoms;
R³ is a C1-C3 alkyl group which may be substituted with one or more halogen atoms, a —C(OR¹⁰)₃ group, a halogen atom, or a hydrogen atom;
R⁵ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
R⁶ is a hydrogen atom;
or N-oxide thereof.

The compound represented by the formula (1), wherein
A¹ is an oxygen atom;
A² is =N(→O)—;
R¹ is a C1-C3 alkyl group which may be substituted with one or more halogen atoms;
R² and R⁴ are both hydrogen atoms;
R³ is a C1-C3 alkyl group which may be substituted with one or more halogen atoms, a —C(OR¹⁰)₃ group, a halogen atom, or a hydrogen atom;
R⁵ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
R⁶ is a hydrogen atom(N-oxide).

The compound represented by the formula (1), wherein
A¹ is an oxygen atom;
A² is =CR⁸—;
R⁸ is a C1-C3 alkoxy group, a C1-C3 alkylsulfanyl group, a halogen atom, or a hydrogen atom;
R¹ is a C1-C3 alkyl group which may be substituted with one or more halogen atoms;
R² and R⁴ are both hydrogen atoms;
R³ is a C1-C3 alkyl group which may be substituted with one or more halogen atoms, a —C(OR¹⁰)₃ group, a halogen atom, or a hydrogen atom;
R⁵ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
R⁶ is a hydrogen atom;
or N-oxide thereof.

The compound represented by the formula (1-2), wherein A²ᵃ is a nitrogen atom; or N-oxide thereof.

The compound represented by the formula (1-2), wherein A²ᵃ is =N(→O)—: (N-oxide).

The compound represented by the formula (1-2), wherein A²ᵃ is =CR⁸ᵃ—; or N-oxide thereof.

The compound represented by the formula (1-2), wherein A²ᵃ is =CH—; or N-oxide thereof.

The compound represented by the formula (1-2), wherein R¹ᵃ is a methyl group; or N-oxide thereof.

The compound represented by the formula (1-2), wherein R¹ᵃ is an ethyl group; or N-oxide thereof.

The compound represented by the formula (1-2), wherein R¹ᵃ is a propyl group; or N-oxide thereof.

The compound represented by the formula (1-2), wherein R¹ᵃ is an isopropyl group; or N-oxide thereof.

The compound represented by the formula (1-2), wherein R³ᵃ is a hydrogen atom; or N-oxide thereof.

The compound represented by the formula (1-2), wherein R³ᵃ is a trifluoromethyl group; or N-oxide thereof.

The compound represented by the formula (1-2), wherein R⁵ᵃ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and R⁶ᵃ is a hydrogen atom; or N-oxide thereof.

The compound represented by the formula (1-2), wherein R⁵ᵃ is a trifluoromethyl group, and R⁶ᵃ is a hydrogen atom; or N-oxide thereof.

The compound represented by the formula (1-2), wherein R⁵ᵃ is —CF₂CF₃, and R⁶ᵃ is a hydrogen atom; or N-oxide thereof.

The compound represented by the formula (1-2), wherein R⁵ᵃ is —SCF₃, and R⁶ᵃ is a hydrogen atom; or N-oxide thereof.

The compound represented by the formula (1-2), wherein R⁵ᵃ is —S(O)CF₃, and R⁶ᵃ is a hydrogen atom; or N-oxide thereof.

The compound represented by the formula (1-2), wherein R⁵ᵃ is —S(O)₂CF₃, and R⁶ᵃ is a hydrogen atom; or N-oxide thereof.

The compound represented by the formula (1-2), wherein
$A^{2a}$ is a nitrogen atom;
$R^{1a}$ is an ethyl group;
$R^{1a}$ is a hydrogen atom;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^{6a}$ is a hydrogen atom;
or N-oxide thereof.

The compound represented by the formula (1-2), wherein
$A^{2a}$ is =N(→O)—;
$R^{1a}$ is an ethyl group;
$R^{3a}$ is a hydrogen atom;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^{6a}$ is a hydrogen atom: (N-oxide).

The compound represented by the formula (1-2), wherein
$A^{2a}$ is =CR$^{8a}$—;
$R^8$ is a C1-C3 alkoxy group, a C1-C3 alkylsulfanyl group, a halogen atom, or a hydrogen atom;
$R^{1a}$ is an ethyl group;
$R^{3a}$ is a hydrogen atom;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^{6a}$ is a hydrogen atom;
or N-oxide thereof.

The compound represented by the formula (1-2), wherein
$A^{2a}$ is a nitrogen atom;
$R^{1a}$ is an ethyl group;
$R^{3a}$ is a trifluoromethyl group;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^{6a}$ is a hydrogen atom;
or N-oxide thereof.

The compound represented by the formula (1-2), wherein
$A^{2a}$ is =N(→O)—;
$R^{1a}$ is an ethyl group;
$R^{3a}$ is a trifluoromethyl group;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and
$R^{6a}$ is a hydrogen atom: (N-oxide).

The compound represented by the formula (1-2), wherein
$A^{2a}$ is =CR$^{8a}$—;
$R^8$ is a C1-C3 alkoxy group, a C1-C3 alkylsulfanyl group, a halogen atom, or a hydrogen atom;
$R^{1a}$ is an ethyl group;
$R^{3a}$ is a trifluoromethyl group;
$R^{5a}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; and
$R^{6a}$ is a hydrogen atom;
or N-oxide thereof.

The compound represented by the formula (1-3), wherein
$A^{2b}$ is a nitrogen atom; or N-oxide thereof.

The compound represented by the formula (1-3), wherein
$A^{2b}$ is =N(→O)—: (N-oxide).

The compound represented by the formula (1-3), wherein
$A^{2b}$ is =CR$^{8b}$—; or N-oxide thereof.

The compound represented by the formula (1-3), wherein
$A^{2b}$ is =CH—; or N-oxide thereof.

The compound represented by the formula (1-3), wherein
$R^{3b}$ is a hydrogen atom; or N-oxide thereof.

The compound represented by the formula (1-3), wherein
$R^{3b}$ is a trifluoromethyl group; or N-oxide thereof.

The compound represented by the formula (1-3), wherein
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom; or N-oxide thereof.

The compound represented by the formula (1-3), wherein
$R^{5b}$ is a trifluoromethyl group; or N-oxide thereof.

The compound represented by the formula (1-3), wherein
$R^{5b}$ is —CF$_2$CF$_3$; or N-oxide thereof.

The compound represented by the formula (1-3), wherein
$R^{5b}$ is —SCF$_3$; or N-oxide thereof.

The compound represented by the formula (1-3), wherein
$R^{5b}$ is —S(O)CF$_3$; or N-oxide thereof.

The compound represented by the formula (1-3), wherein
$R^{5b}$ is —S(O)$_2$CF$_3$; or N-oxide thereof.

The compound represented by the formula (1-3), wherein
$A^{2b}$ is a nitrogen atom;
$R^{2b}$ is a hydrogen atom;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-3), wherein
$A^{2b}$ is =N(→O)—;
$R^{3b}$ is a hydrogen atom; and
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom: (N-oxide).

The compound represented by the formula (1-3), wherein
$A^{2b}$ is =CR$^{8b}$—;
$R^8$ is a C1-C3 alkoxy group, a C1-C3 alkylsulfanyl group, a halogen atom, or a hydrogen atom;
$R^{3b}$ is a hydrogen atom;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-3), wherein
$A^{2b}$ is a nitrogen atom;
$R^{3b}$ is a trifluoromethyl group;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-3), wherein
$A^{2b}$ is =N(→O)—;
$R^{3b}$ is a trifluoromethyl group;
$R^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom(N-oxide).

The compound represented by the formula (1-3), wherein
A$^{2b}$ is =CR$^{8b}$—;
R$^8$ is a C1-C3 alkoxy group, a C1-C3 alkylsulfanyl group, a halogen atom, or a hydrogen atom;
R$^{3b}$ is a trifluoromethyl group;
R$^{5b}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein A$^c$ is a nitrogen atom; or N-oxide thereof.

The compound represented by the formula (1-4), wherein A$^{2c}$ is =N(→O)—: (N-oxide).

The compound represented by the formula (1-4), wherein A$^{2c}$ is =CR$^{8c}$—; or N-oxide thereof.

The compound represented by the formula (1-4), wherein A$^{2c}$ is =CH—; or N-oxide thereof.

The compound represented by the formula (1-4), wherein R$^{3c}$ is a hydrogen atom; or N-oxide thereof.

The compound represented by the formula (1-4), wherein R$^{3c}$ is a trifluoromethyl group; or N-oxide thereof.

The compound represented by the formula (1-4), wherein R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom, and R$^6$c is a hydrogen atom; or N-oxide thereof.

The compound represented by the formula (1-4), wherein R$^{5c}$ is a trifluoromethyl group; or N-oxide thereof.

The compound represented by the formula (1-4), wherein R$^{5c}$ is —CF$_2$CF$_3$; or N-oxide thereof.

The compound represented by the formula (1-4), wherein R$^{5c}$ is —SCF$_3$; or N-oxide thereof.

The compound represented by the formula (1-4), wherein R$^{5c}$ is —S(O)CF$_3$; or N-oxide thereof.

The compound represented by the formula (1-4), wherein R$^{5c}$ is —S(O)$_2$CF$_3$, or N-oxide thereof.

The compound represented by the formula (1-4), wherein
A$^{2c}$ is a nitrogen atom;
R$^{3c}$ is a hydrogen atom;
R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein
A$^{2c}$ is =N(→O)—;
R$^{3c}$ is a hydrogen atom; and
R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom: (N-oxide).

The compound represented by the formula (1-4), wherein
A$^{2c}$ is =CR$^{8c}$—;
R$^8$ is a C1-C3 alkoxy group, C1-C3 alkylsulfanyl group, a halogen atom, or a hydrogen atom;
R$^{3c}$ is a hydrogen atom;
R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein
A$^{2c}$ is a nitrogen atom;
R$^{3c}$ is a trifluoromethyl group; and
R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

The compound represented by the formula (1-4), wherein
A$^{2c}$ is =N(→O)—;
R$^{3c}$ is a trifluoromethyl group; and
R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom: (N-oxide).

The compound represented by the formula (1-4), wherein
A$^{2c}$ is =CR$^{8c}$—;
R$^8$ is a C1-C3 alkoxy group, a C1-C3 alkylsulfanyl group, a halogen atom, or a hydrogen atom;
R$^{3c}$ is a trifluoromethyl group; and
R$^{5c}$ is a C1-C3 perfluoroalkyl group, a C1-C3 perfluoroalkoxy group, a C1-C3 perfluoroalkylsulfanyl group, a C1-C3 perfluoroalkylsulfinyl group, a C1-C3 perfluoroalkylsulfonyl group, or a halogen atom;
or N-oxide thereof.

Next, a process for preparing the present fused heterocyclic compound is explained.

The present fused heterocyclic compound and intermediate compounds can be prepared, for example, according to the below-mentioned (Process 1) to (Process 24).

(Process 1)

A present fused heterocyclic compound of formula (1) wherein n is 1 or 2 can be prepared by oxidizing a present fused heterocyclic compound of formula (1) wherein n is 0.

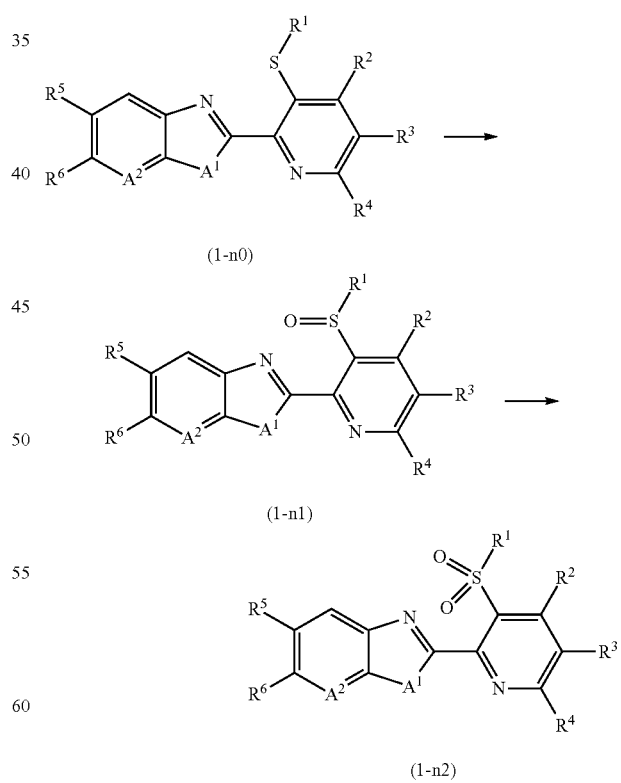

[wherein, each symbol is the same as defined in formula (1)]

A present fused heterocyclic compound of formula (1-n1) (when n is 1 in the formula (1)) can be prepared by oxidizing a present fused heterocyclic compound (1-n0) (when n is 0 in the formula (1)) with an oxidizing agent.

The reaction is usually carried out in the presence of a solvent.

Examples of the solvent to be used in the reaction include aliphatic hydrogenated hydrocarbons such as dichloromethane and chloroform; alcohols such as methanol and ethanol; acetic acid; water; and mixed solvents thereof.

Examples of the oxidizing agent to be used include sodium periodate and m-chloroperoxybenzoic acid.

In the reaction, the oxidizing agent is used usually within a range of 1 to 3 molar ratio(s) as opposed to 1 mole of the present fused heterocyclic compound (1-n0). Preferably, the oxidizing agent is used within a range of 1 to 1.2 molar ratio(s) as opposed to 1 mole of the present fused heterocyclic compound (1-n0).

The reaction temperature is usually within a range of −20 to 80° C. The reaction period of the reaction is usually within a range of 0.1 to 12 hours.

When the reaction is completed, the reaction mixtures are extracted with organic solvent(s), and the resulting organic layers are, if necessary, worked up (for example, washing with an aqueous solution of a reducing agent (such as sodium sulfite and sodium thiosulfate) and/or an aqueous solution of a base (such as sodium hydrogen carbonate), drying and concentration) to isolate the present fused heterocyclic compound (1-n1). The isolated present fused heterocyclic compound (1-n1) may be further purified, for example, by chromatography and recrystallization.

A present fused heterocyclic compound of formula (1-n2) (when n is 2 in the formula (1)) can be prepared by oxidizing the present fused heterocyclic compound of formula (1-n1) (when n is 1 in the formula (1)).

The reaction is usually carried out in the presence of a solvent.

Examples of the solvent to be used in the reaction include aliphatic hydrogenated hydrocarbons such as dichloromethane and chloroform; alcohols such as methanol and ethanol; acids such as acetic acid; water; and mixed solvents thereof.

Examples of the oxidizing agent to be used include m-chloroperoxybenzoic acid and hydrogen peroxide.

In the reaction, the oxidizing agent is used usually within a range of 1 to 4 molar ratio(s) as opposed to 1 mole of the present fused heterocyclic compound (1-n1). Preferably, the oxidizing agent is used within a range of 1 to 2 molar ratio(s) as opposed to 1 mole of the present fused heterocyclic compound (1-n1).

The reaction temperature is usually within a range of −20 to 120° C. The reaction period of the reaction is usually within a range of 0.1 to 12 hours.

When the reaction is completed, the reaction mixtures are extracted with organic solvent(s), and the resulting organic layers are, if necessary, worked up (for example, washing with an aqueous solution of a reducing agent (such as sodium sulfite and sodium thiosulfate), an aqueous solution of a base (such as sodium hydrogen carbonate), drying and concentration) to isolate the present fused heterocyclic compound (1-n2). The isolated present fused heterocyclic compound (1-n2) may be further purified, for example, by chromatography and recrystallization.

Also, the present fused heterocyclic compound of formula (1-n2) (when n is 2 in the formula (1)) can be prepared by oxidizing the present fused heterocyclic compound (1-n0) (when n is 0 in the formula (1)) with an oxidizing agent in one step (one-pot).

The reaction is usually carried out in the presence of a solvent.

Examples of the solvent to be used in the reaction include aliphatic hydrogenated hydrocarbons such as dichloromethane and chloroform; alcohols such as methanol and ethanol; acids such as acetic acid; water; and mixed solvents thereof.

Examples of the oxidizing agent to be used include m-chloroperoxybenzoic acid and hydrogen peroxide.

The reaction may be also carried out, if necessary, in the presence of a catalyst.

Examples of the catalyst to be used include sodium tungstate.

In the reaction, the oxidizing agent is used usually within a range of 2 to 5 molar ratio(s), and the catalyst is used usually within a range of 0.01 to 0.5 molar ratio(s), as opposed to 1 mole of the present fused heterocyclic compound (1-n0). Preferably, the oxidizing agent is used usually within a range of 2 to 3 molar ratio(s), and the catalyst is used usually within a range of 0.01 to 0.5 molar ratio(s), as opposed to 1 mole of the present fused heterocyclic compound (1-n0).

The reaction temperature is usually within a range of 0 to 120° C. The reaction period of the reaction is usually within a range of 0.1 to 12 hours.

When the reaction is completed, the reaction mixtures are extracted with organic solvent(s), and the resulting organic layers are, if necessary, worked up (for example, washing with an aqueous solution of a reducing agent (such as sodium sulfite and sodium thiosulfate) and/or an aqueous solution of a base (such as sodium hydrogen carbonate), drying and concentration) to isolate the present fused heterocyclic compound (1-n2). The isolated present fused heterocyclic compound (1-n2) may be further purified, for example, by chromatography and recrystallization.

(Process 2)

A present fused heterocyclic compound can be prepared by reacting an intermediate compound (M1) with an intermediate compound (M2) or an intermediate compound (M18) to afford an intermediate compound (M3), followed by performing an intramolecular condensation of the obtained intermediate compound (M3). In this reaction, a production of the intermediate compound (M3) and an intramolecular condensation thereon may be occurred concurrently, resulting in no confirmation of the intermediate compound (M3).

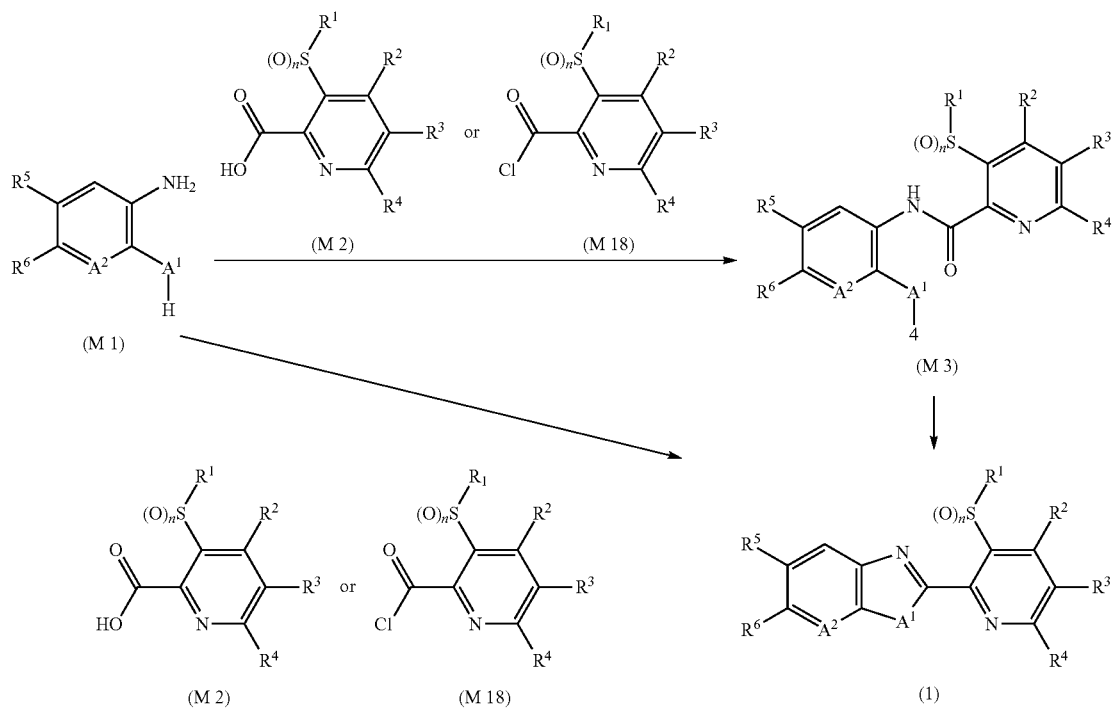

[wherein, each symbol is the same as defined in the formula (1)]

The intermediate compound (M3) may be prepared by reacting the intermediate compound (M1) with the intermediate compound (M2) in the presence of a condensation agent.

This reaction is usually carried out in the presence of a solvent. Examples of the solvent to be used in the reaction include ethers such as 1,4-dioxane, diethyl ether, tetrahydrofuran (hereinafter, sometimes referred to as THF) and methyl tert-butyl ether; halogenated hydrocarbons such as dichloromethane, chloroform, carbon tetrachloride, 1,2-dichloroethane, chlorobenzene; aromatic hydrocarbons such as toluene, benzene and xylene; esters such as ethyl acetate and butyl acetate; nitriles such as acetonitrile; aprotic polar solvents such as N,N-dimethylformamide (hereinafter, sometimes referred to as DMF), N-methylpyrrolidone (hereinafter, sometimes referred to as NMP), 1,3-dimethyl-2-imidazolidinone and dimethyl sulfoxide (hereinafter, sometimes referred to as DMSO); and nitrogen-containing aromatic compounds such as pyridine and quinoline; and mixed solvents thereof.

The condensation agent to be used include 1-ethyl-3-(3-dimethylaminopropyl)carbodiimide hydrochloride (hereinafter, sometimes referred to as EDC hydrochloride), 1,3-dicyclohexylcarbodiimide. The reaction may be also carried out, if necessary, in the presence of a catalyst.

Examples of the catalyst to be used include 1-hydroxybenzotriazole (hereinafter, sometimes referred to as HOBt).

In the reaction, the intermediate compound (M2) is used usually within a range of 0.5 to 2 molar ratio(s), the condensation agent is used usually within a range of 1 to 5 molar ratio(s), and the catalyst is used usually within a range of 0.01 to 1 molar ratio(s), as opposed to 1 mole of the intermediate compound (M1).

The reaction temperature is usually within a range of 0 to 120° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixtures are collected by filtration, to isolate the intermediate compound (M3). The isolated intermediate compound (M3) may be further purified, for example, by recrystallization and chromatography.

Also, the intermediate compound (M3) may be prepared by reacting the intermediate compound (M1) with the intermediate compound (M18).

This reaction is usually carried out in the presence of a solvent.

Examples of the solvent to be used in the reaction include ethers such as THF, ethyleneglycol dimethyl ether, methyl tert-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP and DMSO; and mixed solvents thereof.

The reaction may be also carried out, if necessary, in the presence of a base.

Examples of the base to be used include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

In the reaction, the intermediate compound (M18) is used usually within a range of 1 to 3 molar ratio(s), and the base is used usually within a range of 1 to 10 molar ratio(s), as opposed to 1 mole of the intermediate compound (M1).

The reaction temperature is usually within a range of −20 to 100° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the intermediate compound (M3). The intermediate compound (M3) may be further purified, for example, by chromatography and recrystallization.

The present fused heterocyclic compound (1) can be prepared by performing an intramolecular condensation of the intermediate compound (M3).

The reaction is usually carried out in the presence of a solvent. Examples of the solvent to be used in the reaction include ethers such as 1,4-dioxane, diethyl ether, THF and methyl tert-butyl ether; halogenated hydrocarbons such as dichloromethane, chloroform, carbon tetrachloride, 1,2-dichloroethane and chlorobenzene; aromatic hydrocarbons such as toluene, benzene and xylene; esters such as ethyl acetate and butyl acetate; nitriles such as acetonitrile; aprotic polar solvent such as DMF, NMP, 1,3-dimethyl-2-imidazolidinone and DMSO; nitrogen-containing aromatic compounds such as pyridine and quinoline; and mixed solvents thereof.

In the reaction, if necessary, a condensation agent, an acid, a base or a chlorinating agent may be used.

Examples of the condensation agent to be used include acid anhydrides such as acetic anhydride, trifluoroacetic anhydride; EDC hydrochloride; a mixture of triphenylphosphine, base and carbon tetrachloride or carbon tetrabromide; and a mixture of triphenylphosphine and azodiesters such as diethyl azodicarboxylate.

Examples of the acid to be used include sulfonic acids such as para-toluenesulfonic acid; carboxylic acids such as acetic acid; and polyphosphoric acid.

Examples of the base to be used include pyridine, picoline, 2,6-lutidine and 1,8-diazabicyclo[5.4.0]-7-undecene (hereinafter, sometimes referred to as DBU), nitrogen-containing heterocyclic compounds such as 1,5-diazabicyclo[4.3.0]-5-nonene; tertiary amines such as triethylamine and N,N-diisopropylethylamine; and inorganic bases such as tripotassium phosphate, potassium carbonate and sodium hydride.

Examples of the chlorinating agent to be used include phosphorus oxychloride.

In the reaction, when a condensation agent is used, the condensation agent is used usually within a range of 1 to 5 molar ratio(s), and when an acid is used, the acid is used usually within a range of 0.1 to 5 molar ratio(s), and when a base is used, the base is used usually within a range of 1 to 5 molar ratio(s), and when a chlorinating agent is used, the chlorinating agent is used usually within a range of 1 to 5 molar ratio(s), as opposed to 1 mole of the intermediate compound (M3).

The reaction temperature is usually within a range of 0 to 200° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to afford the present fused heterocyclic compound (1). The isolated the present fused heterocyclic compound (1) may be further purified, for example, by recrystallization and chromatography.

The present fused heterocyclic compound (1) may be prepared in one step (one-pot) by reacting the intermediate compound (M1) with the intermediate compound (M2) in the presence of a condensation agent.

This reaction is usually carried out in the presence of a solvent.

Examples of the solvent to be used in the reaction include ethers such as 1,4-dioxane, diethyl ether, THF, methyl tert-butyl ether; halogenated hydrocarbons such as dichloromethane, chloroform, carbon tetrachloride, 1,2-dichloroethane and chlorobenzene; aromatic hydrocarbons such as toluene, benzene, xylene; esters such as ethyl acetate and butyl acetate; nitriles such as acetonitrile; aprotic polar solvent such as DMF, NMP, 1,3-dimethyl-2-imidazolidinone and DMSO; nitrogen-containing aromatic compounds such as pyridine and quinoline; and mixed solvents thereof.

Examples of the condensation agent to be used include carbodiimides such as EDC hydrochloride and 1,3-dicyclohexylcarbodiimide.

The reaction may be carried out, if necessary, in the presence of a catalyst.

Examples of the catalyst to be used include 1-hydroxybenzotriazole.

In the reaction, the intermediate compound (M2) is used usually within a range of 0.5 to 2 molar ratio(s), the condensation agent is used usually within a range of 1 to 5 molar ratio(s) and the catalyst is used usually within a range of 0.01 to 1 molar ratio(s), as opposed to 1 mole of the intermediate compound (M1).

The reaction temperature is usually within a range of 0 to 200° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to isolate the present fused heterocyclic compound (1). The isolated present fused heterocyclic compound (1) may be further purified, for example, by recrystallization and chromatography.

Also, the present fused heterocyclic compound (1) can be prepared in one step (one-pot) by reacting the intermediate compound (M1) with the intermediate compound (M18).

The reaction is usually carried out in the presence or absence of a solvent.

Examples of the solvent to be used in the reaction include ethers such as THF, ethyleneglycol dimethyl ether, methyl tert-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP and DMSO; and mixed solvents thereof.

The reaction may be also carried out, if necessary, in the presence of a base.

Examples of the base to be used include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

In the reaction, the intermediate compound (M18) is used usually within a range of 1 to 3 molar ratio(s), and the base is usually within a range of 1 to 10 molar ratio(s), as opposed to 1 mole of the intermediate compound (M1).

The reaction temperature is usually within a range of 20 to 200° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the present fused heterocyclic compound (1). The isolated present fused heterocyclic compound (1) may be further purified, for example, by chromatography and recrystallization.

(Process 3)

A present fused heterocyclic compound of formula (P20) (when $A^1$ represents a sulfur atom and $A^2$ represents a nitrogen atom in the formula (1)) can be prepared by reacting an intermediate compound (M9) with an intermediate compound (M2) or an intermediate compound (M18) to afford an intermediate compound (M14), followed by reacting the obtained intermediate compound (M14) with a sulfuring agent.

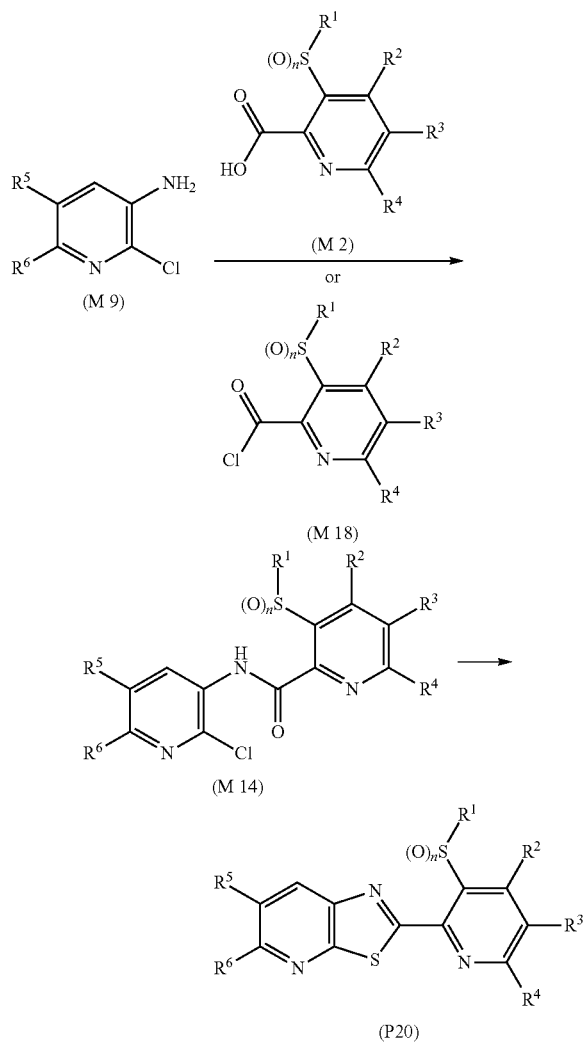

[wherein, each symbol is the same as defined in the formula (1)]

The intermediate compound (M14) can be prepared by reacting the intermediate compound (M9) with the intermediate compound (M2) in the presence of a condensation agent.

The reaction is carried out usually in the presence or absence of a solvent.

Examples of the solvent to be used in the reaction include ethers such as THF, ethyleneglycol dimethyl ether, methyl tert-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP and DMSO; nitrogen-containing aromatic compounds such as pyridine and quinoline; and mixed solvents thereof.

Examples of the condensation agent to be used include carbodiimides such as EDC hydrochloride and 1,3-dicyclohexylcarbodiimide, and BOP reagent (for example, benzotriazol-1-yloxy-trisdimetylamino phosphonium).

In the reaction, the intermediate compound (M2) is used usually within a range of 1 to 3 molar ratio(s) and the condensation agent is used usually within a range of 1 to 5 molar ratio(s), as opposed to 1 mole of the intermediate compound (M9).

The reaction temperature is usually within a range of 0 to 200° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the intermediate compound (M14). The isolated intermediate compound (M14) may be further purified, for example, by chromatography and recrystallization.

Also, the intermediate compound (M14) can be prepared by reacting the intermediate compound (M9) with the intermediate compound (M18).

The reaction is carried out usually in the presence or absence of a solvent. If necessary, the reaction may be also carried out in the presence of a base.

Examples of the solvent to be used in the reaction include ethers such as THF, ethyleneglycol dimethyl ether, methyl tert-butyl ether and 1,4-dioxane, aliphatic hydrocarbons such as hexane, heptane and octane; aromatic hydrocarbons such as toluene and xylene; halogenated hydrocarbons such as chlorobenzene, esters such as ethyl acetate and butyl acetate; nitriles such as acetonitrile; aprotic polar solvents such as DMF, NMP and DMSO; nitrogen-containing aromatic compounds such as pyridine and quinoline; and mixed solvents thereof.

Examples of the base to be used include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine. In the reaction, the intermediate compound (M18) is used usually within a range of 1 to 3 molar ratio(s), and the base is used usually within a range of 1 to 5 molar ratio(s), as opposed to 1 mole of the intermediate compound (M9).

The reaction temperature is usually within a range of 0 to 200° C. The reaction period of the reaction is usually within a range of 0.1 to 24 hours.

When the reaction is completed, the reaction mixtures are added into water and are extracted with organic solvent(s), and the resulting organic layers are, if necessary, worked up (for example, drying and concentration) to isolate the intermediate compound (M14). The isolated intermediate compound (M14) may be further purified, for example, by chromatography and recrystallization.

The present fused heterocyclic compound (P20) can be prepared by reacting the intermediate compound (14) with a sulfurizing agent.

The reaction is carried out in the presence or absence of a solvent.

Examples of the solvent to be used in the reaction include ethers such as 1,4-dioxane, diethyl ether, tetrahydrofuran, methyl tert-butyl ether and diglyme; halogenated hydrocarbons such as dichloromethane, chloroform, carbon tetrachloride, 1,2-dichloroethane and chlorobenzene; aromatic hydrocarbons such as toluene, benzene and xylene; nitriles such as acetonitrile; nitrogen-containing aromatic compounds such as pyridine, picoline, lutidine and quinoline; and mixed solvents thereof.

Examples of the sulfurizing agent to be used include phosphorus pentasulfide and Lawesson's reagent (2,4-bis-(4-methoxyphenyl)-1,3-dithia-2,4-diphosphetane-2,4-disulfide).

In the reaction, the sulfurizing agent is used usually within a range of 1 to 3 molar ratio(s) as opposed to 1 mole of the intermediate compound (M14).

The reaction temperature is usually within a range of 0 to 200° C. The reaction period of the reaction is usually within a range of 1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to isolate the present fused heterocyclic compound (P20). The isolated present heterocyclic compound (P20) may be further purified, for example, by recrystallization and chromatography.
(Process 4)

A present fused heterocyclic compound can be prepared by reacting an intermediate compound (M1) with an intermediate compound (M4) in the presence of an oxidizing agent.

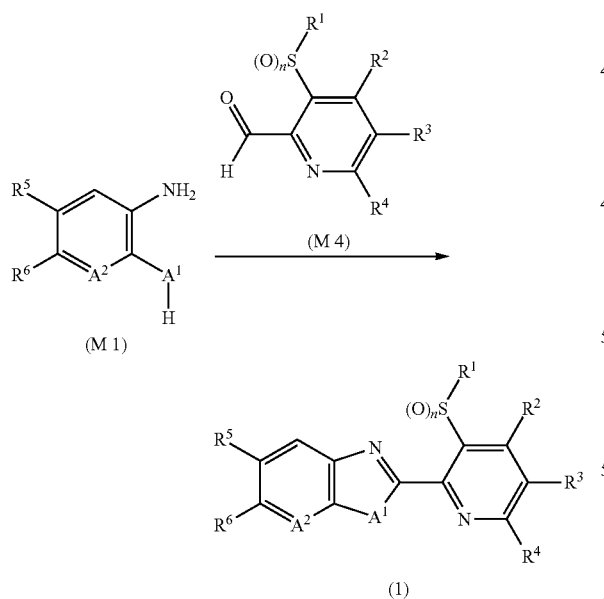

[wherein, each symbol is the same as defined in the formula (1)]

This reaction is usually carried out in the presence of a solvent.

Examples of the solvent to be used in the reaction include alcohols such as methanol and ethanol; ethers such as 1,4-dioxane, diethyl ether, THF and methyl tert-butyl ether; halogenated hydrocarbons such as dichloromethane, chloroform, carbon tetrachloride, 1,2-dichloroethane and chlorobenzene; aromatic hydrocarbons such as toluene, benzene and xylene; esters such as ethyl acetate and butyl acetate; nitriles such as acetonitrile; aprotic polar solvent such as DMF, NMP, 1,3-dimethyl-2-imidazolidinone and DMSO; nitrogen-containing aromatic compounds such as pyridine and quinoline; and mixed solvents thereof.

The reaction may be also carried out, for necessary, in the presence of an acid.

Examples of the acid to be used in the reaction include sulfonic acids such as paratoluenesulfonic acid; carboxylic acids such as acetic acid; and polyphosphoric acid.

The reaction may be also carried out, if necessary, in the presence of a sulfite.

Examples of the sulfite to be used in the reaction include sulfites such as sodium hydrogen sulfite and sodium bisulfite.

Examples of the oxidizing agent to be used include oxygen (for example, molecular oxygen), copper chloride (II) and DDQ.

In the reaction, the intermediate compound (M4) is used usually within a range of 1 to 2 molar ratio(s), the acid is used usually within a range of 0.1 to 2 molar ratio(s), the sulfites is used usually within a range of 1 to 5 molar ratio(s), and the oxidizing agent is used usually within a range of 1 to 5 molar ratio(s), as opposed to one mole of the intermediate compound (M1).

The reaction temperature is usually within a range of 0 to 200° C. The reaction period of the reaction is usually within a range of 1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to isolate the present fused heterocyclic compound (1). The isolated present heterocyclic compound (1) may be further purified, for example, by recrystallization and chromatography.
(Process 5)

A present fused heterocyclic compound (1) (when n is 0 in the formula (1)) can be prepared by reacting an intermediate compound (M6) with a compound (M7) in the presence of a base.

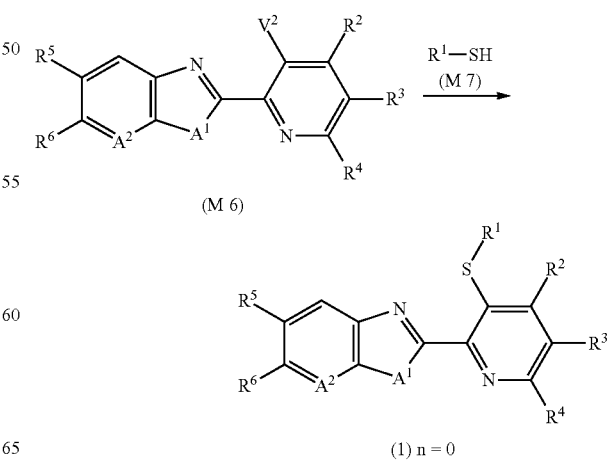

[wherein, V² represents a halogen atom, and the other symbols are the same as defined in the formula (1)]

This reaction is usually carried out in the presence of a solvent.

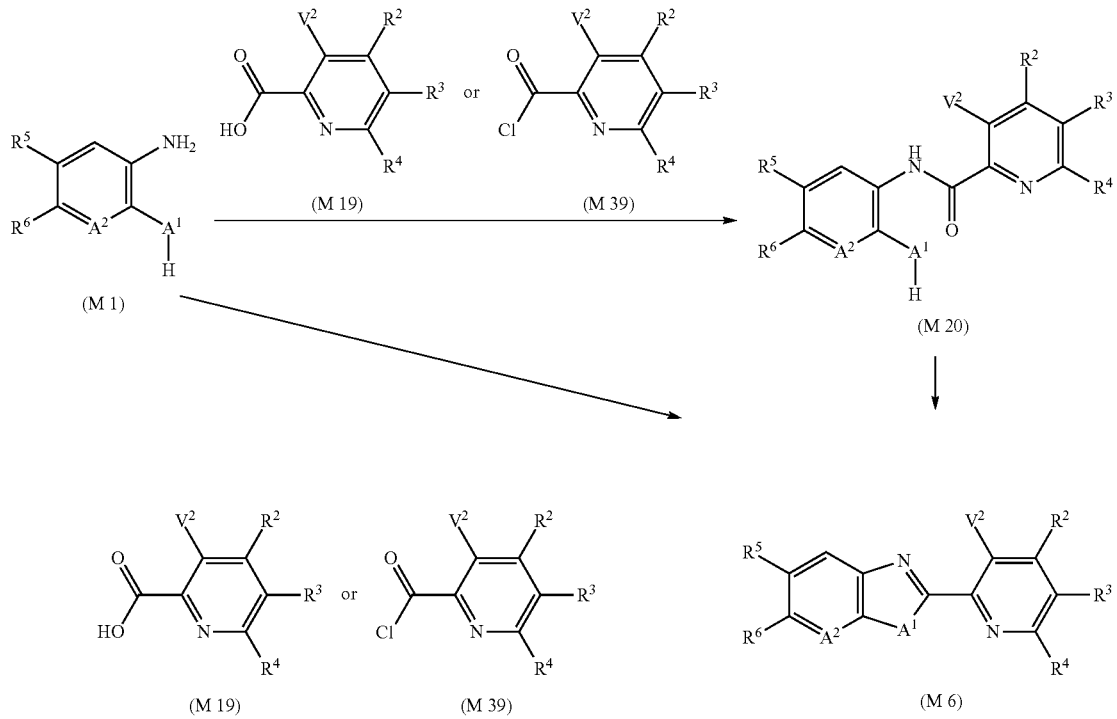

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; water; and mixed solvents thereof.

Examples of the base to be used include alkali metal carbonates such as sodium carbonate and potassium carbonate; and alkali metal hydrides such as sodium hydride.

In the reaction, the compound (M7) is used usually within a range of 1 to 10 molar ratio(s), and the base is used usually within a range of 1 to 10 molar ratio(s), as opposed to 1 mole of the intermediate compound (M6).

The reaction temperature is usually within a range of 0 to 150° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the present fused heterocyclic compound (1) (when n is 0 in the formula (1)). The isolated present fused heterocyclic compound (1) (when n is 0 in the formula (1)) may be further purified, for example, by chromatography and recrystallization.

In the reaction, V² is preferably a fluorine atom and a chlorine atom.

(Process 6)

An intermediate compound (M6) can be prepared by reacting an intermediate compound (M1) with an intermediate compound (M19) or an intermediate compound (M39) to afford an intermediate compound (M20), followed by performing an intramolecular condensation of the obtained intermediate compound (M20). In this reaction, a production of the intermediate compound (M20) and an intramolecular condensation thereon may be occurred concurrently, resulting in no confirmation of the intermediate compound (M20).

[wherein, V² represents a halogen atom, and the other each symbol is the same as defined in the formula (1)]

The intermediate compound (M20) can be prepared by using the intermediate compound (M19) instead of the intermediate compound (M2) according to Process 2.

The intermediate compound (M20) can be prepared by using the intermediate compound (M39) instead of the intermediate compound (M18) according to Process 2.

The intermediate compound (M6) can be prepared by using the intermediate compound (M20) instead of the intermediate compound (M3) according to Process 2.

Also, the intermediate compound (M6) can be prepared by using the intermediate compound (M19) instead of the intermediate compound (M2) according to Process 2 in one step (one-pot).

Also, the intermediate compound (M6) can be also prepared by using the intermediate compound (M39) instead of the intermediate compound (M2) according to Process 2 in one step (one-pot).

In the reaction, V² represents preferably a fluorine atom or a chlorine atom.

(Process 7)

An intermediate compound (M3) (when n is 0 in the formula (M3)) can be prepared by reacting an intermediate compound (M20) with a compound (M7). Also, the obtained intermediate compound (M3) can be performed on intramolecular condensation to afford a present fused heterocyclic compound (1) (when n is 0 in the formula (1)).

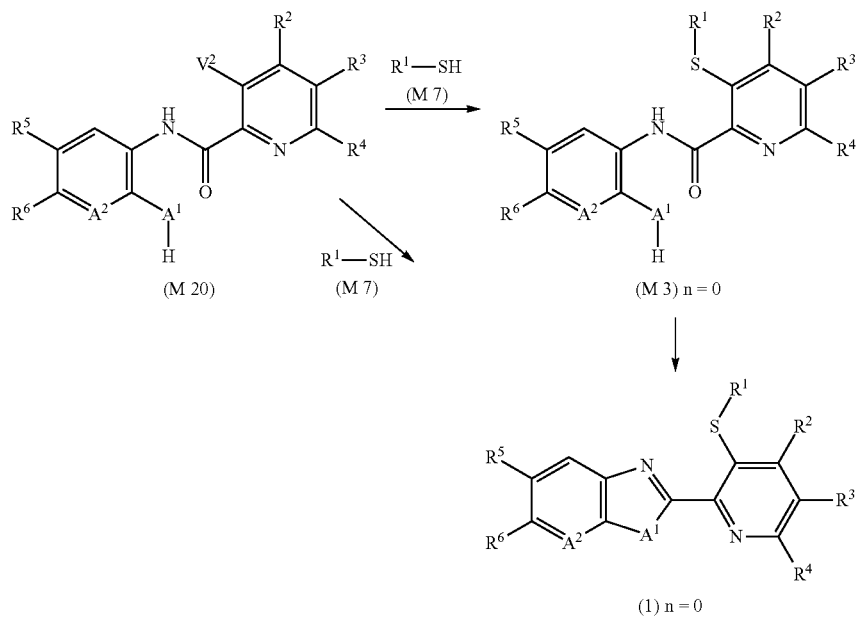

[wherein, $V^2$ represents a halogen atom, and the other each symbol is the same as defined in the formula (1)]

The intermediate compound (M3) (when n is 0 in the formula (M3)) can be prepared by using the intermediate compound (M20) instead of the intermediate compound of formula (M6) according to Process 5.

The present fused heterocyclic compound (1) (when n is 0 in the formula (1)) can be prepared by using the intermediate compound (M3) (when n is 0 in the formula (M3)) instead of the intermediate compound (M3) according to Process 2.

Also, the present fused heterocyclic compound (1) (when n is 0 in the formula (1)) can be also prepared by using the intermediate compound (M20) instead of the intermediate compound (M6) according to Process 5 in one step (one-pot).

In the reaction, $V^2$ represents preferably a fluorine atom or a chlorine atom.

(Process 8)

A present fused heterocyclic compound (1) (when n is 0 in the formula (1)) can be prepared by reacting an intermediate compound (M8) or a disulfide compound thereof, that is, an intermediate compound (M8') with a compound (M17) in the presence of a base.

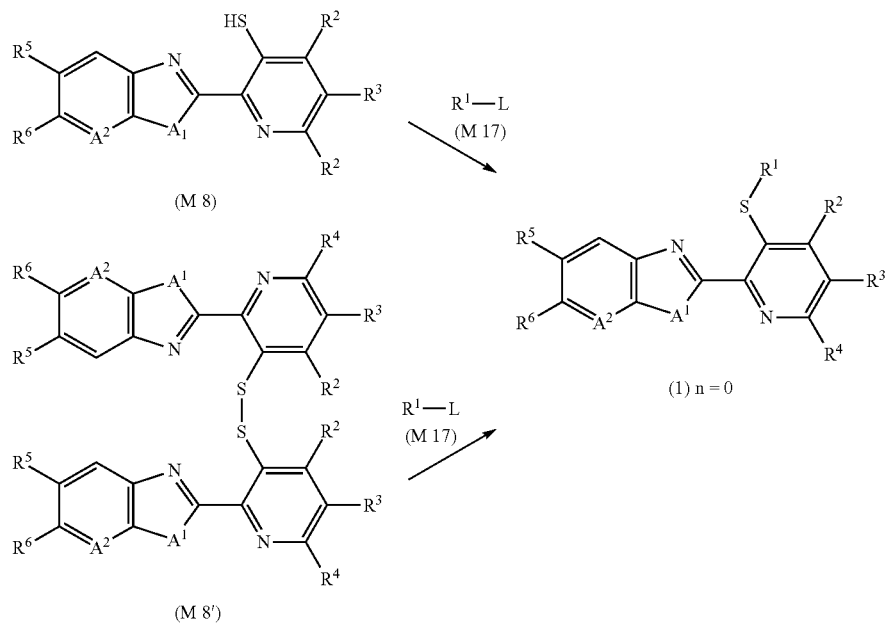

[wherein, L represents a leaving group such as a chlorine atom, a bromine atom, an iodine atom, a trifluoromethanesulfonyloxy group or a methanesulfonyloxy group, and the other each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include an alkali metal or alkaline-earth metal hydrides such as sodium hydride, potassium hydride and calcium hydride; inorganic bases such as sodium carbonate and potassium carbonate; and organic bases such as triethylamine.

When the intermediate compound (M8') being the disulfide compound is used, the reaction is usually carried out in the presence of a reducing agent.

Examples of the reducing agent to be used in the reaction include hydroxymethanesulfinic acid sodium salt (Trade name: Rongalite).

In the reaction, the intermediate compound (M17) is used usually within a range of 1 to 10 molar ratio(s), and the base is used usually within a range of 1 to 10 molar ratio(s), as opposed to 1 mole of the intermediate compound (M8). Also, when the intermediate compound (M8') being the disulfide compound is used, the intermediate compound (M17) is used usually within a range of 2 to 10 molar ratio(s), the base is used usually within a range of 2 to 10 molar ratio(s), and the reducing agent is used usually within a range of 1 to 5 molar ratio(s), as opposed to 1 mole of the intermediate compound (M8').

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (1) (when n is 0 in the formula (1)). The isolated present fused heterocyclic compound (1) (when n is 0 in the formula (1)) may be further purified, for example, by chromatography and recrystallization.

(Process 9)

A present fused heterocyclic compound (1) (when n is 0 in the formula (1)) can be prepared by reacting an intermediate compound (M8') with a compound (M17'-1) or a compound (M17'-2).

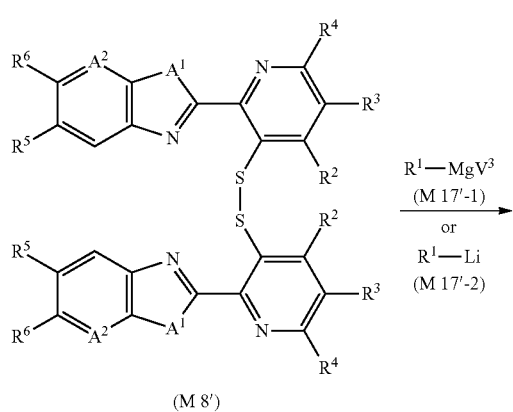

(M 8')

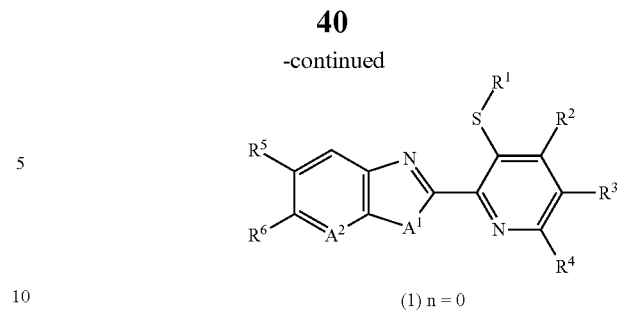

(1) n = 0

[wherein, V³ represents a chlorine atom, a bromine atom or an iodine atom; and the other each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

In the reaction, the compound (M17'-1) is used usually within a range of 1 to 2 molar ratio(s) as opposed to 1 mole of the intermediate compound (M8'). Also, when the compound (M17'-2) is used, the compound (M17'-2) is used usually within a range of 1 to 2 molar ratio(s) as opposed to 1 mole of the intermediate compound (M8').

The reaction temperature is usually within a range of −80 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (1) (when n is 0 in the formula (1)). The isolated present fused heterocyclic compound (1) (when n is 0 in the formula (1)) may be further purified, for example, by chromatography and recrystallization.

(Process 10)

An intermediate compound (M8) can be prepared by reacting an intermediate compound (M6) with a sulfurizing agent. Also, an intermediate compound (M8') being a disulfide compound can be prepared by oxidizing an intermediate compound (M8).

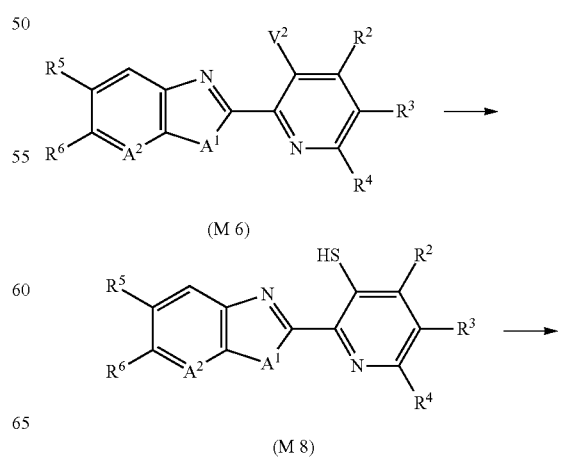

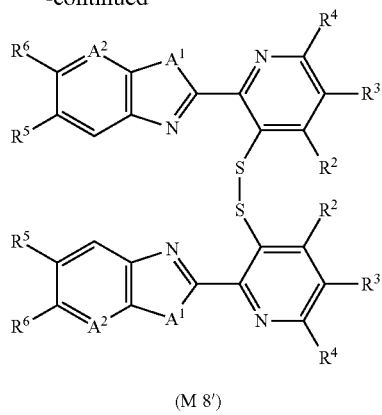

(M 8')

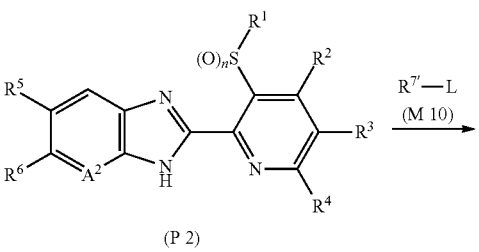

(P 2)

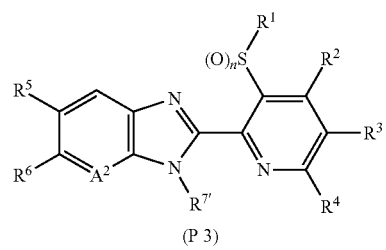

(P 3)

[wherein, $V^2$ represents a halogen atom, and the other each symbol is the same as defined in the formula (1)]

The intermediate compound (M8) can be prepared by using sulfides such as sodium sulfide, sodium hydrogen sulfide or hydrogen sulfide instead of the compound (M7) according to Process 5.

In this reaction, the conversion reaction of the intermediate compound (M8) to the intermediate compound (M8') can easily proceed and the intermediate compound (M8') is sometimes formed during a synthesis of the intermediate compound (M8). In the reaction, $V^2$ is preferably a fluorine atom or a chlorine atom.

The intermediate compound (M8') can be prepared by reacting two molecules of the intermediate compound (M8) in the presence of an oxidizing agent.

This reaction is usually carried out in the presence of a solvent.

Examples of the solvent to be used in the reaction include water; alcohols such as methanol and ethanol; ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; carboxylic acids such as acetic acid; and mixed solvents thereof. Examples of the oxidizing agent to be used include oxygen (such as molecular oxygen), iodine, hydrogen peroxide and potassium ferricyanide.

In the reaction, the oxidizing agent is used usually within a range of 0.5 to 10 molar ratio(s) as opposed to 1 mole of the intermediate compound (M8).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the intermediate compound (M8'). The obtained intermediate compound (M8') may be further purified, for example, by chromatography and recrystallization.

(Process 11)

A present fused heterocyclic compound (P3) (when $A^1$ represents —$NR^{7\prime}$— in the formula (1)) can be prepared by reacting a present fused heterocyclic compound (P2) (when $A^1$ represents —NH— in the formula (1)) with a compound (M10) in the presence of a base.

[wherein, $R^{7\prime}$ represents any group as $R^7$ defined in the formula (1) other than a hydrogen atom, L represents a leaving group such as a chlorine atom, a bromine atom, an iodine atom, a trifluoromethanesulfonyloxy group and a methanesulfonyloxy group; and the other each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include alkali metal or alkaline-earth metal hydrides such as sodium hydride, potassium hydride and calcium hydride; inorganic bases such as sodium carbonate and potassium carbonate; and organic bases such as triethylamine.

In the reaction, the compound (M10) is usually used within a range of 1 to 5 molar ratio(s), and the base is used usually within a range of 1 to 3 molar ratio(s), as opposed to 1 mole of the present fused heterocyclic compound (P2).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (P3). The obtained present fused heterocyclic compound (P3) may be further purified, for example, by chromatography and recrystallization.

(Process 12)

An intermediate compound (M2) can be prepared by hydrolyzing an intermediate compound (M37).

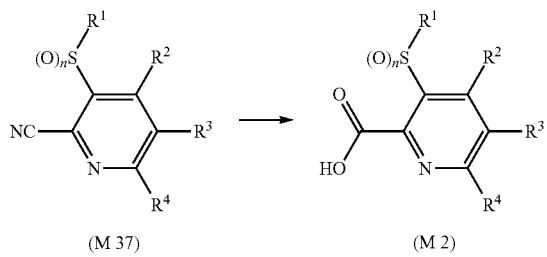

(M 37) → (M 2)

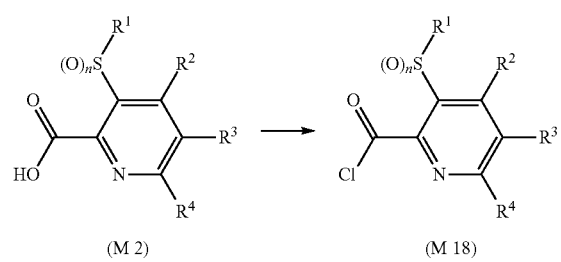

(M 2) → (M 18)

[wherein, each symbol is the same as defined in the formula (1)]

In the case of a hydrolysis with an acid, the reaction is usually carried out by using an aqueous solution of an acid as solvent.

Examples of the acid to be used include mineral acids such as hydrochloric acid, nitric acid, phosphoric acid and sulfuric acid; and organic acids including, for example, organic carboxylic acids such as acetic acid and trifluorocarboxylic acid.

In the reaction, an acid is used usually within a range of 1 to 10 molar ratio(s) as opposed to 1 mole of the intermediate compound (M37).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate intermediate compound (M2). The obtained intermediate compound (M2) may be further purified, for example, by chromatography and recrystallization.

In the case of a hydrolysis with a base, the reaction is usually carried out in a solvent.

Examples of the solvent to be used in the reaction include ethers such as THF, ethyleneglycol dimethyl ether, methyl tert-butyl ether and 1,4-dioxane; alcohols such as methanol and ethanol; water; and mixed solvents thereof.

Examples of the base to be used include alkali metal hydroxides such as sodium hydroxide and potassium hydroxide.

In the reaction, a base is used usually within a range of 1 to 10 molar ratio(s) as opposed to one mole of the intermediate compound (M37).

The reaction temperature is usually within a range of 0 to 120° C. The reaction period of the reaction is usually within a range of 0.1 to 24 hours.

When the reaction is completed, the reaction solutions are acidified and the reaction mixtures are extracted with organic solvent(s), and the resulting organic layers are worked up (for example, drying and concentration) to isolate the intermediate compound (M2). The isolated intermediate compound (M2) may be further purified, for example, by chromatography and recrystallization.

(Process 13)

An intermediate compound (M18) can be prepared by reacting an intermediate compound (M2) with a chlorinating agent.

[wherein, each symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; aliphatic hydrogenated hydrocarbons such as dichloromethane and chloroform; and mixed solvents thereof.

Examples of the chlorinating agent to be used include sulfonyl chloride, oxalyl dichloride and phosphorus oxychloride.

In the reaction, the chlorinating agent is used usually within a range of 1 to 5 molar ratio(s) as opposed to one mole of the intermediate compound (M2).

The reaction temperature is usually within a range of 0 to 100° C. The reaction period of the reaction is usually within a range of 0.1 to 24 hours.

When the reaction is completed, the reaction solvents are distilled off to isolate the intermediate compound (M18).

(Process 14)

An intermediate compound (M2), an intermediate compound (M4) or an intermediate compound (M37) can be prepared by reacting an intermediate compound (M19), an interdicted compound (M22) or an intermediate compound (M36) with a compound (M7), if necessary, followed by oxidizing each the obtained intermediate compound.

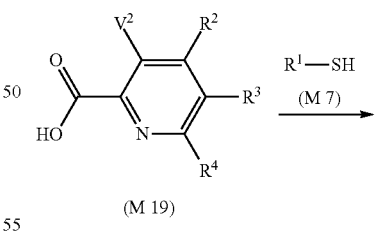

(M 19)

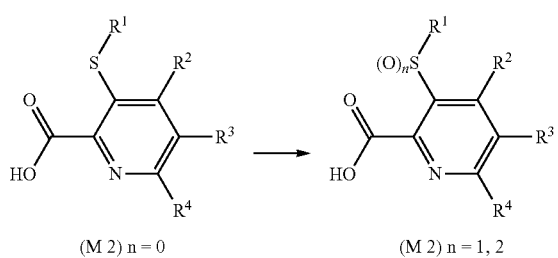

(M 2) n = 0 → (M 2) n = 1, 2

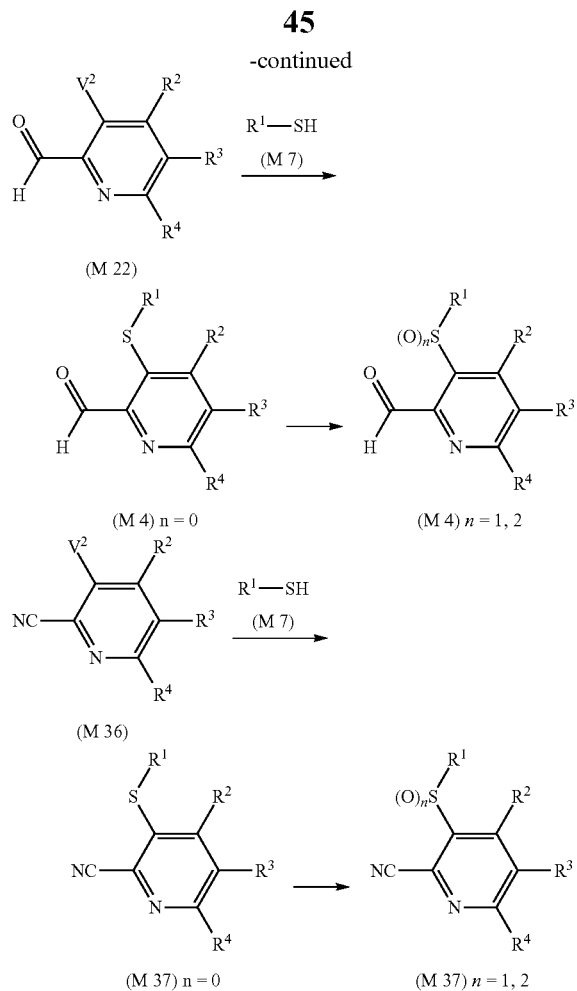

(M 22)

(M 4) n = 0

(M 4) n = 1, 2

(M 36)

(M 37) n = 0

(M 37) n = 1, 2

[wherein, V² represents a halogen atom, and the other each symbol is the same as defined in the formula (1)]

The intermediate compound (M2) (when n is 0) can be prepared by using the intermediate compound (M19) instead of the intermediate compound (M6) according to Process 5.

The intermediate compound (M4) (when n is 0) can be prepared by using the intermediate compound (M22) instead of the intermediate compound (M6) according to Process 5.

The intermediate compound (M37) (when n is 0) can be prepared by using the intermediate compound (M36) instead of the intermediate compound (M6) according to Process 5.

The intermediate compound (M2) (when n is 1 or 2) can be prepared by using the intermediate compound (M2) (when n is 0) instead of the present fused heterocyclic compound (1) (when n is 0) according to Process 1.

The intermediate compound (M4) (when n is 1 or 2) can be prepared by using the intermediate compound (M4) (when n is 0) instead of the present fused heterocyclic compound (1) (when n is 0) according to Process 1.

The intermediate compound (M37) (when n is 1 or 2) can be prepared by using the intermediate compound (M37) (when n is 0) instead of the present fused heterocyclic compound (1) (when n is 0) according to Process 1.

In the reaction, V² represents preferably a fluorine atom or a chlorine atom.

(Process 15)

An intermediate compound (M30) can be prepared by performing a nitration reaction of an intermediate compound (M29) or by reacting an intermediate compound (M33) with a compound (M28). The obtained intermediate compound (M30) can be reduced to afford an intermediate compound (M1) (when A¹ represents —NR⁷— in the formula (M1)).

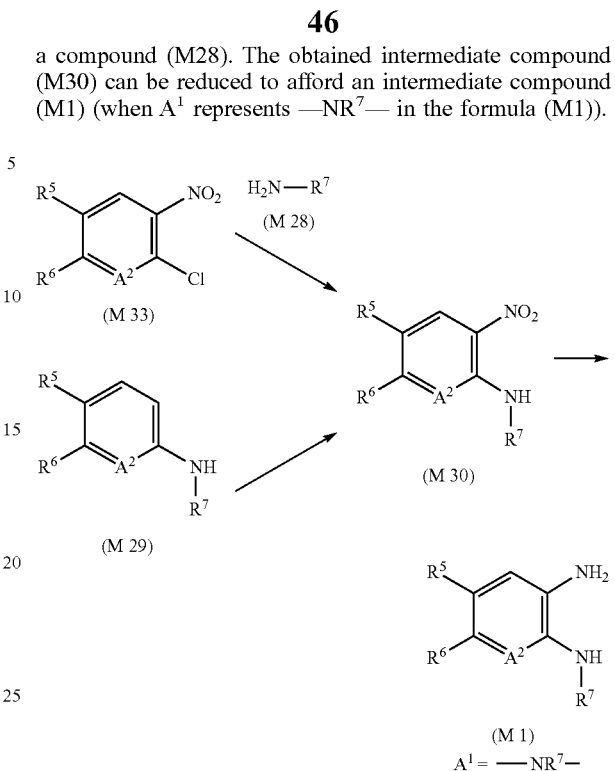

(M 33)

(M 29)

(M 30)

(M 1)
A¹ = —NR⁷—

[wherein, each symbol is the same as defined in the formula (1)]

The intermediate compound (M30) can be prepared by reacting the intermediate compound (M33) with the compound (M28) in the presence of a base.

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

The reaction may be carried out, if necessary, in the presence of a base. Examples of the base to be used include alkali metal hydrides such as sodium hydride; alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

In the reaction, the compound (M28) is used usually within a range of 1 to 10 molar ratio(s), and the base is used usually within a range of 0 to 10 molar ratio(s), as opposed to 1 mole of the intermediate compound (M33).

The reaction temperature is usually within a range of 0 to 150° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the intermediate compound (M30). The isolated intermediate compound (M30) may be further purified, for example, by chromatography and recrystallization.

The intermediate compound (M30) can be prepared by reacting the intermediate compound (M29) with a nitrating agent.

This reaction is usually carried out in the presence of a solvent.

Examples of the solvent to be used in the reaction include aliphatic hydrogenated hydrocarbons such as dichloromethane and chloroform; acids such as acetic acid, concentrated sulfuric acid and concentrated nitric acid; water; and mixed solvents thereof.

The nitrating agent to be used in the reaction includes a concentrated nitric acid.

In the reaction, the nitrating agent is used usually within a range of 1 to 3 molar ratio(s) as opposed to 1 mole of the intermediate compound (M29).

The reaction temperature is usually within a range of −10 to 100° C. The reaction period of the reaction is usually within a range of 0.1 to 24 hours.

When the reaction is completed, the reaction mixtures are added into water and are extracted with organic solvent(s), and the resulting organic layers are worked up (for example, drying and concentration) to isolate the intermediate compound (M30). The isolated intermediate compound (M30) may be further purified, for example, by chromatography and recrystallization.

Also, in the case where in the formula (M30), $R^7$ represents a hydrogen atom, the compounds of formula (M30) wherein $R^7$ represents any group other than a hydrogen atom can be prepared by using the intermediate compound (M30) wherein $R^7$ represents a hydrogen atom instead of the compound (P2) according to Process 11.

The intermediate compound (M1) (when $A^1$ represents —$NR^7$—) can be prepared by reacting the intermediate compound (M30) with hydrogen gas in the presence of a catalyst for hydrogenation.

The reaction is carried out under hydrogen atmosphere of usually 1 to 100 atmospheric pressure(s) and usually in the presence of a solvent.

Examples of the solvent to be used in the reaction include ethers such as THF, ethyleneglycol dimethyl ether, methyl tert-butyl ether and 1,4-dioxane; esters such as ethyl acetate and butyl acetate; alcohols such as methanol and ethanol; water; and mixed solvents thereof.

The catalysts for hydrogenation to be used in the reaction include transition metal compounds such as palladium-carbon, palladium hydroxide, raney nickel and platinum oxide.

In the reaction, the hydrogen gas is used usually within a range of 3 molar ratios, and the catalysts for hydrogenation are used usually within a range of 0.001 to 0.5 molar ratio(s), as opposed to 1 mole of the intermediate compound (M30).

The reaction may be carried out, if necessary, in the presence of an acid or a base and the others.

Examples of the acids to be used in the reaction include acids such as acetic acid and hydrochloric acid, and examples of the base to be used include tertiary amines such as triethylamine and magnesium oxide.

The reaction temperature is usually within a range of −20 to 100° C. The reaction period of the reaction is usually within a range of 0.1 to 24 hours.

When the reaction is completed, the reaction mixtures are filtered and, if necessary, are extracted with organic solvent(s), and the resulting organic layers are worked up (for example, drying and concentration) to isolate the intermediate compound (M1) (when $A^1$ represents —$NR^7$—). The isolated intermediate compound (M1) (when $A^1$ represents —$NR^7$—) may be further purified, for example, by chromatography and recrystallization.

Also, the intermediate compound (M30) can be prepared as mentioned below, for example, by acetylating the intermediate compound (M29) to afford the intermediate compound (M29'), followed by performing a nitration reaction of the obtained intermediate compound (M29') to afford the intermediate compound (M30') and further by hydrolyzing the obtained intermediate compound (M30').

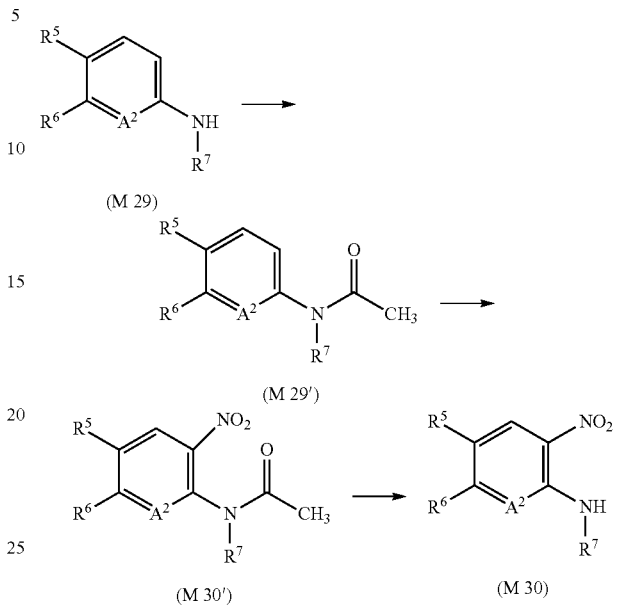

[wherein, each symbol is the same as defined in the formula (1)]

The intermediate compound (M29') can be prepared by reacting the intermediate compound (M29) with an acylating agent.

The reaction is carried out usually in the presence of a solvent or by using the acylating agent as solvent.

Examples of the solvent to be used in the reaction include aliphatic hydrogenated hydrocarbons such as dichloromethane and chloroform; aliphatic hydrogenated hydrocarbons such as dichloromethane and chloroform; ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof. Examples of the acylating agent to be used in the reaction include acetic anhydride and para-acetoxy nitrobenzene.

The reaction may be also carried out, if necessary, in the presence of a base. Examples of the base to be used include tertiary amines such as triethylamine and N,N-diisopropylethylamine; and nitrogen-containing aromatic compounds such as pyridine and 4-dimethylaminopyridine.

In the reaction, the acylating agent is used within a range of 1 or more molar ratio(s), and the base is used usually within a range of 0.1 to 10 molar ratio(s), as opposed to 1 mole of the intermediate compound (M29).

The reaction temperature is usually within a range of 0 to 150° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the intermediate compound (M29'). The isolated intermediate compound (M29') may be further purified, for example, by chromatography and recrystallization.

The intermediate compound (M30') can be prepared by using the intermediate compound (M29') instead of the intermediate compound (M29) according to Process 15.

The intermediate compound (M30) can be prepared by hydrolyzing the intermediate compound (M30') in the presence of an acid or a base.

In the case of a hydrolysis with an acid, the reaction is usually carried out by using an aqueous solution of the acid as solvent.

Examples of the acid to be used in the reaction include mineral acids such as hydrochloric acid and sulfuric acid; and organic acid including, for example, organic carboxylic acids such as acetic acid and trifluoroacetic acid.

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the intermediate compound (M30). The isolated intermediate compound (M30) may be further purified, for example, by chromatography and recrystallization.

In the case of a hydrolysis with a base, the reaction is usually carried out in a solvent.

Examples of the solvent to be used in the reaction include ethers such as THF, ethyleneglycol dimethyl ether, methyl tert-butyl ether and 1,4-dioxane; alcohols such as methanol and ethanol; water; and mixed solvents thereof.

Examples of the base to be used include alkali metal hydroxides such as sodium hydroxide and potassium hydroxide; and hydrazine.

In the reaction, the base is used usually within a range of 1 to 10 molar ratio(s) as opposed to 1 mole of the intermediate compound (M30').

The reaction temperature is usually within a range of 0 to 120° C. The reaction period of the reaction is usually within a range of 0.1 to 24 hours.

When the reaction is completed, the reaction solutions are acidified, and the reaction mixtures are extracted with organic solvent(s), and the resulting organic layers are worked up (for example, drying and concentration) to isolate the intermediate compound (M30). The isolated intermediate compound (M30) may be further purified, for example, by chromatography and recrystallization.

(Process 16)

An intermediate compound (M1) (when $A^1$ represents —$NR^7$—) can be prepared by brominating an intermediate compound (M29) to afford an intermediate compound (M35), followed by aminating the obtained intermediate compound (M35).

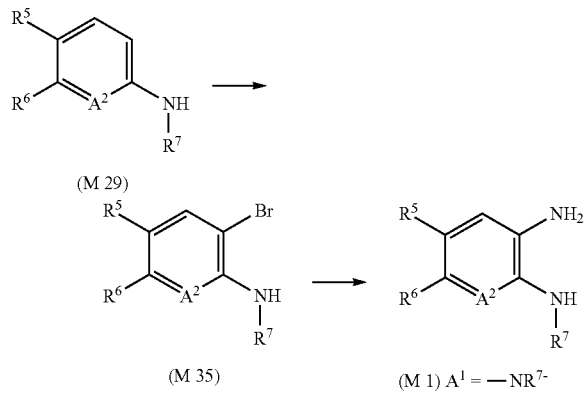

(M 29)
(M 35)
(M 1) $A^1 = —NR^{7-}$

[wherein, each symbol is the same as defined in the formula (1)]

The intermediate compound (M35) can be prepared by reacting the intermediate compound (M29) with a brominating agent.

This reaction is usually carried out in the presence of a solvent.

Examples of the solvent to be used in the reaction include water; acetic acid; ethers such as 1,4-dioxane, diethyl ether and THF; esters such as ethyl acetate and butyl acetate; halogenated hydrocarbons such as dichloromethane, chloroform, carbon tetrachloride and 1,2-dichloroethane; nitriles such as acetonitrile; aprotic polar solvents such as DMF, NMP and DMSO; and mixed solvents thereof.

Examples of the brominating agent to be used include N-bromosuccinimide and bromine.

The brominating agent is used usually within a range of 1 to 3 molar ratio(s) as opposed to 1 mole of the intermediate compound (M29).

The reaction temperature is usually within a range of −10 to 100° C. The reaction period of the reaction is usually within a range of 0.1 to 24 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to afford the intermediate compound (M35). The isolated intermediate compound (M35) may be further purified, for example, by recrystallization and chromatography.

The intermediate compound (M1) (when $A^1$ represents —$NR^7$—) can be prepared by reacting the intermediate compound (M35) with an aminating agent in the presence of a copper compound.

This reaction is usually carried out in the presence of a solvent.

Examples of the solvent to be used in the reaction include water; alcohols such as methanol and ethanol; ethers such as 1,4-dioxane, diethyl ether and THF; esters such as ethyl acetate and butyl acetate; halogenated hydrocarbons such as dichloromethane, chloroform, carbon tetrachloride and 1,2-dichloroethane; nitriles such as acetonitrile; aprotic polar solvents such as DMF, NMP and DMSO; nitrogen-containing aromatic compounds such as pyridine and quinoline; and mixed solvents thereof.

The aminating agent to be used in the reaction includes ammonia, aqueous ammonia and lithium amide.

The copper compound to be used in the reaction includes copper, copper iodide(I), copper oxide(I), copper oxide(II), acetylacetone copper(II), copper acetate(II) and copper sulfate(II).

The reaction may be also carried out, if necessary, in the presence of a ligand.

Examples of the ligand to be used in the reaction include acetylacetone, salen (N,N'-bis(salicylidene)ethylenediamine) and phenanthroline.

The reaction may be also carried out, if necessary, in the presence of a base.

Examples of the base to be used include nitrogen-containing heterocyclic compounds such as pyridine, picoline, 2,6-lutidine, DBU, 1,5-diazabicyclo[4.3.0]-5-nonene; tertiary amines such as triethylamine and N,N-diisopropylethylamine; and inorganic bases such as tripotassium phosphate, potassium carbonate, cesium carbonate and sodium hydroxide.

The aminating agent is used usually within a range of 1 to 5 molar ratio(s), the copper compound is used usually within a range of 0.02 to 0.5 molar ratio(s), the ligand is used usually within a range of 0.02 to 2 molar ratio(s) and the base is used usually within a range of 1 to 5 molar ratio(s), as opposed to 1 mole of the intermediate compound (M35).

The reaction temperature is usually within a range of 30 to 200° C. The reaction period of the reaction is usually within a range of 0.1 to 48 hours.

When the reaction is completed, the reaction mixtures are added into water and are then extracted with organic solvent(s), and the resulting organic layers are concentrated; the reaction mixtures are added into water and the resulting solids are collected by filtration; or the solids formed in the reaction mixture are collected by filtration, to afford the intermediate compound (M1) (when $A^1$ represents —$NR^7$—). The isolated intermediate compound (M1) (when $A^1$ represents —$NR^7$—) may be further purified, for example, by recrystallization and chromatography.

(Process 17)

An intermediate compound (M1) (when $A^1$ represents an oxygen atom) can be prepared by performing a nitration reaction of an intermediate compound (M31) to afford an intermediate compound (M32), followed by reducing the obtained intermediate compound (M32).

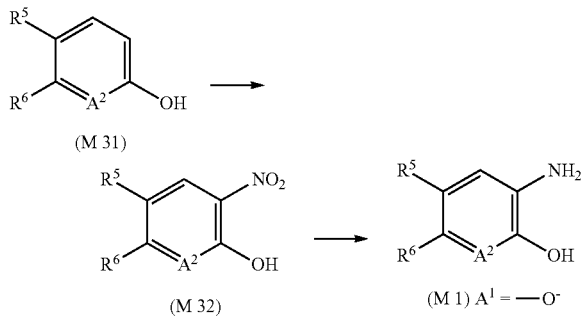

[wherein, each symbol is the same as defined in the formula (1)]

The intermediate compound (M32) can be prepared by using the intermediate compound (M31) instead of the intermediate compound (M29) according to Process 15.

The intermediate compound (M1) (when $A^1$ represents an oxygen atom) can be prepared by using the intermediate compound (M32) instead of the intermediate compound (M30) according to Process 15.

(Process 18)

An intermediate compound (M1) can be prepared by reacting an intermediate compound (M33) with a sulfurizing agent to afford an intermediate compound (M34), followed by reacting the obtained intermediate compound (M34) with a reducing agent.

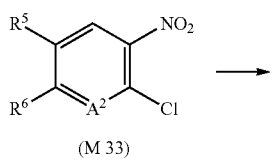

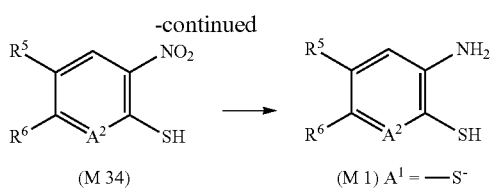

[wherein, each symbol is the same as defined in the formula (1)]

The intermediate compound (M34) can be prepared by reacting the intermediate compound (M33) with a thiourea in the presence of a base.

This reaction is usually carried out in the presence of a solvent.

Examples of the solvent to be used in the reaction include alcohols such as methanol and ethanol; water; and mixed solvents thereof.

Examples of the base to be used include alkali metal hydroxides such as sodium hydroxide and potassium hydroxide.

In the reaction, the thiourea is used usually within a range of 0.5 to 3 molar ratio(s), and the base is used usually within a range of 1 to 10 molar ratio(s), as opposed to 1 mole of the intermediate compound (M33).

The reaction temperature is usually within a range of 0 to 100° C. The reaction period of the reaction is usually within a range of 0.1 to 24 hours.

When the reaction is completed, to the reaction mixtures are added an acid, and the resulting mixtures are extracted with organic solvent(s), and the resulting organic layers are worked up (for example, drying and concentration) to isolate the intermediate compound (M34). The isolated intermediate compound (M34) may be further purified, for example, by chromatography and recrystallization.

The intermediate compound (M1) (when $A^1$ represents a sulfur atom) can be prepared by reacting the intermediate compound (M34) with a reducing agent.

The reduction reaction may be carried out, for example, in the presence of metal powder such as zinc powder; acids such as hydrochloric acid and acetic acid; and water.

This reaction is usually carried out in the presence of a solvent.

Examples of the solvent to be used in the reaction include ethers such as THF, ethyleneglycol dimethyl ether, methyl tert-butyl ether and 1,4-dioxane; esters such as ethyl acetate and butyl acetate; alcohols such as methanol and ethanol; aprotic polar solvents such as DMF, NMP and DMSO; and mixed solvents thereof.

Examples of the reducing agent to be used in the reaction include metal powder such as iron powder, zinc powder and tin dichloride.

In the reaction, the metal powder is used usually within a range of 3 to 10 molar ratio(s) as opposed to 1 mole of the intermediate compound (M34).

The reaction temperature is usually within a range of 0 to 100° C. The reaction period of the reaction is usually within a range of 0.1 to 24 hours.

When the reaction is completed, to the reaction mixtures are added an acid, and the resulting mixtures are extracted with organic solvent(s), and the resulting organic layers are worked up (for example, drying and concentration) to isolate the intermediate compound (M1) wherein $A^1$ represents a sulfur atom. The isolated intermediate compound (M1) wherein $A^1$ represents a sulfur atom may be further purified, for example, by chromatography and recrystallization.

(Process 19)

A compound of formula (1) wherein $R^5$ represents a C1-C6 perfluoroalkyl group, that is, a present fused heterocyclic compound (P7) can be prepared by reacting a compound of formula (1) wherein $R^5$ represents a halogen atom, that is, a present fused heterocyclic compound (P4) with a compound (M11) or a compound (M11') in the presence of a copper compound.

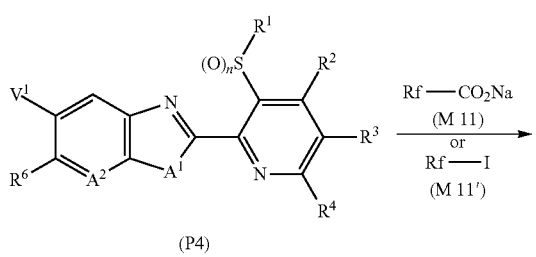

(P4)

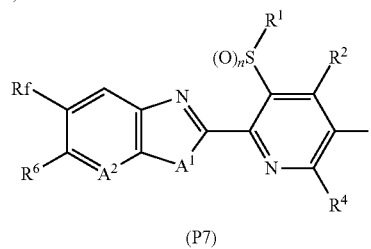

(P7)

[wherein, $V^1$ represents a halogen atom, Rf represents a C1-C6 perfluoroalkyl group, and the other each symbol is the same as defined in the formula (1)]

This reaction is usually carried out in the presence of a solvent.

Examples of the solvent to be used in the reaction include aromatic hydrocarbons such as toluene and xylene; aprotic polar solvents such as DMF, NMP and DMSO; and mixed solvents thereof. Examples of the copper compound to be used in the reaction include copper and copper iodide(I). When the compound (M11) is used in the reaction, the compound (M11) is used usually within a range of 1 to 10 molar ratio(s), the copper compound is used usually within a range of 0.5 to 10 molar ratio(s), as opposed to 1 mole of the present fused heterocyclic compound (P4).

The reaction temperature is usually within a range of 100 to 200° C. The reaction period of the reaction is usually within a range of 0.5 to 48 hours.

In the reaction, when the intermediate compound (M11') is used, a potassium fluoride may be optionally added. The compound (M11') is used usually within a range of 1 to 10 molar ratio(s), the copper compound is used usually within a range of 0.1 to 10 molar ratio(s), and the potassium fluoride is used usually within a range of 0.1 to 5 molar ratio(s), as opposed to 1 mole of the present fused heterocyclic compound (P4).

The reaction temperature is usually within a range of 0 to 150° C. The reaction period of the reaction is usually within a range of 0.5 to 48 hours.

When the reaction is completed, the resulting mixtures are extracted with organic solvent(s), and the resulting organic layers are worked up (for example, drying and concentration) to isolate the present fused heterocyclic compound (P7). The isolated present fused heterocyclic compound (P7) may be further purified, for example, by chromatography and recrystallization. In the reaction, V1 represents preferably a bromine atom and an iodine atom.

(Process 20)

A present fused heterocyclic compound (P9) (when $R^5$ represents a —SH group in the formula (1)) can be prepared by reacting a present fused heterocyclic compound (P4) with a sulfurizing agent. Also, the present fused heterocyclic compound (P9) can be oxidized to afford a disulfide compound thereof, that is, an intermediate compound (P9').

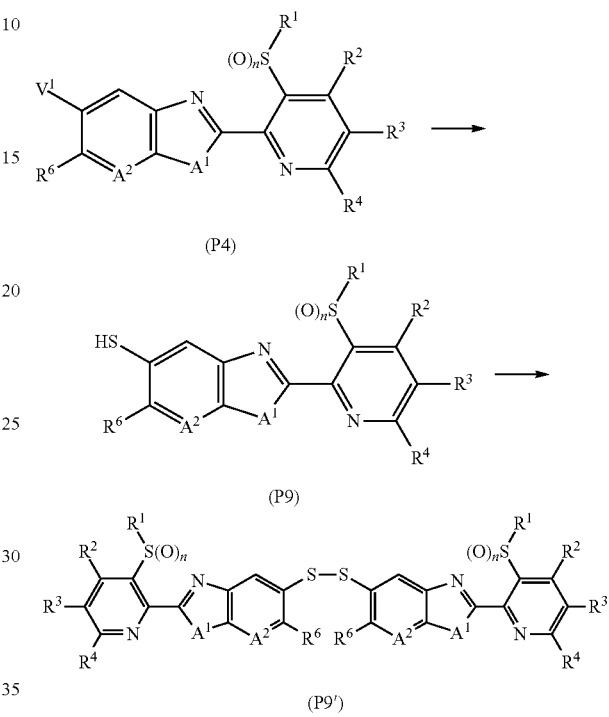

[wherein, $V^1$ represents a halogen atom, and each other symbols are the same as defined in formula (1)]

The present fused heterocyclic compound (P9) can be prepared by reacting the present fused heterocyclic compound (P4) with a thiolating agent in the presence of a catalyst.

This reaction is usually carried out in the presence of a solvent.

Examples of the solvent to be used in the reaction include aromatic hydrocarbons such as toluene and xylene; aprotic polar solvents such as DMF, NMP and DMSO; and mixed solvents thereof.

Examples of the thiolating agent to be used in the reaction include sodium sulfide, sodium sulfide nine hydrates and thiourea.

Examples of the catalyst to be used include copper chloride(I), copper bromide(I) and copper iodide(I).

The reaction may be also carried out, if necessary, in the presence of a ligand.

Examples of the ligand to be used in the reaction include acetylacetone, salen and phenanthroline.

The reaction may be also carried out, if necessary, in the presence of a base.

Examples of the base to be used include inorganic bases such as potassium carbonate, cesium carbonate and tripotassium phosphate; and organic bases such as triethylamine.

In the reaction, the thiolating agent is used usually within a range of 1 to 10 molar ratio(s), the catalyst is used usually within a range of 0.1 to 5 molar ratio(s), the ligand is used usually within a range of 0.1 to 5 molar ratio(s), and the base is used usually within a range of 1 to 2 molar ratio(s), as opposed to 1 mole of the present fused heterocyclic compound (P4).

The reaction temperature is usually within a range of 50 to 200° C. The reaction period of the reaction is usually within a range of 0.5 to 24 hours.

When the reaction is completed, the resulting mixtures are extracted with organic solvent(s), and the resulting organic layers are worked up (for example, drying and concentration) to isolate the present fused heterocyclic compound (P9). The isolated present fused heterocyclic compound (P9) may be further purified, for example, by chromatography and recrystallization. In the reaction, $V^1$ represents preferably a bromine atom and an iodine atom.

In this reaction, the conversion reaction of the intermediate compound (P9) to the intermediate compound (P9') can easily proceed and the intermediate compound (P9') is sometimes formed during a synthesis of the intermediate compound (P9).

The intermediate compound (P9') can be prepared by reacting the present fused heterocyclic compound (P9) with an oxidizing agent.

This reaction is usually carried out in the presence of a solvent.

Examples of the solvent to be used in the reaction include water; alcohols such as methanol and ethanol; ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; carboxylic acids such as acetic acid; and mixed solvents thereof.

Examples of the oxidizing agent to be used include oxygen (for example, molecular oxygen), iodine, hydrogen peroxide and potassium ferricyanide.

In the reaction, the oxidizing agent is used usually within a range of 0.5 to 10 molar ratio(s) as opposed to 1 mole of the present fused heterocyclic compound (P9).

The reaction temperature is usually within a range of 0 to 100° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the intermediate compound (P9'). The isolated intermediate compound (P9') may be further purified, for example, by chromatography and recrystallization.

Also, the present fused heterocyclic compound (P9) can be prepared by thioesterifying the present fused heterocyclic compound (P4) to afford the intermediate compound (P9-1), followed by hydrolyzing the obtained intermediate compound (P9-1).

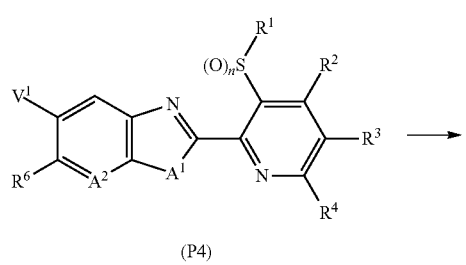

(P4)

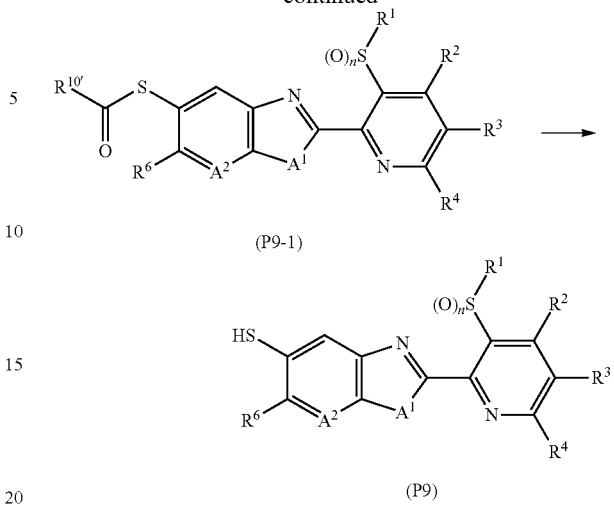

[wherein, $P^{10'}$ represents any group as $R^{10}$ defined in the formula (1) other than a hydrogen atom, and each other symbol is the same as defined in the formula (1)]

The intermediate compound (P9-1) can be prepared by reacting the present fused heterocyclic compound (P4) with a thioesterifying agent in the presence of a base and a catalyst.

This reaction is usually carried out in the presence of a solvent.

Examples of the solvent to be used in the reaction include aromatic hydrocarbons such as toluene and xylene; aprotic polar solvents such as DMF, NMP and DMSO; and mixed solvents thereof.

Examples of the thioesterifying agent include thiobenzoic acid.

Examples of the catalyst to be used include copper chloride(I), copper bromide(I) and copper iodide(I).

The reaction may be carried out, for example, in the presence of a ligand.

Examples of the ligand to be used in the reaction include acetyl acetone, salen and phenanthroline.

Examples of the base to be used include inorganic bases such as potassium carbonate, cesium carbonate, tripotassium phosphate; and organic bases such as triethylamine.

In the reaction, the thioesterifying agent is used usually within a range of 1 to 10 molar ratio(s), the catalyst is used usually within a range of 0.1 to 5 molar ratio(s), the ligand is used usually within a range of 0.1 to 5 molar ratio(s), and the base is used usually within a range of 1 to 2 molar ratio(s), as opposed to 1 mole of the present fused heterocyclic compound (P4).

The reaction temperature is usually within a range of 50 to 200° C. The reaction period of the reaction is usually within a range of 0.5 to 24 hours.

When the reaction is completed, the resulting mixtures are extracted with organic solvent(s), and the resulting organic layers are worked up (for example, drying and concentration) to isolate the intermediate compound (P9-1). The isolated intermediate compound (P9-1) may be further purified, for example, by chromatography and recrystallization.

In the reaction, $V^1$ represents preferably a bromine atom and an iodine atom.

The present fused heterocyclic compound (P9) can be prepared by hydrolyzing the intermediate compound (P9-1).

In the case of a hydrolysis with an acid, the reaction is usually carried out by using an aqueous solution of the acid as solvent.

Examples of the acid to be used in the reaction include mineral acids such as hydrochloric acid, nitric acid, phosphoric acid and sulfuric acid; and organic acid including, for example, organic carboxylic acids such as acetic acid and trifluoroacetic acid.

The reaction temperature is usually within a range of 0 to 100° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the present fused heterocyclic compound (P9). The present fused heterocyclic compound (P9) may be further purified, for example, by chromatography and recrystallization.

In the case of a hydrolysis with a base, the reaction is usually carried out in a solvent.

fused heterocyclic compound (P9) may be further purified, for example, by chromatography and recrystallization.

In this reaction, the conversion reaction of the present fused heterocyclic compound (P9) to the intermediate compound (P9') can easily proceed and the intermediate compound (P9') is sometimes formed during a synthesis of the present fused heterocyclic compound (P9).

(Process 21)

A present fused heterocyclic compound (P10-m0) (when $R^5$ represents a —S(O)$_m$R$^{10}$ group' and also m is 0) can be prepared by reacting a present fused heterocyclic compound (P9) or a disulfide compound thereof, that is, an intermediate compound (P9') with a compound (M13).

The present fused heterocyclic compound (P10-m0) (when m is 0) can be oxidized to afford the present fused heterocyclic compound (P10) (when $R^5$ represents a —S(O)$_m$ R$^{10}$ group' and also m is 1 or 2).

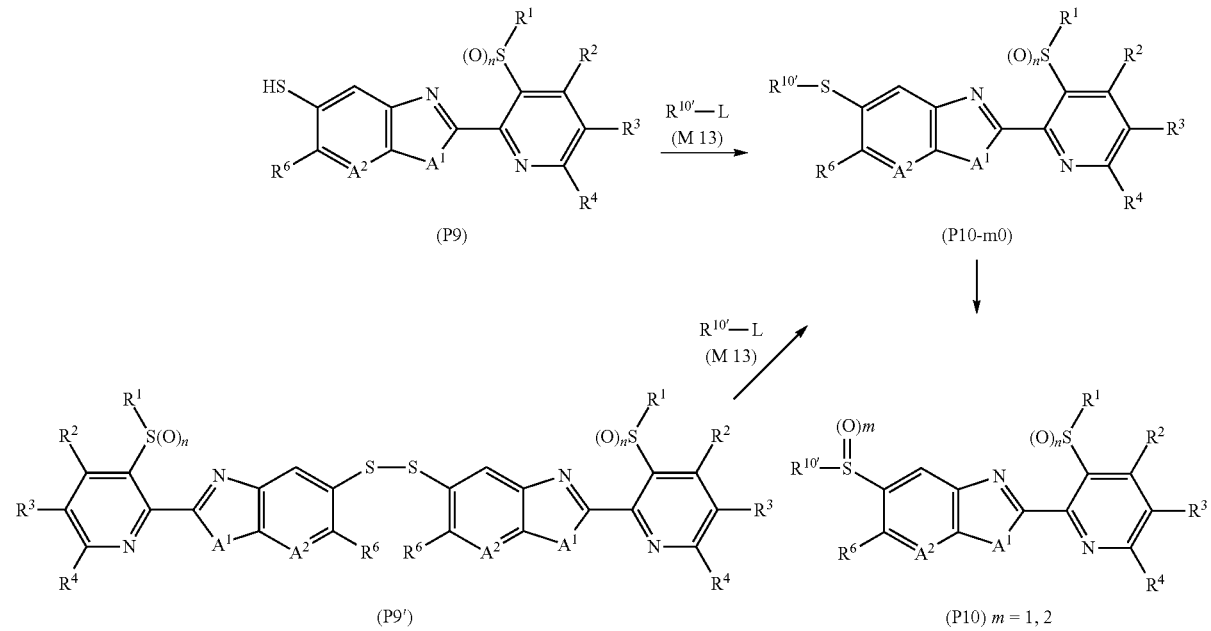

Examples of the solvent to be used in the reaction include ethers such as THF, ethyleneglycol dimethyl ether, methyl tert-butyl ether and 1,4-dioxane; alcohols such as methanol and ethanol; water; and mixed solvents thereof.

Examples of the base to be used include alkali metal hydroxides such as sodium hydroxide and potassium hydroxide.

In the reaction, the base is used usually within a range of 1 to 10 molar ratio(s) as opposed to 1 mole of the intermediate compound (P9-1).

The reaction temperature is usually within a range of 0 to 120° C. The reaction period of the reaction is usually within a range of 0.1 to 24 hours.

When the reaction is completed, the reaction solutions were acidified, the resulting mixtures are extracted with organic solvent(s), and the resulting organic layers are worked up (for example, drying and concentration) to isolate the present fused heterocyclic compound (P9). The present

[wherein, $R^{10'}$ represents any group of $R^{10}$ defined in formula (1) other than a hydrogen atom, L represents a leaving group such as a chlorine atom, a bromine atom, an iodine atom, a trifluoromethanesulfonyloxy group and a methanesulfonyloxy group, and each other symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include an alkali metal or alkaline-earth metal hydrides such as sodium hydride, potassium hydride and calcium hydride; and inorganic bases such as sodium carbonate, potassium carbonate; and organic bases such as triethylamine.

In the case where the intermediate compound (P9') being disulfide compound is used, the reaction is usually carried out in the presence of a reducing agent.

Examples of the reducing agent to be used in the reaction include hydroxymethanesulfinic acid sodium salt (Trade name: Rongalite).

In the reaction, the compound (M13) is usually used within a range of 1 to 10 molar ratio(s), and the base is usually used within a range of 1 to 10 molar ratio(s), as opposed to 1 mole of the present fused heterocyclic compound (P9).

Also, in the case where the intermediate compound (P9') being disulfide compound is used, the compound (M13) is used usually within a range of 2 to 10 molar ratio(s), the base is used usually within a range of 2 to 10 molar ratio(s), and the reducing agent is used usually within a range of 1 to 5 molar ratio(s), as opposed to 1 mole of the intermediate compound (P9').

The reaction temperature is usually within a range of 0 to 100° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the present fused heterocyclic compound (P10-m0) (m is 0). The isolated present fused heterocyclic compound (P10-m0) (m is 0) may be further purified, for example, by chromatography and recrystallization.

Also, among the present fused heterocyclic compound (P10-m0) (when m is 0), the intermediate compound (P9') (when $R^{10'}$ represents a C1-C6 perfluoroalkyl group) can be prepared by reacting the intermediate compound (P9'), a perfluoroalkyl iodide and a reducing agent. This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the reducing agent to be used in the reaction include tetrakis(dimethylamino)ethylene.

Examples of the perfluoroalkyl iodide include trifluoroiodomethane, iodopentafluoroethane and heptafluoro-2-iodopropane.

In the reaction, the perfluoroalkyl iodide is used usually within a range of 2 to 10 molar ratio(s), and the reducing agent is used usually within a range of 1 to 5 molar ratio(s), as opposed to 1 mole of the intermediate compound (P9').

The reaction temperature is usually within a range of −80 to 50° C. The reaction period of the reaction is usually within a range of 0.1 to 24 hours.

When the reaction is completed, the resulting mixtures are extracted with organic solvent(s), and the resulting organic layers are worked up (for example, drying and concentration) to isolate the present fused heterocyclic compound (P10-m0) (when m is 0). The isolated present fused heterocyclic compound (P10-m0) (when m is 0) may be further purified, for example, by chromatography and recrystallization.

Among the present fused heterocyclic compound (P10), the present fused heterocyclic compound wherein m is 1 or 2 can be prepared by reacting the present fused heterocyclic compound (P10-m0) (when m is 0) with an oxidizing agent.

This reaction is usually carried out in a solvent.

Examples of the solvent to be used in the reaction include aliphatic hydrogenated hydrocarbons such as dichloromethane and chloroform; alcohols such as methanol and ethanol; carboxylic acids such as acetic acid; water; and mixed solvents thereof.

Examples of the oxidizing agent to be used include m-chloroperoxybenzoic acid or hydrogen peroxide.

The reaction may be also carried out, if necessary, in the presence of a catalyst.

Examples of the catalyst to be used include sodium tungstate.

In the reaction, the oxidizing agent is used usually within a range of 1 to 5 molar ratio(s), and the catalyst is used usually within a range of 0.01 to 0.5 molar ratio(s), as opposed to 1 mole of the present fused heterocyclic compound (P10-m0) (when m is 0).

In the preparation of the compound wherein m is 1, the oxidizing agent is used usually within a range of 0.8 to 1.2 molar ratio(s), and the catalyst is used usually within a range of 0.05 to 0.2 molar ratio(s), as opposed to 1 mole of the present fused heterocyclic compound (P10-m0) when (m is 0). In the preparation of the compound wherein m is 2, the oxidizing agent is used usually within a range of 1.8 to 5 molar ratio(s), and the catalyst is used usually within a range of 0.05 to 0.2 molar ratio(s), as opposed to 1 mole of the present fused heterocyclic compound (P10-m0) (when m is 0).

The reaction temperature is usually within a range of −20 to 120° C. The reaction period of the reaction is usually within a range of 0.1 to 12 hours.

When the reaction is completed, the resulting mixtures are extracted with organic solvent(s), and if necessary, the resulting organic layers are worked up (for example, washing with an aqueous solution of the reducing agent (for example, sodium sulfite, sodium thiosulfate) and/or an aqueous solution of the base (for example, sodium hydrogen carbonate), drying and concentration) to isolate the present fused heterocyclic compound (P10) (when m is 1 or 2). The isolated present fused heterocyclic compound (P10) (when m is 1 or 2) may be further purified, for example, by chromatography and recrystallization.

(Process 22)

A present fused heterocyclic compound (P11) (when $R^5$ represents —OH) can be prepared via an intermediate compound (P11') from the present fused heterocyclic compound (P4).

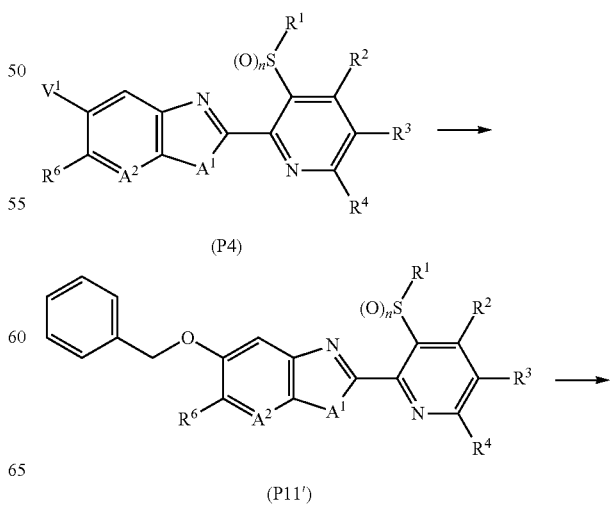

-continued

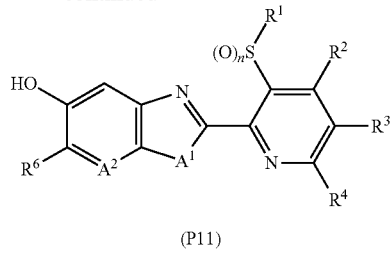

(P11)

[wherein, $V^1$ represents a halogen atom and each other symbol is the same as defined in the formula (1)]

The intermediate compound (P11') can be prepared by reacting the present fused heterocyclic compound (P4) with benzyl alcohol in the presence of a base.

The reaction is usually carried out in the presence of a solvent or by using benzyl alcohol as solvent.

Examples of the solvent to be used in the reaction include aromatic hydrocarbons such as toluene and xylene; aprotic polar solvents such as DMF, NMP and DMSO; and mixed solvents thereof. The reaction may be carried out, if necessary, in the presence of a catalyst. Examples of the catalyst to be used include copper halides such as copper chloride(I), copper bromide(I) and copper iodide(I).

The reaction may be also carried out, if necessary, in the presence of a ligand.

Examples of the ligand to be used in the reaction include acetyl acetone, salen and phenanthroline.

The reaction is usually carried out in the presence of a base.

Examples of the base to be used include inorganic bases such as potassium carbonate, cesium carbonate and tripotassium phosphate.

In the reaction, the benzyl alcohol is used usually within a range of 1 to 10 molar ratio(s), the catalyst is used usually within a range of 0.1 to 5 molar ratio(s), the ligand is used usually within a range of 0.1 to 5 molar ratio(s), and the base is used usually within a range of 1 to 2 molar ratio(s), as opposed to 1 mole of the present fused heterocyclic compound (P4).

The reaction temperature is usually within a range of 50 to 200° C. The reaction period of the reaction is usually within a range of 0.5 to 24 hours.

When the reaction is completed, the resulting mixtures are extracted with organic solvent(s), and the resulting organic layers are worked up (for example, drying and concentration) to isolate the intermediate compound (P11'). The isolated intermediate compound (P11') may be further purified, for example, by chromatography and recrystallization.

In the reaction, $V^1$ represents preferably a bromine atom and an iodine atom.

The present fused heterocyclic compound (P11) can be prepared by reacting the intermediate compound (P11') with hydrogen gas in the presence of a catalyst for hydrogenation.

The reaction is carried out under hydrogen atmosphere of usually 1 to 100 atmospheric pressure(s) and usually in the presence of a solvent.

Examples of the solvent to be used in the reaction include ethers such as THF, ethyleneglycol dimethyl ether, methyl tert-butyl ether and 1,4-dioxane; esters such as ethyl acetate and butyl acetate; alcohols such as methanol and ethanol; water; and mixed solvents thereof.

Examples of the catalyst for hydrogenation to be used in the reaction include transition metal compounds such as palladium-carbon, palladium hydroxide, raney nickel and platinum oxide.

In the reaction, the hydrogen gas is used usually within a range of 3 molar ratios, the catalysts for hydrogenation is used usually within a range of 0.001 to 0.5 molar ratio(s), as opposed to 1 mole of the intermediate compound (P11').

The reaction may be also carried out, if necessary, in the presence of an acid or a base and the others.

Examples of the acids to be used in the reaction include organic acids such as acetic acid and inorganic acids such as hydrochloric acid, and examples of the base to be used include tertiary amines such as triethylamine and metal oxide such as magnesium oxide.

The reaction temperature is usually within a range of −20 to 100° C. The reaction period of the reaction is usually within a range of 0.1 to 24 hours.

When the reaction is completed, the reaction mixtures are filtered and, if necessary, are extracted with organic solvent(s), and the resulting organic layers are worked up (for example, drying and concentration) to isolate the present fused heterocyclic compound (P11). The isolated present fused heterocyclic compound (P11) may be further purified, for example, by chromatography and recrystallization.

(Process 23)

A present fused heterocyclic compound (P12) (when $R^5$ represents a —$OR^{10}$ group' in the formula (1)) can be prepared by reacting the present fused heterocyclic compound (P11) with the compound (M13).

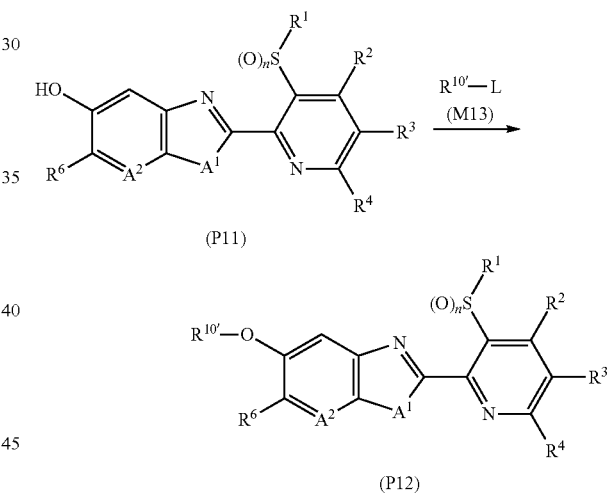

[wherein, $R^{10'}$ represents any group of $R^{10}$ defined in the formula (1) other than a hydrogen atom, and each other symbol is the same as defined in the formula (1)]

This reaction is usually carried out in the presence of a solvent.

Examples of the solvent to be used in the reaction include ethers such as THF, ethyleneglycol dimethyl ether, methyl tert-butyl ether and 1,4-dioxane; aromatic hydrocarbons such as toluene and xylene; nitriles such as acetonitrile; aprotic polar solvents such as DMF, NMP and DMSO; and mixed solvents thereof.

Examples of the base to be used include inorganic bases including an alkali metal or alkaline-earth metal hydrides such as sodium hydride, potassium hydride and calcium hydride; and an alkali metal or alkaline-earth metal carbonates such as sodium carbonate and potassium carbonate; and organic bases such as triethylamine.

In the reaction, the compound (M13) is used usually within a range of 1 to 10 molar ratio(s) and the base is used usually within a range of 1 to 10 molar ratio(s), as opposed to 1 mole of the present fused heterocyclic compound (P11).

The reaction temperature is usually within a range of 0 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present fused heterocyclic compound (P12). The isolated present fused heterocyclic compound (P12) may be further purified, for example, by chromatography and recrystallization.

Also, among the present fused heterocyclic compound (P12), the present fused heterocyclic compound (P12) (when $R^{10'}$ represents a trifluoromethyl group) can be carried out according to the below-mentioned process.

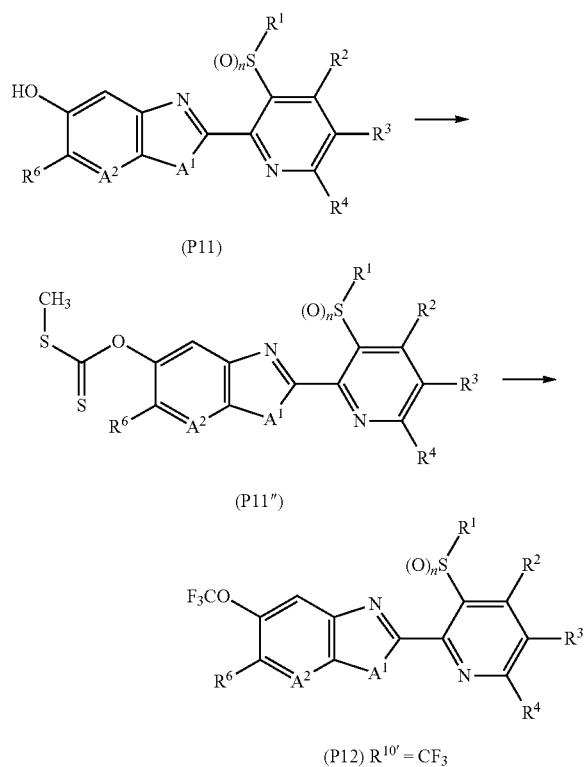

(P11)

(P11″)

(P12) $R^{10'} = CF_3$

[wherein, each symbol is the same as defined in the formula (1)]

The intermediate compound (P11″) can be prepared by reacting the present fused heterocyclic compound (P11) with a base, carbon disulfide and a methylating agent.

The reaction is carried out in the presence of a solvent.

Examples of the solvent to be used in the reaction include aprotic polar solvents such as DMF, NMP and DMSO.

Examples of the base to be used include alkali metal hydrides such as sodium hydride.

Examples of the methylating agent to be used in the reaction include methyl iodide.

In the reaction, the base is used usually within a range of 1 to 2 molar ratio(s), the carbon disulfide is used usually within a range of 1 to 10 molar ratio(s), and the methylating agent is used usually within a range of 1 to 10 molar ratio(s), as opposed to 1 mole of the present fused heterocyclic compound (P11).

The reaction temperature is usually within a range of 0 to 100° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the present fused heterocyclic compound (P11″). The isolated present fused heterocyclic compound (P11″) may be further purified, for example, by chromatography and recrystallization.

Among the present fused heterocyclic compound (P12), the present fused heterocyclic compound (P12) (when $R^{10'}$ represents a trifluoroethyl group) can be prepared by reacting the intermediate compound (P11″) with a fluorinating agent in the presence of a base.

The reaction is usually carried out in the presence of a solvent.

Examples of the solvent to be used in the reaction include halogenated hydrocarbons such as dichloromethane, chloroform, carbon tetrachloride and 1,2-dichloroethane.

The reaction is carried out in the presence of a base and a fluorinating agent.

Examples of the base to be used include 1,3-dibromo-5, 5-dimethylhydantoin.

Examples of the fluorinating agent to be used in the reaction include tetra-n-butylammonium fluoride and hydrogen fluoride pyridine complex.

In the reaction, the base is used usually within a range of 1 to 10 molar ratio(s), and the fluorinating agent is used usually within a range of 1 to 10 molar ratio(s), as opposed to 1 mole of the intermediate compound (P11″).

The reaction temperature is usually within a range of −80 to 50° C. The reaction period of the reaction is usually within a range of 0.5 to 24 hours.

When the reaction is completed, the reaction mixtures are extracted with organic solvent(s), and the resulting organic layers are worked up (for example, drying and concentration) to isolate the present fused heterocyclic compound (P12) (when $R^{10'}$ represents a trifluoromethyl group). The isolated present fused heterocyclic compound (P12) (when $R^{10'}$ represents a trifluoromethyl group) may be further purified, for example, by chromatography and recrystallization.

(Process 24)

Among the present fused heterocyclic compounds and the above-mentioned intermediate compounds, a reaction between the compounds that includes a nitrogen-containing heterocyclic part having lone pair electrons on nitrogen atom and an oxidizing agent may optionally afford N-oxide compounds having the oxidized nitrogen atom.

Examples of the nitrogen-containing heterocyclic part include a pyridine ring.

The reaction may be carried out according to the well-known method, and typically, may be carried out by using an oxidizing agent such as m-chloroperoxybenzoic acid and hydrogen peroxide in solvent(s) including halogenated hydrocarbons such as dichloromethane, chloroform and chlorobenzene; alcohols such as methanol and ethanol; carboxylic acids such as acetic acid; water; and mixed solvents thereof.

The present carboxamide compound is the compound described in, for example, WO 86/02641 pamphlet and WO 92/12970 pamphlet, and can be prepared according to the method described therein.

Specific examples of the present carboxamide compound include the following.

a carboxamide compound represented by the following formula (2a):

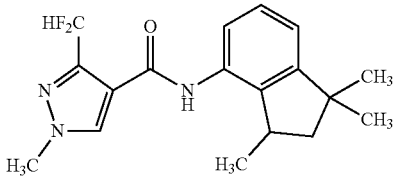

(2a)

(hereinafter, referred to as "Present carboxamide compound (2a)");

a carboxamide compound represented by the following formula (2b):

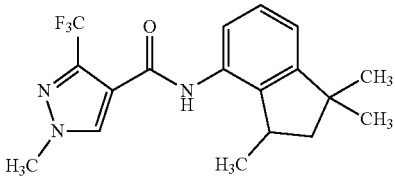

(2b)

(hereinafter, referred to as "Present carboxamide compound (2b)");

a carboxamide compound represented by the following formula (2c):

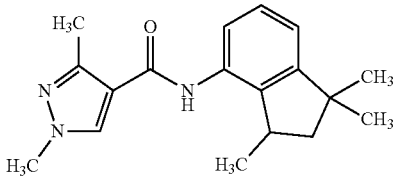

(2c)

(hereinafter, referred to as "Present carboxamide compound (2c)");

a carboxamide compound represented by the following formula (2d):

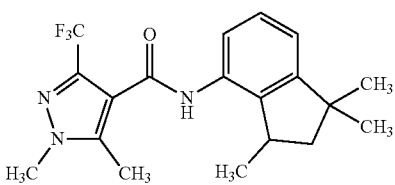

(2d)

(hereinafter, referred to as "Present carboxamide compound (2d)"); and a carboxamide compound represented by the following formula (2e):

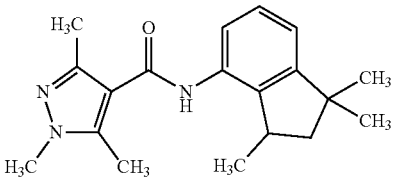

(2e)

(hereinafter, referred to as "Present carboxamide compound (2e)").

Although the pest-controlling composition of the present invention may be a mere mixture of the present fused heterocyclic compound and the present carboxamide compound, the present composition is usually prepared by mixing the present fused heterocyclic compound with the present carboxamide compound and an inert active carrier, and if necessary, adding surfactants and other auxiliary agents for formulation, to formulate into oil solutions, emulsifiable concentrates, flowables, wettable powders, water dispersible granules, dust formulations, granules and the others.

Also, the above-formulated pest-controlling composition may be used as itself or as the pest-controlling agents with adding other inert ingredients.

In the pest-controlling composition of the present invention, the total amounts of the present fused heterocyclic compounds and the present carboxamide compounds are usually within a range of 0.1 to 100% by weight, preferably within a range of 0.2% to 90% by weight, and more preferably within a range of 1 to 80% by weight.

Examples of the inert carrier to be used in the formulation include an inert solid carrier and an inert liquid carrier.

Examples of the above-mentioned inert solid carrier include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol);

acid amides (for example, N,N-dimethylformamide or N,N-dimethylacetamide); halogenated hydrocarbons (for example, dichloromethane, trichloroethane or carbon tetrachloride); sulfoxides (for example, dimethyl sulfoxide); propylene carbonate; and vegetable oils (for example, soybean oil or cottonseed oil).

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

In the pest-controlling composition of the present invention, the content ratio of the present fused heterocyclic compound to the present carboxamide compound is not specifically limited thereto, and include, for example, usually within a range of 1 to 1,000,000 parts by weight of the present carboxamide compound, and preferably within a range of 2 to 10000 parts by weight, as opposed to 1,000 parts by weight of the present fused heterocyclic compound. That is, the content ratio of the present fused heterocyclic compound to the present carboxamide compound is usually within a range of 1,000:1 to 1:1,000 by weight ratio, and preferably within a range of 500:1 to 1:10.

An effective amount of the pest-controlling composition of the present invention can be applied to plants or soils where the plants are cultivated so as to control the pests. Also, a preapplication treatment into plant seeds or bulbs can be also controlled harmful arthropods.

Herein, when the pest-controlling composition of the present invention is applied to plants, an effective amount of the pest-controlling composition of the present invention is applied to plants and/or places where the plants grow, plant seeds or bulbs.

Typical examples of an application method of the pest controlling composition of the present invention include an application to stem and leaf, flower organ or ear of plants (for example, foliage application), an application to nursery (for example, in nursery boxes), an application to the places or soils where plants are cultivated before or after planting, an application to seeds (for example, seed disinfection, seed soaking and seed coating) and an application to bulbs (for example, seed potatoes).

Herein, the plant seeds mean plant seeds in a state before seeding into soils or places where plants are cultivated, and the bulbs means scaly bulbs, solid bulb, root stocks and rhizophore of plants in a state of before planting into soils or places where plants are cultivated.

The pests on which a composition for controlling pests of the present invention has a control efficacy include, for example, harmful insects and harmful mites. The specifical examples are follows:

Hemiptera:
Delphacidae (for example, *Laodelphax striatellus, Nilaparvata lugens*, or *Sogatella furcifera*),
Deltocephalidae (for example, *Nephotettix cincticeps, Nephotettix virescens*, or *Empoasca onukii*),
Aphididae (for example, *Aphis gossypii, Myzus persicae, Brevicoryne brassicae, Aphis spiraecola, Macrosiphum euphorbiae, Aulacorthum solani, Rhopalosiphum padi, Toxoptera citricidus*, or *Hyalopterus pruni*),
Pentatomidae (for example, *Nezara antennata, Riptortus clavetus, Leptocorisa chinensis, Eysarcoris parvus*, or *Halyomorpha mista*),
Aleyrodidae (for example, *Trialeurodes vaporariorum, Bemisia tabaci, Dialeurodes citri*, or *Aleurocanthus spiniferus*).

Lepidoptera:
Pyralidae (for example, *Chilo suppressalis, Tryporyza incertulas, Cnaphalocrocis medinalis, Notarcha derogata, Plodia interpunctella, Ostrinia furnacalis, Hellula undalis*, or *Pediasia teterrellus*),
Noctuidae (for example, *Spodoptera litura, Spodoptera exigua, Mythimna separata, Mamestra brassicae, Agrotis ipsilon, Plusia nigrisigna, Trichoplusia* spp., *Heliothis* spp., or *Helicoverpa* spp.),
Pieridae (for example, *Pieris rapae*),
Tortricidae (for example, *Grapholita molesta, Leguminivora glycinivorella, Matsumuraeses azukivora, Adoxophyes orana fasciata, Adoxophyes honmai., Homona magnanima, Archips fuscocupreanus*, or *Cydia pomonella*).
Gracillariidae (for example, *Caloptilia theivora*, or *Phyllonorycter ringoneella*),
Carposinidae (for example, *Carposina niponensis*),
Lyonetiidae (for example, *Lyonetia* spp.),
Lymantriidae (for example, *Lymantria* spp., or *Euproctis* spp.),
Yponomeutidae (for example, *Plutella xylostella*),
Gelechiidae (for example, *Pectinophora gossypiella*, or *Phthorimaea operculella*);
Arctiidae (for example, *Hyphantria cunea*); and
*Tinea translucens.*

Thysanoptera: *Frankliniella occidentalis, Thrips palmi, Scirtothrips dorsalis, Thrips tabaci, Frankliniella intonsa*, and the others.

Diptera:
Anthomyiidae (for example, *Delia platura*, or *Delia antiqua*);
Agromyzidae (for example, *Agromyza oryzae, Hydrellia griseola, Liriomyza sativae, Liriomyza trifolii*, or *Chromatomyia horticola*);
Chloropidae (for example, *Chlorops oryzae*);
Tephritidae (for example, *Dacus cucurbitae*, or *Ceratitis capitata*);
Drosophilidae.

Coleoptera:
Corn root worms (*Diabrotica* spp.) (for example, *Diabrotica virgifera virgifera*, or *Diabrotica undecimpunctata howardi*);
Scarabaeidae (for example, *Anomala cuprea, Anomala rufocuprea*, or *Popillia japonica*);
Curculionidae (for example, *Sitophilus zeamais, Lissorhoptrus oryzophilus, Echinocnemus squameus, Anthonomus grandis*, or *Sphenophorus venatus*);
Tenebrionidae (for example, *Tenebrio molitor*, or *Tribolium castaneum*);
Chrysomelidae (for example, *Oulema oryzae, Aulacophora femoralis, Phyllotreta striolata*, or *Leptinotarsa decemlineata*);
Epilachna (for example, *Epilachna vigintioctopunctata*);
Scolytidae (for example, *Lyctus brunneus*, or *Tomicus piniperda*);
Bostrichidae;
Ptinidae;

Cerambycidae (for example, *Anoplophora malasiaca*);
Elateridae (*Agriotes* spp.); and
*Paederus fuscipes*.

When a composition for controlling pests of the present invention is used, the application dose as an amount of the present fused heterocyclic compound is usually within a range of 1 to 10000 g per 10000 m$^2$.

The emulsifiable concentrate, the wettable powder, or the flowable formulation etc. of a composition for controlling pests of the present invention is usually applied by diluting it with water in such a way that a concentration of the active ingredient is within a range of 0.01 to 10000 ppm, and then sparging it.

The granular formulation, or the dust formulation etc., is usually applied as itself without diluting it.

These formulations or a water dilution thereof can directly be sparged to pests or plants such as crops to be protected from pests, and also can be used to treat the soil of crop land in order to control pests which live there.

A composition for controlling pests of the present invention can be used in agricultural lands where the following "Plants" are cultivated.

Crops:
corn, rice, wheat, barley, rye, oat, sorghum, cotton, soybean, peanut, buckwheat, beet, colza, sunflower, sugar cane, tobacco, and the others;

Vegetables:
solanaceous vegetables (for example, eggplant, tomato, pimento, pepper or potato),
cucurbitaceous vegetables (for example, cucumber, pumpkin, zucchini, water melon or melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke or lettuce),
liliaceous vegetables (for example, green onion, onion, garlic or asparagus),
ammiaceous vegetables (for example, carrot, parsley, celery or parsnip),
chenopodiaceous vegetables (for example, spinach or Swiss chard),
lamiaceous vegetables (for example, *Perilla frutescens*, mint or basil),
strawberry, sweet potato, *Dioscorea japonica*, *colocasia* or the others;

Fruits:
pomaceous fruits (for example, apple, pear, Japanese pear, Chinese quince or quince),
stone fleshy fruits (for example, peach, plum, nectarine, *Prunus mume*, cherry fruit, apricot or prune),
citrus fruits (for example, *Citrus unshiu*, orange, lemon, lime or grapefruit),
nuts (for example, chestnut, walnuts, hazelnuts, almond, pistachio, cashew nuts or macadamia nuts),
berry fruits (for example, blueberry, cranberry, blackberry or raspberry),
grape, kaki persimmon, olive, Japanese plum, banana, coffee, date palm, coconuts, oil palm and the others;

Trees other than fruit trees:
tea, mulberry,
flowering plant (for example, dwarf azalea, *camellia*, *hydrangea*, sasanqua, *Illicium anisatum*, cherry trees, tulip tree, crape myrtle or fragrant olive),
roadside trees (for example, ash, birch, dogwood, *Eucalyptus*, *Ginkgo biloba*, lilac, maple, *Quercus*, poplar, Judas tree, *Liquidambar formosana*, plane tree, *zelkova*, Japanese arborvitae, fir wood, hemlock, juniper, *Pinus*, *Picea*, *Taxus cuspidate*, elm or Japanese horse chestnut), Sweet *viburnum*, *Podocarpus macrophyllus*, Japanese cedar, Japanese cypress, croton, Japanese spindletree and *Photinia glabra*;

Lawn:
sods (for example, *Zoysia japonica*, *Zoysia matrella*), bermudagrasses (for example, *Cynodon dactylon*),
bent glasses (for example, *Agrostis gigantea*, *Agrostis stolonifera*, *Agrostis capillaris*),
blueglasses (for example, *Poa pratensis*, *Poa trivialis*),
festucae (for example, *Festuca arundinacea* Schreb., *Festuca rubra* L. var. commutata Gaud., *Festuca rubra* L. var. genuina Hack),
ryegrassses (for example, *Lolium multiflorum* Lam, *Lolium perenne* L),
*Dactylis glomerata*, *Phleum pratense*;

Others:
flowers (for example, rose, carnation, *chrysanthemum*, *Eustoma*, *gypsophila*, *gerbera*, marigold, *salvia*, *petunia*, *verbena*, tulip, aster, gentian, lily, pansy, cyclamen, orchid, lily of the valley, lavender, stock, ornamental cabbage, *primula*, poinsettia, *gladiolus*, cattleya, daisy, cymbidium or *begonia*), and
ornamental foliage plants, and the others.

The above-mentioned "Plants" includes genetically modified plants.

EXAMPLES

The following Examples including Production example, Formulation examples, and Test examples serve to illustrate the present invention in more detail, which should not intend to limit the present invention.

Production Examples of the present fused heterocyclic compound are shown below.

The following Production examples of the present fused heterocyclic compound should not intend to limit the present fused heterocyclic compound.

Production Example 1 (1)

A mixture of N2-methyl-5-trifluoromethylpyridine-2,3-diamine 0.76 g, 3-fluoropyridine-2-carboaldehyde 0.50 g, sodium hydrogensulfite 0.50 g, and DMF 3 mL was stirred at 120° C. for 8 hr. To the reaction mixture allowed to cool was added saturated aqueous sodium bicarbonate, and the resulting mixture was extracted with ethyl acetate. The organic layer was washed with water, dried over anhydrous magnesium sulfate, and then concentrated under reduced pressure. The resultant residue was treated with silica gel column chromatography to give 2-(3-fluoropyridin-2-yl)-3-methyl-6-trifluoromethyl-3H-imidazo[4,5-b]pyridine (hereinafter referred to as Intermediate compound (M6-2)) 0.43 g.

Intermediate Compound (M6-2)

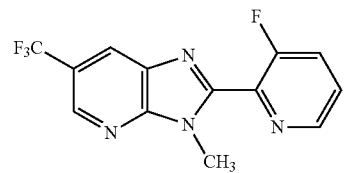 [SMILES: Cn1c(-c2ncccc2F)nc2cc(C(F)(F)F)cnc21]

$^1$H-NMR (CDCl$_3$) δ: 8.75 (1H, d), 8.66-8.63 (1H, m), 8.40 (1H, d), 7.73-7.67 (1H, m), 7.56-7.51 (1H, m), 4.16 (3H, s).

Production Example 1 (2)

To a mixture of Intermediate compound (M6-2) 1.23 g and DMF 3.5 mL at ice temperature was added sodium ethanethiolate 0.48 g, and the resulting mixture was stirred at RT for 2 hr. To the reaction mixture was added water, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-ethylsulfanylpyridin-2-yl)-3-methyl-6-trifluoromethyl-3H-imidazo[4,5-b]pyridine (hereinafter referred to as the present fused heterocyclic compound 1) 1.39 g.
Present Fused Heterocyclic Compound 1

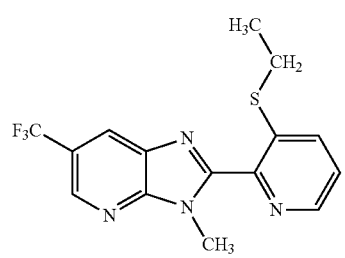

$^1$H-NMR (CDCl$_3$) δ: 8.73 (1H, d), 8.53 (1H, dd), 8.39 (1H, d), 7.80 (1H, dd), 7.40 (1H, dd), 4.04 (3H, s), 2.97 (2H, q), 1.35 (3H, t).

Production Examples 2, 3

To a mixture of 2-(3-ethylsulfanylpyridin-2-yl)-3-methyl-6-trifluoromethyl-3H-imidazo[4,5-b]pyridine (the present fused heterocyclic compound 1) 0.62 g and chloroform 10 mL at ice temperature was added m-chloroperbenzoic acid (65% or more purity) 0.79 g, and then the resulting mixture was stirred at RT for 5 hr. To the reaction mixture was added saturated aqueous sodium bicarbonate, and the reaction mixture was extracted with chloroform. The organic layer was washed with water, and dried over anhydrous magnesium sulfate, and then concentrated under reduced pressure. The resultant residue was treated with silica gel column chromatography to give 2-(3-ethylsulfinylpyridin-2-yl)-3-methyl-6-trifluoromethyl-3H-imidazo[4,5-b]pyridine (hereinafter referred to as the present fused heterocyclic compound 2) 87 mg, and 2-(3-ethylsulfonylpyridin-2-yl)-3-methyl-6-trifluoromethyl-3H-imidazo[4,5-b]pyridine (hereinafter referred to as the present fused heterocyclic compound 3) 0.49 g.
Present Fused Heterocyclic Compound 2

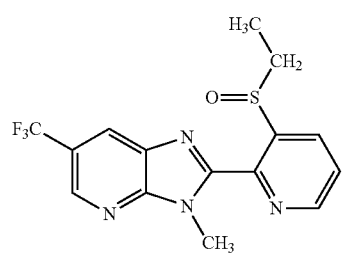

$^1$H-NMR (CDCl$_3$) δ: 8.85 (1H, dd), 8.77 (1H, s), 8.67 (1H, dd), 8.34 (1H, s), 7.69 (1H, dd), 4.36 (3H, s), 3.72-3.62 (1H, m), 3.14-3.04 (1H, m), 1.47 (3H, t).
Present Fused Heterocyclic Compound 3

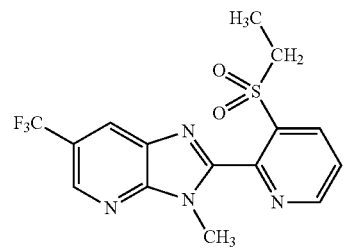

$^1$H-NMR (CDCl$_3$) δ: 9.01 (1H, dd), 8.76 (1H, s), 8.55 (1H, dd), 8.31 (1H, s), 7.74 (1H, dd), 3.88 (3H, s), 3.83 (2H, q), 1.37 (3H, t).

Production Example 4 (1)

A mixture of N2-methyl-5-trifluoromethylpyridine-2,3-diamine 0.70 g, 3-chloro-5-trifluoromethylpyridine-2-carboxylic acid 0.53 g, EDC hydrochloride 0.82 g, HOBt 42 mg, and pyridine 4.5 mL was stirred at 60° C. for 4 hr. To the reaction mixture allowed to cool was added water, and the resulting mixture was extracted with ethyl acetate. The organic layer was washed with water, and dried over anhydrous magnesium sulfate, and then concentrated under reduced pressure to give Intermediate compound (M20-3).
Intermediate Compound (M20-3)

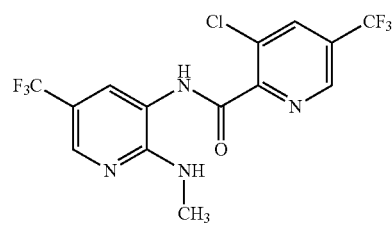 [SMILES: CNc1ncc(C(F)(F)F)cc1NC(=O)c1ncc(C(F)(F)F)cc1Cl]

A mixture of the total amount of the resulting Intermediate compound (M20-3), p-toluenesulfonic acid monohydrate 1.04 g, and N-methylpyrrolidinone 4 mL was stirred with heating at 150° C. for 2.5 hr. To the reaction mixture allowed to cool was added saturated aqueous sodium bicarbonate, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-chloro-5-trifluoromethylpyridin-2-yl)-3-methyl-6-trifluoromethyl-3H-imidazo[4,5-b]pyridine (hereinafter referred to as Intermediate compound (M6-3)) 0.71 g.
Intermediate Compound (M6-3)

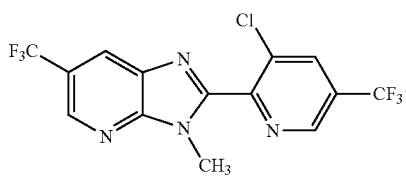 [SMILES: Cn1c(-c2ncc(C(F)(F)F)cc2Cl)nc2cc(C(F)(F)F)cnc21]

¹H-NMR (CDCl₃) δ: 8.96 (1H, d), 8.79 (1H, d), 8.42 (1H, d), 8.22 (1H, d), 4.02 (3H, s).

Production Example 4 (2)

To a mixture of 2-(3-chloro-5-trifluoromethylpyridin-2-yl)-3-methyl-6-trifluoromethyl-3H-imidazo[4,5-b]pyridine (Intermediate compound (M6-3)) 0.71 g and DMF 4 mL at ice temperature was added sodium ethanethiolate 0.24 g, and the resulting mixture was stirred at RT for 1 hr. To the reaction mixture was added water, and the resulting mixture was extracted with ethyl acetate. The organic layer was washed with water, dried over anhydrous magnesium sulfate, and then concentrated under reduced pressure to give 2-(3-ethylsulfanyl-5-trifluoromethylpyridin-2-yl)-3-methyl-6-trifluoromethyl-3H-imidazo[4,5-b]pyridine (hereinafter referred to as the present fused heterocyclic compound 4) 0.76 g.
Present Fused Heterocyclic Compound 4

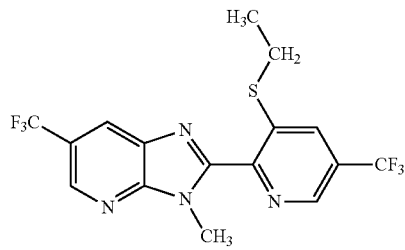 [SMILES: CCSc1cc(C(F)(F)F)cnc1-c1nc2cc(C(F)(F)F)cnc2n1C]

¹H-NMR (CDCl₃) δ: 8.77 (1H, d), 8.75 (1H, d), 8.43 (1H, d), 7.93 (1H, d), 4.11 (3H, s), 3.02 (2H, q), 1.40 (3H, t).

Production Example 5

To a mixture of 2-(3-ethylsulfanyl-5-trifluoromethylpyridin-2-yl)-3-methyl-6-trifluoromethyl-3H-imidazo[4,5-b]pyridine (the present fused heterocyclic compound 4) 0.61 g and chloroform 10 mL at ice temperature was added m-chloroperbenzoic acid (65% or more purity) 0.66 g, and then the mixture was stirred at RT for 10 hr. To the reaction mixture was added aqueous 10% sodium thiosulfate and saturated aqueous sodium bicarbonate, and the reaction mixture was extracted with chloroform. The organic layer was washed with water, dried over anhydrous magnesium sulfate, and then concentrated under reduced pressure to give 2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 5) 0.62 g.
Present Fused Heterocyclic Compound 5

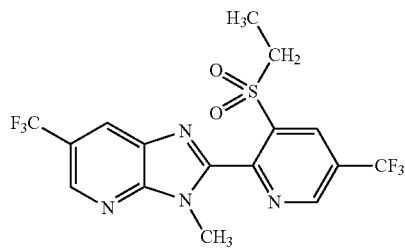 [SMILES: CCS(=O)(=O)c1cc(C(F)(F)F)cnc1-c1nc2cc(C(F)(F)F)cnc2n1C]

¹H-NMR (CDCl₃) δ: 9.25 (1H, d), 8.80 (1H, d), 8.79 (1H, d), 8.34 (1H, d), 3.96 (2H, q), 3.94 (3H, s), 1.42 (3H, t).

Production Example 6

A mixture of 2-(3-ethylsulfanyl-pyridin-2-yl)-6-iodo-3-methyl-3H-imidazo[4,5-b]pyridine 835 mg, sodium pentafluoropropionate 2.0 g, copper iodide 2.0 g, NMP 10 mL, and xylene 50 mL was stirred with heating at 150° C. for 8 hr. The mixture was allowed to cool to RT, and to the mixture was added aqueous 40% ammonia and saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-3-methyl-6-pentafluoroethyl-3H-imidazo[4,5-b]pyridine (hereinafter referred to as the present fused heterocyclic compound 6) 303 mg.
Present Fused Heterocyclic Compound 6

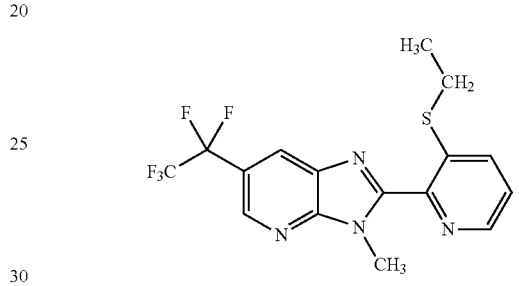

¹H-NMR (CDCl₃) δ: 8.69 (1H, d), 8.52 (1H, dd), 8.40 (1H, d), 7.80 (1H, dd), 7.39 (1H, dd), 4.06 (3H, s), 2.97 (2H, q), 1.34 (3H, t).

Production Examples 7, 8

To a mixture of 2-(3-ethylsulfanyl-pyridin-2-yl)-3-methyl-6-pentafluoroethyl-3H-imidazo[4,5-b]pyridine 254 mg and chloroform 10 mL at ice temperature was added m-chloroperbenzoic acid (65% or more purity) 266 mg. The mixture was allowed to warm to RT, and stirred for 0.5 hr. To the mixture was added saturated aqueous sodium bicarbonate and saturated aqueous sodium thiosulfate, and the mixture was extracted with chloroform. The organic layer was dried over magnesium sulfate, and then concentrated under reduced pressure. The resultant residue was treated with silica gel column chromatography to give 2-(3-ethanesulfinyl-pyridin-2-yl)-3-methyl-6-pentafluoroethyl-3H-imidazo[4,5-b]pyridine (hereinafter referred to as the present fused heterocyclic compound 7) 8 mg and 2-(3-ethanesulfonyl-pyridin-2-yl)-3-methyl-6-pentafluoroethyl-3H-imidazo[4,5-b]pyridine (hereinafter referred to as the present fused heterocyclic compound 8) 235 mg.
Present Fused Heterocyclic Compound 7

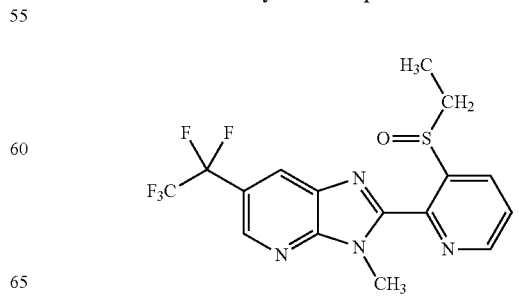

$^1$H-NMR (CDCl$_3$) δ: 8.85 (1H, dd), 8.72 (1H, d), 8.68 (1H, dd), 8.31 (1H, d), 7.69 (1H, dd), 4.36 (3H, s), 3.72-3.61 (1H, m), 3.17-3.06 (1H, m), 1.47 (3H, t).

Present Fused Heterocyclic Compound 8

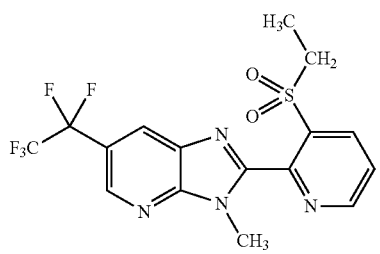

$^1$H-NMR (CDCl$_3$) δ: 9.00 (1H, dd), 8.72 (1H, d), 8.55 (1H, dd), 8.30 (1H, d), 7.73 (1H, dd), 3.89 (3H, s), 3.84 (2H, q), 1.37 (3H, t).

Production Example 9 (1)

To a mixture of 5-iodo-N2-methyl-pyridine-2,3-diamine 1.9 g and pyridine 6 mL was added EDC hydrochloride 1.28 g, HOBt 86 mg, and 3-chloro-pyridine-2-carboxylic acid 1.3 g, and the mixture was stirred at RT for 9 hr. To the reaction mixture was added water, and the precipitated powder was collected by filtration, and washed with chloroform to give 3-chloro-pyridine-2-carboxylic acid (5-iodo-2-methyl-amino-pyridin-3-yl)-amide (hereinafter referred to as Intermediate compound (M20-7)) 3.6 g.

Intermediate Compound (M20-7)

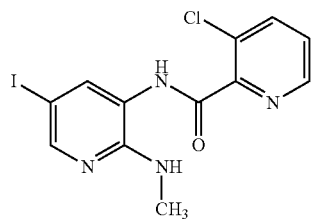 [SMILES: CNc1ncc(I)cc1NC(=O)c1ncccc1Cl]

$^1$H-NMR (DMSO-D$_6$) δ: 9.95 (1H, s), 8.65 (1H, d), 8.15-8.10 (2H, m), 8.00 (1H, d), 7.65 (1H, dd), 6.30 (1H, d), 2.81 (3H, d).

Production Example 9 (2)

A mixture of Intermediate compound (M20-7) 3.4 g, p-toluenesulfonic acid monohydrate 5.8 g, DMF 30 mL, and toluene 120 mL was stirred with heating at 130° C. for 12 hr. The mixture was allowed to cool to RT, and to the mixture was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-chloro-pyridin-2-yl)-6-iodo-3-methyl-3H-imidazo[4,5-b]pyridine (hereinafter referred to as Intermediate compound (M6-7)) 2.0 g.

Intermediate Compound (M6-7)

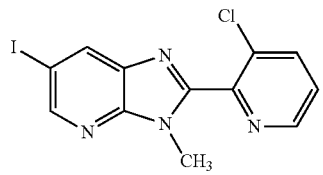 [SMILES: Cn1c(-c2ncccc2Cl)nc2cc(I)cnc21]

$^1$H-NMR (CDCl$_3$) δ: 8.70 (1H, d), 8.66-8.63 (1H, m), 8.47-8.44 (1H, m), 7.95 (1H, d), 7.45 (1H, dd), 3.90 (3H, s).

Production Example 9 (3)

A mixture of Intermediate compound (M6-7) 2.0 g, sodium ethanethiolate 888 mg, and DMF 45 mL was stirred with heating at 50° C. for 12 hr. The mixture was allowed to cool to RT, and to the mixture was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-6-iodo-3-methyl-3H-imidazo[4,5-b]pyridine (hereinafter referred to as the present fused heterocyclic compound 9) 1.0 g.

Present Fused Heterocyclic Compound 9

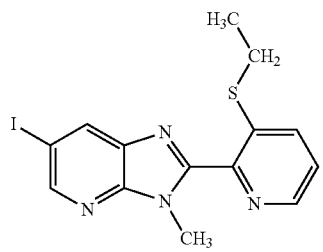

$^1$H-NMR (CDCl$_3$) δ: 8.61 (1H, d), 8.51 (1H, dd), 8.45 (1H, d), 7.76 (1H, dd), 7.37 (1H, dd), 3.96 (3H, s), 2.94 (2H, q), 1.33 (3H, t).

Production Example 10 (1)

A mixture of 3-amino-5-trifluoromethylpyridine-2-thiol 0.45 g, 3-chloro-5-trifluoromethylpyridine-2-carboxylic acid 0.55 g, EDC hydrochloride 0.67 g, HOBt 31 mg, and pyridine 4.5 mL was stirred at 60° C. for 4 hr. The reaction mixture was allowed to cool, and to the reaction mixture was added water, and the resulting mixture was extracted with ethyl acetate. The organic layer was washed with water, and dried over anhydrous magnesium sulfate, and then concentrated under reduced pressure to give Intermediate compound (M20-9).

Intermediate Compound (M20-9)

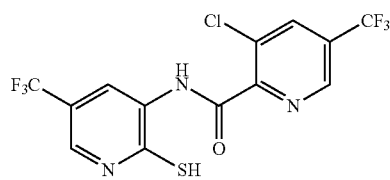 [SMILES: O=C(Nc1cc(C(F)(F)F)cnc1S)c1ncc(C(F)(F)F)cc1Cl]

A mixture of the total amount of the resulting Intermediate compound (M20-9), p-toluenesulfonic acid monohydrate 1.04 g, and N-methylpyrrolidinone 3.5 mL was stirred with heating at 150° C. for 2 hr. To the reaction mixture allowed to cool was added saturated aqueous sodium bicarbonate, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-chloro-5-trifluoromethylpyridin-2-yl)-6-(trifluoromethyl)thiazolo[5,4-b]pyridine (hereinafter referred to as Intermediate compound (M6-9)) 0.29 g.

Intermediate Compound (M6-9)

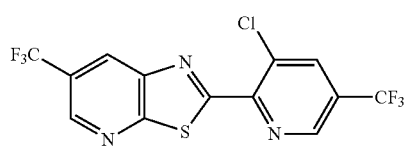 [SMILES: FC(F)(F)c1cnc(-c2nc3cc(C(F)(F)F)cnc3s2)c(Cl)c1]

$^1$H-NMR (CDCl$_3$) δ: 8.94 (1H, d), 8.90 (1H, d), 8.69 (1H, d), 8.19 (1H, d).

Production Example 10 (2)

2-(3-Ethylsulfanyl-5-trifluoromethylpyridin-2-yl)-6-(trifluoromethyl)thiazolo[5,4-b]pyridine (hereinafter referred to as the present fused heterocyclic compound 10) was prepared in a similar manner as described for the preparation of Production example 4 (2) by using Intermediate compound (M6-9) instead of 2-(3-chloro-5-trifluoromethylpyridin-2-yl)-3-methyl-6-trifluoromethyl-3H-imidazo[4,5-b]pyridine (Intermediate compound (M6-3)).

Present Fused Heterocyclic Compound 10

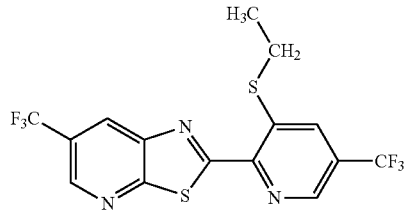 [SMILES: CCSc1cc(C(F)(F)F)cnc1-c1nc2cc(C(F)(F)F)cnc2s1]

$^1$H-NMR (CDCl$_3$) δ: 8.91 (1H, d), 8.70-8.67 (2H, m), 7.91 (1H, s), 3.09 (2H, q), 1.51 (3H, t).

Production Example 11

2-(3-Ethylsulfonyl-5-trifluoromethylpyridin-2-yl)-6-(trifluoromethyl)thiazolo[5,4-b]pyridine (hereinafter referred to as the present fused heterocyclic compound 11) was prepared in a similar manner as described for the preparation of Production example 5 by using 2-(3-ethylsulfanyl-5-trifluoromethylpyridin-2-yl)-6-(trifluoromethyl)thiazolo[5,4-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 11

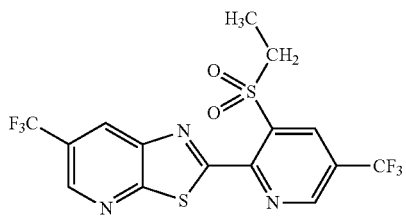 [SMILES: CCS(=O)(=O)c1cc(C(F)(F)F)cnc1-c1nc2cc(C(F)(F)F)cnc2s1]

$^1$H-NMR (CDCl$_3$) δ: 9.19 (1H, d), 8.98 (1H, d), 8.89 (1H, d), 8.61 (1H, d), 4.17 (2H, q), 1.49 (3H, t).

Production Example 12 (1)

A mixture of 3-amino-5-trifluoromethylpyridine-2-thiol 0.45 g, 3-chloropyridine-2-carboxylic acid 0.39 g, EDC hydrochloride 0.67 g, HOBt 31 mg, and pyridine 4 mL was stirred at RT for 12 hr. To the reaction mixture was added water, and the precipitated solid was collected by filtration. The resulting solid was washed with water, and n-hexane, and dried to give 3-chloropyridine-2-carboxylic acid (2-mercapto-5-trifluoromethylpyridin-3-yl)-amide (hereinafter referred to as Intermediate compound (M20-11)) 0.45 g.

Intermediate Compound (M20-11)

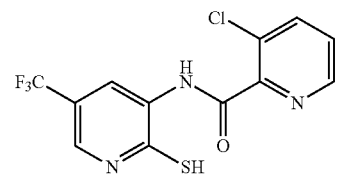 [SMILES: O=C(Nc1cc(C(F)(F)F)cnc1S)c1ncccc1Cl]

Production Example 12 (2)

A mixture of Intermediate compound (M20-11) 0.45 g, p-toluenesulfonic acid monohydrate 0.70 g, and NMP 4 mL was stirred at 150° C. for 2 hr. To the reaction mixture allowed to cool was added saturated aqueous sodium bicarbonate, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-chloropyridin-2-yl)-6-(trifluoromethyl)thiazolo[5,4-b]pyridine (hereinafter referred to as Intermediate compound (M6-11)) 0.47 g.

Intermediate Compound (M6-11)

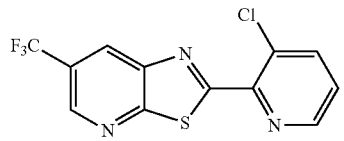 [SMILES: FC(F)(F)c1cnc2sc(-c3ncccc3Cl)nc2c1]

Production Example 12 (3)

2-(3-Ethylsulfanyl-2-yl)-6-(trifluoromethyl)thiazolo[5,4-b]pyridine (hereinafter referred to as the present fused heterocyclic compound 41) was prepared in a similar manner as described for the preparation of Production example 1 (2) by using Intermediate compound (M6-11) instead of 2-(3-fluoropyridin-2-yl)-3-methyl-6-trifluoromethyl-3H-imidazo[4,5-b]pyridine (Intermediate compound (M6-2)).
Present Fused Heterocyclic Compound 41

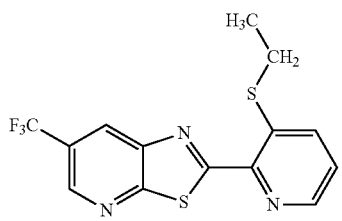 [SMILES: CCSc1cccnc1-c1nc2cc(C(F)(F)F)cnc2s1]

¹H-NMR (CDCl₃) δ: 8.87 (1H, d), 8.64 (1H, d), 8.48 (1H, dd), 7.76 (1H, dd), 7.37 (1H, dd), 3.06 (2H, q), 1.49 (3H, t).

Production Example 12 (4)

To a mixture of 2-(3-ethylsulfanyl-2-yl)-6-(trifluoromethyl)thiazolo[5,4-b]pyridine 0.36 g and chloroform 5 mL was added m-chloroperbenzoic acid (65% or more purity) 0.56 g, and the resulting mixture was stirred at RT for 12 hr. To the reaction mixture was added aqueous 10% sodium thiosulfate and saturated aqueous sodium bicarbonate, and the mixture was extracted with chloroform. The organic layer was washed with water, dried over anhydrous magnesium sulfate, and then concentrated under reduced pressure to give 2-(3-ethylsulfonyl-2-yl)-6-(trifluoromethyl)thiazolo[5,4-b]pyridine (hereinafter referred to as the present fused heterocyclic compound 12) 0.27 g and 2-(3-ethylsulfonyl-2-yl)-6-(trifluoromethyl)thiazolo[5,4-b]pyridine 4-oxide (hereinafter referred to as the present fused heterocyclic compound 22) 91 mg.
Present Fused Heterocyclic Compound 12

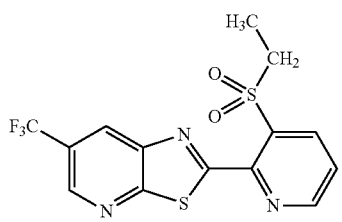 [SMILES: CCS(=O)(=O)c1cccnc1-c1nc2cc(C(F)(F)F)cnc2s1]

¹H-NMR (CDCl₃) δ: 8.98-8.93 (2H, m), 8.66 (1H, dd), 8.57 (1H, d), 7.69 (1H, dd), 4.13 (2H, q), 1.45 (3H, t).
Present Fused Heterocyclic Compound 22

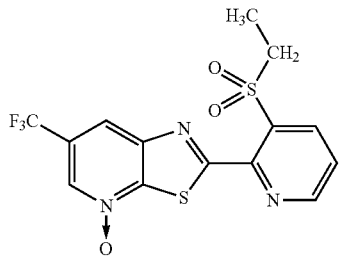 [SMILES: CCS(=O)(=O)c1cccnc1-c1nc2cc(C(F)(F)F)c[n+]([O-])c2s1]

¹H-NMR (CDCl₃) δ: 8.96 (1H, dd), 8.68 (1H, dd), 8.62 (1H, s), 8.20 (1H, s), 7.74 (1H, dd), 4.06 (2H, q), 1.44 (3H, t).

Production Example 13 (1)

A mixture of 2-(3-ethylsulfanyl-pyridin-2-yl)-6-iodo-3-methyl-3H-imidazo[4,5-b]pyridine 1.1 g, copper iodide 160 mg, sodium sulfide nonahydrate 2.7 g, and DMF 10 mL was stirred at 110° C. for 5 hr. To the reaction mixture was added water, and the resulting mixture was extracted with ethyl acetate. The organic layer was dried over sodium sulfate, and then concentrated under reduced pressure. The resultant residue was treated with silica gel column chromatography to give the compound having the formula:

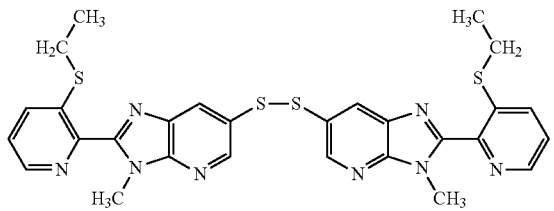 [SMILES: CCSc1cccnc1-c1nc2cc(SSc3cnc4c(c3)nc(-c3ncccc3SCC)n4C)cnc2n1C]

(hereinafter referred to as Intermediate compound (P9'-1)) 710 mg.
Intermediate Compound (P9'-1)

¹H-NMR (DMSO-D₆) δ: 8.56-8.55 (2H, m), 8.53-8.50 (2H, m), 8.38-8.36 (2H, m), 8.04 (2H, d), 7.61-7.56 (2H, m), 3.87 (6H, brs), 3.00 (4H, q), 1.23-1.16 (6H, m).

Production Example 13 (2)

A mixture of Intermediate compound (P9'-1) 710 mg and DMF 12 mL was cooled to −60° C., and to the mixture was added trifluoroiodomethane 10 g. To the mixture was added dropwise tetrakis(dimethylamino)ethylene 1.2 mL at −40° C. The mixture was allowed to warm to −10° C. and stirred at −10° C. for 5 hr. To the reaction mixture was added water, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-3-methyl-6-trifluoromethylsulfanyl-3H-imidazo[4,5-b]pyridine (hereinafter referred to as the present fused heterocyclic compound 13) 530 mg.
Present Fused Heterocyclic Compound 13

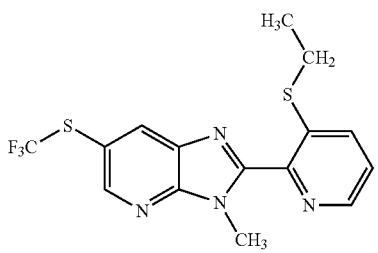 [SMILES: CCSc1cccnc1-c1nc2cc(SC(F)(F)F)cnc2n1C]

¹H-NMR (CDCl₃) δ: 8.67 (1H, d), 8.52 (1H, dd), 8.46 (1H, d), 7.79 (1H, dd), 7.39 (1H, dd), 4.03 (3H, s), 2.97 (2H, q), 1.36 (3H, t).

Production Examples 14, 15

A mixture of 2-(3-ethylsulfanyl-pyridin-2-yl)-3-methyl-6-trifluoromethylsulfanyl-3H-imidazo[4,5-b]pyridine (the present fused heterocyclic compound 13) 200 mg, m-chloroperbenzoic acid (65% or more purity) 230 mg, and chloroform 10 mL was stirred at ice temperature for 5 hr. To the reaction mixture was added saturated aqueous sodium bicarbonate, and the mixture was extracted with chloroform. The organic layer was dried over sodium sulfate, and then concentrated under reduced pressure. The resultant residue was treated with silica gel column chromatography to give 2-(3-ethylsulfinyl-pyridin-2-yl)-3-methyl-6-trifluoromethylsulfanyl-3H-imidazo[4,5-b]pyridine (hereinafter referred to as the present fused heterocyclic compound 14) 89 mg and 2-(3-ethylsulfonyl-pyridin-2-yl)-3-methyl-6-trifluoromethylsulfanyl-3H-imidazo[4,5-b]pyridine (hereinafter referred to as the present fused heterocyclic compound 15) 130 mg.

Present Fused Heterocyclic Compound 14

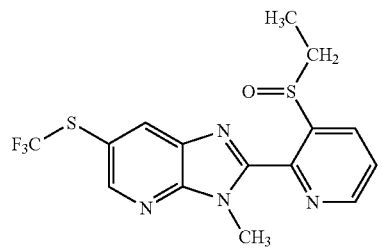 [SMILES: CCS(=O)c1cccnc1-c1nc2cc(SC(F)(F)F)cnc2n1C]

$^1$H-NMR (CDCl$_3$) δ: 8.87-8.83 (1H, m), 8.73-8.64 (2H, m), 8.41 (1H, d), 7.72-7.66 (1H, m), 4.34 (3H, s), 3.72-3.62 (1H, m), 3.17-3.05 (1H, m), 1.47 (3H, t).

Present Fused Heterocyclic Compound 15

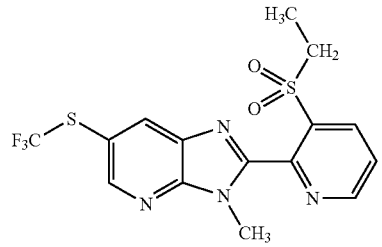 [SMILES: CCS(=O)(=O)c1cccnc1-c1nc2cc(SC(F)(F)F)cnc2n1C]

$^1$H-NMR (CDCl$_3$) δ: 9.01-8.98 (1H, m), 8.71 (1H, d), 8.55-8.52 (1H, m), 8.39 (1H, d), 7.72 (1H, dd), 3.90-3.81 (5H, m), 1.36 (3H, t).

Production Example 16

To a mixture of 2-(3-ethylsulfanyl-pyridin-2-yl)-3-methyl-6-trifluoromethylsulfanyl-3H-imidazo[4,5-b]pyridine (the present fused heterocyclic compound 13) 270 mg, sodium tungstate dihydrate 110 mg, and acetonitrile 5 mL was added aqueous 30% hydrogen peroxide 2 mL at 40° C. The mixture was heated to 80° C. and stirred for 24 hr. To the mixture was added saturated aqueous sodium thiosulfate, and then the resulting mixture was extracted with ethyl acetate. The organic layer was dried over sodium sulfate, and then concentrated under reduced pressure. The resultant residue was treated with silica gel column chromatography to give 2-(3-ethylsulfonyl-pyridin-2-yl)-3-methyl-6-trifluoromethylsulfonyl-3H-imidazo[4,5-b]pyridine (hereinafter referred to as the present fused heterocyclic compound 16) 280 mg.

Present Fused Heterocyclic Compound 16

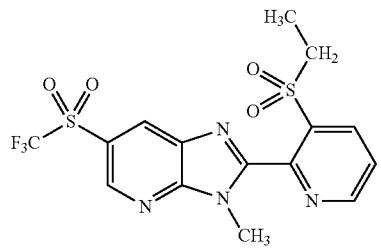 [SMILES: CCS(=O)(=O)c1cccnc1-c1nc2cc(S(=O)(=O)C(F)(F)F)cnc2n1C]

$^1$H-NMR (CDCl$_3$) δ: 9.08 (1H, d), 9.04 (1H, dd), 8.71 (1H, d), 8.57 (1H, dd), 7.79 (1H, dd), 3.93 (3H, s), 3.82 (2H, q), 1.38 (3H, t).

Production Example 17(1)

A mixture of N2-methyl-5-pentafluoroethyl-pyridine-2,3-diamine 590 mg, 3-chloro-5-trifluoromethyl-pyridine-2-carboxylic acid 560 mg, EDC hydrochloride 520 mg, HOBt 35 mg, pyridine 5 mL was stirred at RT for 5 hr. To the reaction mixture was added water, and the resulting mixture was extracted with ethyl acetate. The organic layer was dried over sodium sulfate, and then concentrated under reduced pressure to give Intermediate compound (M20-17).

Intermediate Compound (M20-17)

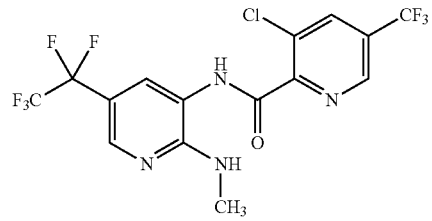 [SMILES: CNc1ncc(C(F)(F)C(F)(F)F)cc1NC(=O)c1ncc(C(F)(F)F)cc1Cl]

The resulting Intermediate compound (M20-17) was dissolved in a mixed solvent of DMF 7.5 mL and toluene 30 mL, and to the resulting mixture was added p-toluenesulfonic acid monohydrate 1.5 g. The mixture was stirred at 160° C. for 6 hr. The reaction mixture allowed to cool to RT, and to the reaction mixture was added saturated aqueous sodium bicarbonate, and then the mixture was extracted with t-butyl methyl ether. The organic layer was dried over sodium sulfate, and then concentrated under reduced pressure. The resultant residue was treated with silica gel column chromatography to give 2-(3-chloro-5-trifluoromethyl-pyridin-2-yl)-3-methyl-6-pentafluoroethyl-3H-imidazo[4,5-b]pyridine (hereinafter referred to as Intermediate compound (M6-17)) 540 mg.

Intermediate Compound (M6-17)

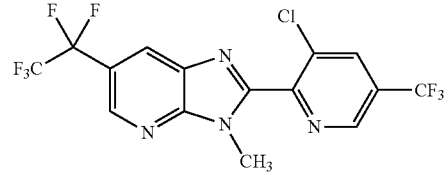 [SMILES: Cn1c(-c2ncc(C(F)(F)F)cc2Cl)nc2cc(C(F)(F)C(F)(F)F)cnc21]

¹H-NMR (CDCl₃) δ: 8.96 (1H, d), 8.74 (1H, d), 8.40 (1H, d), 8.23 (1H, d), 4.03 (3H, s).

Production Example 17(2)

2-(3-Ethylsulfanyl-5-trifluoromethyl-pyridin-2-yl)-3-methyl-6-pentafluoroethyl-3H-imidazo[4,5-b]pyridine (hereinafter referred to as the present fused heterocyclic compound 17) was prepared in a similar manner as described for the preparation of Production example 1 (2) by using Intermediate compound (M6-17) instead of 2-(3-fluoropyridin-2-yl)-3-methyl-6-trifluoromethyl-3H-imidazo[4,5-b]pyridine (Intermediate compound (M6-2)).

Present Fused Heterocyclic Compound 17

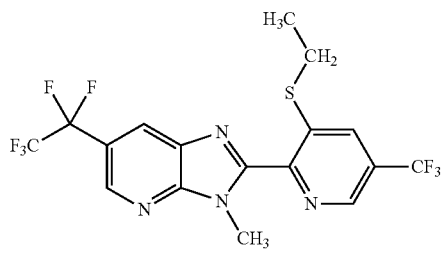 [SMILES: CCSc1cc(C(F)(F)F)cnc1-c1nc2cc(C(F)(F)C(F)(F)F)cnc2n1C]

¹H-NMR (CDCl₃) δ: 8.75 (1H, d), 8.71 (1H, d), 8.42 (1H, d), 7.93 (1H, d), 4.12 (3H, s), 3.03 (2H, q), 1.41 (3H, t).

Production Examples 18, 19

2-(3-Ethylsulfinyl-5-trifluoromethyl-pyridin-2-yl)-3-methyl-6-pentafluoroethyl-3H-imidazo[4,5-b]pyridine (hereinafter referred to as the present fused heterocyclic compound 18) and 2-(3-ethylsulfonyl-5-trifluoromethyl-pyridin-2-yl)-3-methyl-6-pentafluoroethyl-3H-imidazo[4,5-b]pyridine (hereinafter referred to as the present fused heterocyclic compound 19) was prepared in a similar manner as described for the preparation of Production examples 2, 3 by using 2-(3-ethylsulfanyl-5-trifluoromethyl-pyridin-2-yl)-3-methyl-6-pentafluoroethyl-3H-imidazo[4,5-b]pyridine instead of 2-(3-ethylsulfanylpyridin-2-yl)-3-methyl-6-trifluoromethyl-3H-imidazo[4,5-b]pyridine (the present fused heterocyclic compound 1).

Present Fused Heterocyclic Compound 18

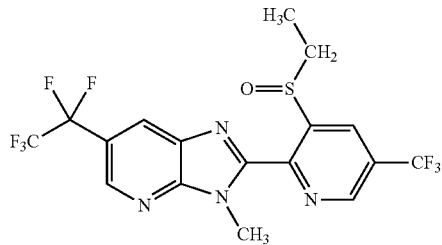 [SMILES: CCS(=O)c1cc(C(F)(F)F)cnc1-c1nc2cc(C(F)(F)C(F)(F)F)cnc2n1C]

¹H-NMR (CDCl₃) δ: 9.10 (1H, d), 8.94 (1H, d), 8.76 (1H, d), 8.36 (1H, d), 4.41 (3H, s), 3.76-3.66 (1H, m), 3.18-3.07 (1H, m), 1.49 (3H, t).

Present Fused Heterocyclic Compound 19

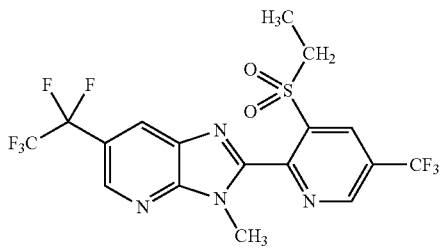 [SMILES: CCS(=O)(=O)c1cc(C(F)(F)F)cnc1-c1nc2cc(C(F)(F)C(F)(F)F)cnc2n1C]

¹H-NMR (CDCl₃) δ: 9.27 (1H, d), 8.80 (1H, d), 8.76 (1H, s), 8.34 (1H, s), 4.01-3.94 (5H, m), 1.41 (3H, t).

Production Example 20

To a mixture of 2-(3-ethylsulfonyl-pyridin-2-yl)-3-methyl-6-trifluoromethylsulfanyl-3H-imidazo[4,5-b]pyridine 500 mg and chloroform 10 mL at ice temperature was added m-chloroperbenzoic acid (65% or more purity) 429 mg, and the mixture was stirred at RT for 1 hr and at 50° C. for 2 hr. To the reaction mixture was added aqueous sodium thiosulfate and aqueous sodium bicarbonate, and the mixture was extracted with chloroform. The organic layer was dried over sodium sulfate, and then concentrated under reduced pressure. The resultant residue was treated with silica gel column chromatography to give 2-(3-ethylsulfonyl-pyridin-2-yl)-3-methyl-6-trifluoromethylsulfinyl-3H-imidazo[4,5-b]pyridine (hereinafter referred to as the present fused heterocyclic compound 20) 353 mg.

Present Fused Heterocyclic Compound 20

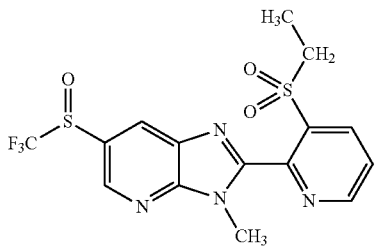 [SMILES: CCS(=O)(=O)c1cccnc1-c1nc2cc(S(=O)C(F)(F)F)cnc2n1C]

¹H-NMR (CDCl₃) δ: 9.02 (1H, dd), 8.77 (1H, d), 8.60-8.52 (2H, m), 7.75 (1H, dd), 3.91 (3H, s), 3.83 (2H, q), 1.38 (3H, t).

Production Example 21 (1)

To a mixture of 4-iodo-2-nitro-phenylamine 2.0 g, 60% sodium hydride (in oil) 330 mg, DMF 20 mL at ice temperature was added dropwise iodomethane 470 μL. The reaction mixture was allowed to warm to RT, and then stirred for 2 hr. To the reaction mixture was added water, and the resulting mixture was extracted with ethyl acetate. The organic layer was dried over sodium sulfate, and then concentrated under reduced pressure. The resultant residue was treated with silica gel column chromatography to give (4-iodo-2-nitro-phenyl)-methyl-amine 2.0 g.

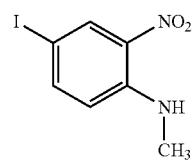

Production Example 21 (2)

A mixture of iron powder 1.7 g, acetic acid 2.2 mL, ethanol 80 mL, and water 25 mL was stirred at 70° C. To the reaction mixture was added dropwise a mixture of (4-iodo-2-nitro-phenyl)-methyl-amine 2.0 g and ethanol 20 mL. After adding dropwise, the mixture was stirred at 70° C. for 6 hr. The reaction mixture was filtered washing with THF. The resulting filtrate was concentrated under reduced pressure. To the resultant residue was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 4-iodo-N1-methyl-benzene-1,2-diamine 1.6 g.

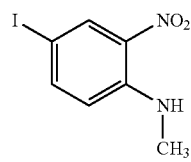

Production Example 21 (3)

A mixture of 4-iodo-N1-methyl-benzene-1,2-diamine 850 mg, 3-chloro-pyridine-2-carboxylic acid 590 mg, EDC hydrochloride 790 mg, HOBt 46 mg, and pyridine 10 mL at 100° C. for 12 hr was stirred. To the reaction mixture was added water, and the resulting mixture was extracted with ethyl acetate. The organic layer was dried over sodium sulfate, and then concentrated under reduced pressure. The resultant residue was treated with silica gel column chromatography to give 2-(3-chloro-pyridin-2-yl)-5-iodo-1-methyl-1H-benzimidazole (hereinafter referred to as Intermediate compound (M6-21)) 930 mg.

Intermediate Compound (M6-21)

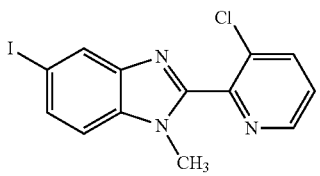 [SMILES: Cn1c(-c2ncccc2Cl)nc2cc(I)ccc21]

Production Example 21 (4)

2-(3-Ethylsulfanyl-pyridin-2-yl)-5-iodo-1-methyl-1H-benzimidazole (hereinafter referred to as the present fused heterocyclic compound 21) was prepared in a similar manner as described for the preparation of Production example 1 (2) by using Intermediate compound (M6-21) instead of 2-(3-fluoropyridin-2-yl)-3-methyl-6-trifluoromethyl-3H-imidazo[4,5-b]pyridine (Intermediate compound (M6-2)).

Present Fused Heterocyclic Compound 21

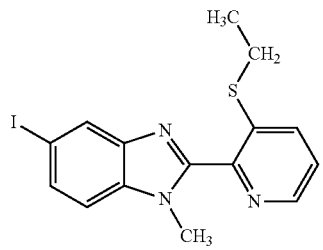 [SMILES: CCSc1cccnc1-c1nc2cc(I)ccc2n1C]

$^1$H-NMR (CDCl$_3$) δ: 8.49 (1H, dd), 8.22 (1H, d), 7.75 (1H, d), 7.62 (1H, dd), 7.35 (1H, dd), 7.21 (1H, d), 3.87 (3H, s), 2.92 (2H, q), 1.32 (3H, t).

Production Example 22 (1)

A mixture of 4-aminophenylsulfurpentafluoride 5.2 g, acetic anhydride 2.7 mL, triethylamine 6.6 mL, and chloroform 20 mL was stirred at RT for 3 hr. To the mixture was added water, and the reaction mixture was extracted with chloroform. The resultant residue was recrystallized by using hexane and ethyl acetate to give 4-acetamidephenyl sulfur pentafluoride 5.4 g.

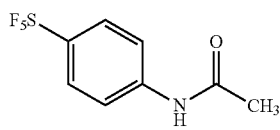

Production Example 22 (2)

To a mixture of 4-acetamidephenyl sulfur pentafluoride 5.4 g and sulfuric acid 15 mL at ice temperature was added dropwise fuming nitric acid 905 mL. After adding dropwise, the mixture was stirred at RT for 3 hr. To ice was poured the reaction mixture, the precipitated crystal was collected by filtration. The crystal was washed with water and dried to give 4-amino-3-nitrophenyl sulfur pentafluoride 5.2 g.

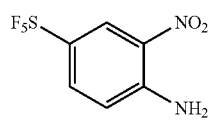

Production Example 22 (3)

To a mixture of 4-amino-3-nitrophenyl sulfur pentafluoride 2.0 g, 60% sodium hydride (in oil) 310 mg and DMF 15 mL at ice temperature was added dropwise iodomethane 447 μL. After adding dropwise, the mixture was stirred at RT for 3 hr. To water was poured the reaction mixture, and then the precipitated solid was collected by filtration. The solid was washed with water and dried to give methyl-(2-nitro-4-pentafluorosulfanyl-phenyl)-amine 2.0 g.

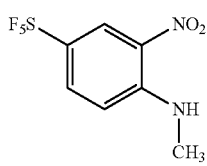

¹H-NMR (CDCl₃) δ: 8.60 (1H, d), 8.28 (1H, brs), 7.78 (1H, dd), 6.89 (1H, d), 3.10 (3H, d).

Production Example 22 (4)

N1-Methyl-4-pentafluorosulfanyl-benzene-1,2-diamine was prepared in a similar manner as described for the preparation of Production example 21 (2) by using methyl-(2-nitro-4-pentafluorosulfanyl-phenyl)-amine instead of (4-iodo-2-nitro-phenyl)-methyl-amine.

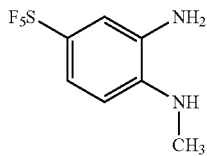

Production Example 22 (5)

3-Chloro-pyridine-2-carboxylic acid (2-methylamino-5-pentafluorosulfanyl-phenyl)-amide (hereinafter referred to as Intermediate compound (M20-23)) was prepared in a similar manner as described for the preparation of Production example 9 (1) by using N1-methyl-4-pentafluorosulfanyl-benzene-1,2-diamine instead of 5-iodo-N2-methyl-pyridine-2,3-diamine.

Intermediate Compound (M20-23)

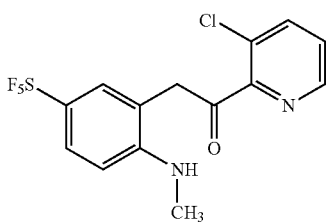

¹H-NMR (CDCl₃) δ: 9.57 (1H, s), 8.55 (1H, dd), 7.91 (1H, dd), 7.81 (1H, d), 7.59 (1H, dd), 7.50-7.45 (1H, m), 6.71 (1H, d), 4.52 (1H, d), 2.93 (3H, d).

Production Example 22 (6)

To a mixture of Intermediate compound (M20-23) 405 mg and DMF 10 mL at ice temperature was added sodium ethanethiolate 193 mg, and then the mixture was stirred at RT for 8 hr and at 60° C. for 2 hr. To the reaction mixture was added water, and the resulting mixture was extracted with ethyl acetate. The organic layer was washed with water, and dried over anhydrous magnesium sulfate, and then concentrated under reduced pressure. The resultant residue was treated with silica gel column chromatography to give 2-(3-ethylsulfanyl-5-trifluoromethyl-pyridin-2-yl)-1-methyl-5-pentafluorosulfanyl-1H-benzimidazole (hereinafter referred to as the present fused heterocyclic compound 23) 411 mg.

Present Fused Heterocyclic Compound 23

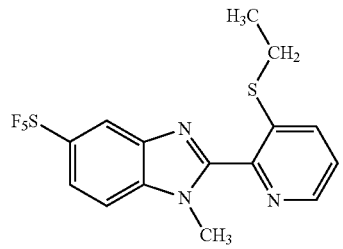

¹H-NMR (CDCl₃) δ: 8.50 (1H, dd), 8.33 (1H, d), 7.79-7.74 (2H, m), 7.46-7.43 (1H, m), 7.37 (1H, dd), 3.92 (3H, s), 2.94 (2H, q), 1.33 (3H, t).

Production Example 23

2-(3-Ethylsulfonyl-pyridin-2-yl)-1-methyl-5-pentafluorosulfanyl-1H-benzimidazole (hereinafter referred to as the present fused heterocyclic compound 24) was prepared in a similar manner as described for the preparation of Production example 11 by using 2-(3-ethylsulfanyl-pyridin-2-yl)-1-methyl-5-pentafluorosulfanyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 24

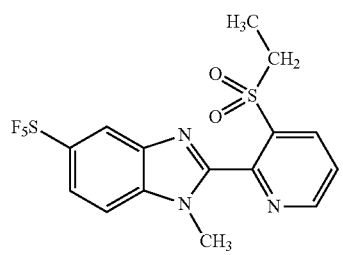

¹H-NMR (CDCl₃) δ: 8.96 (1H, dd), 8.50 (1H, dd), 8.24 (1H, d), 7.79 (1H, dd), 7.68 (1H, dd), 7.48 (1H, d), 3.82 (2H, q), 3.75 (3H, s), 1.34 (3H, t).

Production Example 24 (1)

3-Chloro-5-trifluoromethyl-pyridine-2-carboxylic acid (5-iodo-2-methylamino-pyridin-3-yl)-amide (hereinafter referred to as Intermediate compound (M20-35)) was prepared in a similar manner as described for the preparation of Production example 9 (1) by using 3-chloro-5-trifluoromethyl-pyridine-2-carboxylic acid instead of 3-chloro-pyridine-2-carboxylic acid.

Intermediate Compound (M20-35)

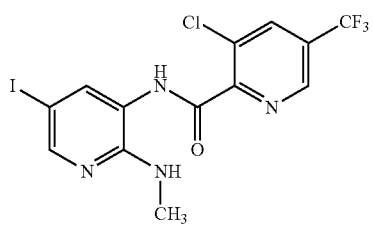 [SMILES: CNc1ncc(I)cc1NC(=O)c1ncc(C(F)(F)F)cc1Cl]

¹H-NMR (CDCl₃) δ: 9.33 (1H, s), 8.80 (1H, d), 8.28 (1H, d), 8.17 (1H, d), 8.00 (1H, d), 4.60 (1H, s), 3.01 (3H, d).

Production Example 24 (2)

2-(3-Chloro-5-trifluoromethyl-pyridin-2-yl)-6-iodo-3-methyl-3H-imidazo[4,5-b]pyridine (hereinafter referred to as Intermediate compound (M6-35)) was prepared in a similar manner as described for the preparation of Production example 9 (2) by using Intermediate compound (M20-35) instead of 3-chloro-pyridine-2-carboxylic acid (5-iodo-2-methylamino-pyridin-3-yl)-amide (Intermediate compound (M20-7)).

Intermediate Compound (M6-35)

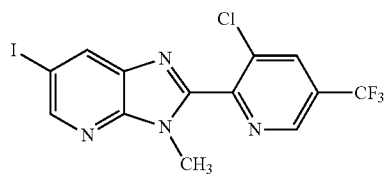 [SMILES: Cn1c(-c2ncc(C(F)(F)F)cc2Cl)nc2cc(I)cnc21]

¹H-NMR (CDCl₃) δ: 8.95 (1H, s), 8.68 (1H, s), 8.49 (1H, s), 8.20 (1H, s), 3.95 (3H, s).

Production Example 24 (3)

2-(3-Ethylsulfanyl-5-trifluoromethyl-pyridin-2-yl)-6-iodo-3-methyl-3H-imidazo[4,5-b]pyridine (hereinafter referred to as the present fused heterocyclic compound 42) was prepared in a similar manner as described for the preparation of Production example 1 (2) by using Intermediate compound (M6-35) instead of 2-(3-fluoropyridin-2-yl)-3-methyl-6-trifluoromethyl-3H-imidazo[4,5-b]pyridine (Intermediate compound (M6-2)).

Present Fused Heterocyclic Compound 42

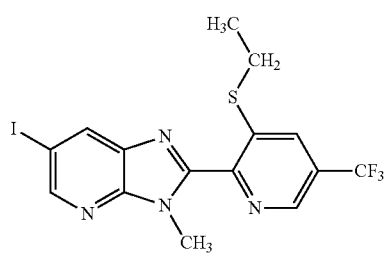 [SMILES: CCSc1cc(C(F)(F)F)cnc1-c1nc2cc(I)cnc2n1C]

¹H-NMR (CDCl₃) δ: 8.73 (1H, s), 8.65 (1H, d), 8.49 (1H, d), 7.91 (1H, s), 4.04 (3H, s), 3.01 (2H, q), 1.39 (3H, t).

Production Example 24 (4)

A mixture of 2-(3-ethylsulfanyl-5-trifluoromethyl-pyridin-2-yl)-6-iodo-3-methyl-3H-imidazo[4,5-b]pyridine 900 mg, thiobenzoic acid 320 μL, copper iodide 45 mg, 1,10-phenanthroline 85 mg, diisopropylethylamine 940 μL, and toluene 25 mL was stirred at 110° C. for 8 hr. To the reaction mixture was added water, and the resulting mixture was extracted with ethyl acetate. The organic layer was dried over sodium sulfate, and then concentrated under reduced pressure. The resultant residue was treated with silica gel column chromatography to give thiobenzoic acid S-[2-(3-ethylsulfanyl-5-trifluoromethyl-pyridin-2-yl)-3-methyl-3H-imidazo[4,5-b]pyridine]ester 990 mg.

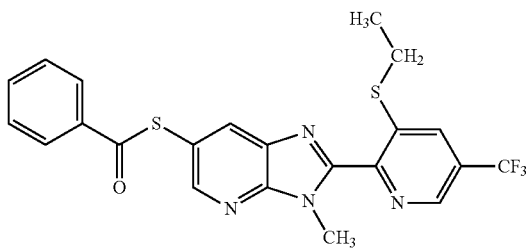 [SMILES: CCSc1cc(C(F)(F)F)cnc1-c1nc2cc(SC(=O)c3ccccc3)cnc2n1C]

¹H-NMR (CDCl₃) δ: 8.74 (1H, s), 8.54 (1H, d), 8.33 (1H, d), 8.07 (2H, dd), 7.92 (1H, s), 7.63 (1H, t), 7.51 (2H, t), 4.10 (3H, s), 3.01 (2H, q), 1.39 (3H, t).

Production Example 24 (5)

A mixture of thiobenzoic acid S-[2-(3-ethylsulfanyl-5-trifluoromethyl-pyridin-2-yl)-3-methyl-3H-imidazo[4,5-b]pyridine]ester 1.8 g, potassium carbonate 1.1 g, and methanol 20 mL was stirred at RT for 4.5 hr. To the reaction mixture was added saturated aqueous ammonium chloride, and the resulting mixture was extracted with ethyl acetate. The organic layer was washed with saturated aqueous sodium bicarbonate, dried over sodium sulfate, and concentrated under reduced pressure to give 2-(3-ethylsulfanyl-5-trifluoromethyl-pyridin-2-yl)-3-methyl-3H-imidazo[4,5-b]pyridine-6-thiol (hereinafter referred to as the present fused heterocyclic compound 43) 1.2 g.

Present Fused Heterocyclic Compound 43

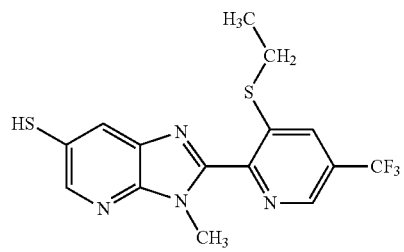 [SMILES: CCSc1cc(C(F)(F)F)cnc1-c1nc2cc(S)cnc2n1C]

¹H-NMR (CDCl₃) δ: 8.73 (1H, s), 8.46 (1H, d), 8.19 (1H, d), 7.90 (1H, s), 4.04 (3H, s), 3.01 (2H, q), 1.39 (3H, t).

Production Example 24 (6)

A mixture of 2-(3-ethylsulfanyl-5-trifluoromethyl-pyridin-2-yl)-3-methyl-3H-imidazo[4,5-b]pyridine-6-thiol 1.2 g, iodine 20 mg, and DMF 30 mL was stirred at RT for 12 hr under air atmosphere. The reaction mixture was concentrated, and the resultant residue was treated with silica gel column chromatography to give a compound having the formula:

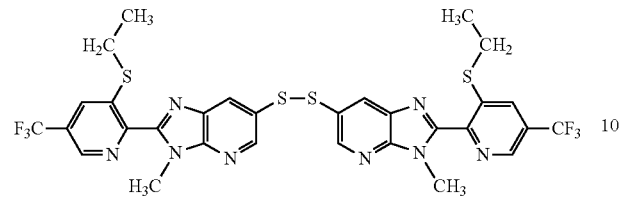

(hereinafter referred to as Intermediate compound (P9'-4)) 800 mg.

Intermediate Compound (P9'-4)

$^1$H-NMR (CDCl$_3$) δ: 8.73 (2H, s), 8.52 (2H, d), 8.35 (2H, d), 7.91 (2H, d), 4.06 (6H, s), 3.04-2.98 (4H, m), 1.39 (6H, t).

Production Example 24 (7)

2-(3-Ethylsulfanyl-5-trifluoromethyl-pyridin-2-yl)-3-methyl-6-trifluoromethylsulfanyl-3H-imidazo[4,5-b]pyridine (hereinafter referred to as the present fused heterocyclic compound 28) was prepared in a similar manner as described for the preparation of Production example 13 (2) by using Intermediate compound (P9'-4) instead of Intermediate compound (P9'-1).

Present Fused Heterocyclic Compound 28

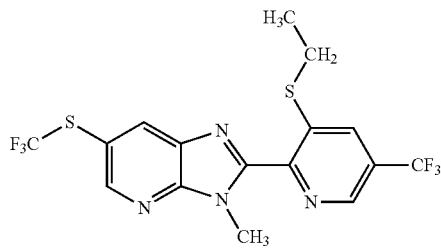 [SMILES: CCSc1cc(C(F)(F)F)cnc1-c1nc2cc(SC(F)(F)F)cnc2n1C]

$^1$H-NMR (CDCl$_3$) δ: 8.75 (1H, d), 8.71 (1H, d), 8.50 (1H, d), 7.93 (1H, d), 4.10 (3H, s), 3.03 (2H, q), 1.41 (3H, t).

Production Example 24 (8)

To a mixture of 2-(3-ethylsulfanyl-5-trifluoromethyl-pyridin-2-yl)-3-methyl-6-trifluoromethylsulfanyl-3H-imidazo[4,5-b]pyridine 299 mg and chloroform 30 mL at ice temperature was added m-chloroperbenzoic acid (65% or more purity) 0.34 g, and the mixture was stirred at ice temperature for 5 hr. To the reaction mixture was added saturated aqueous sodium bicarbonate and saturated aqueous sodium thiosulfate, and the reaction mixture was extracted with chloroform. The organic layer was dried over magnesium sulfate, and then concentrated under reduced pressure. The resultant residue was treated with silica gel column chromatography to give 2-(3-ethylsulfonyl-5-trifluoromethyl-pyridin-2-yl)-3-methyl-6-trifluoromethylsulfanyl-3H-imidazo[4,5-b]pyridine (hereinafter referred to as the present fused heterocyclic compound 44) 0.24 g.

Present Fused Heterocyclic Compound 44

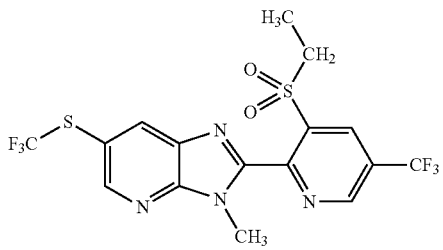 [SMILES: CCS(=O)(=O)c1cc(C(F)(F)F)cnc1-c1nc2cc(SC(F)(F)F)cnc2n1C]

$^1$H-NMR (CDCl$_3$) δ: 9.24 (1H, d), 8.79 (1H, d), 8.74 (1H, d), 8.40 (1H, d), 3.97 (2H, q), 3.93 (3H, s), 1.42 (3H, t).

Production Example 24 (9)

2-(3-Ethylsulfonyl-5-trifluoromethyl-pyridin-2-yl)-3-methyl-6-trifluoromethylsulfonyl-3H-imidazo[4,5-b]pyridine (hereinafter referred to as the present fused heterocyclic compound 25) was prepared in a similar manner as described for the preparation of Production example 16 by using 2-(3-ethylsulfanyl-5-trifluoromethyl-pyridin-2-yl)-3-methyl-6-trifluoromethylsulfanyl-3H-imidazo[4,5-b]pyridine instead of 2-(3-ethylsulfanyl-pyridin-2-yl)-3-methyl-6-trifluoromethylsulfanyl-3H-imidazo[4,5-b]pyridine (the present fused heterocyclic compound 13).

Present Fused Heterocyclic Compound 25

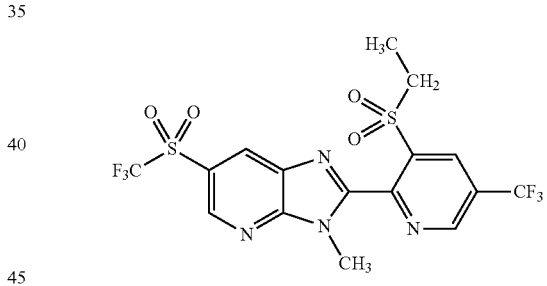

$^1$H-NMR (CDCl$_3$) δ: 9.28 (1H, d), 9.10 (1H, d), 8.80 (1H, d), 8.72 (1H, d), 3.98 (3H, s), 3.93 (2H, q), 1.43 (3H, t).

Production Example 25

A mixture of 2-(3-ethylsulfanyl-pyridin-2-yl)-5-iodo-1-methyl-1H-benzimidazole 340 mg, copper iodide 410 mg, sodium pentafluoropropionate 800 mg, NMP 5 mL, xylene 5 mL was stirred at 160° C. for 5 hr. The reaction mixture was allowed to cool to RT, and then to the reaction mixture was added saturated aqueous sodium bicarbonate and aqueous 28% ammonia, and the mixture was extracted with t-butyl methyl ether. The organic layer was dried over sodium sulfate, and then concentrated under reduced pressure. The resultant residue was treated with silica gel column chromatography to give 2-(3-ethylsulfanyl-pyridin-2-yl)-1-methyl-5-pentafluoroethyl-1H-benzimidazole (hereinafter referred to as the present fused heterocyclic compound 26) 240 mg.

Present Fused Heterocyclic Compound 26

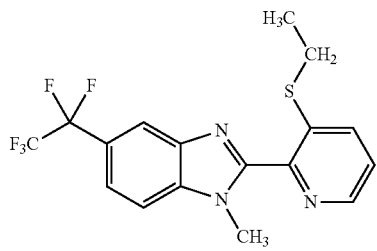 [SMILES: CCSc1cccnc1-c1nc2cc(C(F)(F)C(F)(F)F)ccc2n1C]

$^1$H-NMR (CDCl$_3$) δ: 8.50 (1H, dd), 8.16 (1H, s), 7.77 (1H, dd), 7.57 (1H, d), 7.53 (1H, d), 7.36 (1H, dd), 3.93 (3H, s), 2.94 (2H, q), 1.33 (3H, t).

Production Example 26

2-(3-Ethylsulfonyl-pyridin-2-yl)-1-methyl-5-pentafluoroethyl-1H-benzimidazole (hereinafter referred to as the present fused heterocyclic compound 27) was prepared in a similar manner as described for the preparation of Production example 5 by using 2-(3-ethylsulfanyl-pyridin-2-yl)-1-methyl-5-pentafluoroethyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 27

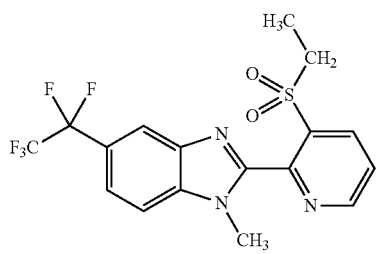 [SMILES: CCS(=O)(=O)c1cccnc1-c1nc2cc(C(F)(F)C(F)(F)F)ccc2n1C]

$^1$H-NMR (CDCl$_3$) δ: 8.98 (1H, dd), 8.53 (1H, dd), 8.06 (1H, s), 7.70 (1H, dd), 7.60 (1H, d), 7.56 (1H, d), 3.86-3.78 (5H, m), 1.34 (3H, t).

Production Example 27

To a mixture of 2-(3-ethylsulfanyl-5-trifluoromethylpyridin-2-yl)-3-methyl-6-trifluoromethylsulfanyl-3H-imidazo[4,5-b]pyridine 0.18 g and chloroform 4 mL at ice temperature was added m-chloroperbenzoic acid (65% or more purity) 0.21 g, and the mixture was stirred at ice temperature for 5 min. To the reaction mixture was added saturated aqueous sodium bicarbonate and saturated aqueous sodium thiosulfate, and the reaction mixture was extracted with chloroform. The organic layer was dried over magnesium sulfate, and then concentrated under reduced pressure. The resultant residue was treated with silica gel column chromatography to give 2-(3-ethylsulfanyl-5-trifluoromethyl-pyridin-2-yl)-3-methyl-6-trifluoromethylsulfanyl-3H-imidazo[4,5-b]pyridine (hereinafter referred to as the present fused heterocyclic compound 29) 0.16 g.

Present Fused Heterocyclic Compound 29

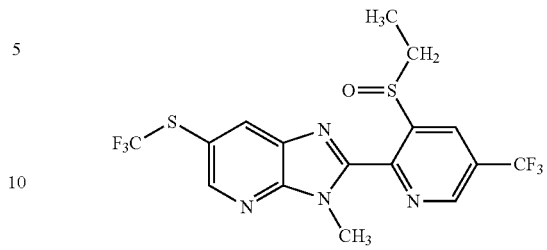

$^1$H-NMR (CDCl$_3$) δ: 9.10-9.07 (1H, m), 8.94-8.91 (1H, m), 8.77-8.74 (1H, m), 8.46-8.44 (1H, m), 4.38 (3H, s), 3.76-3.65 (1H, m), 3.16-3.05 (1H, m), 1.49 (3H, t).

Production Example 28 (1)

3-Chloro-pyridine-2-carboxylic acid (2-methylamino-5-trifluoromethyl-phenyl)-amide (hereinafter referred to as Intermediate compound (M20-29)) was prepared in a similar manner as described for the preparation of Production example 9 (1) by using N1-methyl-4-trifluoromethyl-benzene-1,2-diamine instead of 5-iodo-N2-methyl-pyridine-2,3-diamine.

Intermediate Compound (M20-29)

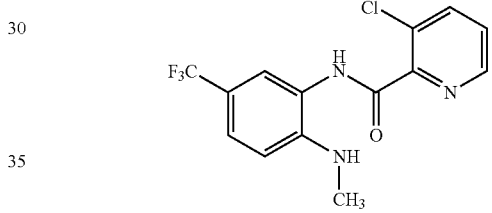

$^1$H-NMR (CDCl$_3$) δ: 9.56 (1H, s), 8.55-8.54 (1H, m), 7.91 (1H, dd), 7.70 (1H, d), 7.49-7.43 (3H, m), 6.79 (1H, d), 2.93 (3H, d).

Production Example 28 (2)

A mixture of Intermediate compound (M20-29) 800 mg, sodium ethanethiolate 350 mg, and DMF 10 mL was stirred at 100° C. for 5 hr. To the reaction mixture was added saturated aqueous sodium bicarbonate, and the resulting mixture was extracted with ethyl acetate. The organic layer was dried over sodium sulfate, and then concentrated under reduced pressure. The resultant residue was treated with silica gel column chromatography to give 2-(3-ethylsulfanyl-pyridin-2-yl)-1-methyl-5-trifluoromethyl-1H-benzimidazole (hereinafter referred to as the present fused heterocyclic compound 30) 410 mg.

Present Fused Heterocyclic Compound 30

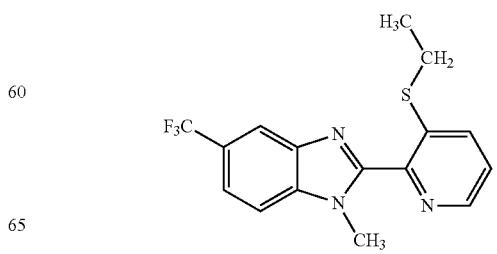

¹H-NMR (CDCl₃) δ: 8.51 (1H, dd), 8.17 (1H, d), 7.78 (1H, dd), 7.61 (1H, dd), 7.52 (1H, d), 7.38 (1H, dd), 3.93 (3H, s), 2.94 (2H, q), 1.33 (3H, t).

Production Examples 29, 30

2-(3-Ethylsulfinyl-pyridin-2-yl)-1-methyl-5-trifluoromethyl-1H-benzimidazole (hereinafter referred to as the present fused heterocyclic compound 31) and 2-(3-ethylsulfonyl-pyridine-2-yl)-1-methyl-5-trifluoromethyl-1H-benzimidazole (hereinafter referred to as the present fused heterocyclic compound 32) were prepared in a similar manner as described for the preparation of Production examples 2, 3 by using 2-(3-ethylsulfanyl-pyridin-2-yl)-1-methyl-5-trifluoromethyl-1H-benzimidazole instead of 2-(3-ethylsulfanylpyridin-2-yl)-3-methyl-6-trifluoromethyl-3H-imidazo[4,5-b]pyridine.

Present Fused Heterocyclic Compound 31

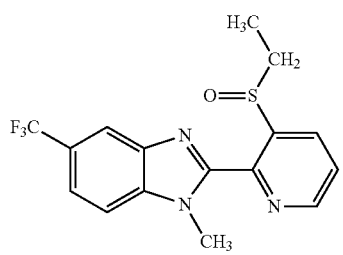 [SMILES: CCS(=O)c1cccnc1-c1nc2cc(C(F)(F)F)ccc2n1C]

¹H-NMR (CDCl₃) δ: 8.77 (1H, d), 8.61 (1H, d), 8.05 (1H, s), 7.61 (1H, dd), 7.55 (1H, d), 7.48 (1H, d), 4.20 (3H, s), 3.73-3.61 (1H, m), 3.11-3.00 (1H, m), 1.47 (3H, t).

Present Fused Heterocyclic Compound 32

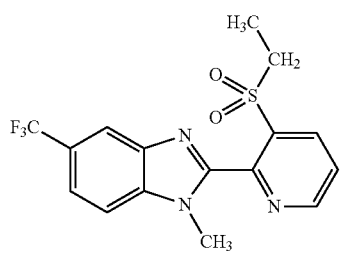

¹H-NMR (CDCl₃) δ: 8.95 (1H, dd), 8.50 (1H, dd), 8.09 (1H, d), 7.66 (1H, dd), 7.61 (1H, d), 7.53 (1H, d), 3.83 (2H, q), 3.75 (3H, s), 1.33 (3H, t).

Production Example 31 (1)

3-Chloro-5-trifluoromethyl-pyridine-2-carboxylic acid (2-methylamino-5-trifluoromethyl-phenyl)-amide (hereinafter referred to as Intermediate compound (M20-31)) was prepared in a similar manner as described for the preparation of Production example 9 (1) by using N1-methyl-4-trifluoromethyl-benzene-1,2-diamine instead of 5-iodo-N2-methyl-pyridine-2,3-diamine and by using 3-chloro-5-trifluoromethylpyridine-2-carboxylic acid instead of 3-chloro-pyridine-2-carboxylic acid.

Intermediate Compound (M20-31)

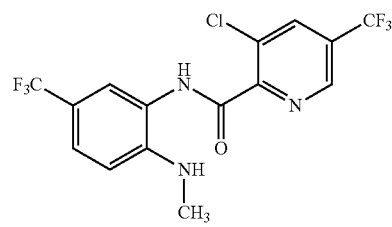 [SMILES: CNc1ccc(C(F)(F)F)cc1NC(=O)c1ncc(C(F)(F)F)cc1Cl]

¹H-NMR (CDCl₃) δ: 9.42 (1H, s), 8.80 (1H, d), 8.16 (1H, d), 7.71 (1H, s), 7.47 (1H, d), 6.81 (1H, d), 4.32 (1H, s), 2.93 (3H, d).

Production Example 31 (2)

2-(3-Ethylsulfanyl-5-trifluoromethyl-pyridin-2-yl)-1-methyl-5-trifluoromethyl-1H-benzimidazole (hereinafter referred to as the present fused heterocyclic compound 33) and 3-ethylsulfanyl-5-trifluoromethyl-pyridine-2-carboxylic acid (2-methylamino-5-trifluoromethyl-phenyl)-amide (hereinafter referred to as Intermediate compound (M3-32)) was prepared in a similar manner as described for the preparation of Production example 28 (2) by using Intermediate compound (M20-31) instead of 3-chloro-pyridine-2-carboxylic acid (2-methylamino-5-trifluoromethyl-phenyl)-amide (Intermediate compound (M20-29)).

Present Fused Heterocyclic Compound 33

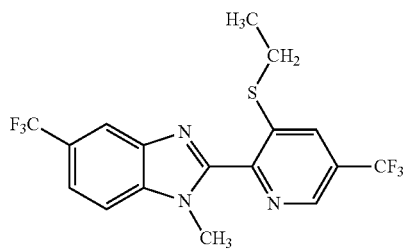 [SMILES: CCSc1cc(C(F)(F)F)cnc1-c1nc2cc(C(F)(F)F)ccc2n1C]

¹H-NMR (CDCl₃) δ: 8.72 (1H, d), 8.21 (1H, d), 7.91 (1H, d), 7.63 (1H, d), 7.54 (1H, d), 4.00 (3H, s), 3.00 (2H, q), 1.38 (3H, t).

Intermediate Compound (M3-32)

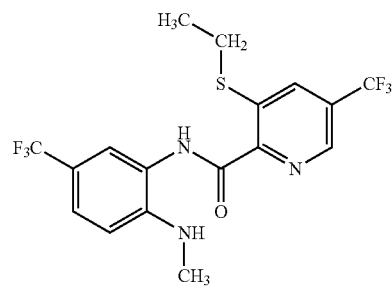 [SMILES: CCSc1cc(C(F)(F)F)cnc1C(=O)Nc1cc(C(F)(F)F)ccc1NC]

¹H-NMR (CDCl₃) δ: 9.64 (1H, s), 8.53 (1H, d), 7.86 (1H, s), 7.76 (1H, d), 7.41 (1H, dd), 6.76 (1H, d), 4.35 (1H, d), 2.96 (2H, q), 2.90 (3H, d), 1.44 (3H, t).

Production Examples 32, 33

2-(3-Ethylsulfinyl-5-trifluoromethyl-pyridin-2-yl)-1-methyl-5-trifluoromethyl-1H-benzimidazole (hereinafter referred to as the present fused heterocyclic compound 34) and 2-(3-ethylsulfonyl-5-trifluoromethyl-pyridin-2-yl)-1-methyl-5-trifluoromethyl-1H-benzimidazole (hereinafter referred to as the present fused heterocyclic compound 35) was prepared in a similar manner as described for the preparation of Production examples 2, 3 by using 2-(3-ethylsulfanyl-5-trifluoromethyl-pyridin-2-yl)-1-methyl-5-trifluoromethyl-1H-benzimidazole instead of 2-(3-ethylsulfanylpyridin-2-yl)-3-methyl-6-trifluoromethyl-3H-imidazo[4,5-b]pyridine (the present fused heterocyclic compound 1).

Present Fused Heterocyclic Compound 34

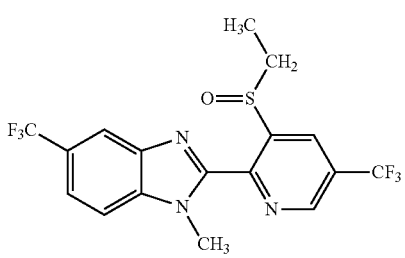 [SMILES: CCS(=O)c1cc(C(F)(F)F)cnc1-c1nc2cc(C(F)(F)F)ccc2n1C]

¹H-NMR (CDCl₃) δ: 9.05 (1H, d), 8.91 (1H, d), 8.12 (1H, d), 7.67 (1H, dd), 7.60 (1H, d), 4.32 (3H, s), 3.80-3.70 (1H, m), 3.15-3.05 (1H, m), 1.51 (3H, t).

Present Fused Heterocyclic Compound 35

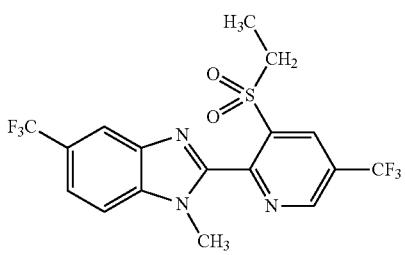 [SMILES: CCS(=O)(=O)c1cc(C(F)(F)F)cnc1-c1nc2cc(C(F)(F)F)ccc2n1C]

¹H-NMR (CDCl₃) δ: 9.22 (1H, d), 8.77 (1H, d), 8.10 (1H, d), 7.66 (1H, dd), 7.57 (1H, d), 3.98 (2H, q), 3.84 (3H, s), 1.40 (3H, t).

Production Examples 34, 35

To a mixture of 2-(3-ethylsulfonylpyridin-2-yl)-3-methyl-6-trifluoromethyl-3H-imidazo[4,5-b]pyridine 550 mg and chloroform 15 mL was added m-chloroperbenzoic acid (65% or more purity) 750 mg, and the mixture was heated to reflux for 20 hr. To the reaction mixture was added aqueous 10% sodium thiosulfate, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfonyl-1-oxypyridin-2-yl)-3-methyl-6-trifluoromethyl-3H-imidazo[4,5-b]pyridine (hereinafter referred to as the present fused heterocyclic compound 36) 168 mg and 2-(3-ethylsulfonylpyridin-2-yl)-3-methyl-6-trifluoromethyl-3H-imidazo[4,5-b]pyridine 4-oxide (hereinafter referred to as the present fused heterocyclic compound 37) 73 mg.

Present Fused Heterocyclic Compound 36

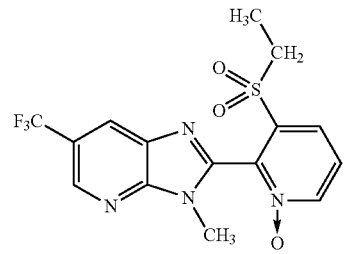 [SMILES: CCS(=O)(=O)c1ccc[n+]([O-])c1-c1nc2cc(C(F)(F)F)cnc2n1C]

¹H-NMR (CDCl₃) δ: 8.79 (1H, d), 8.54 (1H, dd), 8.33 (1H, d), 7.99 (1H, dd), 7.69 (1H, dd), 3.85-3.74 (4H, m), 3.52-3.42 (1H, m), 1.34 (3H, t).

Present Fused Heterocyclic Compound 37

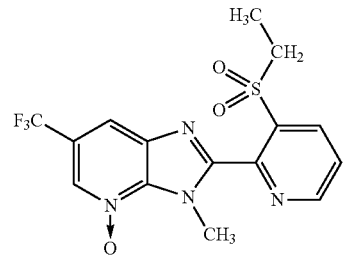 [SMILES: CCS(=O)(=O)c1cccnc1-c1nc2cc(C(F)(F)F)c[n+]([O-])c2n1C]

¹H-NMR (CDCl₃) δ: 9.03 (1H, dd), 8.53 (1H, dd), 8.47 (1H, d), 7.92 (1H, d), 7.77 (1H, dd), 4.29 (3H, s), 3.69 (2H, q), 1.36 (3H, t).

Production Example 36 (1)

2-(3-Chloro-5-trifluoromethyl-pyridin-2-yl)-5-iodo-1-methyl-1H-benzimidazole (hereinafter referred to as Intermediate compound (M6-41)) was prepared in a similar manner as described for the preparation of Production example 4 (1) by using 4-iodo-N1-methyl-benzene-1,2-diamine instead of N2-methyl-5-trifluoromethylpyridine-2,3-diamine.

Intermediate Compound (M6-41)

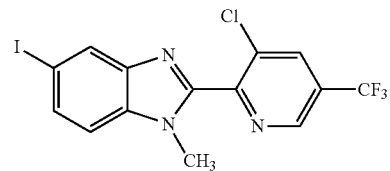 [SMILES: Cn1c(-c2ncc(C(F)(F)F)cc2Cl)nc2cc(I)ccc21]

¹H-NMR (CDCl₃) δ: 8.92 (1H, d), 8.23 (1H, d), 8.17 (1H, d), 7.66 (1H, dd), 7.23 (1H, d), 3.85 (3H, s).

Production Example 36 (2)

2-(3-Ethylsulfanyl-5-trifluoromethyl-pyridin-2-yl)-5-iodo-1-methyl-1H-benzimidazole (hereinafter referred to as the present fused heterocyclic compound 45) was prepared in a similar manner as described for the preparation of Production example 1 (2) by using Intermediate compound (M6-41) instead of 2-(3-fluoropyridin-2-yl)-3-methyl-6-trifluoromethyl-3H-imidazo[4,5-b]pyridine.

Present Fused Heterocyclic Compound 45

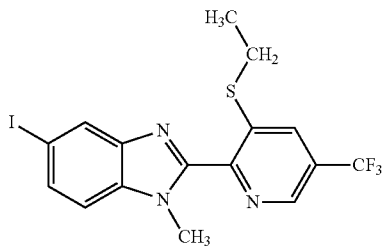

Production Example 36 (3)

2-(3-Ethylsulfanyl-5-trifluoromethyl-pyridin-2-yl)-1-methyl-5-pentafluoroethyl-1H-benzimidazole (hereinafter referred to as the present fused heterocyclic compound 38) was prepared in a similar manner as described for the preparation of Production example 25 by using 2-(3-ethylsulfanyl-5-trifluoromethyl-pyridin-2-yl)-5-iodo-1-methyl-1H-benzimidazole instead of 2-(3-ethylsulfanyl-pyridin-2-yl)-5-iodo-1-methyl-1H-benzimidazole.

Present Fused Heterocyclic Compound 38

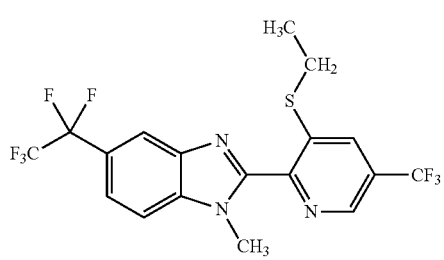

$^1$H-NMR (CDCl$_3$) δ: 8.72 (1H, d), 8.20 (1H, s), 7.91 (1H, d), 7.60 (1H, d), 7.55 (1H, d), 4.00 (3H, s), 3.01 (2H, q), 1.39 (3H, t).

Production Examples 37, 38

2-(3-Ethylsulfinyl-5-trifluoromethyl-pyridin-2-yl)-1-methyl-5-pentafluoroethyl-1H-benzimidazole (hereinafter referred to as the present fused heterocyclic compound 39) and 2-(3-ethylsulfonyl-5-trifluoromethyl-pyridin-2-yl)-1-methyl-5-pentafluoroethyl-1H-benzimidazole (hereinafter referred to as the present fused heterocyclic compound 40) was prepared in a similar manner as described for the preparation of Production examples 2, 3 by using 2-(3-ethylsulfanyl-5-trifluoromethyl-pyridin-2-yl)-1-methyl-5-pentafluoroethyl-1H-benzimidazole instead of 2-(3-ethylsulfanylpyridin-2-yl)-3-methyl-6-trifluoromethyl-3H-imidazo[4,5-b]pyridine.

Present Fused Heterocyclic Compound 39

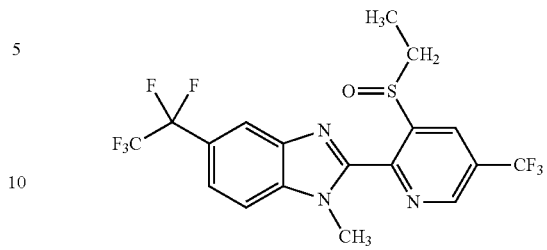

$^1$H-NMR (CDCl$_3$) δ: 9.05 (1H, d), 8.91 (1H, d), 8.10 (1H, s), 7.66-7.60 (2H, m), 4.33 (3H, s), 3.80-3.69 (1H, m), 3.17-3.07 (1H, m), 1.50 (3H, t).

Present Fused Heterocyclic Compound 40

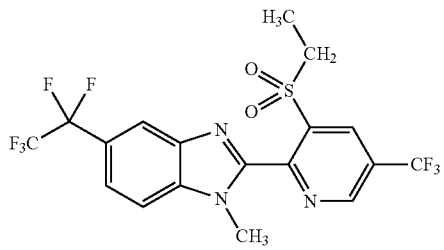

$^1$H-NMR (CDCl$_3$) δ: 9.22 (1H, d), 8.77 (1H, d), 8.08 (1H, s), 7.63 (1H, d), 7.58 (1H, d), 3.99 (2H, q), 3.84 (3H, s), 1.40 (3H, t).

Production Example 39 (1)

To a mixture of methyl-(2-nitro-4-trifluoromethyl-phenyl)-amine 16 g and acetonitrile 200 mL at ice temperature was added N-bromosuccinimide 15 g. The reaction mixture was stirred at RT for 5 hr. To the resulting reaction mixture was added saturated aqueous sodium bicarbonate, and the resulting mixture was extracted with ethyl acetate. The organic layer was dried over magnesium sulfate, and then concentrated under reduced pressure. The resultant residue was treated with silica gel column chromatography to give (2-bromo-6-nitro-4-trifluoromethyl-phenyl)-methyl-amine 15 g.

(2-bromo-6-nitro-4-trifluoromethyl-phenyl)-methyl-amine

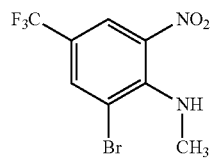

$^1$H-NMR (CDCl$_3$) δ: 8.12 (1H, s), 7.86 (1H, s), 6.48 (1H, brs), 3.07 (3H, d).

Production Example 39 (2)

While a mixture of iron powder 11 g, acetic acid 12 mL, THF 40 mL, and water 10 mL was stirred with heating at 70° C., to the mixture was added dropwise another mixture of (2-bromo-6-nitro-4-trifluoromethyl-phenyl)-methyl-amine 10 g and THF 50 mL. After adding dropwise, the mixture was stirred with heating at 70° C. for 3 hr. The resulting reaction mixture was filtered using Celite with washing with THF. The resulting filtrate was concentrated under reduced pressure. To the resultant residue was added aqueous 10% sodium hydroxide, and the resulting mixture was extracted with ethyl acetate. The organic layer was dried over magnesium sulfate, and then concentrated under reduced pressure to give 3-bromo-N2-methyl-5-trifluoromethyl-benzene-1,2-diamine 11 g.

3-Bromo-N2-methyl-5-trifluoromethyl-benzene-1,2-diamine

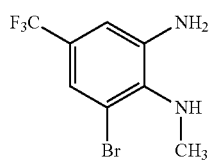

Production Example 39 (3)

3-Chloro-pyridine-2-carboxylic acid (3-bromo-2-methyl-amino-5-trifluoromethyl-phenyl)-amide (hereinafter referred to as Intermediate compound (M20-43)) was prepared in a similar manner as described for the preparation of Production example 9 (1) by using 3-bromo-N2-methyl-5-trifluoromethyl-benzene-1,2-diamine instead of 5-iodo-N2-methyl-pyridine-2,3-diamine.

Intermediate Compound (M20-43)

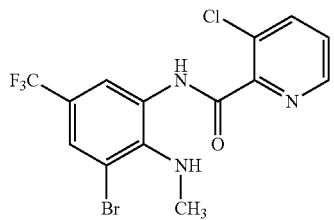 [SMILES: CNc1c(Br)cc(C(F)(F)F)cc1NC(=O)c1ncccc1Cl]

$^1$H-NMR (CDCl$_3$) δ: 10.63 (1H, s), 8.77 (1H, d), 8.58 (1H, dd), 7.91 (1H, dd), 7.56 (1H, d), 7.47 (1H, dd), 3.75-3.68 (1H, m), 2.83 (3H, d).

Production Example 39 (4)

2-(3-Ethylsulfanyl-pyridin-2-yl)-7-bromo-1-methyl-5-trifluoromethyl-1H-benzimidazole (hereinafter referred to as the present fused heterocyclic compound 75), 3-ethylsulfanyl-pyridine-2-carboxylic acid (3-bromo-2-methylamino-5-trifluoromethyl-phenyl)-amide (hereinafter referred to as Intermediate compound (M3-42)), and 2-(3-chloro-pyridin-2-yl)-7-bromo-1-methyl-5-trifluoromethyl-1H-benzimidazole (hereinafter referred to as Intermediate compound (M6-43)) were prepared in a similar manner as described for the preparation of Production example 28 (2) by using Intermediate compound (M20-43) instead of Intermediate compound (M20-29).

Present Fused Heterocyclic Compound 75

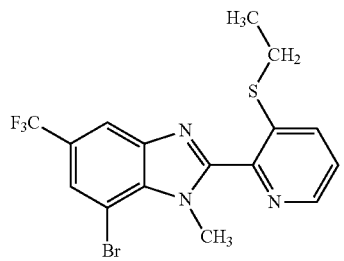 [SMILES: CCSc1cccnc1-c1nc2cc(C(F)(F)F)cc(Br)c2n1C]

$^1$H-NMR (CDCl$_3$) δ: 8.54 (1H, dd), 8.08 (1H, d), 7.79 (1H, dd), 7.72 (1H, d), 7.40 (1H, dd), 4.13 (3H, s), 2.94 (2H, q), 1.32 (3H, t).

Intermediate Compound (M3-42)

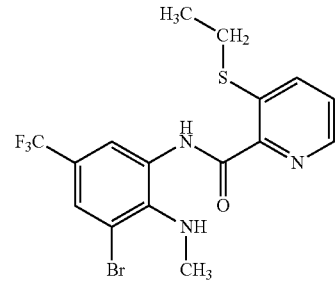 [SMILES: CCSc1cccnc1C(=O)Nc1cc(C(F)(F)F)cc(Br)c1NC]

$^1$H-NMR (CDCl$_3$) δ: 10.80 (1H, s), 8.82 (1H, s), 8.38 (1H, dd), 7.74 (1H, d), 7.54 (1H, s), 7.42 (1H, dd), 3.75-3.65 (1H, brm), 2.97 (2H, q), 2.82 (3H, d), 1.45 (3H, t).

Intermediate Compound (M6-43)

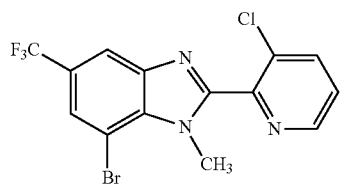 [SMILES: Cn1c(-c2ncccc2Cl)nc2cc(C(F)(F)F)cc(Br)c21]

$^1$H-NMR (CDCl$_3$) δ: 8.71 (1H, dd), 8.08 (1H, d), 7.95 (1H, dd), 7.74 (1H, d), 7.47 (1H, dd), 4.09 (3H, s).

Production Example 40

2-(3-Ethylsulfonyl-pyridin-2-yl)-7-bromo-1-methyl-5-trifluoromethyl-1H-benzimidazole (hereinafter referred to as the present fused heterocyclic compound 46) was prepared in a similar manner as described for the preparation of Production example 5 by using 2-(3-ethylsulfanyl-pyridin-2-yl)-7-bromo-1-methyl-5-trifluoromethyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 46

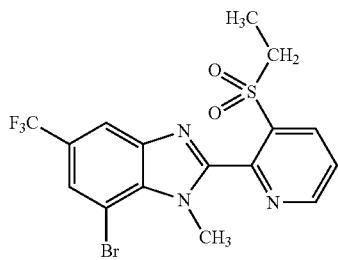

¹H-NMR (CDCl₃) δ: 8.99 (1H, dd), 8.51 (1H, dd), 8.00 (1H, d), 7.75 (1H, d), 7.72 (1H, dd), 4.03 (3H, s), 3.73 (2H, q), 1.33 (3H, t).

Production Examples 41, 42

A mixture of 2-(3-ethylsulfanyl-5-trifluoromethylpyridin-2-yl)-3-methyl-6-trifluoromethyl-3H-imidazo[4,5-b]pyridine (the present fused heterocyclic compound 4) 1.0 g, m-chloroperbenzoic acid (65% or more purity) 2.72 g, and chloroform 5 mL was refluxed for 8 hr, and to the mixture was added m-chloroperbenzoic acid (65% or more purity) 2.0 g, and then the mixture was further refluxed for 5 hr. To the reaction mixture allowed to cool was added aqueous 10% sodium thiosulfate, and the reaction mixture was extracted with chloroform. The organic layer was washed with saturated aqueous sodium bicarbonate, dried over anhydrous magnesium sulfate, and then concentrated under reduced pressure to give 2-(3-ethylsulfonyl-5-trifluoromethylpyridin-2-yl)-3-methyl-6-trifluoromethyl-3H-imidazo[4,5-b]pyridine 4-oxide (hereinafter referred to as the present fused heterocyclic compound 48) 362 mg and 2-(3-ethylsulfonyl-1-oxy-5-trifluoromethylpyridin-2-yl)-3-methyl-6-trifluoromethyl-3H-imidazo[4,5-b]pyridine (hereinafter referred to as the present fused heterocyclic compound 51) 45 mg.

Present Fused Heterocyclic Compound 48

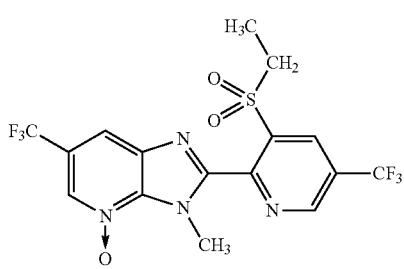 [SMILES: CCS(=O)(=O)c1cc(C(F)(F)F)cnc1-c1nc2cc(C(F)(F)F)c[n+]([O-])c2n1C]

¹H-NMR (CDCl₃) δ: 9.27 (1H, d), 8.76 (1H, d), 8.49 (1H, d), 7.94 (1H, d), 4.33 (3H, s), 3.80 (2H, q), 1.40 (3H, t).

Present Fused Heterocyclic Compound 51

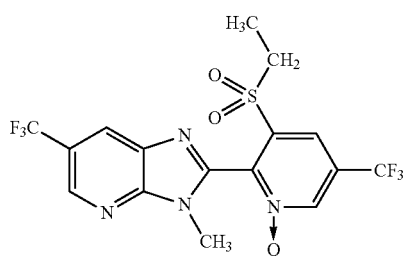 [SMILES: CCS(=O)(=O)c1cc(C(F)(F)F)c[n+]([O-])c1-c1nc2cc(C(F)(F)F)cnc2n1C]

¹H-NMR (CDCl₃) δ: 8.75 (1H, s), 8.50 (1H, s), 8.12 (1H, s), 7.94 (1H, s), 4.28 (3H, s), 3.75-3.65 (1H, m), 3.55-3.44 (1H, m), 1.38 (3H, t).

Production Example 43 (1)

A mixture of 2-chloro-3-nitro-5-trifluoromethylpyridine 2.60 g, 2, 2, 2-trifluoroethylamine 0.79 g, N,N-diisopropylethylamine 1.04 g, and N-methyl-2-pyrrolidone 5 mL was stirred at RT for 10 hr. To the reaction mixture was added aqueous 10% citric acid, and the resulting mixture was extracted with ethyl acetate. The organic layer was washed with water, and dried over sodium sulfate, and then concentrated under reduced pressure to give (3-nitro-5-trifluoromethylpyridin-2-yl)-(2, 2, 2-trifluoroethyl)amine 1.83 g.

(3-Nitro-5-trifluoromethylpyridin-2-yl)-(2, 2, 2-trifluoroethyl)amine

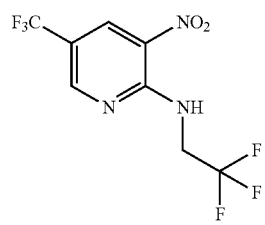 [SMILES: O=[N+]([O-])c1cc(C(F)(F)F)cnc1NCC(F)(F)F]

¹H-NMR (CDCl₃) δ: 8.72 (1H, d), 8.68 (1H, d), 8.59 (1H, brs), 4.54-4.41 (2H, m).

Production Example 43 (2)

To a mixture of iron powder 2.12 g, ethanol 6 mL, water 4 mL, and acetic acid 0.1 mL was added dropwise another mixture of (3-nitro-5-trifluoromethylpyridin-2-yl)-(2, 2, 2-trifluoroethyl)amine 1.83 g and ethanol 10 mL at 70° C., and then the resulting mixture was stirred at 70° C. for 1 hr. The reaction mixture allowed to cool was filtered, and then the filtrate was extracted with ethyl acetate and water. The organic layer was washed with water, and dried over sodium sulfate, and then concentrated under reduced pressure to give N2-(2, 2, 2-trifluoroethyl)-5-trifluoromethylpyridine-2, 3-diamine 1.59 g.

N2-(2, 2, 2-Trifluoroethyl)-5-trifluoromethylpyridine-2,3-diamine

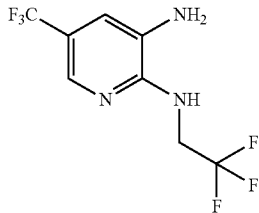 [SMILES: Nc1cc(C(F)(F)F)cnc1NCC(F)(F)F]

¹H-NMR (CDCl₃) δ: 8.04-8.02 (1H, m), 7.10-7.07 (1H, m), 4.81 (1H, brs), 4.31-4.20 (2H, m), 3.34 (2H, brs).

Production Example 43 (3)

A mixture of N2-(2, 2, 2-trifluoroethyl)-5-trifluoromethylpyridine-2,3-diamine 0.52 g, 3-ethylsulfanylpyridine-2-carboxylic acid 0.37 g, EDC hydrochloride 0.46 g, HOBt 27 mg, and pyridine 2 mL was stirred at RT for 3 hr. To the reaction mixture was added aqueous 10% citric acid, and the resulting mixture was extracted with ethyl acetate. The organic layer was washed with water, and dried over sodium sulfate, and then concentrated under reduced pressure to give 3-ethylsulfanylpyridine-2-carboxylic acid [2-(2, 2, 2-trifluoroethyl)amino-5-trifluoromethylpyridin-3-yl]amide (hereinafter referred to as Intermediate compound (M3-43)) 0.75 g.

Intermediate Compound (M3-43)

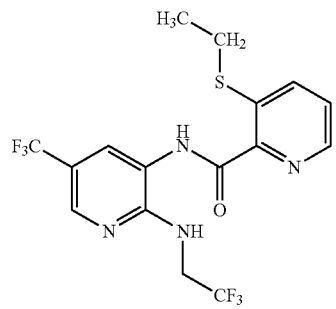 [SMILES: CCSc1cccnc1C(=O)Nc1cc(C(F)(F)F)cnc1NCC(F)(F)F]

Production Example 43 (4)

A mixture of Intermediate compound (M3-43) 0.75 g and acetic acid 5 mL was stirred with heating to reflux for 2 days. The mixture was cooled to RT, and then concentrated under reduced pressure. The crude product was treated with silica gel column chromatography to give 2-(3-ethylsulfanylpyridin-2-yl)-3-(2, 2, 2-trifluoroethyl)-6-trifluoromethyl-3H-imidazo[4,5-b]pyridine (hereinafter referred to as the present fused heterocyclic compound 65) 0.53 g.

Present Fused Heterocyclic Compound 65

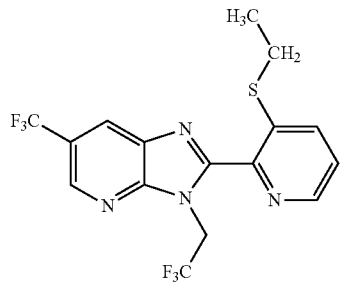 [SMILES: CCSc1cccnc1-c1nc2cc(C(F)(F)F)cnc2n1CC(F)(F)F]

¹H-NMR (CDCl₃) δ: 8.77-8.74 (1H, m), 8.48 (1H, dd), 8.45-8.42 (1H, m), 7.82 (1H, dd), 7.40 (1H, dd), 5.64 (2H, q), 2.99 (2H, q), 1.35 (3H, t).

Production Example 44 (1)

A mixture of N2-(2, 2, 2-trifluoroethyl)-5-trifluoromethylpyridine-2,3-diamine 0.52 g, 3-ethylsulfanyl-5-trifluoromethylpyridine-2-carboxylic acid 0.50 g, EDC hydrochloride 0.46 g, HOBt 27 mg, and pyridine 2 mL was stirred at RT for 3 hr. To the reaction mixture was added aqueous 10% citric acid, and the resulting mixture was extracted with ethyl acetate. The organic layer was washed with water, and dried over sodium sulfate, and then concentrated under reduced pressure to give 3-ethylsulfanyl-5-trifluoromethylpyridine-2-carboxylic acid [2-(2, 2, 2-trifluoroethyl)amino-5-trifluoromethylpyridin-3-yl]amide (hereinafter referred to as Intermediate compound (M3-44)) 0.89 g.

Intermediate Compound (M3-44)

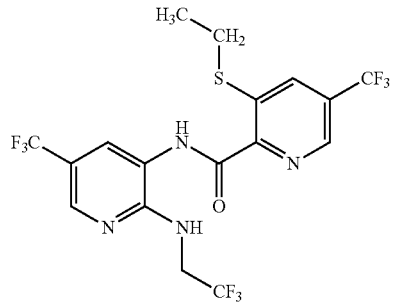 [SMILES: CCSc1cc(C(F)(F)F)cnc1C(=O)Nc1cc(C(F)(F)F)cnc1NCC(F)(F)F]

Production Example 44 (2)

A mixture of Intermediate compound (M3-44) 0.89 g, p-toluenesulfonic acid·monohydrate 1.14 g, N-methyl-2-pyrrolidone 10 mL, and xylene 10 mL was heated to reflux for 8 hr with removing water using Dean-Stark apparatus. The reaction mixture was allowed to cool, and then to the reaction mixture was added water, and the resulting mixture was extracted with ethyl acetate. The organic layer was washed with water, and dried over sodium sulfate, and then concentrated under reduced pressure. The crude product was treated with silica gel column chromatography to give 2-(3-ethylsulfanyl-5-trifluoromethylpyridin-2-yl)-3-(2, 2, 2-trifluoroethyl)-6-trifluoromethyl-3H-imidazo[4,5-b]pyridine (hereinafter referred to as the present fused heterocyclic compound 66) 0.76 g.

Present Fused Heterocyclic Compound 66

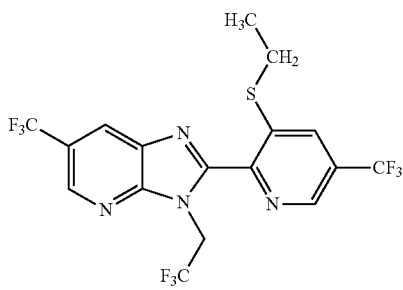 [SMILES: CCSc1cc(C(F)(F)F)cnc1-c1nc2cc(C(F)(F)F)cnc2n1CC(F)(F)F]

¹H-NMR (CDCl₃) δ: 8.80 (1H, d), 8.70 (1H, d), 8.48 (1H, d), 7.96 (1H, d), 5.67 (2H, q), 3.04 (2H, q), 1.40 (3H, t).

Production Example 45

To a mixture of the present fused heterocyclic compound 65 0.32 g and chloroform 2 mL at ice temperature was added m-chloroperbenzoic acid (65% or more purity) 0.36 g, and then the mixture was allowed to warm to RT, and stirred for 1 hr. To the mixture was added saturated aqueous sodium bicarbonate and saturated aqueous sodium thiosulfate, and the reaction mixture was extracted with chloroform. The organic layer was washed with water, and dried over sodium sulfate, and then concentrated under reduced pressure. The crude product was treated with silica gel column chromatography to give 2-(3-ethylsulfonylpyridin-2-yl)-3-(2, 2, 2-trifluoroethyl)-6-trifluoromethyl-3H-imidazo[4,5-b]pyridine (hereinafter referred to as the present fused heterocyclic compound 67) 0.32 g.

Present Fused Heterocyclic Compound 67

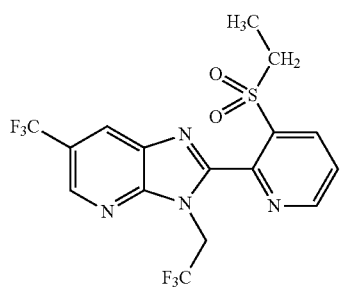 [SMILES: CCS(=O)(=O)c1cccnc1-c1nc2cc(C(F)(F)F)cnc2n1CC(F)(F)F]

¹H-NMR (CDCl₃) δ: 8.98 (1H, dd), 8.80 (1H, d), 8.59 (1H, dd), 8.37 (1H, d), 7.75 (1H, dd), 5.31 (2H, q), 3.95 (2H, q), 1.40 (3H, t).

Production Example 46

To a mixture of the present fused heterocyclic compound 66 (0.32 g) and chloroform 2 mL at ice temperature was added m-chloroperbenzoic acid (65% or more purity) 0.31 g, and then the mixture was allowed to warm to RT, and stirred for 1 hr. To the mixture was added saturated aqueous sodium bicarbonate and saturated aqueous sodium thiosulfate, and the reaction mixture was extracted with chloroform. The organic layer was washed with water, and dried over sodium sulfate, and then concentrated under reduced pressure. The resulting crude product was washed with hexane to give 2-(3-ethylsulfonyl-5-trifluoromethylpyridin-2-yl)-3-(2, 2, 2-trifluoroethyl)-6-trifluoromethyl-3H-imidazo[4,5-b]pyridine (hereinafter referred to as the present fused heterocyclic compound 68) 0.28 g.

Present Fused Heterocyclic Compound 68

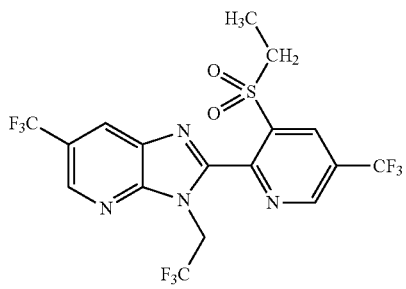 [SMILES: CCS(=O)(=O)c1cc(C(F)(F)F)cnc1-c1nc2cc(C(F)(F)F)cnc2n1CC(F)(F)F]

¹H-NMR (CDCl₃) δ: 9.22 (1H, d), 8.83-8.83 (2H, m), 8.40 (1H, d), 5.36 (2H, q), 4.05 (2H, q), 1.45 (3H, t).

Production Example 47 (1)

A mixture of 2-chloro-5-iodopyridine 20.0 g, sodium pentafluoropropionate 77.8 g, copper iodide (I) 31.8 g, xylene 84 mL, and N-methylpyrrolidone 84 mL was heated to 160° C., and stirred with heating to reflux for 6 hr. The reaction mixture was cooled to RT, and then to the reaction mixture was added water. The mixture was extracted with methyl-tert-butyl ether. The organic layer was dried over sodium sulfate, and then concentrated under reduced pressure to give 2-chloro-5-pentafluoroethylpyridine.

2-Chloro-5-pentafluoroethylpyridine

¹H-NMR (CDCl₃) δ: 8.65-8.62 (1H, m), 7.85-7.81 (1H, m), 7.48-7.44 (1H, m)

Production Example 47 (2)

A mixture of a half amount of 2-chloro-5-pentafluoroethylpyridine prepared in Production example 47 (1), zinc cyanide (II) 14.4 g, tetrakis(triphenylphosphine)palladium 2.42 g, and N-methylpyrrolidone 84 mL was heated to 80° C., and stirred with heating for 2.5 hr. The reaction mixture was cooled to RT, and then to the mixture was added water and methyl-tert-butyl ether. The mixture was filtrated with Celite (Trademark) to remove the resulting precipitate, and the resultant residue was washed with methyl-tert-butyl ether. The filtrate was extracted with methyl-tert-butyl ether, and the organic layer was dried over sodium sulfate, and then concentrated under reduced pressure. The crude product was treated with silica gel column chromatography to give 2-cyano-5-pentafluoroethylpyridine 4.19 g.

2-Cyano-5-pentafluoroethylpyridine

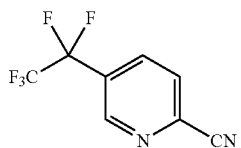 [SMILES: N#Cc1ccc(C(F)(F)C(F)(F)F)cn1]

$^1$H-NMR (CDCl$_3$) δ: 8.97-8.96 (1H, m), 8.12-8.09 (1H, m), 7.90-7.87 (1H, m)

Production Example 47 (3)

A mixture of water 17 mL and concentrated sulfuric acid 17 mL was heated to 100° C., and to the mixture was added dropwise 2-cyano-5-pentafluoroethylpyridine 3.81 g with heating, and then the mixture was stirred at 100° C. for 2.5 hr. The mixture was cooled to RT, and then the reaction mixture was added to iced water. The precipitated solid was collected by filtration, and washed with water. The resulting solid was dried under reduced pressure to give 5-pentafluoropyridine-2-carboxylic acid 3.52 g.

5-Pentafluoropyridine-2-carboxylic Acid

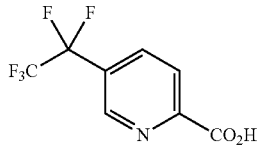 [SMILES: O=C(O)c1ccc(C(F)(F)C(F)(F)F)cn1]

$^1$H-NMR (CDCl$_3$) δ: 8.92-8.88 (1H, m), 8.44-8.39 (1H, m), 8.25-8.20 (1H, m)

Production Example 47 (4)

A mixture of tetramethylpiperidine 5.5 mL and THF 58 mL was cooled to −78° C., and then a solution of 1.6 M n-butyllithium in hexane was added dropwise into the mixture. The mixture was allowed to warm to RT, and then stirred for 10 min. The mixture was cooled to −78° C. again, and to the mixture was added dropwise a solution of 5-pentafluoropyridine-2-carboxylic acid 3.52 g in THF, and the mixture was stirred at −78° C. for 1 hr. To the mixture was added dropwise diethyldisulfide 4.0 mL at −78° C. Then the mixture was allowed to warm to RT and was stirred for 1 hr. To the reaction mixture was added 1N hydrochloric acid, and then to the mixture was added aqueous 5 N sodium hydroxide. The aqueous layer was washed with methyl-tert-butyl ether. To the aqueous layer was added 12 N hydrochloric acid, and the precipitated solid was collected by filtration and dissolved in methyl-tert-butyl ether. The mixture was dried over sodium sulfate, and then concentrated under reduced pressure to give 3-ethylsulfanyl-5-pentafluoroethylpyridine-2-carboxylic acid (hereinafter referred to as Intermediate compound (M2-7)) 1.99 g.

Intermediate Compound (M2-7)

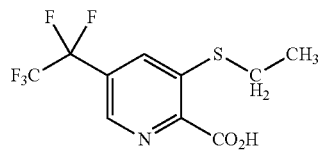

$^1$H-NMR (CDCl$_3$) δ: 8.51-8.50 (1H, m), 7.89-7.87 (1H, m), 3.01 (2H, q), 1.46 (3H, t)

Production Example 47 (5)

A mixture of N2-methyl-5-trifluoromethylpyridine-2,3-diamine 0.50 g, Intermediate compound (M2-7) 0.79 g, EDC hydrochloride 0.37 g, HOBt 35 mg, and pyridine 5 mL was stirred at RT for 3 hr. To the reaction mixture was added water, and the mixture was extracted with methyl-tert-butyl ether. The organic layer was dried over magnesium sulfate, and then concentrated under reduced pressure to give 3-ethylsulfanyl-5-pentafluoroethylpyridine-2-carboxylic acid (2-methylamino-5-trifluoromethylpyridin-3-yl)amide (hereinafter referred to as Intermediate compound (M3-45)).

Intermediate Compound (M3-45)

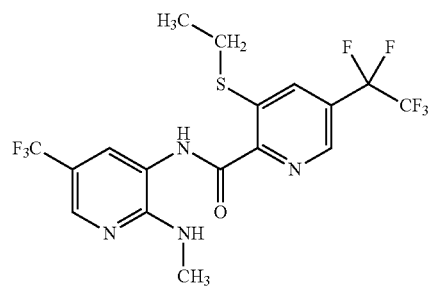 [SMILES: CCSc1cc(C(F)(F)C(F)(F)F)cnc1C(=O)Nc1cc(C(F)(F)F)cnc1NC]

$^1$H-NMR (CDCl$_3$) δ: 9.57 (1H, brs), 8.54-8.52 (1H, m), 8.37-8.35 (1H, m), 7.94-7.92 (1H, m), 7.89-7.87 (1H, m), 4.97 (1H, brs), 3.08 (3H, d), 2.99 (2H, q), 1.45 (3H, t)

A mixture of the total amount of the resulting Intermediate compound (M3-45) and acetic acid 5 mL was heated to 120° C., and stirred with heating to reflux for 3 hr. The mixture was cooled to RT, and then concentrated under reduced pressure. The crude product was treated with silica gel column chromatography to give 2-(3-ethylsulfanyl-5-pentafluoroethylpyridin-2-yl)-3-methyl-6-trifluoromethyl-3H-imidazo[4,5-b]pyridine (hereinafter referred to as the present fused heterocyclic compound 71) 0.77 g.

Present Fused Heterocyclic Compound 71

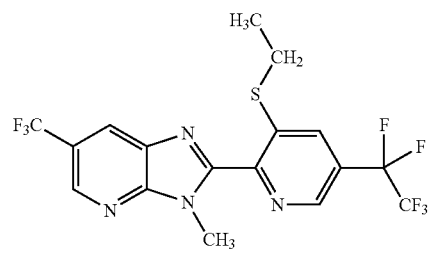 [SMILES: CCSc1cc(C(F)(F)C(F)(F)F)cnc1-c1nc2cc(C(F)(F)F)cnc2n1C]

$^1$H-NMR (CDCl$_3$) δ: 8.78-8.76 (1H, m), 8.71-8.69 (1H, m), 8.44-8.42 (1H, m), 7.91-7.89 (1H, m), 4.13 (3H, s), 3.02 (2H, q), 1.39 (3H, t)

Production Example 48

To a mixture of the present fused heterocyclic compound 71 0.47 g and chloroform 10 mL at ice temperature was added m-chloroperbenzoic acid (65% or more purity) 0.57 g, and then the mixture was allowed to warm to RT and stirred for 1 hr. To the mixture was added saturated aqueous sodium bicarbonate and saturated aqueous sodium thiosulfate, and the reaction mixture was extracted with chloroform. The organic layer was dried over sodium sulfate, and then concentrated under reduced pressure. The crude product was treated with silica gel column chromatography to give 2-(3-ethylsulfonyl-5-pentafluoroethylpyridin-2-yl)-3-methyl-6-trifluoromethyl-3H-imidazo[4,5-b]pyridine (hereinafter referred to as the present fused heterocyclic compound 72) 0.39 g.
Present Fused Heterocyclic Compound 72

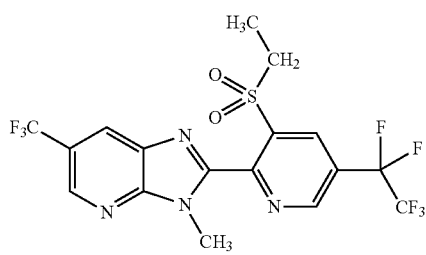 [SMILES: CCS(=O)(=O)c1cc(C(F)(F)C(F)(F)F)cnc1-c1nc2cc(C(F)(F)F)cnc2n1C]

$^1$H-NMR (CDCl$_3$) δ: 9.21-9.19 (1H, m), 8.81-8.79 (1H, m), 8.76-8.75 (1H, m), 8.35-8.33 (1H, m), 3.99-3.93 (5H, m), 1.41 (3H, t)

Production Example 49

A mixture of N2-methyl-5-pentafluoroethylpyridine-2,3-diamine 0.50 g, Intermediate compound (M2-7) 0.62 g, EDC hydrochloride 0.29 g, HOBt 28 mg, and pyridine 4 mL was stirred at RT for 3 hr. To the reaction mixture was added water, and the mixture was extracted with methyl-tert-butyl ether. The organic layer was dried over magnesium sulfate, and then concentrated under reduced pressure to give 3-ethylsulfanyl-5-pentafluoroethylpyridine-2-carboxylic acid (2-methylamino-5-pentafluoroethylpyridin-3-yl)amide (hereinafter referred to as Intermediate compound (M3-46)).
Intermediate Compound (M3-46)

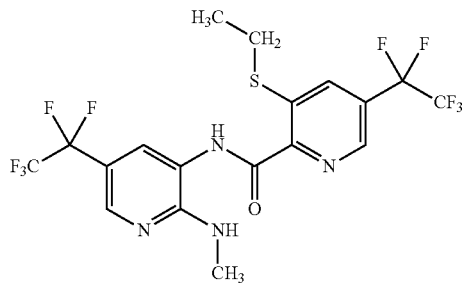 [SMILES: CCSc1cc(C(F)(F)C(F)(F)F)cnc1C(=O)Nc1cc(C(F)(F)C(F)(F)F)cnc1NC]

$^1$H-NMR (CDCl$_3$) δ: 9.59 (1H, brs), 8.54-8.52 (1H, m), 8.32-8.30 (1H, m), 7.89-7.87 (1H, m), 7.85-7.83 (1H, m), 5.04 (1H, brs), 3.09 (3H, d), 2.99 (2H, q), 1.45 (3H, t)

A mixture of the total amount of the resulting Intermediate compound (M3-46) and acetic acid 4 mL was heated to 120° C. and stirred with heating to reflux for 3 hr. The mixture was cooled to RT, and then concentrated under reduced pressure. The crude product was treated with silica gel column chromatography to give 2-(3-ethylsulfanyl-5-pentafluoroethylpyridin-2-yl)-3-methyl-6-pentafluoroethyl-3H-imidazo[4,5-b]pyridine (hereinafter referred to as the present fused heterocyclic compound 73) 0.84 g.
Present Fused Heterocyclic Compound 73

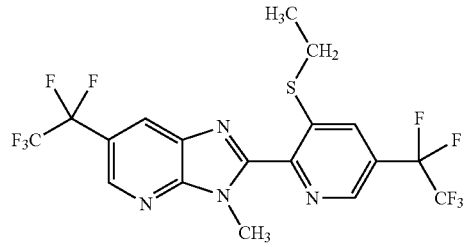 [SMILES: CCSc1cc(C(F)(F)C(F)(F)F)cnc1-c1nc2cc(C(F)(F)C(F)(F)F)cnc2n1C]

$^1$H-NMR (CDCl$_3$) δ: 8.72-8.69 (2H, m), 8.42-8.41 (1H, m), 7.90-7.89 (1H, m), 4.15-4.12 (3H, m), 3.02 (2H, q), 1.40 (3H, t)

Production Example 50

To a mixture of the present fused heterocyclic compound 73 0.54 g and chloroform 11 mL at ice temperature was added m-chloroperbenzoic acid (65% or more purity) 0.59 g, and then the mixture was allowed to warm to RT and stirred for 1 hr. To the mixture was added saturated aqueous sodium bicarbonate and saturated aqueous sodium thiosulfate, and the reaction mixture was extracted with chloroform. The organic layer was dried over sodium sulfate, and then concentrated under reduced pressure.

The crude product was treated with silica gel column chromatography to give 2-(3-ethylsulfonyl-5-pentafluoroethylpyridin-2-yl)-3-methyl-6-pentafluoroethyl-3H-imidazo[4,5-b]pyridine (hereinafter referred to as the present fused heterocyclic compound 74) 0.34 g.
Present Fused Heterocyclic Compound 74

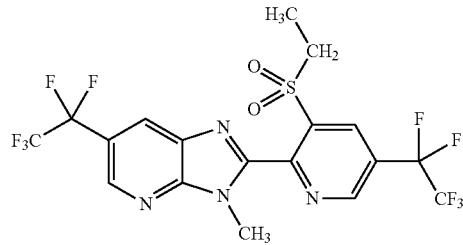 [SMILES: CCS(=O)(=O)c1cc(C(F)(F)C(F)(F)F)cnc1-c1nc2cc(C(F)(F)C(F)(F)F)cnc2n1C]

$^1$H-NMR (CDCl$_3$) δ: 9.21-9.20 (1H, m), 8.77-8.74 (2H, m), 8.32-8.31 (1H, m), 4.00-3.94 (5H, m), 1.41 (3H, t)

Production Example 51

2-(3-Ethylsulfonylpyridin-2-yl)-1-methyl-5-trifluoromethoxy-1H-benzimidazole (hereinafter referred to as the present fused heterocyclic compound 50) was prepared in a similar manner as described for the preparation of Production example 5 by using 2-(3-ethylsulfanylpyridin-2-yl)-1-methyl-5-trifluoromethoxy-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 50

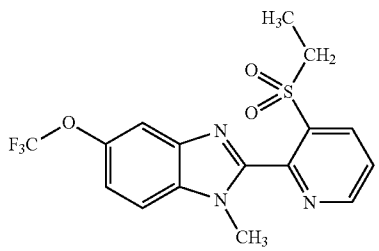 [SMILES: CCS(=O)(=O)c1cccnc1-c1nc2cc(OC(F)(F)F)ccc2n1C]

¹H-NMR (CDCl₃) δ: 8.93 (1H, dd), 8.49 (1H, dd), 7.68-7.62 (2H, m), 7.43 (1H, d), 7.25 (1H, d), 3.84 (2H, q), 3.73 (3H, s), 1.31 (3H, q).

Production Example 52

2-(3-Ethylsulfonylpyridin-2-yl)-5-trifluoromethyl-benzothiazole (hereinafter referred to as the present fused heterocyclic compound 53) was prepared in a similar manner as described for the preparation of Production example 5 by using 2-(3-ethylsulfanylpyridin-2-yl)-5-trifluoromethyl-benzothiazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 53

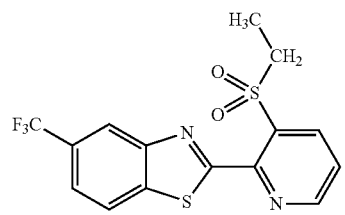 [SMILES: CCS(=O)(=O)c1cccnc1-c1nc2cc(C(F)(F)F)ccc2s1]

¹H-NMR (CDCl₃) δ: 8.92 (1H, dd), 8.65 (1H, dd), 8.37 (1H, s), 8.11 (1H, d), 7.72 (1H, dd), 7.66 (1H, dd), 4.19 (2H, q), 1.45 (3H, t).

Production Example 53

2-(3-Ethylsulfonylpyridin-2-yl)-6-trifluoromethyl-oxazolo[5,4-b]pyridine (hereinafter referred to as the present fused heterocyclic compound 81) was prepared in a similar manner as described for the preparation of Production example 5 by using 2-(3-ethylsulfanylpyridin-2-yl)-6-trifluoromethyl-oxazolo[5,4-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 81

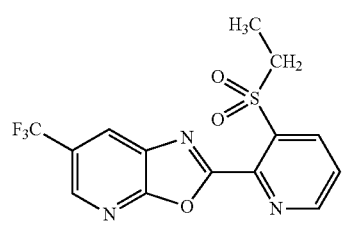 [SMILES: CCS(=O)(=O)c1cccnc1-c1nc2cc(C(F)(F)F)cnc2o1]

¹H-NMR (CDCl₃) δ: 9.06 (1H, dd), 8.79 (1H, d), 8.58 (1H, dd), 8.43 (1H, d), 7.78 (1H, dd), 3.88 (2H, q), 1.44 (3H, t).

Production Example 54

2-(3-Ethylsulfonylpyridin-2-yl)-5-trifluoromethyl-benzoxazole (hereinafter referred to as the present fused heterocyclic compound 85) was prepared in a similar manner as described for the preparation of Production example 5 by using 2-(3-ethylsulfanylpyridin-2-yl)-5-trifluoromethyl-benzoxazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 85

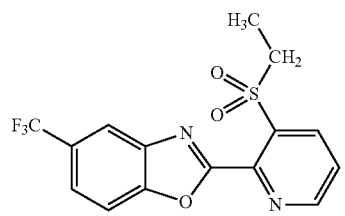 [SMILES: CCS(=O)(=O)c1cccnc1-c1nc2cc(C(F)(F)F)ccc2o1]

¹H-NMR (CDCl₃) δ: 9.03 (1H, dd), 8.60 (1H, dd), 8.16-8.13 (1H, m), 7.82-7.71 (3H, m), 4.01 (2H, q), 1.43 (3H, t).

Production Example 55

To phosphorus oxychloride 2.04 g at ice temperature was added the present fused heterocyclic compound 48 (0.20 g), and the mixture was stirred at 110° C. for 2 hr. The reaction mixture was allowed to cool to RT, and to the reaction mixture at ice temperature was added saturated aqueous sodium bicarbonate, and the resulting mixture was extracted with ethyl acetate. The organic layer was dried over anhydrous magnesium sulfate, and then concentrated under reduced pressure. The resultant residue was treated with silica gel column chromatography to give 5-chloro-2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 89) 0.21 g.
Present Fused Heterocyclic Compound 89

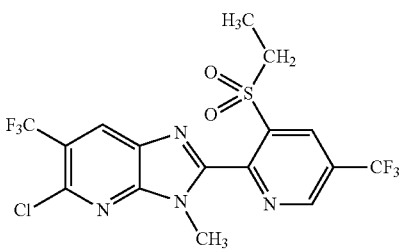 [SMILES: CCS(=O)(=O)c1cc(C(F)(F)F)cnc1-c1nc2cc(C(F)(F)F)c(Cl)nc2n1C]

¹H-NMR (CDCl₃) δ: 9.25 (1H, d), 8.78 (1H, d), 8.43 (1H, s), 3.97-3.87 (5H, m), 1.41 (3H, t).

Production Example 56

To a mixture of the present fused heterocyclic compound 89 (0.20 g) and NMP 0.5 mL was added dimethylamine (in methanol, 2.0 mol/L) 0.3 mL, and the mixture was stirred at RT for 1 hr and at 50° C. for 3 hr. To the reaction mixture allowed to cool to RT was added dimethylamine (in methanol, 2.0 mol/L) 0.3 mL, and the mixture was stirred at 50° C. for 3 hr. To the reaction mixture allowed to cool to RT was added water, and the resulting mixture was extracted with ethyl acetate. The organic layer was dried over anhydrous magnesium sulfate, and then concentrated under reduced pressure. The resultant residue was treated with silica gel column chromatography to give 5-dimethylamino-2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 99) 0.03 g.

Present Fused Heterocyclic Compound 99

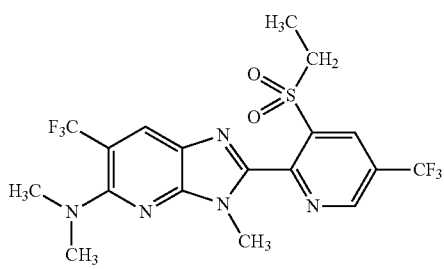 [SMILES: CCS(=O)(=O)c1cc(C(F)(F)F)cnc1-c1nc2cc(C(F)(F)F)c(N(C)C)nc2n1C]

$^1$H-NMR (CDCl$_3$) δ: 9.20 (1H, d), 8.76 (1H, d), 8.26 (1H, s), 4.02 (2H, q), 3.84 (3H, s), 3.04 (6H, s), 1.41 (3H, t).

Production Example 57

7-Cyano-2-(3-ethylsulfonylpyridin-2-yl)-1-methyl-5-trifluoromethyl-1H-benzimidazole (hereinafter referred to as the present fused heterocyclic compound 130) was prepared in a similar manner as described for the preparation of Production example 5 by using 7-cyano-2-(3-ethylsulfanylpyridin-2-yl)-1-methyl-5-trifluoromethyl-1H-benzimidazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 130

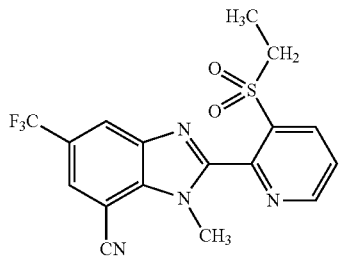 [SMILES: CCS(=O)(=O)c1cccnc1-c1nc2cc(C(F)(F)F)cc(C#N)c2n1C]

$^1$H-NMR (CDCl$_3$) δ: 9.02 (1H, dd), 8.54 (1H, dd), 8.28 (1H, s), 7.95 (1H, s), 7.77 (1H, dd), 4.06 (3H, s), 3.74 (2H, q), 1.35 (3H, t).

Production Example 58

2-(5-Chloro-3-ethylsulfonylpyridin-2-yl)-3-methyl-6-pentafluoroethyl-3H-imidazo[4,5-b]pyridine (hereinafter referred to as the present fused heterocyclic compound 312) was prepared in a similar manner as described for the preparation of Production example 5 by using 2-(5-chloro-3-ethylsulfanylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 312

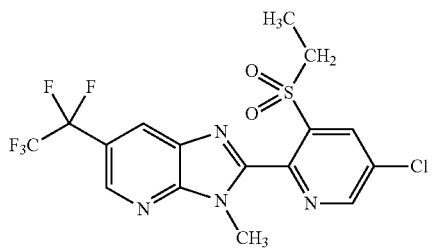 [SMILES: CCS(=O)(=O)c1cc(Cl)cnc1-c1nc2cc(C(F)(F)C(F)(F)F)cnc2n1C]

$^1$H-NMR (CDCl$_3$) δ: 8.95 (1H, d), 8.72-8.71 (1H, m), 8.53 (1H, d), 8.30-8.28 (1H, m), 3.94-3.87 (5H, m), 1.40 (3H, t)

To a mixture of the present fused heterocyclic compound 48 (0.30 g), triethylamine 0.14 mL, and acetonitrile 1 mL, trimethylsilyl cyanide 0.35 mL was added, and the mixture was stirred at 110° C. for 3 hr. To the reaction mixture allowed to cool to RT was added water, and the resulting mixture was extracted with ethyl acetate. The organic layer was dried over anhydrous magnesium sulfate, and then concentrated under reduced pressure. The resultant residue was treated with silica gel column chromatography to give 5-cyano-2-(3-ethylsulfonyl-5-trifluoromethylpyridin-2-yl)-3-methyl-6-trifluoromethyl-3H-imidazo[4,5-b]pyridine (hereinafter referred to as the present fused heterocyclic compound 399) 0.23 g.

Present Fused Heterocyclic Compound 399

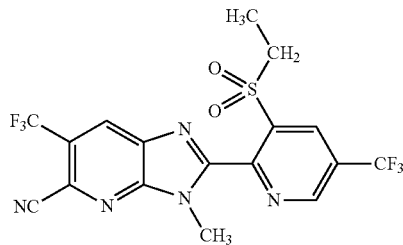

$^1$H-NMR (CDCl$_3$) δ: 9.28 (1H, d), 8.79 (1H, d), 8.48 (1H, s), 3.96 (3H, s), 3.89 (2H, q), 1.42 (3H, t).

Production Example 60

To a mixture of 2-(3-ethylsulfanylpyridin-2-yl)-1-methyl-7-methylsulfanyl-5-trifluoromethyl-1H-benzimidazole 0.11 g and chloroform 5 mL at ice temperature was added m-chloroperbenzoic acid (65% or more purity) 0.32 g, and then the resulting mixture was stirred at RT for 5 hr. The reaction mixture was cooled at ice temperature, and to the mixture was added m-chloroperbenzoic acid (65% or more purity) 0.32 g, and then the mixture was stirred at RT for 3 hr. To the reaction mixture was added aqueous 10% sodium thiosulfate and saturated aqueous sodium bicarbonate, and the reaction mixture was extracted with chloroform. The organic layer was washed with water, dried over anhydrous magnesium sulfate, and then concentrated under reduced pressure to give 2-(3-ethylsulfonylpyridin-2-yl)-1-methyl-7- methylsulfonyl-5-trifluoromethyl-1H-benzimidazole (hereinafter referred to as the present fused heterocyclic compound 404) 0.62 g.

Present Fused Heterocyclic Compound 404

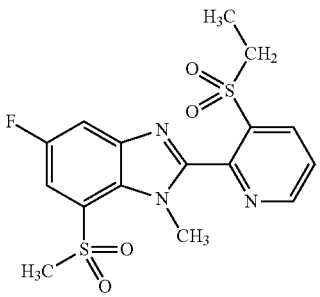 [SMILES: CCS(=O)(=O)c1cccnc1-c1nc2cc(F)cc(S(C)(=O)=O)c2n1C]

$^1$H-NMR (CDCl$_3$) δ: 9.08-8.97 (1H, m), 8.58-8.46 (1H, m), 8.41-8.26 (2H, m), 7.84-7.70 (1H, m), 4.12 (3H, s), 3.72-3.59 (2H, m), 3.33 (3H, s), 1.39-1.22 (3H, m).

Production Example 61

To a mixture of the present fused heterocyclic compound 19 (2.0 g) and chloroform 20 mL at ice temperature was added m-chloroperbenzoic acid (65% or more purity) 3.03 g, and then the mixture was stirred with heating to reflux for 3 hr. The reaction mixture was cooled at ice temperature, and to the mixture was added m-chloroperbenzoic acid (65% or more purity) 3.03 g, and then the mixture was stirred with heating to reflux for 3 hr. The reaction mixture was cooled at ice temperature, and to the mixture was added m-chloroperbenzoic acid (65% or more purity) 3.03 g, and then the mixture was stirred with heating to reflux for 3 hr. To the reaction mixture allowed to cool to RT was added aqueous 10% sodium thiosulfate and saturated aqueous sodium bicarbonate, and the reaction mixture was extracted with chloroform. The organic layer was washed with water, dried over anhydrous magnesium sulfate, and then concentrated under reduced pressure to give 2-(3-ethylsulfonyl-5-trifluoromethyl-pyridin-2-yl)-3-methyl-6-pentafluoroethyl-3H-imidazo[4,5-b]pyridine 4-oxide (hereinafter referred to as the present fused heterocyclic compound 409) 1.10 g.

Present Fused Heterocyclic Compound 409

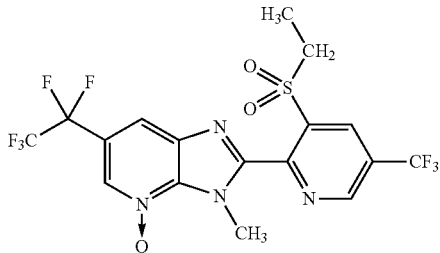 [SMILES: CCS(=O)(=O)c1cc(C(F)(F)F)cnc1-c1nc2cc(C(F)(F)C(F)(F)F)c[n+]([O-])c2n1C]

$^1$H-NMR (CDCl$_3$) δ: 9.27 (1H, d), 8.77 (1H, d), 8.45 (1H, s), 7.92 (1H, s), 4.34 (3H, s), 3.81 (2H, q), 1.40 (3H, t).

Production Example 62

To a mixture of the present fused heterocyclic compound 19 (0.65 g), methanol 6 mL, THF 6 mL, and water 2 mL was added sodium hydroxide 0.54 g, and the mixture was stirred with heating to reflux for 1 day. To the reaction mixture allowed to cool to RT was added water, and the resulting mixture was extracted with ethyl acetate. The organic layer was dried over anhydrous magnesium sulfate, and then concentrated under reduced pressure. The resultant residue was treated with silica gel column chromatography to give 2-(3-ethylsulfonyl-5-trimethoxymethyl-pyridin-2-yl)-3-methyl-6-pentafluoroethyl-3H-imidazo[4,5-b]pyridine (hereinafter referred to as the present fused heterocyclic compound 414) 0.25 g.

Present Fused Heterocyclic Compound 414

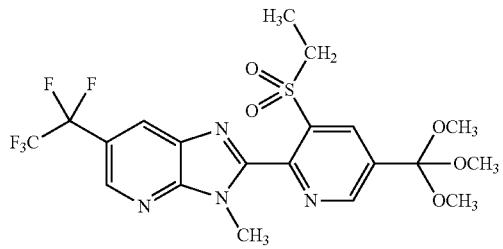 [SMILES: CCS(=O)(=O)c1cc(C(OC)(OC)OC)cnc1-c1nc2cc(C(F)(F)C(F)(F)F)cnc2n1C]

$^1$H-NMR (CDCl$_3$) δ: 9.16 (1H, d), 8.74 (1H, d), 8.70 (1H, d), 8.31 (1H, d), 3.93 (3H, s), 3.88 (2H, q), 3.28 (9H, s), 1.38 (3H, t).

Production Example 63

2-(3-Methylsulfonyl-5-trifluoromethylpyridin-2-yl)-3-methyl-6-pentafluoroethyl-3H-imidazo[4,5-b]pyridine (hereinafter referred to as the present fused heterocyclic compound 419) was prepared in a similar manner as described for the preparation of Production example 5 by using 2-(3-methylsulfanyl-5-trifluoromethylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 419

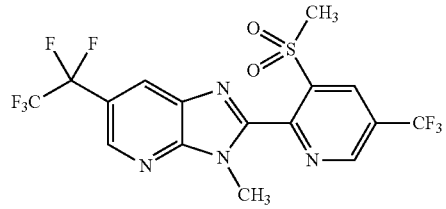 [SMILES: Cn1c(-c2ncc(C(F)(F)F)cc2S(C)(=O)=O)nc2cc(C(F)(F)C(F)(F)F)cnc21]

$^1$H-NMR (CDCl$_3$) δ: 9.25 (1H, s), 8.85 (1H, s), 8.75 (1H, s), 8.32 (1H, s), 3.96 (3H, s), 3.73 (3H, s)

Production Example 64

2-(3-Propylsulfonyl-5-trifluoromethylpyridin-2-yl)-3-methyl-6-pentafluoroethyl-3H-imidazo[4,5-b]pyridine (hereinafter referred to as the present fused heterocyclic compound 421) was prepared in a similar manner as described for the preparation of Production example 5 by using 2-(3-propylsulfanyl-5-trifluoromethylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).

Present Fused Heterocyclic Compound 421

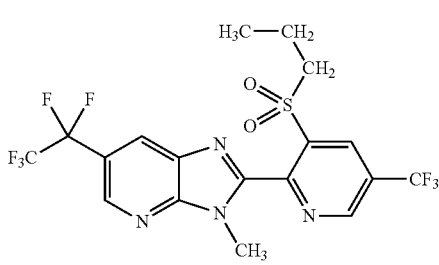 [SMILES: CCCS(=O)(=O)c1cc(C(F)(F)F)cnc1-c1nc2cc(C(F)(F)C(F)(F)F)cnc2n1C]

¹H-NMR (CDCl₃) δ: 9.24 (1H, s), 8.79 (1H, s), 8.74 (1H, s), 8.31 (1H, s), 3.95-3.88 (5H, m), 1.92-1.81 (2H, m), 1.13 (3H, t)

Production Example 65

2-(3-Isopropylsulfonyl-5-trifluoromethylpyridin-2-yl)-3-methyl-6-pentafluoroethyl-3H-imidazo[4,5-b]pyridine (hereinafter referred to as the present fused heterocyclic compound 423) was prepared in a similar manner as described for the preparation of Production example 5 by using 2-(3-isopropylsulfanyl-5-trifluoromethylpyridin-2-yl)-3-methyl-6-pentafluoroethyl-3H-imidazo[4,5-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 423

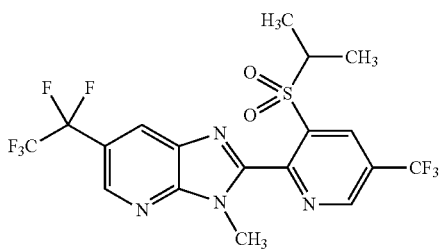 [SMILES: CC(C)S(=O)(=O)c1cc(C(F)(F)F)cnc1-c1nc2cc(C(F)(F)C(F)(F)F)cnc2n1C]

¹H-NMR (CDCl₃) δ: 9.24 (1H, s), 8.75 (2H, d), 8.31 (1H, s), 4.71-4.60 (1H, m), 3.93 (3H, s), 1.39 (6H, d)

Production Example 66

2-(3-Ethylsulfonylpyridin-2-yl)-6-pentafluoroethyl-oxazolo[5,4-b]pyridine (hereinafter referred to as the present fused heterocyclic compound 464) was prepared in a similar manner as described for the preparation of Production example 5 by using 2-(3-ethylsulfanylpyridin-2-yl)-6-pentafluoroethyl-oxazolo[5,4-b]pyridine instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 464

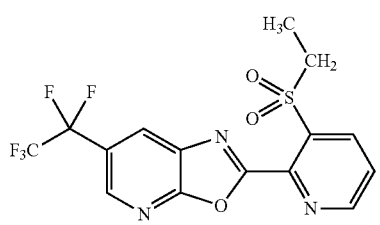 [SMILES: CCS(=O)(=O)c1cccnc1-c1nc2cc(C(F)(F)C(F)(F)F)cnc2o1]

¹H-NMR (CDCl₃) δ: 9.07 (1H, dd), 8.74 (1H, d), 8.59 (1H, dd), 8.41 (1H, d), 7.80 (1H, dd), 3.91 (2H, q), 1.45 (3H, t).

Production Example 67

2-(3-Ethylsulfonylpyridin-2-yl)-5-pentafluoroethyl-benzoxazole (hereinafter referred to as the present fused heterocyclic compound 467) was prepared in a similar manner as described for the preparation of Production example 5 by using 2-(3-ethylsulfanylpyridin-2-yl)-5-pentafluoroethyl-benzoxazole instead of 2-(3-ethylsulfanyl-5-trifluoromethylpyridin-2-yl)-3-methyl-6-trifluoromethyl-3H-imidazo[4,5-b]pyridine (the present fused heterocyclic compound 4).
Present Fused Heterocyclic Compound 467

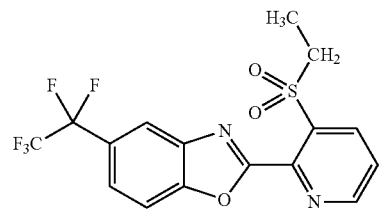 [SMILES: CCS(=O)(=O)c1cccnc1-c1nc2cc(C(F)(F)C(F)(F)F)ccc2o1]

¹H-NMR (CDCl₃) δ: 9.04 (1H, dd), 8.61 (1H, dd), 8.12 (1H, d), 7.82 (1H, d), 7.75 (1H, dd), 7.72 (1H, dd), 4.04 (2H, q), 1.44 (3H, t).

Production Example 68(1)

A mixture of 2-amino-4-(trifluoromethylsulfanyl)phenol 1.0 g, 3-ethylsulfanylpicolinic acid 0.87 g, EDC hydrochloride 1.10 g, and chloroform 10 mL was stirred at RT for 30 min. To the reaction mixture was added water, and the resulting mixture was extracted with ethyl acetate. The organic layer was washed with saturated aqueous sodium bicarbonate and brine, dried over anhydrous magnesium sulfate, and then concentrated under reduced pressure. The resultant residue was treated with silica gel column chromatography to give 3-ethylsulfanyl-N-[2-hydroxy-5-(trifluoromethylsulfanyl)phenyl]picolinamide 1.32 g.

3-Ethylsulfanyl-N-[2-hydroxy-5-(trifluoromethylsulfanyl)phenyl]picolinamide

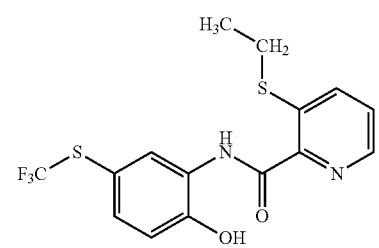 [SMILES: CCSc1cccnc1C(=O)Nc1cc(SC(F)(F)F)ccc1O]

¹H-NMR (CDCl₃) δ: 10.40 (1H, brs), 9.63 (1H, s), 8.36 (1H, dd), 7.75 (1H, dd), 7.53 (1H, d), 7.45 (1H, dd), 7.41 (1H, dd), 7.08 (1H, d), 2.97 (2H, q), 1.44 (3H, t).

Production Example 68(2)

A mixture of 3-ethylsulfanyl-N-[2-hydroxy-5-(trifluoromethylsulfanyl)phenyl]picolinamide 1.23 g, di-2- methoxyethyl azodicarboxylate (hereinafter referred to as DMEAD) 1.28 g, triphenylphosphine 1.39 g, and THF 30 mL was stirred at RT for 1 hr and at 50° C. for 1 hr. The reaction mixture allowed to cool to RT was concentrated under reduced pressure, and to the mixture was added water. The resulting mixture was extracted with ethyl acetate. The organic layer was washed with saturated aqueous sodium bicarbonate and brine, dried over anhydrous magnesium sulfate, and then concentrated under reduced pressure. The resultant residue was treated with silica gel column chromatography to give 2-(3-ethylsulfanylpyridin-2-yl)-5-(trifluoromethylsulfanyl)benzoxazole (hereinafter referred to as the present fused heterocyclic compound 441) 1.21 g.

Present Fused Heterocyclic Compound 441

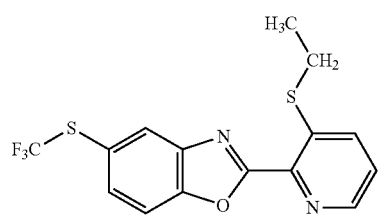 [SMILES: CCSc1cccnc1-c1nc2cc(SC(F)(F)F)ccc2o1]

$^1$H-NMR (CDCl$_3$) δ: 8.59 (1H, dd), 8.27 (1H, s), 7.78 (1H, dd), 7.75-7.69 (2H, m), 7.42 (1H, dd), 3.07 (2H, q), 1.47 (3H, t).

Production Example 69

To a mixture of the present fused heterocyclic compound 441 (1.06 g) and chloroform 30 mL at ice temperature was added m-chloroperbenzoic acid (65% or more purity) 1.47 g, and then the mixture was stirred at RT for 6 hr. To the reaction mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfonylpyridin-2-yl)-5-(trifluoromethylsulfanyl)benzoxazole (hereinafter referred to as the present fused heterocyclic compound 443) 0.87 g and 2-(3-ethylsulfonylpyridin-2-yl)-5-(trifluoromethylsulfinyl)benzoxazole (hereinafter referred to as the present fused heterocyclic compound 444) 0.17 g.

Present Fused Heterocyclic Compound 443

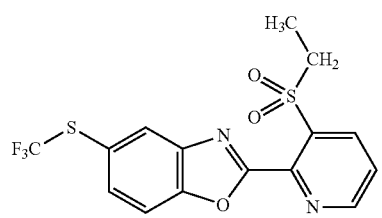 [SMILES: CCS(=O)(=O)c1cccnc1-c1nc2cc(SC(F)(F)F)ccc2o1]

$^1$H-NMR (CDCl$_3$) δ: 9.03 (1H, dd), 8.60 (1H, dd), 8.19 (1H, d), 7.80-7.71 (3H, m), 4.02 (2H, q), 1.43 (3H, t).

Present Fused Heterocyclic Compound 444

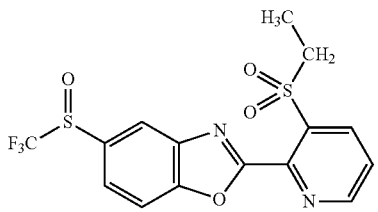 [SMILES: CCS(=O)(=O)c1cccnc1-c1nc2cc(S(=O)C(F)(F)F)ccc2o1]

$^1$H-NMR (CDCl$_3$) δ: 9.04 (1H, dd), 8.61 (1H, dd), 8.35 (1H, d), 7.96-7.86 (2H, m), 7.77 (1H, dd), 4.01 (2H, q), 1.44 (3H, t).

Production Example 70

To a mixture of the present fused heterocyclic compound 443 (0.35 g) and chloroform 8 mL at ice temperature was added m-chloroperbenzoic acid (65% or more purity) 0.43 g, and then the mixture was stirred at 40° C. for 6 hr. The reaction mixture was allowed to cool to RT, and to the mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. To the resultant residue was added acetonitrile 4 mL, sodium tungstate dihydrate 30 mg, and aqueous hydrogen peroxide (30%) 4 mL, and the mixture was stirred at 80° C. for 6 hr. The reaction mixture was allowed to cool to RT, and to the mixture was added water. The precipitated solid was removed by filtration, and to the filtrate was added aqueous 10% sodium sulfite. The resulting mixture was extracted with ethyl acetate. The organic layer was washed with water and brine, dried over anhydrous magnesium sulfate, and then concentrated under reduced pressure. The resultant residue was treated with silica gel column chromatography to give 2-(3-ethylsulfonylpyridin-2-yl)-5-(trifluoromethylsulfonyl)benzoxazole (hereinafter referred to as the present fused heterocyclic compound 445) 0.35 g.

Present Fused Heterocyclic Compound 445

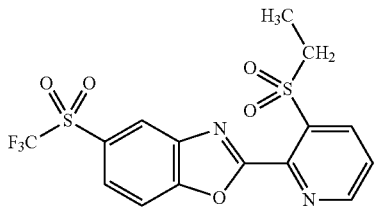 [SMILES: CCS(=O)(=O)c1cccnc1-c1nc2cc(S(=O)(=O)C(F)(F)F)ccc2o1]

$^1$H-NMR (CDCl$_3$) δ: 9.05 (1H, dd), 8.61 (1H, dd), 8.59 (1H, d), 8.17 (1H, dd), 7.96 (1H, d), 7.80 (1H, dd), 3.98 (2H, q), 1.45 (3H, t).

Production Example 71 (1)

A mixture of 2-amino-4-(trifluoromethylsulfanyl)phenol 1.0 g, 3-chloro-5-trifluoromethylpicolinic acid 1.08 g, EDC hydrochloride 1.10 g, and chloroform 10 mL was stirred at RT for 1 hr. To the reaction mixture was added water, and the resulting mixture was extracted with ethyl acetate. The organic layer was washed with saturated aqueous sodium bicarbonate, water, and brine, dried over anhydrous magnesium sulfate, and then concentrated under reduced pressure to give 3-chloro-5-trifluoromethyl-N-[2-hydroxy-5-(trifluoromethylsulfanyl)phenyl]picolinamide 1.94 g.

3-chloro-5-trifluoromethyl-N-[2-hydroxy-5-(trifluoromethylsulfanyl)phenyl]picolinamide

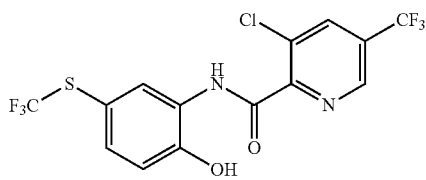 [SMILES: O=C(Nc1cc(SC(F)(F)F)ccc1O)c1ncc(C(F)(F)F)cc1Cl]

$^1$H-NMR (CDCl$_3$) δ: 8.78 (1H, d), 8.15 (1H, d), 8.09 (1H, d), 7.37 (1H, dd), 7.04 (1H, d).

Production Example 71 (2)

To a mixture of 3-chloro-5-trifluoromethyl-N-[2-hydroxy-5-(trifluoromethylsulfanyl)phenyl]picolinamide 1.93 g, DMF 6 mL, THF 1 mL, and ethyl mercaptan 0.38 mL at ice temperature was added potassium tert-butoxide 0.62 g, and the mixture was stirred at RT for 2 hr. To the reaction mixture was added water, and the resulting mixture was extracted with ethyl acetate. The organic layer was washed with water and brine, dried over anhydrous magnesium sulfate, and then concentrated under reduced pressure. The resultant residue was treated with silica gel column chromatography to give 3-ethylsulfanyl-5-trifluoromethyl-N-[2-hydroxy-5-(trifluoromethylsulfanyl)phenyl]picolinamide 1.45 g.

3-Ethylsulfanyl-5-trifluoromethyl-N-[2-hydroxy-5-(trifluoromethylsulfanyl)phenyl]picolinamide

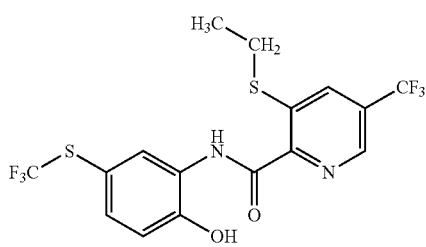 [SMILES: CCSc1cc(C(F)(F)F)cnc1C(=O)Nc1cc(SC(F)(F)F)ccc1O]

$^1$H-NMR (CDCl$_3$) δ: 10.31 (1H, s), 8.96 (1H, brs), 8.58 (1H, d), 7.91 (1H, d), 7.70 (1H, d), 7.43 (1H, dd), 7.07 (1H, d), 3.00 (2H, q), 1.47 (3H, t).

Production Example 71 (3)

A mixture of 3-ethylsulfanyl-5-trifluoromethyl-N-[2-hydroxy-5-(trifluoromethylsulfanyl)phenyl]picolinamide 1.45 g, DMEAD 1.19 g, triphenylphosphine 1.29 g, and THF 30 mL was stirred at RT for 1 hr and at 50° C. for 1 hr. The reaction mixture allowed to cool to RT was concentrated under reduced pressure, and then to the residue was added water, the resulting mixture was extracted with ethyl acetate. The organic layer was washed with saturated aqueous sodium bicarbonate and brine, dried over anhydrous magnesium sulfate, and then concentrated under reduced pressure. The resultant residue was treated with silica gel column chromatography to give 2-(3-ethylsulfanyl-5-trifluoromethylpyridin-2-yl)-5-(trifluoromethylsulfanyl)benzoxazole (hereinafter referred to as the present fused heterocyclic compound 451) 1.31 g.

Present Fused Heterocyclic Compound 451

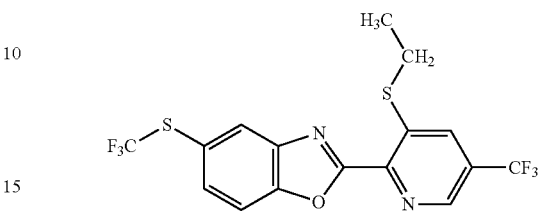

$^1$H-NMR (CDCl$_3$) δ: 8.78 (1H, d), 8.30 (1H, s), 7.94 (1H, d), 7.77-7.75 (2H, m), 3.11 (2H, q), 1.51 (3H, t).

Production Example 72

To a mixture of the present fused heterocyclic compound 451 (1.13 g) and chloroform 25 mL at ice temperature was added m-chloroperbenzoic acid (65% or more purity) 0.56 g, and then the mixture was stirred at 0° C. for 40 min. To the reaction mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfinyl-5-trifluoromethylpyridin-2-yl)-5-(trifluoromethylsulfanyl)benzoxazole (hereinafter referred to as the present fused heterocyclic compound 452) 1.01 g.

Present Fused Heterocyclic Compound 452

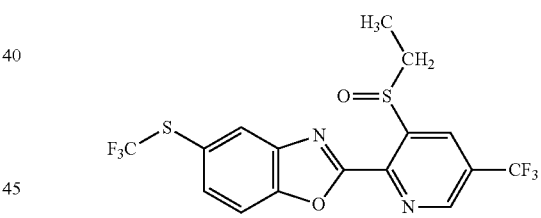

$^1$H-NMR (CDCl$_3$) δ: 9.13 (1H, d), 8.91 (1H, d), 8.25 (1H, s), 7.85-7.79 (2H, m), 3.60-3.49 (1H, m), 3.13-3.02 (1H, m), 1.44 (3H, t).

Production Example 73

To a mixture of the present fused heterocyclic compound 452 (1.01 g) and chloroform 20 mL at ice temperature was added m-chloroperbenzoic acid (65% or more purity) 0.56 g, and then the mixture was stirred at RT for 6 hr. To the reaction mixture was added m-chloroperbenzoic acid (65% or more purity) 0.20 g, and then the reaction mixture was stirred at RT for 3 hr. To the reaction mixture was added aqueous 10% sodium sulfite, and the reaction mixture was extracted with chloroform. The organic layer was washed with saturated aqueous sodium bicarbonate, and dried over anhydrous magnesium sulfate, and then concentrated under reduced pressure. The resultant residue was treated with silica gel column chromatography to give 2-(3-ethylsulfonyl-5-trifluoromethylpyridin-2-yl)-5-(trifluoromethylsulfanyl)benzoxazole (hereinafter referred to as the present fused heterocyclic compound 453) 0.53 g and 2-(3-ethylsulfonyl-5-trifluoromethylpyridin-2-yl)-5-(trifluoromethylsulfinyl)benzoxazole (hereinafter referred to as the present fused heterocyclic compound 454) 0.48 g.

Present Fused Heterocyclic Compound 453

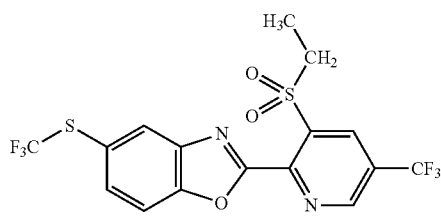 [SMILES: CCS(=O)(=O)c1cc(C(F)(F)F)cnc1-c1nc2cc(SC(F)(F)F)ccc2o1]

¹H-NMR (CDCl₃) δ: 9.25 (1H, d), 8.84 (1H, d), 8.22 (1H, d), 7.82 (1H, dd), 7.77 (1H, d), 4.11 (2H, q), 1.47 (3H, t).

Present Fused Heterocyclic Compound 454

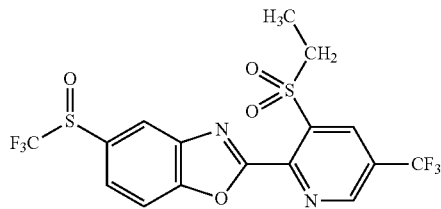 [SMILES: CCS(=O)(=O)c1cc(C(F)(F)F)cnc1-c1nc2cc(S(=O)C(F)(F)F)ccc2o1]

¹H-NMR (CDCl₃) δ: 9.27 (1H, d), 8.85 (1H, d), 8.39 (1H, s), 7.96 (1H, d), 7.92 (1H, d), 4.09 (2H, q), 1.48 (3H, t).

Production Example 74

The present fused heterocyclic compound 454 (0.26 g), acetonitrile 4 mL, sodium tungstate dihydrate 18 mg, and aqueous hydrogen peroxide (30%) 3.5 mL was mixed, and the mixture was stirred at 85° C. for 5 hr. The reaction mixture was allowed to cool to RT, and to the mixture was added aqueous hydrogen peroxide (30%) 0.5 mL, and the mixture was stirred at 85° C. for 3 hr. The reaction mixture was allowed to cool to RT, and to the mixture was added water. The precipitated solid was removed by filtration, and to the filtrate was added aqueous 10% sodium sulfite. The resulting mixture was extracted with ethyl acetate. The organic layer was washed with water and brine, dried over anhydrous magnesium sulfate, and then concentrated under reduced pressure. The resultant residue was treated with silica gel column chromatography to give 2-(3-ethylsulfonyl-5-trifluoromethylpyridin-2-yl)-5-(trifluoromethylsulfonyl)benzoxazole (hereinafter referred to as the present fused heterocyclic compound 455) 0.24 g.

Present Fused Heterocyclic Compound 455

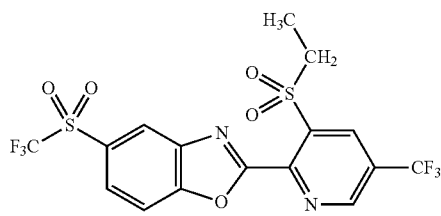 [SMILES: CCS(=O)(=O)c1cc(C(F)(F)F)cnc1-c1nc2cc(S(=O)(=O)C(F)(F)F)ccc2o1]

¹H-NMR (CDCl₃) δ: 9.28 (1H, d), 8.84 (1H, d), 8.62 (1H, d), 8.21 (1H, dd), 8.00 (1H, d), 4.05 (2H, q), 1.49 (3H, t).

Production Example 75 (1)

A mixture of tert-butanol 27 mL and potassium hydroxide 3.15 g was stirred with heating to reflux for 1 hr. To the mixture was added 2-chloro-5-trifluoromethylsulfanylpyridine 6.0 g and tert-butanol 3 mL with dropping funnel, and the mixture was stirred with heating to reflux for 5 hr. The reaction mixture was allowed to cool to RT, and to the mixture was added concentrated hydrochloric acid. The precipitated solid was removed by filtration and washed with ethanol. The resulting filtrate was concentrated under reduced pressure. To the residue was added 1 N hydrochloric acid. The solid was collected by filtration and washed with water, and then with hexane, and dried to give 2-hydroxy-5-trifluoromethylsulfanylpyridine 4.42 g.

2-Hydroxy-5-trifluoromethylsulfanylpyridine

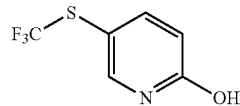

¹H-NMR (CDCl₃) δ: 7.73 (1H, d), 7.62 (1H, dd), 6.61 (1H, d).

Production Example 75 (2)

To a mixture of 2-hydroxy-5-trifluoromethylsulfanylpyridine 2 g and concentrated sulfuric acid 10 mL at ice temperature was added fuming nitric acid 0.74 mL, and the mixture was stirred at 60° C. for 2 hr. The reaction mixture was allowed to cool to RT, and then to ice water 50 mL was poured the mixture, and then the resulting mixture was extracted with ethyl acetate. The organic layer was washed with brine, and dried over anhydrous sodium sulfate, and concentrated under reduced pressure. The resulting solid was washed with tert-butyl methyl ether to give 2-hydroxy-3-nitro-5-trifluoromethylsulfinylpyridine 2.13 g.

2-Hydroxy-3-nitro-5-trifluoromethylsulfinylpyridine

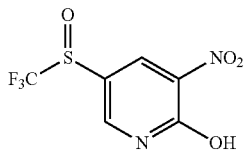 [SMILES: O=[N+]([O-])c1cc(S(=O)C(F)(F)F)cnc1O]

¹H-NMR (DMSO-D₆) δ: 8.67 (1H, brs), 8.59 (1H, brs).

Production Example 75 (3)

A mixture of iron powder 4.6 g, acetic acid 0.5 mL, ethanol 20 mL, and water 15 mL was stirred at 70° C. To the mixture was added 2-hydroxy-3-nitro-5-trifluoromethylsulfinylpyridine 2 g, and the mixture was stirred at 70° C. for 2 hr. The reaction mixture was allowed to cool to RT and filtrated through Celite (Trademark). The filtrates were concentrated under reduced pressure, and to the resultant residue was added saturated aqueous sodium bicarbonate. The resulting mixture was extracted with ethyl acetate. The organic layer was dried over anhydrous sodium sulfate, and concentrated under reduced pressure. The resulting solid was washed with tert-butyl methyl ether to give 3-amino-2-hydroxy-5-trifluoromethylsulfinylpyridine 1.45 g.

3-Amino-2-hydroxy-5-trifluoromethylsulfinylpyridine

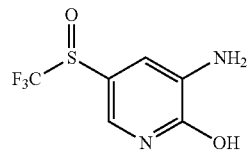 [SMILES: Nc1cc(S(=O)C(F)(F)F)cnc1O]

$^1$H-NMR (DMSO-D$_6$) δ: 12.23 (1H, brs), 7.49 (1H, s), 6.68 (1H, s), 5.72 (2H, brs).

Production Example 75 (4)

A mixture of 3-amino-2-hydroxy-5-trifluoromethylsulfinylpyridine 0.63 g, 3-ethylsulfanylpicolinic acid 0.55 g, EDC hydrochloride 0.68 g and pyridine 20 ml was stirred at RT 3 hr. To the reaction mixture was added water, the mixture was stirred at RT for 30 min. The precipitated solids were collected by filtration, and concentrated under reduced pressure to give 3-ethylsulfanyl-N-[2-hydroxy-5-trifluoromethylsulfinylpyridin-3-yl]picolinamide 0.73 g.

3-Ethylsulfanyl-N-[2-hydroxy-5-trifluoromethylsulfinylpyridin-3-yl]picolinamide

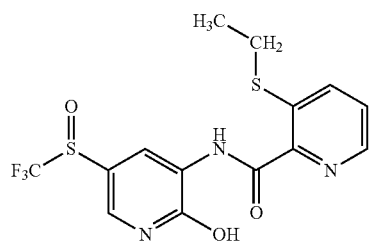 [SMILES: CCSc1cccnc1C(=O)Nc1cc(S(=O)C(F)(F)F)cnc1O]

$^1$H-NMR (DMSO-D$_6$) δ: 10.83 (1H, s), 8.71 (1H, s), 8.48 (1H, dd), 8.09 (1H, d), 7.98 (1H, d), 7.65 (1H, dd), 2.99 (2H, q), 1.31 (3H, t).

Production Example 75 (5)

A mixture of 3-ethylsulfanyl-N-[2-hydroxy-5-trifluoromethylsulfinylpyridin-3-yl]picolinamide 0.67 g, DMEAD 0.64 g, triphenylphosphine 0.68 g, and THF 40 mL was stirred at 50° C. for 3 hr. The reaction mixture allowed to cool to RT was concentrated under reduced pressure, and to the mixture was added water, and the mixture was extracted with ethyl acetate. The organic layer was washed with saturated aqueous ammonium chloride and brine, dried over anhydrous sodium sulfate, and concentrated under reduced pressure. The resultant residue is treated with silica gel column chromatography to give 2-(3-ethylsulfanylpyridin-2-yl)-6-(trifluoromethylsulfinyl)oxazolo[5,4-b]pyridine 0.59 g (hereinafter referred to as the present fused heterocyclic compound 474).

Present Fused Heterocyclic Compound 474

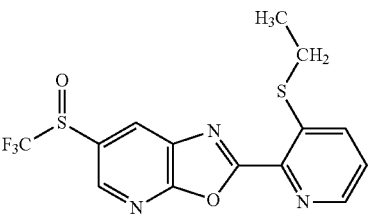 [SMILES: CCSc1cccnc1-c1nc2cc(S(=O)C(F)(F)F)cnc2o1]

$^1$H-NMR (CDCl$_3$) δ: 8.76 (1H, d), 8.70 (1H, d), 8.64 (1H, dd), 7.82 (1H, dd), 7.47 (1H, dd), 3.09 (2H, q), 1.47 (3H, t).

Production Example 76

To a mixture of the present fused heterocyclic compound 474 (0.43 g) and chloroform 30 mL at ice temperature was added m-chloroperbenzoic acid (65% or more purity) 0.53 g, and then the mixture was stirred at RT for 5 hr. To the reaction mixture was added aqueous 10% sodium sulfite, and the mixture was extracted with chloroform. The organic layer was washed with saturated aqueous sodium bicarbonate, dried over anhydrous sodium sulfate, and then concentrated under reduced pressure. The resultant residue was treated with silica gel column chromatography to give 2-(3-ethylsulfonylpyridin-2-yl)-6-(trifluoromethylsulfinyl)oxazolo[5,4-b]pyridine (hereinafter referred to as the present fused heterocyclic compound 439) 0.34 g.

Present Fused Heterocyclic Compound 439

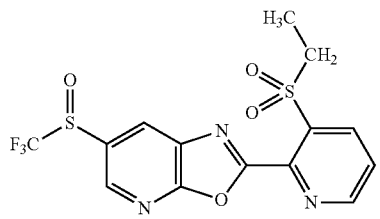 [SMILES: CCS(=O)(=O)c1cccnc1-c1nc2cc(S(=O)C(F)(F)F)cnc2o1]

$^1$H-NMR (CDCl$_3$) δ: 9.08 (1H, dd), 8.80 (1H, d), 8.69 (1H, d), 8.60 (1H, dd), 7.81 (1H, dd), 3.91 (2H, q), 1.45 (3H, t).

Production Example 77

The present fused heterocyclic compound 439 (0.17 g), acetonitrile 4 mL, sodium tungstate dihydrate 14 mg, and aqueous hydrogen peroxide (30%) 4 mL was mixed, and the mixture was stirred at 80° C. for 4 hr. To the reaction mixture allowed to cool to RT was added water, and the precipitated solid was collected by filtration, and the solids and aqueous 10% sodium sulfite were mixed, and the mixture was extracted with ethyl acetate. The organic layer was washed with water and brine, dried over anhydrous sodium sulfate, and concentrated under reduced pressure. The resultant residue is treated with silica gel column chromatography to give 2-(3-ethylsulfonylpyridin-2-yl)-6-(trifluoromethylsulfonyl)oxazolo[5,4-b]pyridine (hereinafter referred to as the present fused heterocyclic compound 440) 0.09 g.

Present Fused Heterocyclic Compound 440

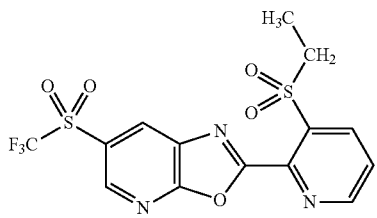 [SMILES: CCS(=O)(=O)c1cccnc1-c1nc2cc(S(=O)(=O)C(F)(F)F)cnc2o1]

$^1$H-NMR (CDCl$_3$) δ: 9.13 (1H, dd), 9.09 (1H, dd), 8.79 (1H, d), 8.60 (1H, dd), 7.83 (1H, dd), 3.88 (2H, q), 1.46 (3H, t).

Production Example 78 (1)

A mixture of 3-amino-2-hydroxy-5-trifluoromethylsulfinylpyridine 0.67 g, 3-ethylsulfanyl-5-trifluoromethylpicolinic acid 0.75 g, EDCI hydrochloride 0.68 g and pyridine 20 mL was stirred at RT for 1.5 hr. To the reaction mixture was added water, and the mixture was stirred at RT for 30 min. The precipitated solids were collected by filtration and dried under reduced pressure to give 3-ethylsulfanyl-5-trifluoromethyl-N-[2-hydroxy-5-trifluoromethylsulfinylpyridin-3-yl]picolinamide.

3-Ethylsulfanyl-5-trifluoromethyl-N-[2-hydroxy-5-trifluoromethylsulfinylpyridin-3-yl]picolinamide 1.28 g

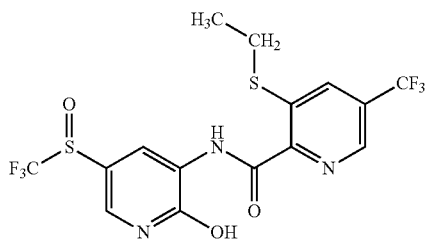 [SMILES: CCSc1cc(C(F)(F)F)cnc1C(=O)Nc1cc(S(=O)C(F)(F)F)cnc1O]

$^1$H-NMR (CDCl$_3$) δ: 10.99 (1H, dd), 8.90 (1H, s), 8.68 (1H, s), 7.91 (1H, s), 7.81 (1H, s), 3.02 (2H, q), 1.48 (3H, t).

Production Example 78 (2)

A mixture of 3-ethylsulfanyl-5-trifluoromethyl-N-[2-hydroxy-5-trifluoromethylsulfinylpyridin-3-yl]picolinamide (1.24 g), DMEAD 1.01 g, triphenylphosphine 1.06 g, and THF 40 mL was stirred at 50° C. for 3 hr. The reaction mixture allowed to cool to RT was concentrated under reduced pressure, and to the mixture is added water, and the mixture was extracted with ethyl acetate. The organic layer was washed with saturated aqueous ammonium chloride and brine, dried over anhydrous magnesium sulfate, and concentrated under reduced pressure. The resultant residue was treated with silica gel column chromatography to give 2-(3-ethylsulfanyl-5-trifluoromethylpyridin-2-yl)-6-(trifluoromethylsulfinyl)oxazolo[5,4-b]pyridine (hereinafter referred to as the present fused heterocyclic compound 478) 0.94 g.

Present Fused Heterocyclic Compound 478

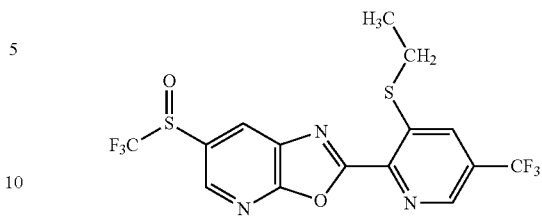

$^1$H-NMR (CDCl$_3$) δ: 8.83 (1H, d), 8.81 (1H, d), 8.75 (1H, d), 7.97 (1H, d), 3.13 (2H, q), 1.51 (3H, t).

Production Example 79

To a mixture of the present fused heterocyclic compound 478 (0.74 g) and chloroform 30 mL at ice temperature was added m-chloroperbenzoic acid (65% or more purity) 0.77 g, and then the mixture was stirred at RT 4 hr. To the reaction mixture was added aqueous 10% sodium sulfite, and the mixture was extracted with chloroform. The organic layer was washed with saturated aqueous sodium bicarbonate, dried over anhydrous sodium sulfate, and concentrated under reduced pressure. The resultant residue was treated with silica gel column chromatography to give 2-(3-ethylsulfonyl-5-trifluoromethylpyridin-2-yl)-6-(trifluoromethylsulfinyl)oxazolo[5,4-b]pyridine (hereinafter referred to as the present fused heterocyclic compound 449) 0.75 g.

Present Fused Heterocyclic Compound 449

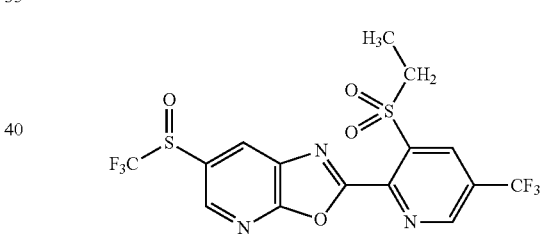

$^1$H-NMR (CDCl$_3$) δ: 9.31 (1H, d), 8.84-8.81 (2H, m), 8.73 (1H, d), 3.98 (2H, q), 1.49 (3H, t).

Production Example 80

The present fused heterocyclic compound 449 (0.14 g), acetonitrile 4 mL, sodium tungstate dihydrate 27 mg, and aqueous hydrogen peroxide (30%) 4 mL were mixed, and the mixture was stirred at 80° C. for 5 hr. To the reaction mixture allowed to cool to RT was added water, and the precipitated solids were collected by filtration. The solids and aqueous 10% sodium sulfite were mixed and the mixture was extracted with ethyl acetate. The organic layer was washed with water and brine, dried over anhydrous sodium sulfate, and concentrated under reduced pressure. The resultant residue was treated with silica gel column chromatography to give 2-(3-ethylsulfonyl-5-trifluoromethylpyridin-2-yl)-6-(trifluoromethylsulfonyl)oxazolo[5,4-b]pyridine (hereinafter referred to as the present fused heterocyclic compound 450) 0.21 g.

131

Present Fused Heterocyclic Compound 450

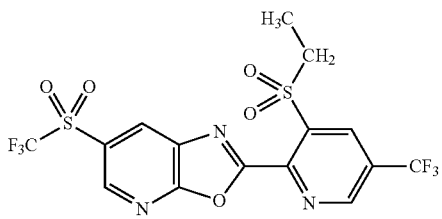 [SMILES: CCS(=O)(=O)c1cc(C(F)(F)F)cnc1-c1nc2cc(S(=O)(=O)C(F)(F)F)cnc2o1]

¹H-NMR (CDCl₃) δ: 9.32 (1H, d), 9.17 (1H, d), 8.85-8.82 (2H, m), 3.95 (2H, q), 1.50 (3H, t).

Production Example 81

To a mixture of the present fused heterocyclic compound 440 (1 mmol) and chloroform 10 mL at ice temperature is added m-chloroperbenzoic acid (65% or more purity) 5 mmol, and then the mixture is stirred with heating to reflux for 6 hr. To the reaction mixture allowed to cool to RT is added m-chloroperbenzoic acid (65% or more purity) 5 mmol, and then the mixture is stirred with heating to reflux for 6 hr. To the reaction mixture allowed to cool to RT is added aqueous 10% sodium sulfite, and the mixture is extracted with chloroform. The organic layer is washed with saturated aqueous sodium bicarbonate, dried over anhydrous magnesium sulfate, and concentrated under reduced pressure. The resultant residue is treated with silica gel column chromatography to give 2-(3-ethylsulfonylpyridin-2-yl)-6-(trifluoromethylsulfonyl)oxazolo[5,4-b]pyridine 4-oxide (hereinafter referred to as the present fused heterocyclic compound 456) and 2-(3-ethylsulfonyl-1-oxy-pyridin-2-yl)-6-(trifluoromethylsulfonyl)oxazolo[5,4-b]pyridine (hereinafter referred to as the present fused heterocyclic compound 458).

Present Fused Heterocyclic Compound 456

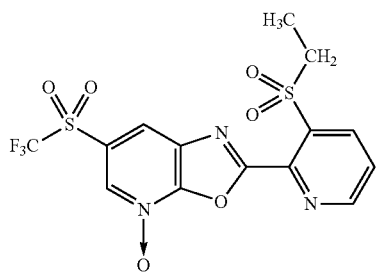 [SMILES: CCS(=O)(=O)c1cccnc1-c1nc2cc(S(=O)(=O)C(F)(F)F)c[n+]([O-])c2o1]

Present Fused Heterocyclic Compound 458

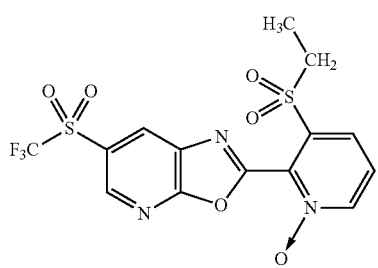 [SMILES: CCS(=O)(=O)c1ccc[n+]([O-])c1-c1nc2cc(S(=O)(=O)C(F)(F)F)cnc2o1]

132

Compounds as described in the above Production example, and compounds which are prepared in a similar manner as described for the preparation of the above Production examples are listed in the following tables.

Examples of the combinations of R¹, R², R³, R⁴, R⁵, R⁶, A¹, A², and n in the compound represented by the formula (1):

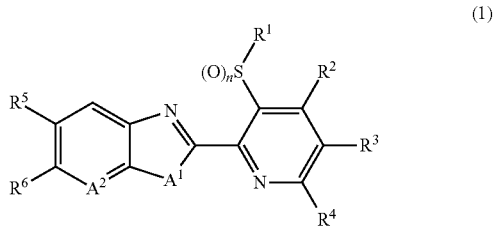

(1)

are shown below in [Table 1] to [Table 20].

TABLE 1

| No. | R¹ | R² | R³ | R⁴ | R⁵ | R⁶ | A¹ | A² | n |
|---|---|---|---|---|---|---|---|---|---|
| 1 | Et | H | H | H | CF₃ | H | NMe | N | 0 |
| 2 | Et | H | H | H | CF₃ | H | NMe | N | 1 |
| 3 | Et | H | H | H | CF₃ | H | NMe | N | 2 |
| 4 | Et | H | CF₃ | H | CF₃ | H | NMe | N | 0 |
| 5 | Et | H | CF₃ | H | CF₃ | H | NMe | N | 2 |
| 6 | Et | H | H | H | CF₂CF₃ | H | NMe | N | 0 |
| 7 | Et | H | H | H | CF₂CF₃ | H | NMe | N | 1 |
| 8 | Et | H | H | H | CF₂CF₃ | H | NMe | N | 2 |
| 9 | Et | H | H | H | I | H | NMe | N | 0 |
| 10 | Et | H | CF₃ | H | CF₃ | H | S | N | 0 |
| 11 | Et | H | CF₃ | H | CF₃ | H | S | N | 2 |
| 12 | Et | H | H | H | CF₃ | H | S | N | 2 |
| 13 | Et | H | H | H | SCF₃ | H | NMe | N | 0 |
| 14 | Et | H | H | H | SCF₃ | H | NMe | N | 1 |
| 15 | Et | H | H | H | SCF₃ | H | NMe | N | 2 |
| 16 | Et | H | H | H | SO₂CF₃ | H | NMe | N | 2 |
| 17 | Et | H | CF₃ | H | CF₂CF₃ | H | NMe | N | 0 |
| 18 | Et | H | CF₃ | H | CF₂CF₃ | H | NMe | N | 1 |
| 19 | Et | H | CF₃ | H | CF₂CF₃ | H | NMe | N | 2 |
| 20 | Et | H | H | H | SOCF₃ | H | NMe | N | 2 |
| 21 | Et | H | H | H | I | H | NMe | CH | 0 |
| 22* | Et | H | H | H | CF₃ | H | S | N | 2 |
| 23 | Et | H | H | H | SF₅ | H | NMe | CH | 0 |
| 24 | Et | H | H | H | SF₅ | H | NMe | CH | 2 |
| 25 | Et | H | CF₃ | H | SO₂CF₃ | H | NMe | N | 2 |

TABLE 2

| No. | R¹ | R² | R³ | R⁴ | R⁵ | R⁶ | A¹ | A² | n |
|---|---|---|---|---|---|---|---|---|---|
| 26 | Et | H | H | H | CF₂CF₃ | H | NMe | CH | 0 |
| 27 | Et | H | H | H | CF₂CF₃ | H | NMe | CH | 2 |
| 28 | Et | H | CF₃ | H | SCF₃ | H | NMe | N | 0 |
| 29 | Et | H | CF₃ | H | SCF₃ | H | NMe | N | 1 |
| 30 | Et | H | H | H | CF₃ | H | NMe | CH | 0 |
| 31 | Et | H | H | H | CF₃ | H | NMe | CH | 1 |
| 32 | Et | H | H | H | CF₃ | H | NMe | CH | 2 |
| 33 | Et | H | CF₃ | H | CF₃ | H | NMe | CH | 0 |
| 34 | Et | H | CF₃ | H | CF₃ | H | NMe | CH | 1 |
| 35 | Et | H | CF₃ | H | CF₃ | H | NMe | CH | 2 |
| 36* | Et | H | H | H | CF₃ | H | NMe | N | 0 |
| 37* | Et | H | H | H | CF₃ | H | NMe | N | 2 |
| 38 | Et | H | CF₃ | H | CF₂CF₃ | H | NMe | CH | 0 |
| 39 | Et | H | CF₃ | H | CF₂CF₃ | H | NMe | CH | 1 |
| 40 | Et | H | CF₃ | H | CF₂CF₃ | H | NMe | CH | 2 |
| 41 | Et | H | H | H | CF3 | H | S | N | 0 |
| 42 | Et | H | CF₃ | H | I | H | NMe | N | 0 |
| 43 | Et | H | CF₃ | H | SH | H | NMe | N | 0 |
| 44 | Et | H | CF₃ | H | SCF₃ | H | NMe | N | 2 |
| 45 | Et | H | CF₃ | H | I | H | NMe | CH | 0 |

TABLE 2-continued

| No. | R¹ | R² | R³ | R⁴ | R⁵ | R⁶ | A¹ | A² | n |
|---|---|---|---|---|---|---|---|---|---|
| 46 | Et | H | H | H | $CF_3$ | H | NMe | CBr | 2 |
| 47* | Et | H | H | H | $CF_2CF_3$ | H | NMe | CH | 2 |
| 48* | Et | H | $CF_3$ | H | $CF_3$ | H | NMe | N | 2 |
| 49 | Et | H | H | H | $OCF_3$ | H | NMe | CH | 0 |
| 50 | Et | H | H | H | $OCF_3$ | H | NMe | CH | 2 |

TABLE 3

| No. | R¹ | R² | R³ | R⁴ | R⁵ | R⁶ | A¹ | A² | n |
|---|---|---|---|---|---|---|---|---|---|
| 51* | Et | H | $CF_3$ | H | $CF_3$ | H | NMe | N | 2 |
| 52 | Et | H | H | H | $CF_3$ | H | S | CH | 0 |
| 53 | Et | H | H | H | $CF_3$ | H | S | CH | 2 |
| 54 | Et | H | $CF_3$ | H | $CF_3$ | H | S | CH | 0 |
| 55 | Et | H | $CF_3$ | H | $CF_3$ | H | S | CH | 2 |
| 56 | Et | H | H | H | $CF_3$ | OMe | NMe | CH | 2 |
| 57 | Et | H | H | H | $C(OH)_2CF_3$ | H | NMe | N | 0 |
| 58 | Et | H | H | H | $C(OH)_2CF_3$ | H | NMe | N | 2 |
| 59 | Et | H | $CF_3$ | H | $CO_2Me$ | H | NMe | N | 0 |
| 60 | Et | H | $CF_3$ | H | $SOCF_3$ | H | NMe | N | 2 |
| 61 | Et | H | H | H | $SCF_3$ | H | NMe | CH | 0 |
| 62 | Et | H | H | H | $SCF_3$ | H | NMe | CH | 1 |
| 63 | Et | H | H | H | $SCF_3$ | H | NMe | CH | 2 |
| 64 | Et | H | H | H | $SO_2CF_3$ | H | NMe | CH | 2 |
| 65 | Et | H | H | H | $CF_3$ | H | $NCH_2CF_3$ | N | 0 |
| 66 | Et | H | $CF_3$ | H | $CF_3$ | H | $NCH_2CF_3$ | N | 0 |
| 67 | Et | H | H | H | $CF_3$ | H | $NCH_2CF_3$ | N | 2 |
| 68 | Et | H | $CF_3$ | H | $CF_3$ | H | $NCH_2CF_3$ | N | 2 |
| 69 | Et | H | $CF_3$ | H | $CO_2Me$ | H | NMe | N | 2 |
| 70* | Et | H | $CF_3$ | H | $CO_2Me$ | H | NMe | N | 2 |
| 71 | Et | H | $CF_2CF_3$ | H | $CF_3$ | H | NMe | N | 0 |
| 72 | Et | H | $CF_2CF_3$ | H | $CF_3$ | H | NMe | N | 2 |
| 73 | Et | H | $CF_2CF_3$ | H | $CF_2CF_3$ | H | NMe | N | 0 |
| 74 | Et | H | $CF_2CF_3$ | H | $CF_2CF_3$ | H | NMe | N | 2 |
| 75 | Et | H | H | H | $CF_3$ | H | NMe | CBr | 0 |

TABLE 4

| No. | R¹ | R² | R³ | R⁴ | R⁵ | R⁶ | A¹ | A² | n |
|---|---|---|---|---|---|---|---|---|---|
| 76 | Et | H | H | H | $CF_3$ | H | NH | N | 0 |
| 77 | Et | H | H | H | $CF_3$ | H | NH | N | 2 |
| 78 | Et | H | $CF_3$ | H | $CF_3$ | H | NH | N | 0 |
| 79 | Et | H | $CF_3$ | H | $CF_3$ | H | NH | N | 2 |
| 80 | Et | H | H | H | $CF_3$ | H | O | N | 0 |
| 81 | Et | H | H | H | $CF_3$ | H | O | N | 2 |
| 82 | Et | H | $CF_3$ | H | $CF_3$ | H | O | N | 0 |
| 83 | Et | H | $CF_3$ | H | $CF_3$ | H | O | N | 2 |
| 84 | Et | H | H | H | $CF_3$ | H | O | CH | 0 |
| 85 | Et | H | H | H | $CF_3$ | H | O | CH | 2 |
| 86 | Et | H | $CF_3$ | H | $CF_3$ | H | O | CH | 0 |
| 87 | Et | H | $CF_3$ | H | $CF_3$ | H | O | CH | 2 |
| 88 | Et | H | H | H | $CF_3$ | H | Cl | NMe | N | 2 |
| 89 | Et | H | $CF_3$ | H | $CF_3$ | H | Cl | NMe | N | 2 |

TABLE 4-continued

| No. | R¹ | R² | R³ | R⁴ | R⁵ | R⁶ | A¹ | A² | n |
|---|---|---|---|---|---|---|---|---|---|
| 90 | Et | H | H | H | $CF_3$ | OC(O)Me | NMe | N | 2 |
| 91 | Et | H | $CF_3$ | H | $CF_3$ | OC(O)Me | NMe | N | 2 |
| 92 | Et | H | H | H | $CF_3$ | OH | NMe | N | 2 |
| 93 | Et | H | $CF_3$ | H | $CF_3$ | OH | NMe | N | 2 |
| 94 | Et | H | H | H | $CF_3$ | OMe | NMe | N | 2 |
| 95 | Et | H | $CF_3$ | H | $CF_3$ | OMe | NMe | N | 2 |
| 96 | Et | H | H | H | $CF_3$ | SMe | NMe | N | 2 |
| 97 | Et | H | $CF_3$ | H | $CF_3$ | SMe | NMe | N | 2 |
| 98 | Et | H | H | H | $CF_3$ | $NMe_2$ | NMe | N | 2 |
| 99 | Et | H | $CF_3$ | H | $CF_3$ | $NMe_2$ | NMe | N | 2 |
| 100 | $CH_2CycPr$ | H | H | H | $CF_3$ | H | NMe | N | 2 |

TABLE 5

| No. | R¹ | R² | R³ | R⁴ | R⁵ | R⁶ | A¹ | A² | n |
|---|---|---|---|---|---|---|---|---|---|
| 101 | $CH_2CycPr$ | H | $CF_3$ | H | $CF_3$ | H | NMe | N | 2 |
| 102 | $CF_3$ | H | H | H | $CF_3$ | H | NMe | N | 2 |
| 103 | $CF_3$ | H | $CF_3$ | H | $CF_3$ | H | NMe | N | 2 |
| 104 | $CH_2CF_3$ | H | H | H | $CF_3$ | H | NMe | N | 2 |
| 105 | $CH_2CF_3$ | H | $CF_3$ | H | $CF_3$ | H | NMe | N | 2 |
| 106 | Et | Cl | H | H | $CF_3$ | H | NMe | N | 2 |
| 107 | Et | H | Cl | H | $CF_3$ | H | NMe | N | 2 |
| 108 | Et | H | H | Cl | $CF_3$ | H | NMe | N | 2 |
| 109 | Et | H | $OCF_3$ | H | $CF_3$ | H | NMe | N | 2 |
| 110 | Et | H | $SCF_3$ | H | $CF_3$ | H | NMe | N | 2 |
| 111 | Et | H | $SOCF_3$ | H | $CF_3$ | H | NMe | N | 2 |
| 112 | Et | H | $SO_2CF_3$ | H | $CF_3$ | H | NMe | N | 2 |

TABLE 5-continued

| No. | R¹ | R² | R³ | R⁴ | R⁵ | R⁶ | A¹ | A² | n |
|---|---|---|---|---|---|---|---|---|---|
| 113 | Et | H | CF(CF₃)₂CF₃ | H | CF₃ | H | NMe | N | 2 |
| 114 | Et | H | CF₂CF₂CF₃ | H | CF₃ | H | NMe | N | 2 |
| 115 | Et | H | Br | H | CF₃ | H | NMe | N | 2 |
| 116 | Et | H | I | H | CF₃ | H | NMe | N | 2 |
| 117 | Et | H | Me | H | CF₃ | H | NMe | N | 2 |
| 118 | Et | H | OMe | H | CF₃ | H | NMe | N | 2 |
| 119 | Et | H | H | H | CF(CF₃)₂ | H | NMe | N | 2 |
| 120 | Et | H | CF₃ | H | CF(CF₃)₂ | H | NMe | N | 2 |
| 121 | Et | H | CF₃ | H | SF₅ | H | NMe | N | 2 |
| 122 | Et | H | H | H | CF₂CF₂CF₃ | H | NMe | N | 2 |
| 123 | Et | H | CF₃ | H | CF₂CF₂CF₃ | H | NMe | N | 2 |
| 124 | Et | H | H | H | SCF₂CF₃ | H | NMe | N | 2 |
| 125 | Et | H | CF₃ | H | SCF₂CF₃ | H | NMe | N | 2 |

TABLE 6

| No. | R¹ | R² | R³ | R⁴ | R⁵ | R⁶ | A¹ | A² | n |
|---|---|---|---|---|---|---|---|---|---|
| 126 | Et | H | H | H | SO₂CF₂CF₃ | H | NMe | N | 2 |
| 127 | Et | H | CF₃ | H | SO₂CF₂CF₃ | H | NMe | N | 2 |
| 128 | Et | H | H | H | CF₃ | H | NCH₂OMe | N | 2 |
| 129 | Et | H | CF₃ | H | CF₃ | H | NCH₂OMe | N | 2 |
| 130 | Et | H | H | H | CF₃ | H | NMe | CCN | 2 |
| 131 | Et | H | CF₃ | H | CF₃ | H | NMe | CCN | 2 |
| 132 | Et | H | H | H | CF₃ | H | NMe | CF | 2 |
| 133 | Et | H | CF₃ | H | CF₃ | H | NMe | CF | 2 |
| 134 | Et | H | H | H | CF₃ | H | NMe | CMe | 2 |
| 135 | Et | H | CF₃ | H | CF₃ | H | NMe | CMe | 2 |
| 136 | Et | H | H | H | CF₃ | H | NMe | COMe | 2 |
| 137 | Et | H | CF₃ | H | CF₃ | H | NMe | COMe | 2 |
| 138 | Et | H | H | H | CF₃ | H | NMe | CSCH₂CH₃ | 2 |
| 139 | Et | H | CF₃ | H | CF₃ | H | NMe | CSCH₂CH₃ | 2 |
| 140 | Et | H | H | H | CF₃ | H | NMe | CSO₂CH₂CH₃ | 2 |
| 141 | Et | H | CF₃ | H | CF₃ | H | NMe | CSO₂CH₂CH₃ | 2 |
| 142 | Me | H | H | H | CF₃ | H | NMe | N | 0 |
| 143 | Me | H | H | H | CF₃ | H | NMe | N | 1 |
| 144 | Me | H | H | H | CF₃ | H | NMe | N | 2 |
| 145 | Pr | H | H | H | CF₃ | H | NMe | N | 0 |
| 146 | Pr | H | H | H | CF₃ | H | NMe | N | 1 |
| 147 | Pr | H | H | H | CF₃ | H | NMe | N | 2 |
| 148 | iPr | H | H | H | CF₃ | H | NMe | N | 0 |
| 149 | iPr | H | H | H | CF₃ | H | NMe | N | 1 |
| 150 | iPr | H | H | H | CF₃ | H | NMe | N | 2 |

TABLE 7

| No. | R¹ | R² | R³ | R⁴ | R⁵ | R⁶ | A¹ | A² | n |
|---|---|---|---|---|---|---|---|---|---|
| 151 | tBu | H | H | H | CF₃ | H | NMe | N | 0 |
| 152 | tBu | H | H | H | CF₃ | H | NMe | N | 1 |
| 153 | tBu | H | H | H | CF₃ | H | NMe | N | 2 |
| 154 | CF₃ | H | H | H | CF₃ | H | NMe | N | 0 |
| 155 | CF₃ | H | H | H | CF₃ | H | NMe | N | 1 |
| 156 | Et | H | H | H | CF₃ | H | NEt | N | 0 |
| 157 | Et | H | H | H | CF₃ | H | NEt | N | 1 |
| 158 | Et | H | H | H | CF₃ | H | NEt | N | 2 |
| 159 | Et | H | H | H | CF₃ | H | NPr | N | 0 |
| 160 | Et | H | H | H | CF₃ | H | NPr | N | 1 |
| 161 | Et | H | H | H | CF₃ | H | NPr | N | 2 |
| 162 | Et | H | H | H | CF₃ | H | NiPr | N | 0 |
| 163 | Et | H | H | H | CF₃ | H | NiPr | N | 1 |
| 164 | Et | H | H | H | CF₃ | H | NiPr | N | 2 |
| 165 | Et | H | H | H | CF₃ | H | NCycPr | N | 0 |
| 166 | Et | H | H | H | CF₃ | H | NCycPr | N | 1 |
| 167 | Et | H | H | H | CF₃ | H | NCycPr | N | 2 |
| 168 | Et | H | H | H | CF₃ | H | NCH₂OEt | N | 0 |
| 169 | Et | H | H | H | CF₃ | H | NCH₂OEt | N | 1 |
| 170 | Et | H | H | H | CF₃ | H | NCH₂OEt | N | 2 |
| 171 | Et | H | H | H | CF₃ | H | NCH₂OMe | N | 0 |
| 172 | Et | H | H | H | Me | H | NMe | N | 0 |
| 173 | Et | H | H | H | Me | H | NMe | N | 1 |
| 174 | Et | H | H | H | Me | H | NMe | N | 2 |
| 175 | Et | H | H | H | Br | H | NMe | N | 0 |

TABLE 8

| No. | R¹ | R² | R³ | R⁴ | R⁵ | R⁶ | A¹ | A² | n |
|---|---|---|---|---|---|---|---|---|---|
| 176 | Et | H | H | H | Br | H | NMe | N | 1 |
| 177 | Et | H | H | H | Br | H | NMe | N | 2 |
| 178 | Et | H | H | H | I | H | NMe | N | 1 |
| 179 | Et | H | H | H | I | H | NMe | N | 2 |
| 180 | Et | H | H | H | CN | H | NMe | N | 0 |
| 181 | Et | H | H | H | CN | H | NMe | N | 1 |
| 182 | Et | H | H | H | CN | H | NMe | N | 2 |
| 183 | Et | H | H | H | CHO | H | NMe | N | 0 |
| 184 | Et | H | H | H | CF₂H | H | NMe | N | 0 |
| 185 | Et | H | H | H | CF₂H | H | NMe | N | 1 |
| 186 | Et | H | H | H | CF₂H | H | NMe | N | 2 |
| 187 | Me | H | H | H | CF₃ | H | NMe | CH | 0 |
| 188 | Et | H | H | H | CF₃ | H | NMe | CCl | 0 |
| 189 | Et | H | H | H | CF₃ | H | NMe | CCl | 1 |

TABLE 8-continued

| No. | R¹ | R² | R³ | R⁴ | R⁵ | R⁶ | A¹ | A² | n |
|---|---|---|---|---|---|---|---|---|---|
| 190 | Et | H | H | H | CF₃ | H | NMe | CCl | 2 |
| 191 | Et | H | H | H | CF₃ | H | NMe | CBr | 1 |
| 192 | Me | H | H | H | CF₃ | H | O | CH | 0 |
| 193 | Et | H | H | H | CF₃ | H | O | CH | 1 |
| 194 | Et | H | H | H | CF₃ | H | O | N | 1 |
| 195 | Me | H | H | H | CF₃ | H | S | CH | 0 |
| 196 | Et | H | H | H | CF₃ | H | S | CH | 1 |
| 197 | Et | Cl | H | H | CF₃ | H | NMe | N | 0 |
| 198 | Et | Cl | H | H | CF₃ | H | NMe | N | 1 |
| 199 | Et | H | H | H | COCF₃ | H | NMe | N | 0 |
| 200 | Et | H | H | H | Cl | H | NMe | N | 0 |

TABLE 9

| No. | R¹ | R² | R³ | R⁴ | R⁵ | R⁶ | A¹ | A² | n |
|---|---|---|---|---|---|---|---|---|---|
| 201 | Et | H | H | H | Cl | H | NMe | N | 1 |
| 202 | Et | H | H | H | Cl | H | NMe | N | 2 |
| 203 | Et | H | H | H | Br | H | NMe | N | 0 |
| 204 | Et | H | H | SEt | CF₃ | H | NMe | N | 0 |
| 205 | Et | H | H | H | CF₃ | H | NCH₂OEt | CH | 0 |
| 206 | Et | H | H | H | CF₃ | H | NCH₂CO₂Me | N | 0 |
| 207 | Et | H | H | H | CF₃ | H | NCH₂CO₂Et | N | 0 |
| 208 | Et | H | H | H | CF₃ | H | N(CH₂)₂OMe | N | 0 |
| 209 | Et | H | H | H | CF₃ | H | NBu | N | 0 |
| 210 | Et | H | H | H | CF₃ | H | NCO₂tBu | N | 0 |
| 211 | Et | H | H | H | CH(OH)CF₃ | H | NMe | N | 0 |
| 212 | Et | H | H | H | CHFCF₃ | H | NMe | N | 0 |
| 213 | Et | H | F | H | CF₃ | H | NMe | N | 0 |
| 214 | Et | H | F | H | CF₃ | H | NMe | N | 1 |
| 215 | Et | H | F | H | CF₃ | H | NMe | N | 2 |
| 216 | Et | OMe | H | H | CF₃ | H | NMe | N | 0 |
| 217 | Et | OMe | H | H | CF₃ | H | NMe | N | 1 |
| 218 | Et | H | OMe | H | CF₃ | H | NMe | N | 0 |
| 219 | Et | H | OMe | H | CF₃ | H | NMe | N | 1 |
| 220 | Et | H | OH | H | CF₃ | H | NMe | N | 0 |
| 221 | Et | H | H | H | NH₂ | H | NMe | N | 0 |
| 222 | Et | H | H | H | CHFCF₃ | H | NMe | N | 1 |
| 223 | Et | H | H | H | CHFCF₃ | H | NMe | N | 2 |
| 224 | Et | H | H | H | CF₂CF₂CF₃ | H | NMe | N | 0 |
| 225 | Et | H | H | H | CF₂CF₂CF₃ | H | NMe | N | 1 |

TABLE 10

| No. | R¹ | R² | R³ | R⁴ | R⁵ | R⁶ | A¹ | A² | n |
|---|---|---|---|---|---|---|---|---|---|
| 226 | Et | Cl | H | H | CF₂CF₃ | H | NMe | N | 1 |
| 227 | Et | Cl | H | H | CF₂CF₃ | H | NMe | N | 2 |
| 228 | Et | H | Cl | H | CF₃ | H | NMe | N | 0 |
| 229 | Et | H | Cl | H | CF₃ | H | NMe | N | 1 |
| 230 | Et | H | Cl | H | CF₂CF₃ | H | NMe | N | 1 |
| 231 | Et | H | H | Cl | CF₃ | H | NMe | N | 0 |
| 232 | Et | H | H | Cl | CF₃ | H | NMe | N | 1 |
| 233 | Et | H | H | OMe | CF₃ | H | NMe | N | 0 |
| 234 | Et | H | H | OMe | CF₃ | H | NMe | N | 1 |
| 235 | Et | H | H | OMe | CF₃ | H | NMe | N | 2 |
| 236 | Et | H | H | H | SH | H | NMe | N | 0 |
| 237 | Et | H | H | H | Et | H | NMe | N | 0 |
| 238 | Et | H | H | H | iPr | H | NMe | N | 0 |
| 239 | Et | H | H | H | NHEt | H | NMe | N | 0 |
| 240 | Et | H | H | H | NEt₂ | H | NMe | N | 0 |
| 241 | Et | H | H | H | tBu | H | NMe | N | 0 |
| 242 | Et | H | H | H | H | CF₃ | NMe | N | 0 |
| 243 | Et | F | H | H | CF₃ | H | NMe | N | 0 |
| 244 | Et | F | H | H | CF₃ | H | NMe | N | 1 |
| 245 | Et | F | H | H | CF₃ | H | NMe | N | 2 |
| 246 | Et | H | H | H | H | CF₃ | NMe | N | 1 |
| 247 | Et | H | H | H | H | CF₃ | NMe | N | 2 |
| 248 | Et | H | H | H | NMe₂ | H | NMe | N | 0 |
| 249 | Et | H | H | H | NHCOMe | H | NMe | N | 0 |
| 250 | Et | H | H | H | CH₂CF₃ | H | NMe | N | 0 |

TABLE 11

| No. | R¹ | R² | R³ | R⁴ | R⁵ | R⁶ | A¹ | A² | n |
|---|---|---|---|---|---|---|---|---|---|
| 251 | Et | H | H | H | NMeCOMe | H | NMe | N | 0 |
| 252 | Et | H | H | H | NH2 | H | NMe | N | 1 |
| 253 | Et | H | CF₃ | H | CF₃ | H | NMe | N | 0 |
| 254 | Et | H | H | H | NHCOCF₃ | H | NMe | N | 0 |
| 255 | Et | H | H | H | NHCOCF₃ | H | NMe | N | 1 |
| 256 | Et | H | H | H | NHCOCF₃ | H | NMe | N | 2 |
| 257 | Et | H | H | H | CF₃ | H | S | N | 1 |
| 258 | CH₂CF₃ | H | H | H | CF₃ | H | NMe | N | 0 |
| 259 | CH₂CF₃ | H | H | H | CF₃ | H | NMe | N | 1 |
| 260 | Et | Me | H | H | CF₃ | H | NMe | N | 0 |
| 261 | Et | Me | H | H | CF₃ | H | NMe | N | 1 |
| 262 | Et | Me | H | H | CF₃ | H | NMe | N | 2 |
| 263 | Et | H | Me | H | CF₃ | H | NMe | N | 0 |
| 264 | Et | H | Me | H | CF₃ | H | NMe | N | 1 |
| 265 | Et | H | H | CF₃ | CF₃ | H | NMe | N | 0 |
| 266 | Et | H | H | CF₃ | CF₃ | H | NMe | N | 1 |
| 267 | Et | H | H | CF₃ | CF₃ | H | NMe | N | 2 |
| 268 | Et | H | Br | H | CF₃ | H | NMe | N | 0 |
| 269 | Et | H | Br | H | CF₃ | H | NMe | N | 1 |
| 270 | Et | H | CN | H | CF₃ | H | NMe | N | 0 |
| 271 | Et | H | CN | H | CF₃ | H | NMe | N | 1 |
| 272 | Et | H | CN | H | CF₃ | H | NMe | N | 2 |
| 273 | Et | H | CF₂CF₃ | H | CF₃ | H | NMe | N | 1 |
| 274 | Et | H | CHO | H | CF₃ | H | NMe | N | 0 |
| 275 | Et | H | H | H | SMe | H | NMe | N | 0 |

TABLE 12

| No. | R¹ | R² | R³ | R⁴ | R⁵ | R⁶ | A¹ | A² | n |
|---|---|---|---|---|---|---|---|---|---|
| 276 | Et | H | H | H | SO₂Me | H | NMe | N | 2 |
| 277 | Et | H | H | H | SEt | H | NMe | N | 0 |
| 278 | Et | H | H | H | SO₂Et | H | NMe | N | 2 |
| 279 | Et | H | H | H | SO₂iPr | H | NMe | N | 2 |
| 280 | Et | H | H | H | SCH₂CF₃ | H | NMe | N | 0 |
| 281 | Et | H | H | H | SO₂CH₂CF₃ | H | NMe | N | 2 |
| 282 | Et | H | H | H | SCF₂CF₃ | H | NMe | N | 0 |

TABLE 12-continued

| No. | R¹ | R² | R³ | R⁴ | R⁵ | R⁶ | A¹ | A² | n |
|---|---|---|---|---|---|---|---|---|---|
| 283 | Et | H | H | H | SCF$_2$CF$_2$CF$_3$ | H | NMe | N | 0 |
| 284 | Et | H | H | H | SCF(CF$_3$)$_2$ | H | NMe | N | 0 |
| 285 | Et | H | H | H | CH(OH)CF$_3$ | H | NMe | N | 0 |
| 286 | Et | H | H | H | CH(Cl)CF$_3$ | H | NMe | N | 0 |
| 287 | Et | H | H | H | OH | H | NMe | N | 0 |
| 288 | Et | H | H | H | OH | H | NMe | N | 2 |
| 289 | Et | H | H | H | OCF$_2$Br | H | NMe | N | 2 |
| 290 | Et | H | H | H | OCF$_3$ | H | NMe | N | 2 |
| 291 | Et | H | H | H | SCF$_2$CF$_3$ | H | NMe | N | 1 |
| 292 | Et | H | H | H | SCF$_2$CF$_2$CF$_3$ | H | NMe | N | 1 |
| 293 | Et | H | H | H | SCF$_2$CF$_2$CF$_3$ | H | NMe | N | 2 |
| 294 | Et | H | H | H | StBu | H | NMe | N | 0 |
| 295 | Et | H | H | H | SO$_2$tBu | H | NMe | N | 2 |
| 296 | Et | H | CF$_3$ | H | Br | H | NMe | N | 0 |
| 297 | Et | H | CF$_3$ | H | Br | H | NMe | N | 1 |
| 298 | Et | H | CF$_3$ | H | Br | H | NMe | N | 2 |
| 299 | Et | H | I | H | CF$_2$CF$_3$ | H | NMe | N | 2 |
| 300 | Et | H | NO$_2$ | H | CF$_3$ | H | NMe | N | 0 |

TABLE 13

| No. | R¹ | R² | R³ | R⁴ | R⁵ | R⁶ | A¹ | A² | n |
|---|---|---|---|---|---|---|---|---|---|
| 301 | Et | H | NO$_2$ | H | CF$_3$ | H | NMe | N | 1 |
| 302 | Et | H | NO$_2$ | H | CF$_3$ | H | NMe | N | 2 |
| 303 | Et | H | I | H | SCF$_3$ | H | NMe | N | 2 |
| 304 | Et | H | I | H | SO$_2$CF$_3$ | H | NMe | N | 2 |
| 305 | Et | H | Br | H | CF$_2$CF$_3$ | H | NMe | N | 2 |
| 306 | Et | H | Cl | H | CF$_3$ | H | S | N | 0 |
| 307 | Et | H | Cl | H | CF$_3$ | H | S | N | 2 |
| 308 | Et | H | H | H | C(OH)(CF$_3$)$_2$ | H | NMe | N | 0 |
| 309 | Et | H | H | H | C(Cl)(CF$_3$)$_2$ | H | NMe | N | 0 |
| 310 | Et | H | H | H | C(Cl)(CF$_3$)$_2$ | H | NMe | N | 1 |
| 311 | Et | H | H | H | C(Cl)(CF$_3$)$_2$ | H | NMe | N | 2 |
| 312 | Et | H | Cl | H | CF$_2$CF$_3$ | H | NMe | N | 2 |
| 313 | Et | H | H | H | H | CF(CF$_3$)$_2$ | NMe | CH | 0 |
| 314 | Et | H | H | H | CF(CF$_3$)$_2$ | H | NMe | CH | 0 |
| 315 | Et | H | CF$_3$ | H | I | H | NMe | N | 2 |
| 316 | Et | H | H | H | CF$_2$CF$_3$ | H | NMe | CH | 1 |
| 317 | Et | H | H | H | SF$_5$ | H | NMe | CH | 1 |

TABLE 13-continued

| No. | R¹ | R² | R³ | R⁴ | R⁵ | R⁶ | A¹ | A² | n |
|---|---|---|---|---|---|---|---|---|---|
| 318 | Et | H | CF$_3$ | H | SF$_5$ | H | NMe | CH | 0 |
| 319 | Et | H | CF$_3$ | H | SF$_5$ | H | NMe | CH | 1 |
| 320 | Et | H | Me | H | CF$_2$CF$_3$ | H | NMe | N | 0 |
| 321 | Et | H | Me | H | CF$_2$CF$_3$ | H | NMe | N | 1 |
| 322 | Et | H | Me | H | CF$_2$CF$_3$ | H | NMe | N | 2 |
| 323 | Et | H | H | H | I | H | S | N | 0 |
| 324 | Et | H | CF$_3$ | H | I | H | S | N | 0 |
| 325 | Et | H | H | H | CF$_2$CF$_3$ | H | S | N | 0 |

TABLE 14

| No. | R¹ | R² | R³ | R⁴ | R⁵ | R⁶ | A¹ | A² | n |
|---|---|---|---|---|---|---|---|---|---|
| 326 | Et | H | CF$_3$ | H | CF$_2$CF$_3$ | H | S | N | 0 |
| 327 | Et | H | H | H | CF$_2$CF$_3$ | H | S | N | 2 |
| 328 | Et | H | CF$_3$ | H | CF$_2$CF$_3$ | H | S | N | 2 |
| 329 | Et | H | Et | H | CF$_3$ | H | NMe | N | 2 |
| 330 | Et | H | H | H | SO$_2$NMe$_2$ | H | NMe | N | 1 |
| 331 | Et | H | H | H | SO$_2$NMe$_2$ | H | NMe | N | 2 |
| 332 | Et | H | H | H | CF$_3$ | H | NMe | CNH$_2$ | 0 |
| 333 | Et | H | Br | H | SCF$_3$ | H | NMe | N | 0 |
| 334 | Et | H | H | H | CF$_3$ | H | NMe | CNMe$_2$ | 0 |
| 335 | Et | H | CF$_3$ | H | CF$_3$ | H | NMe | CNH$_2$ | 0 |
| 336 | Et | H | CF$_3$ | H | CF$_3$ | H | NMe | CNMe$_2$ | 0 |
| 337 | Et | H | SF$_5$ | H | CF$_3$ | H | NMe | N | 0 |
| 338 | Et | H | SF$_5$ | H | CF$_3$ | H | NMe | N | 1 |
| 339 | Et | H | SF$_5$ | H | CF$_3$ | H | NMe | N | 2 |
| 340 | Et | H | H | H | CF(CF$_3$)$_2$ | H | NH | CH | 0 |
| 341 | Et | H | H | H | Br | H | NMe | N | 0 |
| 342 | Et | H | H | H | Br | H | NMe | N | 1 |
| 343 | Et | H | H | H | Br | H | NMe | N | 2 |
| 344 | Et | H | H | H | Br | H | NMe | N | 0 |
| 345 | Et | H | H | H | CF$_3$ | H | NH | N | 1 |
| 346 | Et | H | H | H | CF$_3$ | H | NH | CH | 0 |
| 347 | Et | H | CF$_3$ | H | CF$_3$ | H | NEt | N | 2 |
| 348 | Et | H | CF$_3$ | H | CF$_3$ | H | NCH$_2$CN | N | 2 |
| 349 | Et | H | CF$_3$ | H | CF$_3$ | H | NCH$_2$OEt | N | 2 |
| 350 | Et | H | CF$_3$ | H | CF$_3$ | H | NPr | N | 2 |

TABLE 15

| No. | R¹ | R² | R³ | R⁴ | R⁵ | R⁶ | A¹ | A² | n |
|---|---|---|---|---|---|---|---|---|---|
| 351 | Et | H | CF$_3$ | H | CF$_3$ | H | N(CH$_2$)$_3$CH$_3$ | N | 2 |
| 352 | Et | H | CF$_3$ | H | CF$_3$ | H | NCH$_2$CO$_2$Me | N | 2 |
| 353 | Et | H | CF$_3$ | H | CF$_3$ | H | NCO$_2$tBu | N | 2 |
| 354 | Et | H | CF$_3$ | H | CF$_3$ | H | NCO$_2$Me | N | 2 |
| 355 | Et | H | CF$_3$ | H | CF$_3$ | H | NCOMe | N | 2 |
| 356 | Et | H | OCF$_3$ | H | CF$_3$ | H | NMe | N | 0 |
| 357 | Et | H | OCF$_3$ | H | CF$_3$ | H | NMe | N | 1 |
| 358 | Et | H | CF$_2$CF$_2$CF$_2$CF$_3$ | H | CF$_3$ | H | NMe | N | 2 |
| 359 | Et | H | NH$_2$ | H | CF$_3$ | H | NMe | N | 2 |
| 360 | Et | H | NHCOCF$_3$ | H | CF$_3$ | H | NMe | N | 2 |
| 361 | Et | H | iPr | H | CF$_3$ | H | NMe | N | 2 |
| 362 | Et | H | CHO | H | CF$_3$ | H | NMe | N | 2 |
| 363 | Bu | H | H | H | CF$_3$ | H | NMe | N | 0 |
| 364 | CH$_2$CN | H | H | H | CF$_3$ | H | NMe | N | 0 |
| 365 | CH$_2$tBu | H | H | H | CF$_3$ | H | NMe | N | 0 |
| 366 | CH$_2$CH$_2$CN | H | H | H | CF$_3$ | H | NMe | N | 0 |
| 367 | CH$_2$CycBu | H | H | H | CF$_3$ | H | NMe | N | 0 |
| 368 | CF$_2$Br | H | H | H | CF$_3$ | H | NMe | N | 0 |
| 369 | Et | H | CF$_2$H | H | CF$_3$ | H | NMe | N | 2 |
| 370 | Et | H | CH$_2$OH | H | CF$_3$ | H | NMe | N | 2 |
| 371 | Bu | H | H | H | CF$_3$ | H | NMe | N | 2 |
| 372 | CH$_2$CN | H | H | H | CF$_3$ | H | NMe | N | 2 |
| 373 | CH$_2$tBu | H | H | H | CF$_3$ | H | NMe | N | 2 |
| 374 | CH$_2$CH$_2$CN | H | H | H | CF$_3$ | H | NMe | N | 2 |
| 375 | CH$_2$CycBu | H | H | H | CF$_3$ | H | NMe | N | 2 |

TABLE 16

| No. | $R^1$ | $R^2$ | $R^3$ | $R^4$ | $R^5$ | $R^6$ | $A^1$ | $A^2$ | n |
|---|---|---|---|---|---|---|---|---|---|
| 376 | CF$_2$Br | H | H | H | CF$_3$ | H | NMe | N | 2 |
| 377 | Et | H | CH$_2$F | H | CF$_3$ | H | NMe | N | 2 |
| 378 | Et | H | H | H | H | CF$_3$ | S | N | 0 |
| 379 | Et | H | H | H | CF$_3$ | H | S | N | 2 |
| 380 | Et | H | OCF$_3$ | H | CF$_2$CF$_3$ | H | NMe | N | 0 |
| 381 | Et | H | OCF$_3$ | H | CF$_2$CF$_3$ | H | NMe | N | 1 |
| 382 | Et | H | OCF$_3$ | H | CF$_2$CF$_3$ | H | NMe | N | 2 |
| 383 | Et | H | CF$_3$ | H | CF$_3$ | H | NMe | CMe | 0 |
| 384 | Et | H | CF$_3$ | H | CF$_3$ | H | NMe | CMe | 1 |
| 385 | Et | H | CF$_3$ | H | CF$_3$ | H | NMe | CF | 0 |
| 386 | Et | H | CF$_3$ | H | CF$_3$ | H | NMe | CF | 1 |
| 387 | CH$_2$CycPr | H | H | H | CF$_3$ | H | NMe | N | 0 |
| 388 | CH$_2$CycPr | H | H | H | CF$_3$ | H | NMe | N | 1 |
| 389 | Et | H | CF$_3$ | H | CF$_3$ | H | NMe | CBr | 0 |
| 390 | Et | H | CF$_3$ | H | CF$_3$ | H | NMe | CSCH$_2$CH$_3$ | 0 |
| 391 | Et | H | OCF$_3$ | H | SCF$_3$ | H | NMe | N | 0 |
| 392 | Et | H | OCF$_3$ | H | SCF$_3$ | H | NMe | N | 1 |
| 393 | Et | H | OCF$_3$ | H | SCF$_3$ | H | NMe | N | 2 |
| 394 | Et | H | CF$_3$ | H | CF$_3$ | H | NMe | CBr | 1 |
| 395 | Et | H | CF$_3$ | H | CF$_3$ | H | NMe | CBr | 2 |
| 396 | Et | H | H | H | COMe | H | NMe | N | 0 |
| 397 | Et | H | H | H | COMe | H | NMe | N | 2 |
| 398 | Et | H | H | H | CF$_3$ | CN | NMe | N | 2 |
| 399 | Et | H | CF$_3$ | H | CF$_3$ | CN | NMe | N | 2 |
| 400* | Et | H | H | H | CF$_3$ | H | NMe | N | 2 |

TABLE 17

| No. | $R^1$ | $R^2$ | $R^3$ | $R^4$ | $R^5$ | $R^6$ | $A^1$ | $A^2$ | n |
|---|---|---|---|---|---|---|---|---|---|
| 401* | Et | H | CF$_3$ | H | CF$_3$ | H | NMe | N | 2 |
| 402 | Et | H | H | H | CF$_3$ | H | NMe | COMe | 0 |
| 403 | Et | H | H | H | CF$_3$ | H | NMe | CSCH$_3$ | 0 |
| 404 | Et | H | H | H | CF$_3$ | H | NMe | CSO$_2$CH$_3$ | 2 |
| 405 | Et | H | H | H | CF$_3$ | H | NMe | CSO$_2$CH$_2$CF$_3$ | 2 |
| 406 | Et | H | H | H | CF$_3$ | H | NMe | CCN | 0 |
| 407 | Et | H | CF$_3$ | H | CF$_3$ | COOH | NMe | N | 2 |
| 408 | Et | H | CF$_3$ | H | CF$_3$ | CONH$_2$ | NMe | N | 2 |
| 409* | Et | H | CF$_3$ | H | CF$_2$CF$_3$ | H | NMe | N | 2 |
| 410* | Et | H | CF$_3$ | H | CF$_2$CF$_3$ | H | NMe | N | 2 |
| 411 | Et | H | CF$_3$ | H | COOH | H | NMe | N | 0 |
| 412 | Et | H | H | H | CF$_3$ | H | NMe | CCN | 1 |
| 413 | Et | H | H | H | CF$_3$ | H | NH | CCF$_3$ | 0 |
| 414 | Et | H | C(OCH$_3$)$_3$ | H | CF$_2$CF$_3$ | H | NMe | N | 2 |
| 415 | Et | H | H | H | H | CF$_3$ | NMe | CH | 0 |
| 416 | Et | H | H | H | H | CF$_3$ | NMe | CH | 2 |
| 417 | Et | H | H | H | CF$_3$ | H | NMe | CCF$_3$ | 2 |
| 418 | Me | H | CF$_3$ | H | CF$_2$CF$_3$ | H | NMe | N | 0 |
| 419 | Me | H | CF$_3$ | H | CF$_2$CF$_3$ | H | NMe | N | 2 |
| 420 | Pr | H | CF$_3$ | H | CF$_2$CF$_3$ | H | NMe | N | 0 |
| 421 | Pr | H | CF$_3$ | H | CF$_2$CF$_3$ | H | NMe | N | 2 |
| 422 | iPr | H | CF$_3$ | H | CF$_2$CF$_3$ | H | NMe | N | 0 |
| 423 | iPr | H | CF$_3$ | H | CF$_2$CF$_3$ | H | NMe | N | 2 |
| 424 | Bu | H | CF$_3$ | H | CF$_2$CF$_3$ | H | NMe | N | 0 |
| 425 | Bu | H | CF$_3$ | H | CF$_2$CF$_3$ | H | NMe | N | 2 |

TABLE 18

| No. | $R^1$ | $R^2$ | $R^3$ | $R^4$ | $R^5$ | $R^6$ | $A^1$ | $A^2$ | n |
|---|---|---|---|---|---|---|---|---|---|
| 426 | CH(CH$_3$)CH$_2$CH$_3$ | H | CF$_3$ | H | CF$_2$CF$_3$ | H | NMe | N | 0 |
| 427 | CH(CH$_3$)CH$_2$CH$_3$ | H | CF$_3$ | H | CF$_2$CF$_3$ | H | NMe | N | 2 |
| 428 | CH$_2$CH(CH$_3$)$_2$ | H | CF$_3$ | H | CF$_2$CF$_3$ | H | NMe | N | 0 |
| 429 | CH$_2$CH(CH$_3$)$_2$ | H | CF$_3$ | H | CF$_2$CF$_3$ | H | NMe | N | 2 |
| 430 | tBu | H | CF$_3$ | H | CF$_2$CF$_3$ | H | NMe | N | 0 |
| 431 | tBu | H | CF$_3$ | H | CF$_2$CF$_3$ | H | NMe | N | 2 |
| 432 | CH$_2$CF$_3$ | H | CF$_3$ | H | CF$_2$CF$_3$ | H | NMe | N | 0 |
| 433 | CH$_2$CF$_3$ | H | CF$_3$ | H | CF$_2$CF$_3$ | H | NMe | N | 2 |
| 434 | Et | H | CF$_3$ | H | CN | H | NMe | N | 0 |

TABLE 18-continued

| No. | R¹ | R² | R³ | R⁴ | R⁵ | R⁶ | A¹ | A² | n |
|---|---|---|---|---|---|---|---|---|---|
| 435 | Et | H | H | H | CF₃ | H | NMe | CCF₃ | 0 |
| 436 | Et | H | H | H | SCF₃ | H | O | N | 0 |
| 437 | Et | H | H | H | SCF₃ | H | O | N | 1 |
| 438 | Et | H | H | H | SCF₃ | H | O | N | 2 |
| 439 | Et | H | H | H | S(O)CF₃ | H | O | N | 2 |
| 440 | Et | H | H | H | S(O)₂CF₃ | H | O | N | 2 |
| 441 | Et | H | H | H | SCF₃ | H | O | CH | 0 |
| 442 | Et | H | H | H | SCF₃ | H | O | CH | 1 |
| 443 | Et | H | H | H | SCF₃ | H | O | CH | 2 |
| 444 | Et | H | H | H | S(O)CF₃ | H | O | CH | 2 |
| 445 | Et | H | H | H | S(O)₂CF₃ | H | O | CH | 2 |
| 446 | Et | H | CF₃ | H | SCF₃ | H | O | N | 0 |
| 447 | Et | H | CF₃ | H | SCF₃ | H | O | N | 1 |
| 448 | Et | H | CF₃ | H | SCF₃ | H | O | N | 2 |
| 449 | Et | H | CF₃ | H | S(O)CF₃ | H | O | N | 2 |
| 450 | Et | H | CF₃ | H | S(O)₂CF₃ | H | O | N | 2 |

TABLE 19

| No. | R¹ | R² | R³ | R⁴ | R⁵ | R⁶ | A¹ | A² | n |
|---|---|---|---|---|---|---|---|---|---|
| 451 | Et | H | CF₃ | H | SCF₃ | H | O | CH | 0 |
| 452 | Et | H | CF₃ | H | SCF₃ | H | O | CH | 1 |
| 453 | Et | H | CF₃ | H | SCF₃ | H | O | CH | 2 |
| 454 | Et | H | CF₃ | H | S(O)CF₃ | H | O | CH | 2 |
| 455 | Et | H | CF₃ | H | S(O)₂CF₃ | H | O | CH | 2 |
| 456* | Et | H | H | H | S(O)₂CF₃ | H | O | N | 2 |
| 457* | Et | H | CF₃ | H | S(O)₂CF₃ | H | O | N | 2 |
| 458* | Et | H | H | H | S(O)₂CF₃ | H | O | N | 2 |
| 459* | Et | H | H | H | S(O)₂CF₃ | H | O | CH | 2 |
| 460* | Et | H | CF₃ | H | S(O)₂CF₃ | H | O | N | 2 |
| 461* | Et | H | CF₃ | H | S(O)₂CF₃ | H | O | CH | 2 |
| 462 | Et | H | H | H | CF₂CF₃ | H | O | N | 0 |
| 463 | Et | H | H | H | CF₂CF₃ | H | O | N | 1 |
| 464 | Et | H | H | H | CF₂CF₃ | H | O | N | 2 |
| 465 | Et | H | H | H | CF₂CF₃ | H | O | CH | 0 |
| 466 | Et | H | H | H | CF₂CF₃ | H | O | CH | 1 |
| 467 | Et | H | H | H | CF₂CF₃ | H | O | CH | 2 |
| 468 | Et | H | CF₃ | H | CF₂CF₃ | H | O | N | 0 |
| 469 | Et | H | CF₃ | H | CF₂CF₃ | H | O | N | 1 |
| 470 | Et | H | CF₃ | H | CF₂CF₃ | H | O | N | 2 |
| 471 | Et | H | CF₃ | H | CF₂CF₃ | H | O | CH | 0 |
| 472 | Et | H | CF₃ | H | CF₂CF₃ | H | O | CH | 1 |
| 473 | Et | H | CF₃ | H | CF₂CF₃ | H | O | CH | 2 |
| 474 | Et | H | H | H | S(O)CF₃ | H | O | N | 0 |
| 475 | Et | H | H | H | S(O)₂CF₃ | H | O | N | 0 |

TABLE 20

| No. | R¹ | R² | R³ | R⁴ | R⁵ | R⁶ | A¹ | A² | n |
|---|---|---|---|---|---|---|---|---|---|
| 476 | Et | H | H | H | S(O)CF₃ | H | O | CH | 0 |
| 477 | Et | H | H | H | S(O)₂CF₃ | H | O | CH | 0 |
| 478 | Et | H | CF₃ | H | S(O)CF₃ | H | O | N | 0 |
| 479 | Et | H | CF₃ | H | S(O)₂CF₃ | H | O | N | 0 |
| 480 | Et | H | CF₃ | H | S(O)CF₃ | H | O | CH | 0 |
| 481 | Et | H | CF₃ | H | S(O)₂CF₃ | H | O | CH | 0 |

In [Table 1] to [Table 20], the symbol "*" in the leftmost column denotes that the present fused heterocyclic compound is a N-oxide. Specifically, the following compounds are included.

Present Fused Heterocyclic Compound 22

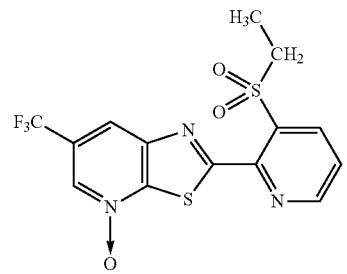 [SMILES: CCS(=O)(=O)c1cccnc1-c1nc2cc(C(F)(F)F)c[n+]([O-])c2s1]

Present Fused Heterocyclic Compound 36

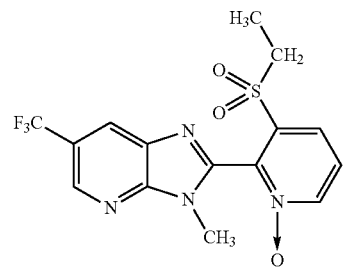 [SMILES: CCS(=O)(=O)c1ccc[n+]([O-])c1-c1nc2cc(C(F)(F)F)cnc2n1C]

Present Fused Heterocyclic Compound 37

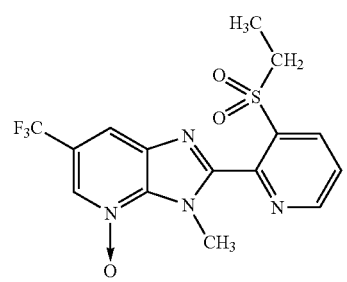 [SMILES: CCS(=O)(=O)c1cccnc1-c1nc2cc(C(F)(F)F)c[n+]([O-])c2n1C]

Present Fused Heterocyclic Compound 47
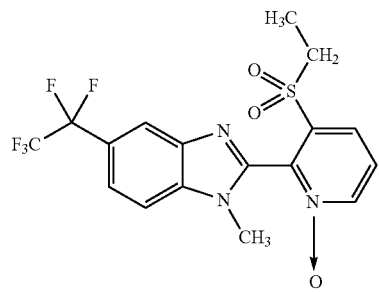 [SMILES: CCS(=O)(=O)c1cccnc1-c1nc2cc(C(F)(F)C(F)(F)F)ccc2n1C ; O]
Present Fused Heterocyclic Compound 48
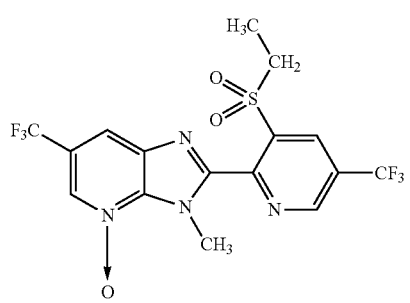 [SMILES: CCS(=O)(=O)c1cc(C(F)(F)F)cnc1-c1nc2cc(C(F)(F)F)cnc2n1C ; O]
Present Fused Heterocyclic Compound 51
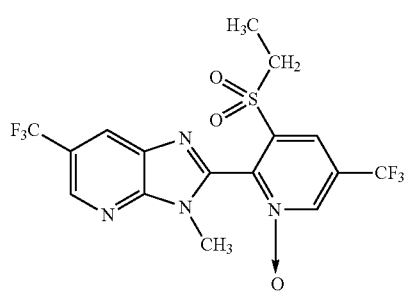 [SMILES: CCS(=O)(=O)c1cc(C(F)(F)F)cnc1-c1nc2cc(C(F)(F)F)cnc2n1C ; O]
Present Fused Heterocyclic Compound 70
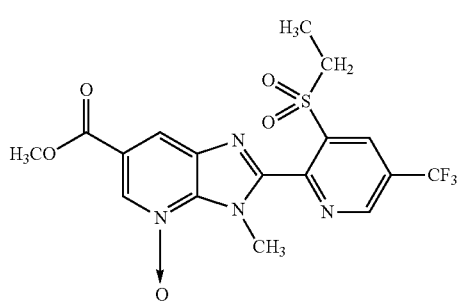 [SMILES: CCS(=O)(=O)c1cc(C(F)(F)F)cnc1-c1nc2cc(C(=O)OC)cnc2n1C ; O]
Present Fused Heterocyclic Compound 400
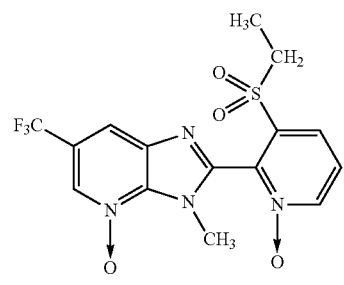 [SMILES: CCS(=O)(=O)c1ccc[n+]([O-])c1-c1nc2cc(C(F)(F)F)c[n+]([O-])c2n1C]
Present Fused Heterocyclic Compound 401
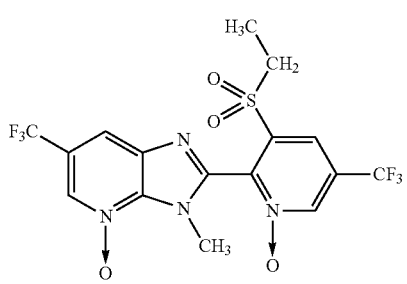 [SMILES: CCS(=O)(=O)c1cc(C(F)(F)F)c[n+]([O-])c1-c1nc2cc(C(F)(F)F)c[n+]([O-])c2n1C]
Present Fused Heterocyclic Compound 409
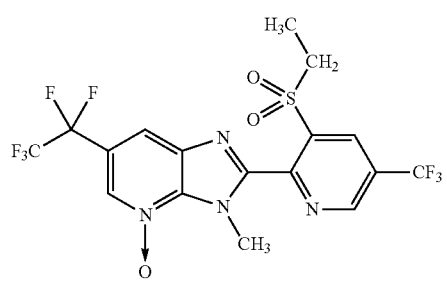 [SMILES: CCS(=O)(=O)c1cc(C(F)(F)F)cnc1-c1nc2cc(C(F)(F)C(F)(F)F)c[n+]([O-])c2n1C]
Present Fused Heterocyclic Compound 410
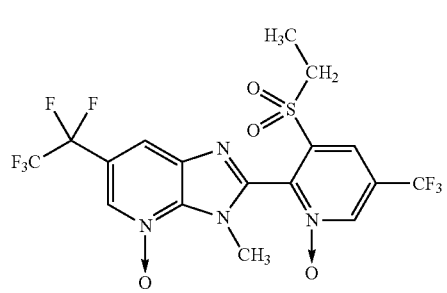 [SMILES: CCS(=O)(=O)c1cc(C(F)(F)F)c[n+]([O-])c1-c1nc2cc(C(F)(F)C(F)(F)F)c[n+]([O-])c2n1C]

Present Fused Heterocyclic Compound 456

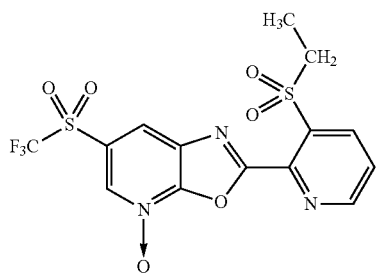 [SMILES: CCS(=O)(=O)c1cccnc1-c1nc2cc(S(=O)(=O)C(F)(F)F)c[n+]([O-])c2o1]

Present Fused Heterocyclic Compound 457

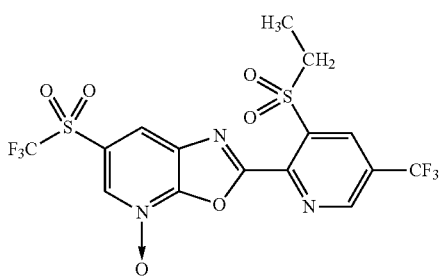 [SMILES: CCS(=O)(=O)c1cc(C(F)(F)F)cnc1-c1nc2cc(S(=O)(=O)C(F)(F)F)c[n+]([O-])c2o1]

Present Fused Heterocyclic Compound 458

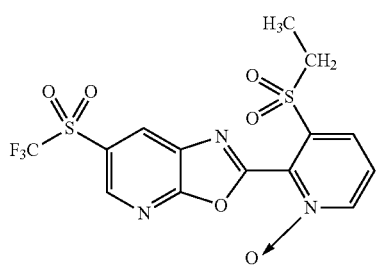 [SMILES: CCS(=O)(=O)c1cccnc1-c1nc2cc(S(=O)(=O)C(F)(F)F)cnc2o1 ; O]

Present Fused Heterocyclic Compound 459

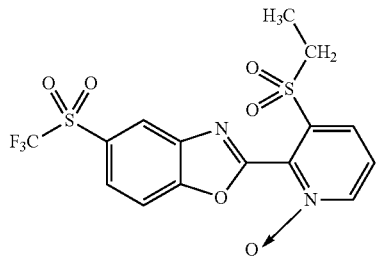 [SMILES: CCS(=O)(=O)c1cccnc1-c1nc2cc(S(=O)(=O)C(F)(F)F)ccc2o1 ; O]

Present Fused Heterocyclic Compound 460

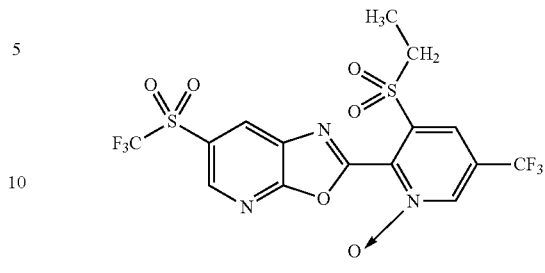

Present Fused Heterocyclic Compound 461

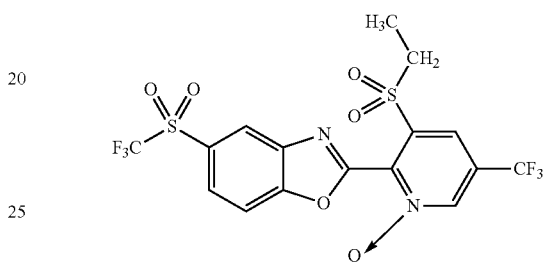

In [Table 1] to [Table 20],
Me represents a methyl group;
Et represents an ethyl group;
Pr represents a propyl group;
Bu represents a butyl group;
tBu represents a tertiary butyl group;
iPr represents an isopropyl group;
CycPr represents cyclopropyl group.
Formulation Examples are shown below.

Formulation Example 1

Five (5) parts of one compound selected from the present fused heterocyclic compounds 1 to 481, 10 parts of the present carboxamide compound (2a), 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain each formulation.

Formulation Example 2

Five (5) parts of one compound selected from the present fused heterocyclic compounds 1 to 481, 10 parts of the present carboxamide compound (2e), 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain each formulation.

Formulation Example 3

Ten (10) parts of one compound selected from the present fused heterocyclic compounds 1 to 481, 0.1 parts of the present carboxamide compound (2a), 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain each formulation.

Formulation Example 4

Ten (10) parts of one compound selected from the present fused heterocyclic compounds 1 to 481, 0.1 parts of the present carboxamide compound (2e), 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain each formulation.

Formulation Example 5

Ten (10) parts of one compound selected from the present fused heterocyclic compounds 1 to 481, 2 parts of the present carboxamide compound (2a), 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of aqueous solution containing 0.05 parts of xanthane gum and 0.1 parts of magnesium aluminium silicate so as to give a total amount of 90 parts, and then 10 parts of propylene glycol is added thereto. The mixture is stirred to obtain each formulation.

Formulation Example 6

Ten (10) parts of one compound selected from the present fused heterocyclic compounds 1 to 481, 2 parts of the present carboxamide compound (2e), 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of aqueous solution containing 0.05 parts of xanthane gum and 0.1 parts of magnesium aluminium silicate so as to give a total amount of 90 parts, and then 10 parts of propylene glycol is added thereto. The mixture is stirred to obtain each formulation.

Formulation Example 7

Ten (10) parts of one compound selected from the present fused heterocyclic compounds 1 to 481, 10 parts of the present carboxamide compound (2a), 3 parts of calcium lignin sulfonate, 2 parts of sodium lauryl sulfate, and the rest parts of synthetic hydrated silicon oxide are well mixed while grinding to obtain 100 parts of each wettable powder.

Formulation Example 8

Ten (10) parts of one compound selected from the present fused heterocyclic compounds 1 to 481, 10 parts of the present carboxamide compound (2e), 3 parts of calcium lignin sulfonate, 2 parts of sodium lauryl sulfate, and the rest parts of synthetic hydrated silicon oxide are well mixed while grinding to obtain 100 parts of each wettable powder.

Formulation Example 9

One (1) parts of one compound selected from the present fused heterocyclic compounds 1 to 481, 0.5 parts of the present carboxamide compound (2a), 1 parts of synthetic hydrated silicon oxide fine powder, 2 parts of calcium lignin sulfonate, 30 parts of bentonite, and the rest parts of kaolin clay are mixed. Then, to this mixture is added a suitable amount of water, and the mixture is further stirred, granulated by a granulator, and dried under ventilation to obtain each granule.

Formulation Example 10

One (1) parts of one compound selected from the present fused heterocyclic compounds 1 to 481, 0.5 parts of the present carboxamide compound (2e), 1 parts of synthetic hydrated silicon oxide fine powder, 2 parts of calcium lignin sulfonate, 30 parts of bentonite, and the rest parts of kaolin clay are mixed. Then, to this mixture is added a suitable amount of water, and the mixture is further stirred, granulated by a granulator, and dried under ventilation to obtain each granule.

Test Example 1

One (1) mg of any one of the present fused heterocyclic compounds 3, 4, 5, 9, 15, 16, 17, 18, 19, 20, 22, 25, 27, 28, 29, 34, 36, 39, 48, 50, 53, 71, 72, 74, 81, 85, 89, 99, 130, 312, 399, 404, 409, 414, 419, 421, 423, 443, 444, 445, 464 and 467 was dissolved in 10 μL of mixed solvent of xylene, dimethylformamide, and surfactant (Trade name: Sorpol 3005X, manufactured by TOHO CHEMICAL INDUSTRY CO. LTD) (4:4:1 (volume ratio)). Then, the mixture was diluted with water containing 0.02% (v/v) of the spreading agent (Trade name: Sindain, manufactured by Sumitomo Chemical Company, Limited) so as to give a given concentration.

One (1) mg of the present carboxamide compound (2a) was dissolved in 10 μL of mixed solvent of xylene, dimethylformamide, and surfactant (Trade name: Sorpol 3005X, manufactured by TOHO CHEMICAL INDUSTRY CO. LTD) (4:4:1 (volume ratio)). Then, the mixture was diluted with water containing 0.02% (v/v) of the spreading agent (Trade name: Sindain, manufactured by Sumitomo Chemical Company, Limited) so as to give a given concentration.

The resulting water-diluted solution of the present fused heterocyclic compound and the resulting water-diluted solution of the present carboxamide compound (2a) were mixed to prepare a test solution.

Leaf disks (1.5 cm in diameter) of cabbage (*Brassicae oleracea*) were placed in each well of 24-well microplates (manufactured by Becton Dickinson), and 40 μL of the test solution was applied per well (hereinafter, referred to as "treated group"). An untreated group was prepared by applying 40 μL of water containing 0.02% (v/v) of the spreading agent (Trade name: Sindain, manufactured by Sumitomo Chemical Company, Limited) only into a well.

After air drying, five diamondback moth (*Plutella xylostella*) (2nd instar larva) were released per well, and the wells were covered with a paper towel and then covered with a lid. At 2 days after the release, the number of surviving insects was counted on each well.

The mortality of the treated group and the mortality of the untreated group were calculated by the following equation 1), respectively. One replication test was performed on each group.

Mortality (%)=(Total number of Tested insects−Number of Surviving insects)/Total number of Tested insects×100    Equation 1)

The results are shown in Tables 21 to 25.

TABLE 21

| Composition | Concentration (ppm) | Mortality (%) |
|---|---|---|
| Present fused heterocyclic compound 3 + Present carboxamide compound (2a) | 200 + 2000 | 100 |
| Present fused heterocyclic compound 3 + Present carboxamide compound (2a) | 500 + 500 | 100 |
| Present fused heterocyclic compound 3 + Present carboxamide compound (2a) | 500 + 1 | 100 |
| Present fused heterocyclic compound 4 + Present carboxamide compound (2a) | 200 + 2000 | 100 |
| Present fused heterocyclic compound 4 + Present carboxamide compound (2a) | 500 + 500 | 100 |
| Present fused heterocyclic compound 4 + Present carboxamide compound (2a) | 500 + 1 | 100 |
| Present fused heterocyclic compound 5 + Present carboxamide compound (2a) | 200 + 2000 | 100 |
| Present fused heterocyclic compound 5 + Present carboxamide compound (2a) | 500 + 500 | 100 |
| Present fused heterocyclic compound 5 + Present carboxamide compound (2a) | 500 + 1 | 100 |
| Present fused heterocyclic compound 9 + Present carboxamide compound (2a) | 200 + 2000 | 100 |
| Present fused heterocyclic compound 9 + Present carboxamide compound (2a) | 500 + 500 | 100 |
| Present fused heterocyclic compound 9 + Present carboxamide compound (2a) | 500 + 1 | 100 |
| Present fused heterocyclic compound 15 + Present carboxamide compound (2a) | 200 + 2000 | 100 |
| Present fused heterocyclic compound 15 + Present carboxamide compound (2a) | 500 + 500 | 100 |
| Present fused heterocyclic compound 15 + Present carboxamide compound (2a) | 500 + 1 | 100 |
| Present fused heterocyclic compound 16 + Present carboxamide compound (2a) | 200 + 2000 | 100 |
| Present fused heterocyclic compound 16 + Present carboxamide compound (2a) | 500 + 500 | 100 |
| Present fused heterocyclic compound 16 + Present carboxamide compound (2a) | 500 + 1 | 100 |
| Present fused heterocyclic compound 17 + Present carboxamide compound (2a) | 200 + 2000 | 100 |
| Present fused heterocyclic compound 17 + Present carboxamide compound (2a) | 500 + 500 | 100 |
| Present fused heterocyclic compound 17 + Present carboxamide compound (2a) | 500 + 1 | 100 |
| Present fused heterocyclic compound 18 + Present carboxamide compound (2a) | 200 + 2000 | 100 |
| Present fused heterocyclic compound 18 + Present carboxamide compound (2a) | 500 + 500 | 100 |
| Present fused heterocyclic compound 18 + Present carboxamide compound (2a) | 500 + 1 | 100 |
| Present fused heterocyclic compound 19 + Present carboxamide compound (2a) | 200 + 2000 | 100 |
| Present fused heterocyclic compound 19 + Present carboxamide compound (2a) | 500 + 500 | 100 |
| Present fused heterocyclic compound 19 + Present carboxamide compound (2a) | 500 + 1 | 100 |
| Untreated group | — | 0 |

TABLE 22

| Composition | Concentration (ppm) | Mortality (%) |
|---|---|---|
| Present fused heterocyclic compound 20 + Present carboxamide compound (2a) | 200 + 2000 | 100 |
| Present fused heterocyclic compound 20 + Present carboxamide compound (2a) | 500 + 500 | 100 |
| Present fused heterocyclic compound 20 + Present carboxamide compound (2a) | 500 + 1 | 100 |
| Present fused heterocyclic compound 22 + Present carboxamide compound (2a) | 200 + 2000 | 100 |
| Present fused heterocyclic compound 22 + Present carboxamide compound (2a) | 500 + 500 | 100 |
| Present fused heterocyclic compound 22 + Present carboxamide compound (2a) | 500 + 1 | 100 |
| Present fused heterocyclic compound 25 + Present carboxamide compound (2a) | 200 + 2000 | 100 |
| Present fused heterocyclic compound 25 + Present carboxamide compound (2a) | 500 + 500 | 100 |
| Present fused heterocyclic compound 25 + Present carboxamide compound (2a) | 500 + 1 | 100 |
| Present fused heterocyclic compound 27 + Present carboxamide compound (2a) | 200 + 2000 | 100 |
| Present fused heterocyclic compound 27 + Present carboxamide compound (2a) | 500 + 500 | 100 |
| Present fused heterocyclic compound 27 + Present carboxamide compound (2a) | 500 + 1 | 100 |
| Present fused heterocyclic compound 28 + Present carboxamide compound (2a) | 200 + 2000 | 100 |
| Present fused heterocyclic compound 28 + Present carboxamide compound (2a) | 500 + 500 | 100 |
| Present fused heterocyclic compound 28 + Present carboxamide compound (2a) | 500 + 1 | 100 |
| Present fused heterocyclic compound 29 + Present carboxamide compound (2a) | 200 + 2000 | 100 |
| Present fused heterocyclic compound 29 + Present carboxamide compound (2a) | 500 + 500 | 100 |
| Present fused heterocyclic compound 29 + Present carboxamide compound (2a) | 500 + 1 | 100 |
| Present fused heterocyclic compound 34 + Present carboxamide compound (2a) | 200 + 2000 | 100 |
| Present fused heterocyclic compound 34 + Present carboxamide compound (2a) | 500 + 500 | 100 |
| Present fused heterocyclic compound 34 + Present carboxamide compound (2a) | 500 + 1 | 100 |
| Present fused heterocyclic compound 36 + Present carboxamide compound (2a) | 200 + 2000 | 100 |
| Present fused heterocyclic compound 36 + Present carboxamide compound (2a) | 500 + 500 | 100 |
| Present fused heterocyclic compound 36 + Present carboxamide compound (2a) | 500 + 1 | 100 |
| Present fused heterocyclic compound 39 + Present carboxamide compound (2a) | 200 + 2000 | 100 |
| Present fused heterocyclic compound 39 + Present carboxamide compound (2a) | 500 + 500 | 100 |
| Present fused heterocyclic compound 39 + Present carboxamide compound (2a) | 500 + 1 | 100 |
| Untreated group | — | 0 |

TABLE 23

| Composition | Concentration (ppm) | Mortality (%) |
|---|---|---|
| Present fused heterocyclic compound 48 + Present carboxamide compound (2a) | 200 + 2000 | 100 |
| Present fused heterocyclic compound 48 + Present carboxamide compound (2a) | 500 + 500 | 100 |
| Present fused heterocyclic compound 48 + Present carboxamide compound (2a) | 500 + 1 | 100 |
| Present fused heterocyclic compound 50 + Present carboxamide compound (2a) | 200 + 2000 | 100 |
| Present fused heterocyclic compound 50 + Present carboxamide compound (2a) | 500 + 500 | 100 |
| Present fused heterocyclic compound 50 + Present carboxamide compound (2a) | 500 + 1 | 100 |
| Present fused heterocyclic compound 53 + Present carboxamide compound (2a) | 200 + 2000 | 100 |
| Present fused heterocyclic compound 53 + Present carboxamide compound (2a) | 500 + 500 | 100 |
| Present fused heterocyclic compound 53 + Present carboxamide compound (2a) | 500 + 1 | 100 |
| Present fused heterocyclic compound 71 + Present carboxamide compound (2a) | 200 + 2000 | 100 |
| Present fused heterocyclic compound 71 + Present carboxamide compound (2a) | 500 + 500 | 100 |
| Present fused heterocyclic compound 71 + Present carboxamide compound (2a) | 500 + 1 | 100 |

TABLE 23-continued

| Composition | Concentration (ppm) | Mortality (%) |
|---|---|---|
| Present fused heterocyclic compound 72 + Present carboxamide compound (2a) | 200 + 2000 | 100 |
| Present fused heterocyclic compound 72 + Present carboxamide compound (2a) | 500 + 500 | 100 |
| Present fused heterocyclic compound 72 + Present carboxamide compound (2a) | 500 + 1 | 100 |
| Present fused heterocyclic compound 74 + Present carboxamide compound (2a) | 200 + 2000 | 100 |
| Present fused heterocyclic compound 74 + Present carboxamide compound (2a) | 500 + 500 | 100 |
| Present fused heterocyclic compound 74 + Present carboxamide compound (2a) | 500 + 1 | 100 |
| Present fused heterocyclic compound 81 + Present carboxamide compound (2a) | 200 + 2000 | 100 |
| Present fused heterocyclic compound 81 + Present carboxamide compound (2a) | 500 + 500 | 100 |
| Present fused heterocyclic compound 81 + Present carboxamide compound (2a) | 500 + 1 | 100 |
| Present fused heterocyclic compound 85 + Present carboxamide compound (2a) | 200 + 2000 | 100 |
| Present fused heterocyclic compound 85 + Present carboxamide compound (2a) | 500 + 500 | 100 |
| Present fused heterocyclic compound 85 + Present carboxamide compound (2a) | 500 + 1 | 100 |
| Present fused heterocyclic compound 89 + Present carboxamide compound (2a) | 200 + 2000 | 100 |
| Present fused heterocyclic compound 89 + Present carboxamide compound (2a) | 500 + 500 | 100 |
| Present fused heterocyclic compound 89 + Present carboxamide compound (2a) | 500 + 1 | 100 |
| Untreated group | — | 0 |

TABLE 24

| Composition | Concentration (ppm) | Mortality (%) |
|---|---|---|
| Present fused heterocyclic compound 99 + Present carboxamide compound (2a) | 200 + 2000 | 100 |
| Present fused heterocyclic compound 99 + Present carboxamide compound (2a) | 500 + 500 | 100 |
| Present fused heterocyclic compound 99 + Present carboxamide compound (2a) | 500 + 1 | 100 |
| Present fused heterocyclic compound 130 + Present carboxamide compound (2a) | 200 + 2000 | 100 |
| Present fused heterocyclic compound 130 + Present carboxamide compound (2a) | 500 + 500 | 100 |
| Present fused heterocyclic compound 130 + Present carboxamide compound (2a) | 500 + 1 | 100 |
| Present fused heterocyclic compound 312 + Present carboxamide compound (2a) | 200 + 2000 | 100 |
| Present fused heterocyclic compound 312 + Present carboxamide compound (2a) | 500 + 500 | 100 |
| Present fused heterocyclic compound 312 + Present carboxamide compound (2a) | 500 + 1 | 100 |
| Present fused heterocyclic compound 399 + Present carboxamide compound (2a) | 200 + 2000 | 100 |
| Present fused heterocyclic compound 399 + Present carboxamide compound (2a) | 500 + 500 | 100 |
| Present fused heterocyclic compound 399 + Present carboxamide compound (2a) | 500 + 1 | 100 |
| Present fused heterocyclic compound 404 + Present carboxamide compound (2a) | 200 + 2000 | 100 |
| Present fused heterocyclic compound 404 + Present carboxamide compound (2a) | 500 + 500 | 100 |
| Present fused heterocyclic compound 404 + Present carboxamide compound (2a) | 500 + 1 | 100 |
| Present fused heterocyclic compound 409 + Present carboxamide compound (2a) | 200 + 2000 | 100 |
| Present fused heterocyclic compound 409 + Present carboxamide compound (2a) | 500 + 500 | 100 |
| Present fused heterocyclic compound 409 + Present carboxamide compound (2a) | 500 + 1 | 100 |
| Present fused heterocyclic compound 414 + Present carboxamide compound (2a) | 200 + 2000 | 100 |
| Present fused heterocyclic compound 414 + Present carboxamide compound (2a) | 500 + 500 | 100 |
| Present fused heterocyclic compound 414 + Present carboxamide compound (2a) | 500 + 1 | 100 |
| Present fused heterocyclic compound 419 + Present carboxamide compound (2a) | 200 + 2000 | 100 |
| Present fused heterocyclic compound 419 + Present carboxamide compound (2a) | 500 + 500 | 100 |
| Present fused heterocyclic compound 419 + Present carboxamide compound (2a) | 500 + 1 | 100 |
| Present fused heterocyclic compound 421 + Present carboxamide compound (2a) | 200 + 2000 | 100 |
| Present fused heterocyclic compound 421 + Present carboxamide compound (2a) | 500 + 500 | 100 |
| Present fused heterocyclic compound 421 + Present carboxamide compound (2a) | 500 + 1 | 100 |
| Untreated group | — | 0 |

TABLE 25

| Composition | Concentration (ppm) | Mortality (%) |
|---|---|---|
| Present fused heterocyclic compound 423 + Present carboxamide compound (2a) | 200 + 2000 | 100 |
| Present fused heterocyclic compound 423 + Present carboxamide compound (2a) | 500 + 500 | 100 |
| Present fused heterocyclic compound 423 + Present carboxamide compound (2a) | 500 + 1 | 100 |
| Present fused heterocyclic compound 443 + Present carboxamide compound (2a) | 200 + 2000 | 100 |
| Present fused heterocyclic compound 443 + Present carboxamide compound (2a) | 500 + 500 | 100 |
| Present fused heterocyclic compound 443 + Present carboxamide compound (2a) | 500 + 1 | 100 |
| Present fused heterocyclic compound 444 + Present carboxamide compound (2a) | 200 + 2000 | 100 |
| Present fused heterocyclic compound 444 + Present carboxamide compound (2a) | 500 + 500 | 100 |
| Present fused heterocyclic compound 444 + Present carboxamide compound (2a) | 500 + 1 | 100 |
| Present fused heterocyclic compound 445 + Present carboxamide compound (2a) | 200 + 2000 | 100 |
| Present fused heterocyclic compound 445 + Present carboxamide compound (2a) | 500 + 500 | 100 |
| Present fused heterocyclic compound 445 + Present carboxamide compound (2a) | 500 + 1 | 100 |
| Present fused heterocyclic compound 464 + Present carboxamide compound (2a) | 200 + 2000 | 100 |
| Present fused heterocyclic compound 464 + Present carboxamide compound (2a) | 500 + 500 | 100 |
| Present fused heterocyclic compound 464 + Present carboxamide compound (2a) | 500 + 1 | 100 |
| Present fused heterocyclic compound 467 + Present carboxamide compound (2a) | 200 + 2000 | 100 |
| Present fused heterocyclic compound 467 + Present carboxamide compound (2a) | 500 + 500 | 100 |
| Present fused heterocyclic compound 467 + Present carboxamide compound (2a) | 500 + 1 | 100 |
| Untreated group | — | 0 |

A composition for controlling pests of the present invention can control pests.

The invention claimed is:

1. A composition for controlling pests comprising a compound represented by the formula (1-4) or N-oxide thereof and a compound represented by the formula (2);

the formula (1-4):

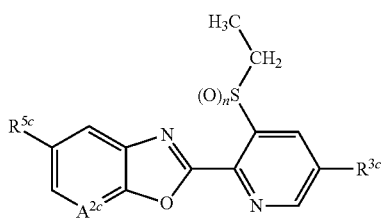

(1-4)

wherein $A^{2c}$ represents a nitrogen atom or $=CR^{8c}-$;

$R^{3c}$ represents a $-C(OR^{10c})_3$ group, a halogen atom, a hydrogen atom, or a C1-C3 alkyl group which may be substituted with one or more halogen atoms;

$R^{5c}$ represents a C1-C3 haloalkyl group, a $-OR^{20c}$ group, a $-S(O)_mR^{20c}$ group, or a halogen atom;

$R^{8c}$ represents a $-S(O)_m{}^{10c}$ group, a cyano group, a halogen atom, or a hydrogen atom;

$R^{10c}$ independently represents a C1-C3 alkyl group which may be substituted with one or more halogen atoms;

$R^{20c}$ represents a C1-C3 haloalkyl group;

each m independently represents 0, 1 or 2; and n represents 0, 1 or 2;

the formula (2):

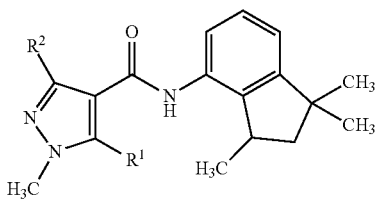

(2)

wherein $R^1$ represents a hydrogen atom or a methyl group; and $R^2$ represents a methyl group, a difluoromethyl group, or a trifluoromethyl group.

2. The composition for controlling pests according to claim 1, wherein in the compound represented by the formula (1-4) or N-oxide thereof, $R^{3c}$ is a halogen atom or a hydrogen atom;

$R^{5c}$ is a C1-C3 perfluoroalkyl group, a $-OR^{30c}$ group, or a $-S(O)_mR^{30c}$ group, $R^{30c}$ is a C1-C3 perfluoroalkyl group, and $R^{8c}$ is a halogen atom or a hydrogen atom.

3. The composition for controlling pests according to claim 1 wherein a weight ratio of the compound represented by the formula (1-4) to the compound represented by the formula (2) is in the range of 1,000:1 to 1:1,000.

4. The composition for controlling pests according to claim 1 wherein a weight ratio of the compound represented by the formula (1-4) to the compound represented by the formula (2) is in the range of 500:1 to 1:10.

5. A method for controlling pests, which comprises the step of applying an effective amount of the composition for controlling pests according to claim 1 to plants, plant seeds, bulbs, or a soil where plants grow.

* * * * *